(12) United States Patent
Arevalos et al.

(10) Patent No.: US 11,865,270 B2
(45) Date of Patent: Jan. 9, 2024

(54) BODILY FLUID MANAGEMENT SYSTEM

(71) Applicant: Starling Medical, Inc., Houston, TX (US)

(72) Inventors: Christopher Alex Arevalos, Houston, TX (US); Sylvie Kalikoff, Houston, TX (US); Hannah McKenney, Houston, TX (US); William Andrew Hendricks, III, Houston, TX (US); Patricia Thai, Pearland, TX (US); Kunj Sheth, San Francisco, CA (US)

(73) Assignee: Starling Medical, Inc., Houston, TX (US)

( * ) Notice: Subject to any disclaimer, the term of this patent is extended or adjusted under 35 U.S.C. 154(b) by 0 days.

(21) Appl. No.: 17/866,383

(22) Filed: Jul. 15, 2022

(65) Prior Publication Data

US 2022/0362509 A1  Nov. 17, 2022

Related U.S. Application Data

(63) Continuation of application No. PCT/US2022/025421, filed on Apr. 19, 2022, and a
(Continued)

(51) Int. Cl.
*A61M 25/00* (2006.01)
*A61M 5/20* (2006.01)
(Continued)

(52) U.S. Cl.
CPC .......... *A61M 25/0017* (2013.01); *A61M 1/69* (2021.05); *A61M 5/20* (2013.01); *A61M 39/22* (2013.01);
(Continued)

(58) Field of Classification Search
CPC .................. A61M 1/69; A61M 39/22; A61M 2202/0496; A61B 5/20; A61B 5/207;
(Continued)

(56) References Cited

U.S. PATENT DOCUMENTS 3,503,400 A  3/1970 Osthagen et al.
3,575,158 A  4/1971 Summers
(Continued)

FOREIGN PATENT DOCUMENTS

EP  0258690 B1  3/1992
EP  0357846 B1  11/1992
(Continued)

OTHER PUBLICATIONS

International Preliminary Report on Patentability for International Application No. PCT/US2021/013933 dated Jul. 28, 2022, 8 pages.
(Continued)

*Primary Examiner* — Adam Marcetich
(74) *Attorney, Agent, or Firm* — Cooley LLP

(57) ABSTRACT

In some embodiments, an external bladder management system that is configured to reside within a urine collection receptacle (e.g., a toilet) includes a body that houses a fluid testing chamber. The fluid testing chamber is fluidically coupled to a fluid inlet and a fluid outlet. The system further includes a fluid capturing funnel fluidically coupled to and extending from the body and configured to couple the body to the urine collection receptacle. The system further includes an optical sensor disposed within the body and including (1) an emitter configured to convey light across the fluid testing chamber, and (2) an optical detector capable of measuring an intensity of the light as the light exits the fluid testing chamber. The fluid inlet, fluid testing chamber,
(Continued)

and fluid outlet are collectively configured to encourage a laminar flow profile of the fluid as it flows through the fluid testing chamber.

39 Claims, 78 Drawing Sheets

Related U.S. Application Data continuation-in-part of application No. PCT/US2021/013933, filed on Jan. 19, 2021.

(60) Provisional application No. 63/323,203, filed on Mar. 24, 2022, provisional application No. 63/176,674, filed on Apr. 19, 2021, provisional application No. 62/961,976, filed on Jan. 16, 2020.

(51) Int. Cl.
*A61M 1/00* (2006.01)
*A61M 39/22* (2006.01)

(52) U.S. Cl.
CPC .............. *A61M 2202/0496* (2013.01); *A61M 2205/331* (2013.01); *A61M 2205/3317* (2013.01); *A61M 2205/3592* (2013.01); *A61M 2206/11* (2013.01)

(58) Field of Classification Search
CPC ............. A61B 5/208; A61F 2013/8473; A61F 2013/8476; A61F 2013/8488; A61F 2013/8491
See application file for complete search history.

(56) References Cited

U.S. PATENT DOCUMENTS

| | | | |
|---|---|---|---|
| 3,731,670 A | 5/1973 | Loe | |
| 3,812,841 A | 5/1974 | Isaacson | |
| 4,284,412 A * | 8/1981 | Hansen | G01N 33/56972 436/805 |
| 4,553,533 A | 11/1985 | Leighton | |
| 4,745,929 A * | 5/1988 | Silver | A61B 5/208 604/323 |
| 4,762,798 A * | 8/1988 | Deutsch | G01N 21/75 436/67 |
| 5,004,454 A | 4/1991 | Beyar et al. | |
| 5,030,199 A | 7/1991 | Barwick et al. | |
| 5,041,092 A | 8/1991 | Barwick | |
| 5,107,133 A * | 4/1992 | Klainer | G01N 21/253 250/573 |
| 5,140,999 A | 8/1992 | Ardito | |
| 5,167,237 A | 12/1992 | Rabin et al. | |
| 5,269,802 A | 12/1993 | Garber | |
| 5,366,506 A | 11/1994 | Davis | |
| 5,520,636 A | 5/1996 | Korth et al. | |
| 5,562,598 A | 10/1996 | Whalen et al. | |
| 5,624,374 A | 4/1997 | Von Iderstein | |
| 5,701,916 A | 12/1997 | Kulisz et al. | |
| 5,718,686 A | 2/1998 | Davis | |
| 5,770,454 A * | 6/1998 | Essenpreis | G01N 21/49 436/164 |
| 5,833,707 A | 11/1998 | McIntyre et al. | |
| 5,971,967 A | 10/1999 | Willard | |
| 6,066,088 A | 5/2000 | Davis | |
| 6,110,111 A | 8/2000 | Barnard | |
| 6,417,750 B1 | 7/2002 | Sohn | |
| 6,527,702 B2 | 3/2003 | Whalen et al. | |
| 6,599,237 B1 | 7/2003 | Singh | |
| 6,623,421 B1 | 9/2003 | Rivero Rodriguez et al. | |
| 6,652,569 B1 | 11/2003 | Taylor et al. | |
| 6,673,051 B2 | 1/2004 | Flinchbaugh | |
| 6,701,918 B2 | 3/2004 | Fariss et al. | |
| 6,764,519 B2 | 7/2004 | Whitmore, III | |
| 6,821,291 B2 | 11/2004 | Bolea et al. | |
| 6,913,244 B1 | 7/2005 | Atkinson et al. | |
| 7,001,327 B2 | 2/2006 | Whalen et al. | |
| 7,041,139 B2 | 5/2006 | Bluni et al. | |
| 7,610,093 B2 | 10/2009 | Gerber et al. | |
| 8,097,007 B2 | 1/2012 | Evans et al. | |
| 8,328,877 B2 | 12/2012 | Gellman | |
| 8,366,674 B2 | 2/2013 | Frassica et al. | |
| 8,858,460 B2 | 10/2014 | Connors et al. | |
| 9,662,058 B2 | 5/2017 | Burnett et al. | |
| 9,707,065 B2 | 7/2017 | Kunz | |
| 9,707,068 B2 | 7/2017 | Drager et al. | |
| 9,775,698 B2 | 10/2017 | Herrera et al. | |
| 9,839,373 B2 | 12/2017 | Connolly et al. | |
| 9,931,060 B2 | 4/2018 | Connolly et al. | |
| 9,950,138 B2 | 4/2018 | O'Callaghan et al. | |
| 10,010,392 B1 | 7/2018 | Zukowski | |
| D835,784 S | 12/2018 | Orr et al. | |
| 10,383,606 B1 | 8/2019 | McCord et al. | |
| 10,390,989 B2 | 8/2019 | Sanchez et al. | |
| 2004/0147871 A1 | 7/2004 | Burnett | |
| 2005/0131547 A1 | 6/2005 | Segura et al. | |
| 2005/0243303 A1 * | 11/2005 | Pettersson | A61B 5/14557 356/39 |
| 2005/0261605 A1 * | 11/2005 | Shemer | G01N 21/31 600/584 |
| 2006/0073606 A1 | 4/2006 | Fukuda | |
| 2006/0111691 A1 | 5/2006 | Bolmsjo et al. | |
| 2006/0247724 A1 | 11/2006 | Gerber et al. | |
| 2008/0312538 A1 * | 12/2008 | Shahar | A61B 7/026 600/459 |
| 2010/0312225 A1 | 12/2010 | Armistead | |
| 2011/0106060 A1 | 5/2011 | Atkinson et al. | |
| 2012/0157759 A1 | 6/2012 | Wirbisky et al. | |
| 2013/0302212 A1 * | 11/2013 | Wakui | G01N 21/51 422/82.05 |
| 2015/0359522 A1 * | 12/2015 | Recht | G01N 21/6486 600/573 |
| 2017/0086728 A1 * | 3/2017 | Hidas | A61B 5/0022 |
| 2017/0095323 A1 | 4/2017 | Garcia | |
| 2017/0102336 A1 * | 4/2017 | Takinami | G01N 21/8483 |
| 2017/0135622 A1 * | 5/2017 | Shimokawa | G01F 1/075 |
| 2017/0156838 A1 | 6/2017 | Herrera et al. | |
| 2017/0307525 A1 * | 10/2017 | Langhoff | G01N 21/03 |
| 2017/0370826 A1 * | 12/2017 | Coombs | G01N 21/0303 |
| 2018/0080923 A1 * | 3/2018 | Hall | G01N 21/59 |
| 2018/0163388 A1 | 6/2018 | Staton et al. | |
| 2018/0229015 A1 | 8/2018 | Pisano et al. | |
| 2019/0117116 A1 | 4/2019 | Connolly et al. | |
| 2019/0145963 A1 * | 5/2019 | Zait | G01N 33/56972 436/63 |
| 2019/0231244 A1 * | 8/2019 | Swan | A61B 5/202 |
| 2019/0302099 A1 * | 10/2019 | Pollak | G01N 21/0303 |
| 2019/0366329 A1 * | 12/2019 | John | B01L 3/508 |
| 2020/0205717 A1 | 7/2020 | Yang et al. | |
| 2020/0390422 A1 * | 12/2020 | Hall | G01N 33/5005 |
| 2021/0048385 A1 * | 2/2021 | Shimokita | G01N 21/27 |
| 2021/0093243 A1 * | 4/2021 | Stanton | A61B 5/024 |
| 2021/0311018 A1 * | 10/2021 | Harrington | G01N 21/3577 |
| 2022/0022810 A1 * | 1/2022 | Hall | A61B 5/0075 |
| 2022/0192565 A1 * | 6/2022 | Cheng | A61B 5/208 |

FOREIGN PATENT DOCUMENTS

| | | |
|---|---|---|
| FR | 2655536 A1 | 6/1991 |
| WO | WO-2018027102 A1 | 2/2018 |
| WO | WO-2018144463 A1 | 8/2018 |

OTHER PUBLICATIONS

International Search Report and Written Opinion for International Application No. PCT/US2021/013933 dated Apr. 1, 2021, 9 pages.
International Search Report and Written Opinion for International Application No. PCT/US2022/025421, dated Aug. 18, 2022, 11 pages.

(56) References Cited

OTHER PUBLICATIONS

Invitation to Pay for International Application No. PCT/US2022/025421 dated Jun. 23, 2022, 2 pages.

* cited by examiner

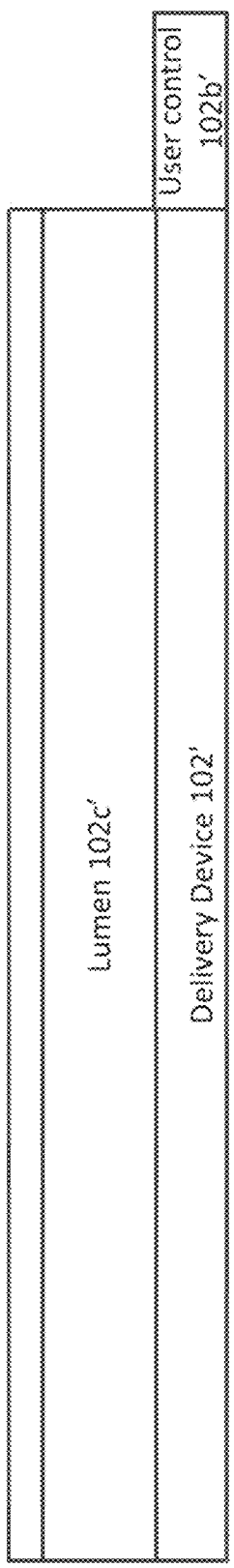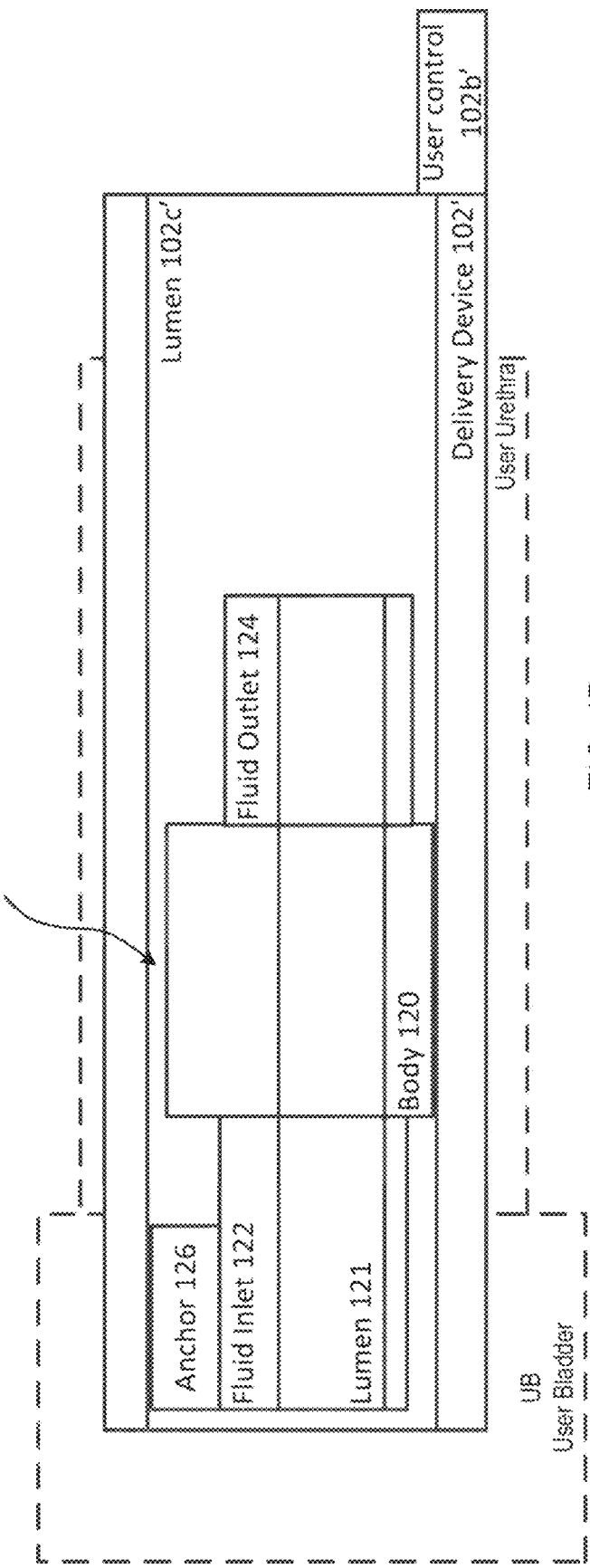

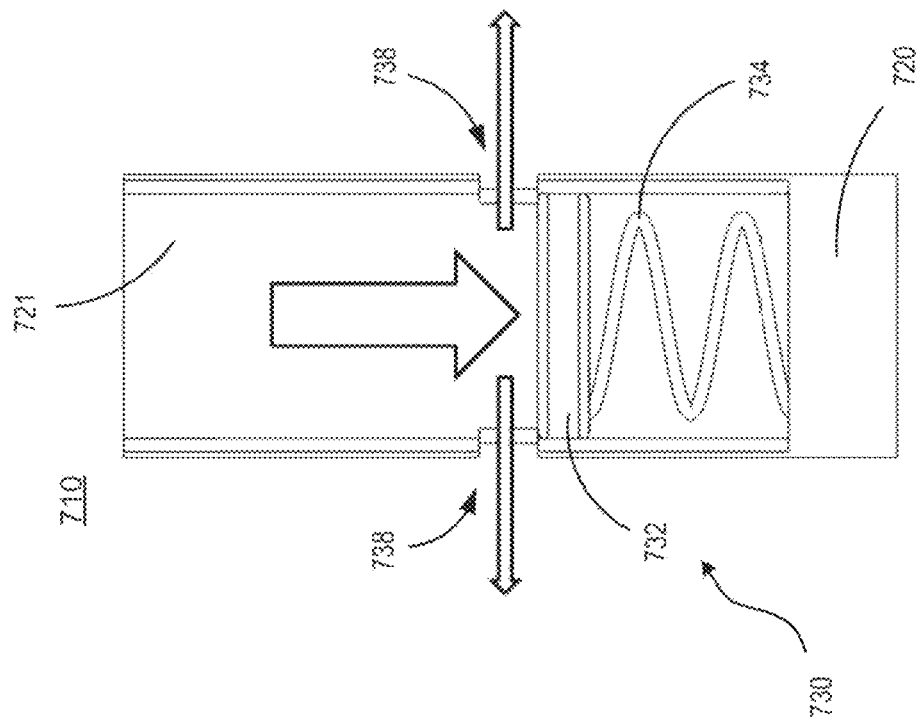
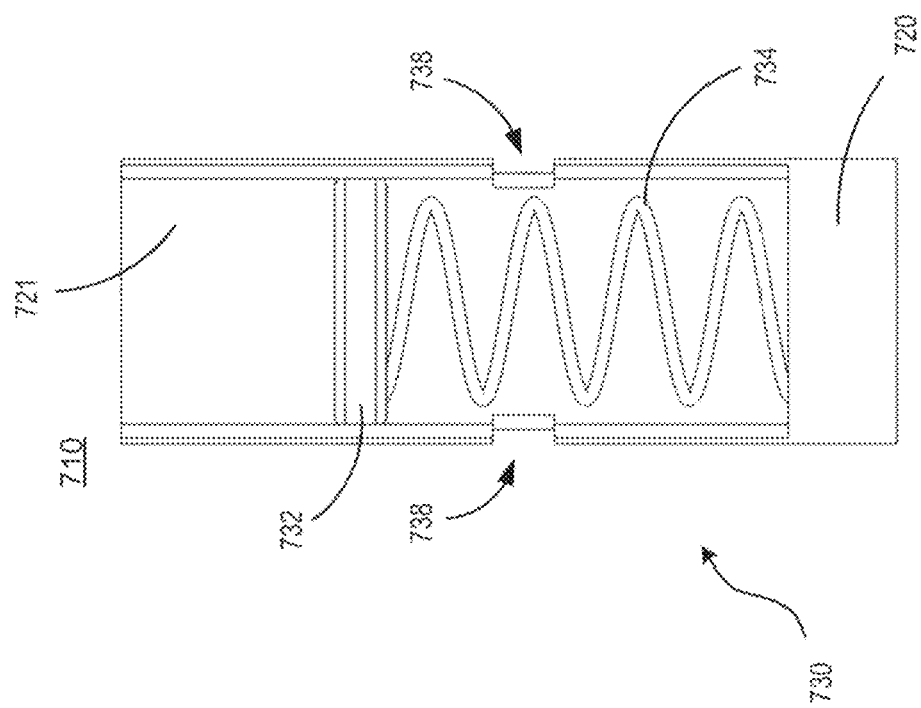

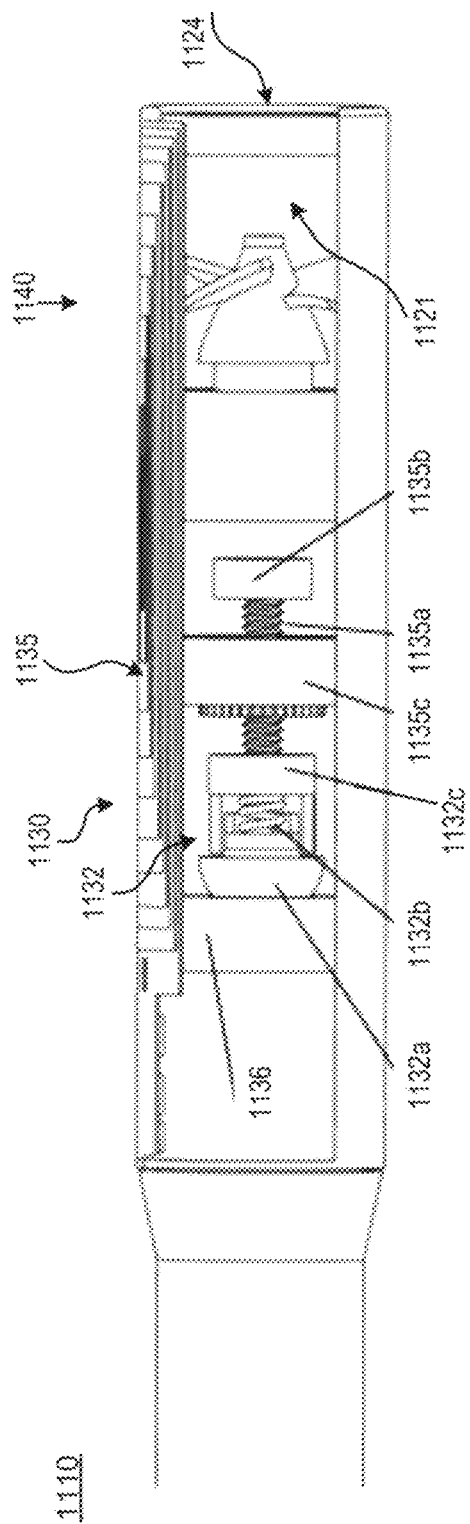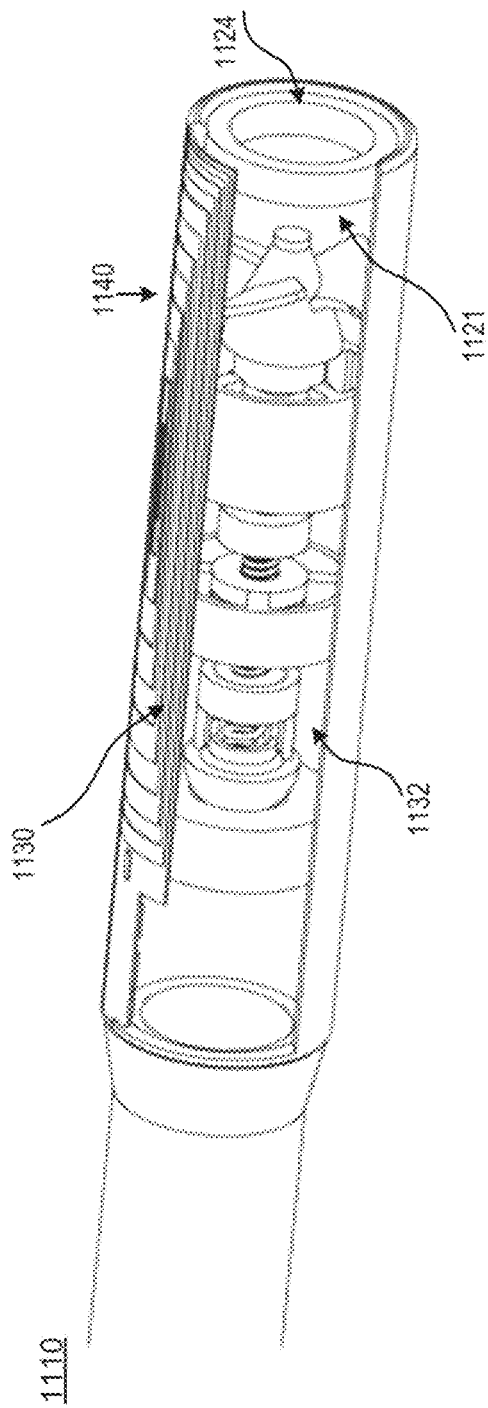
FIG. 15A
FIG. 15B

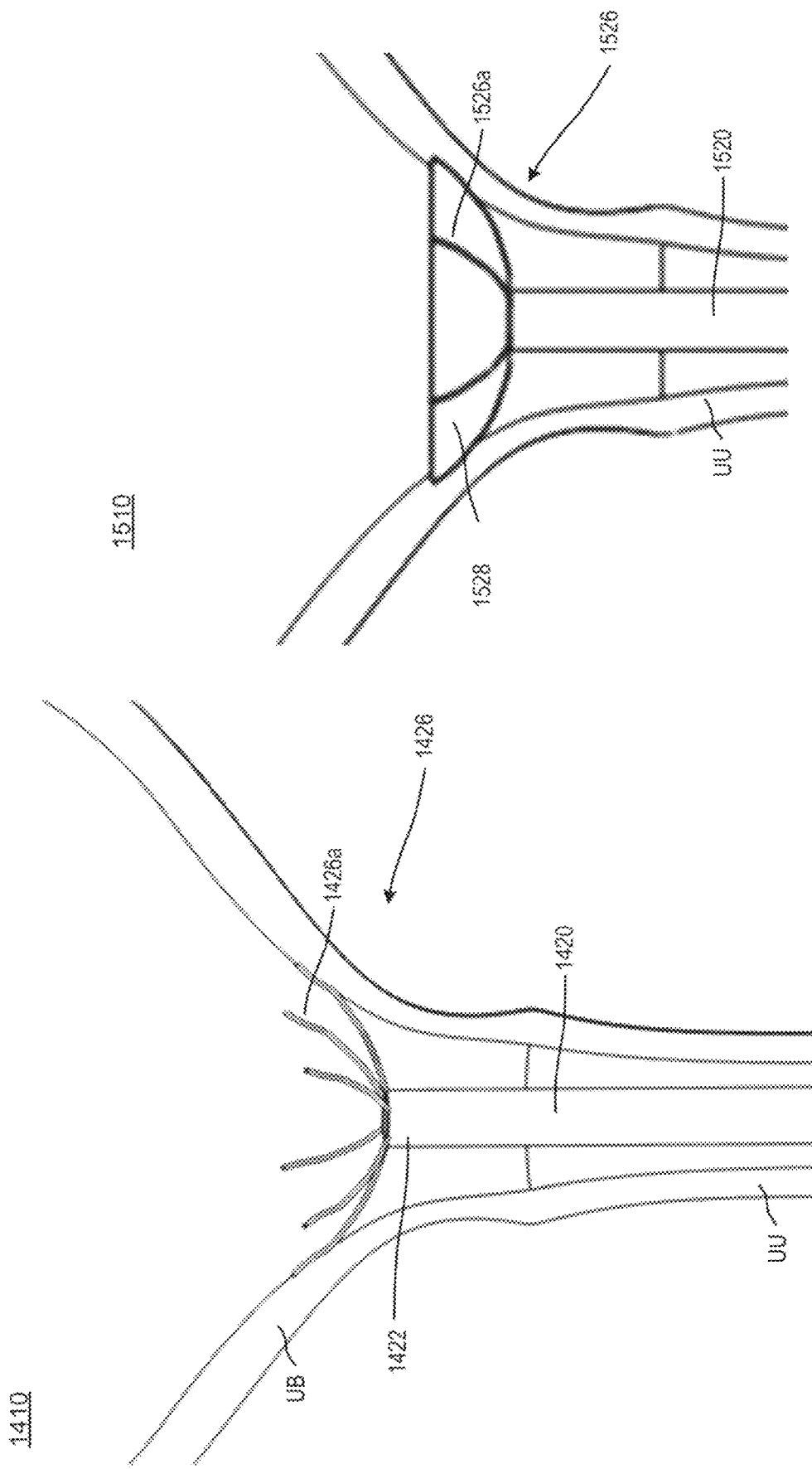

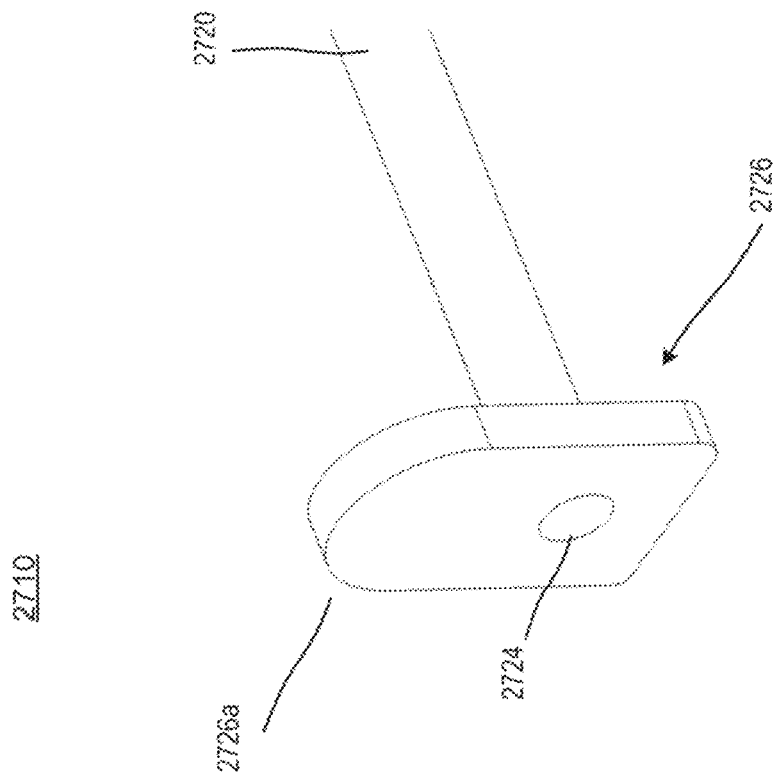
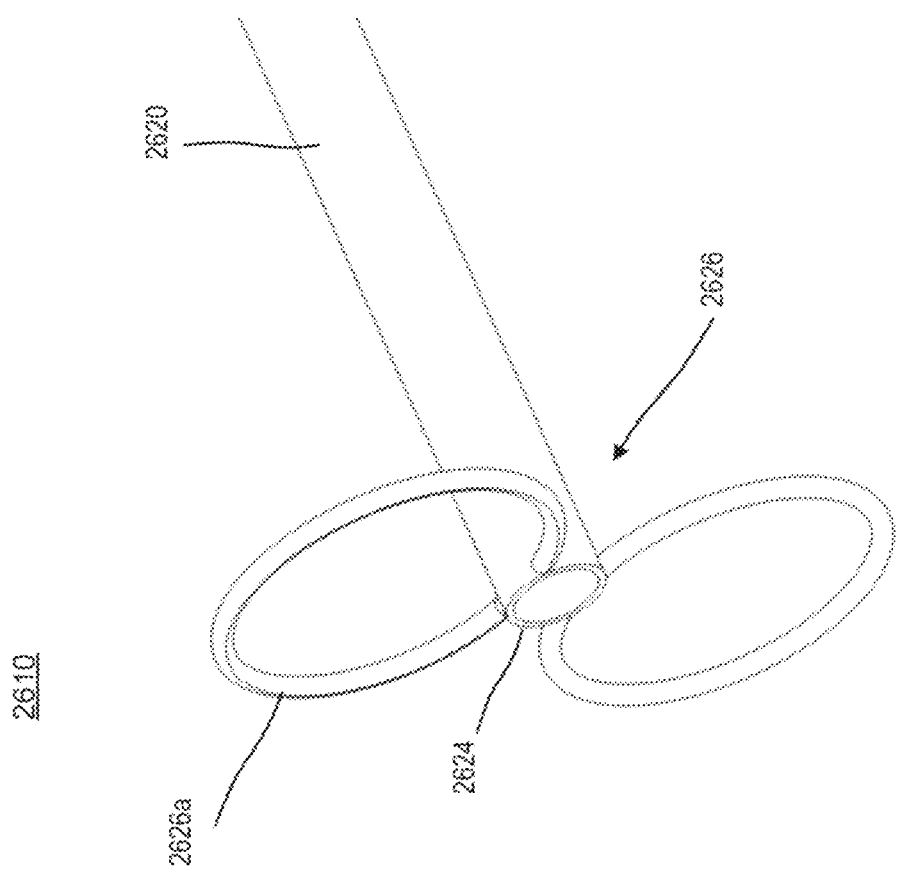

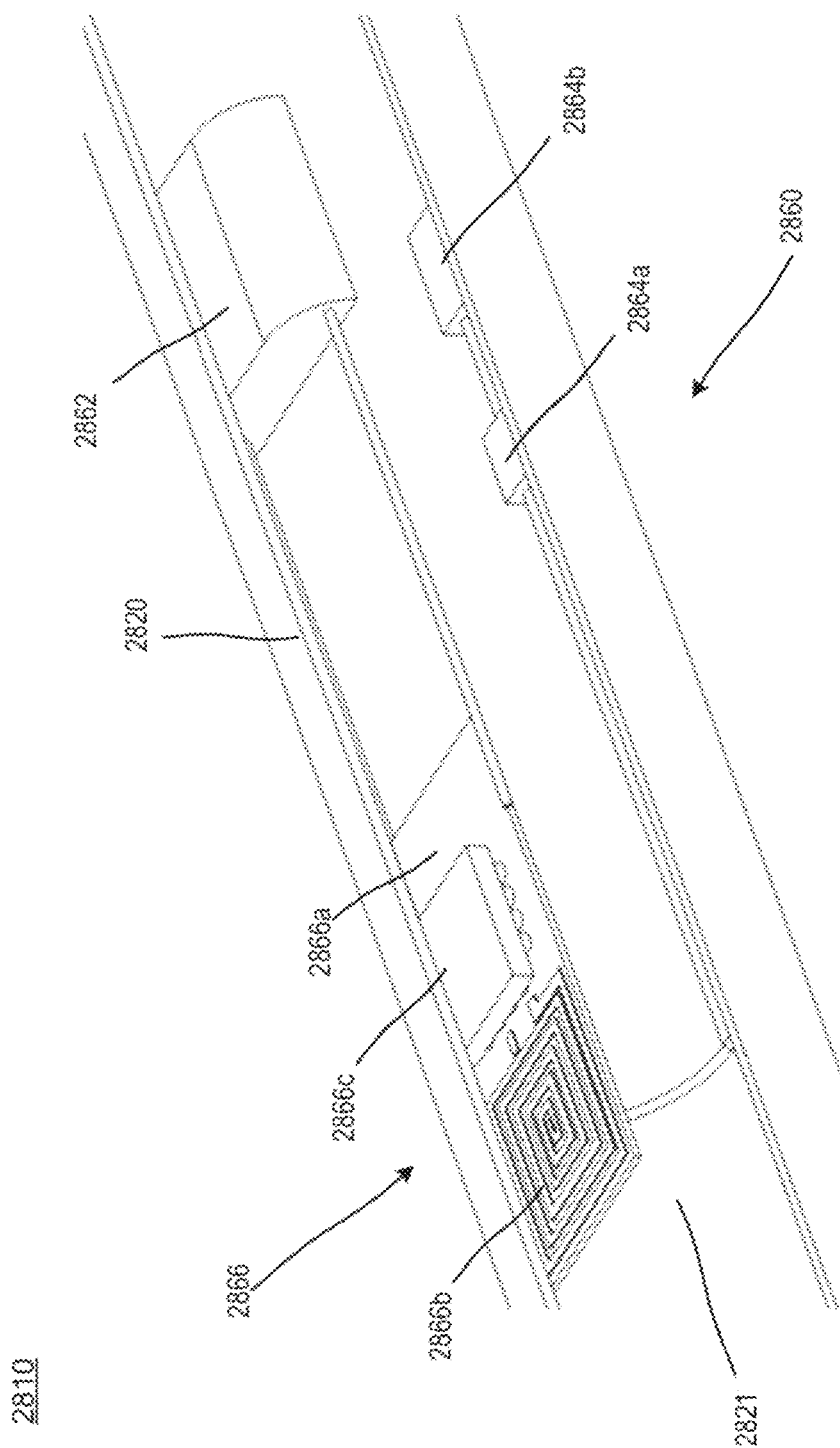

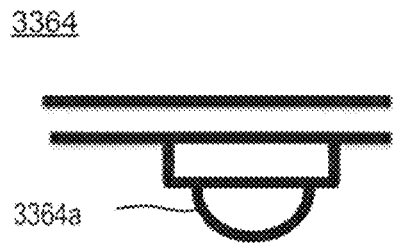
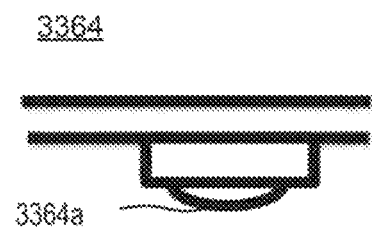
FIG. 37A  FIG. 37B
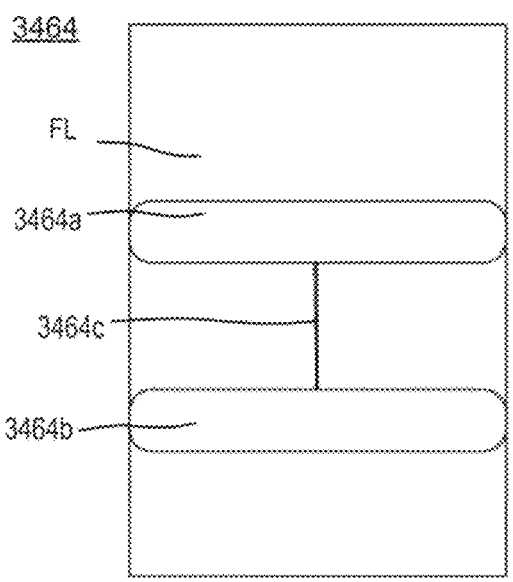
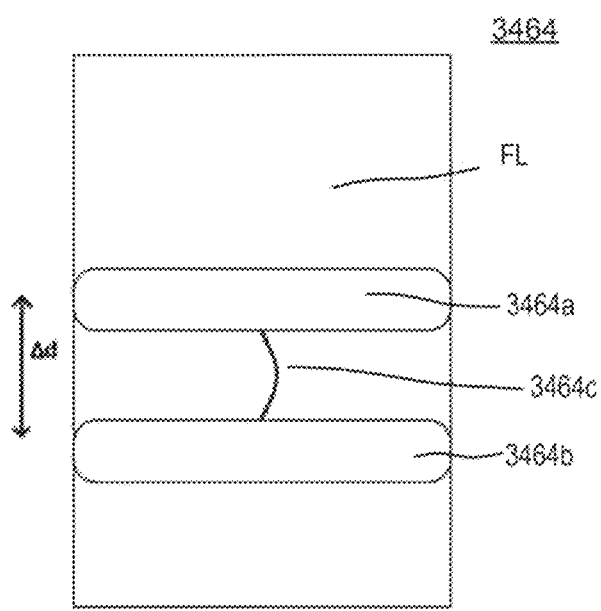
FIG. 38A  FIG. 38B

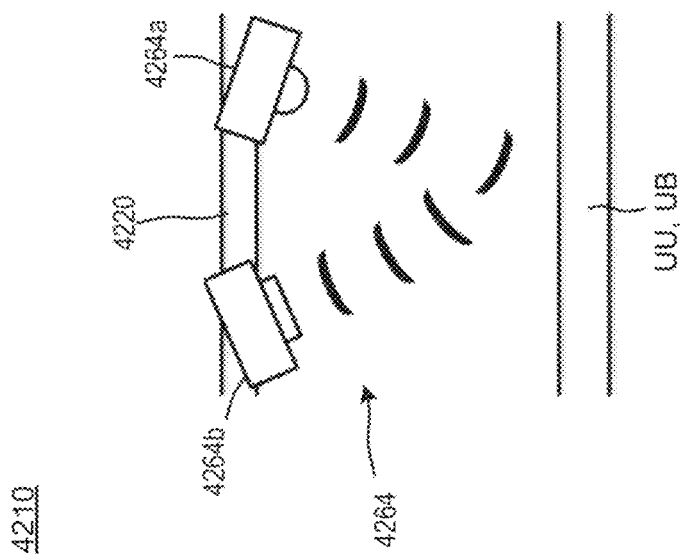

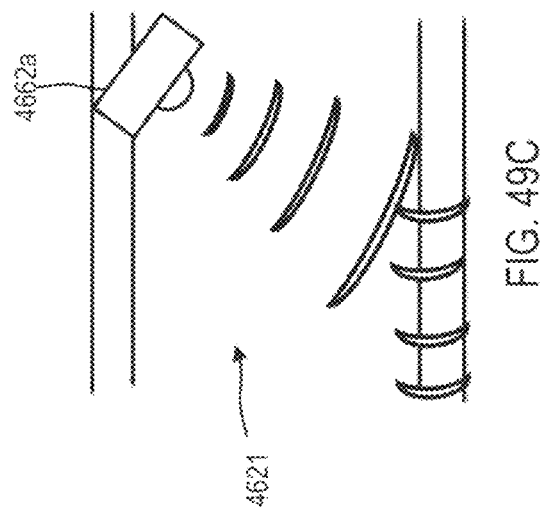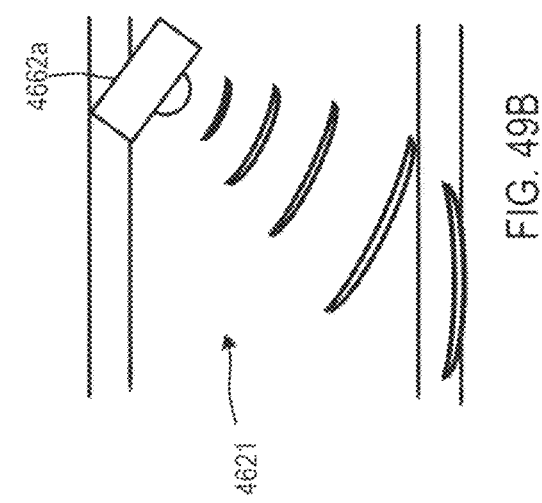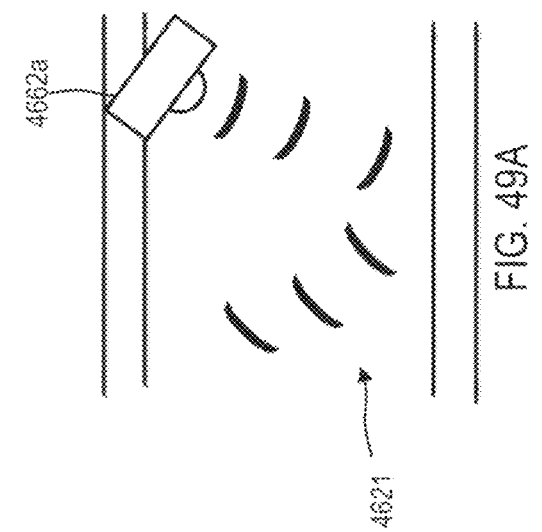

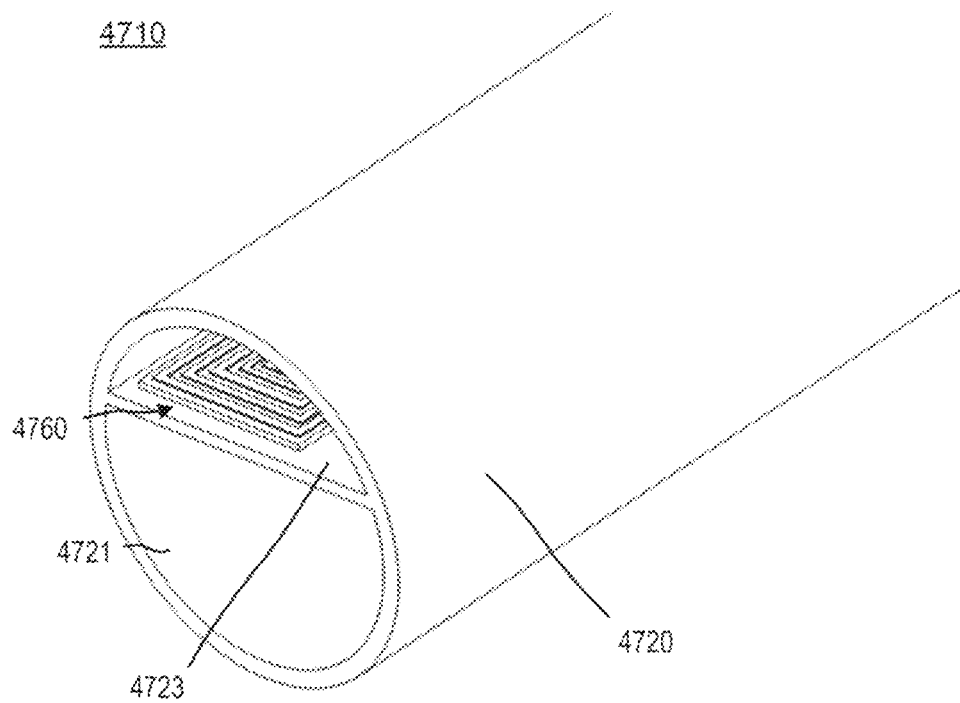
FIG. 50A
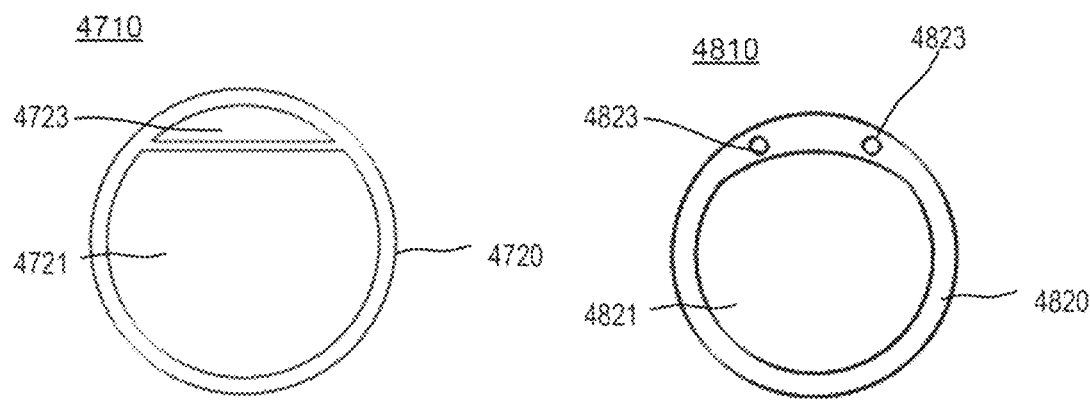
FIG. 50B
FIG. 51

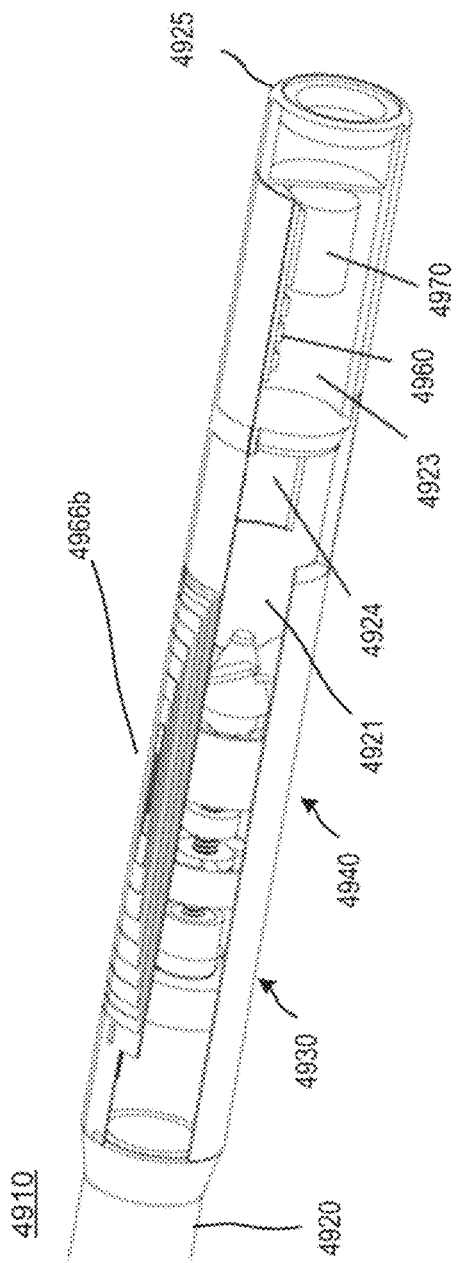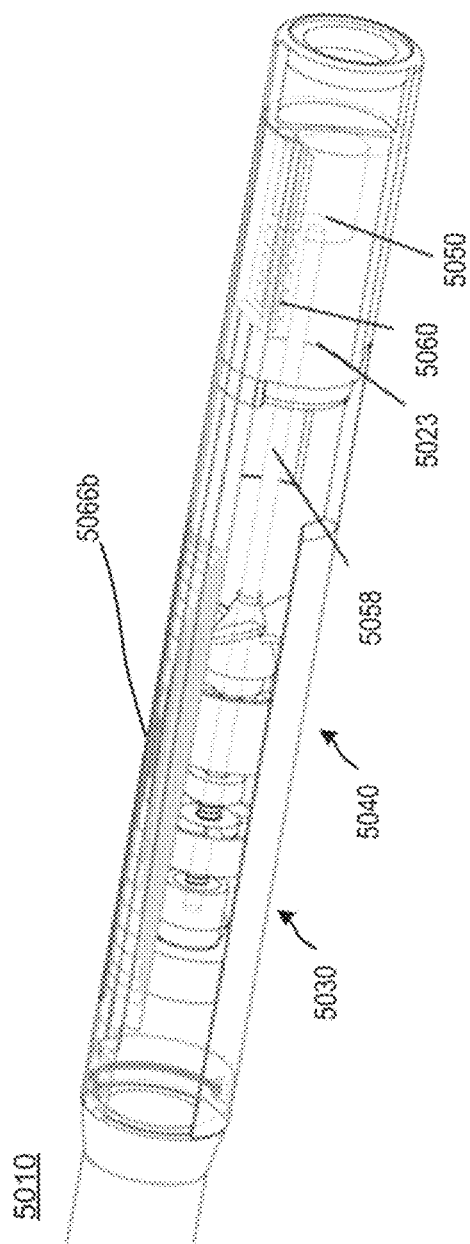

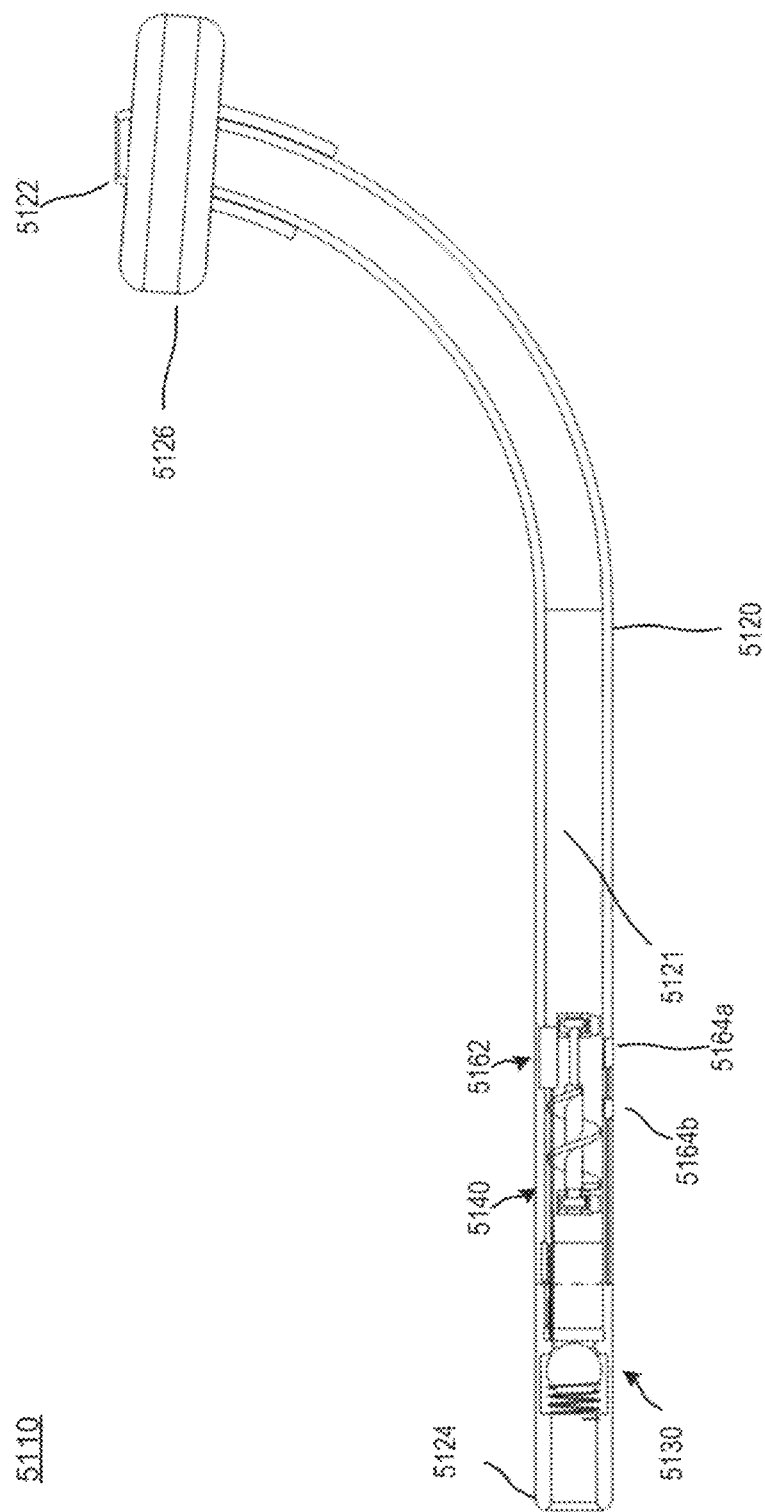

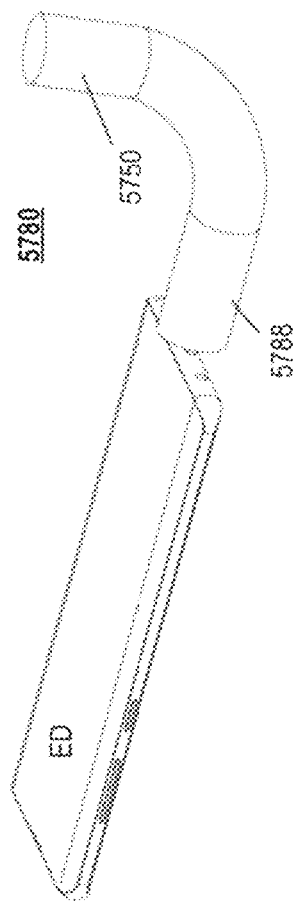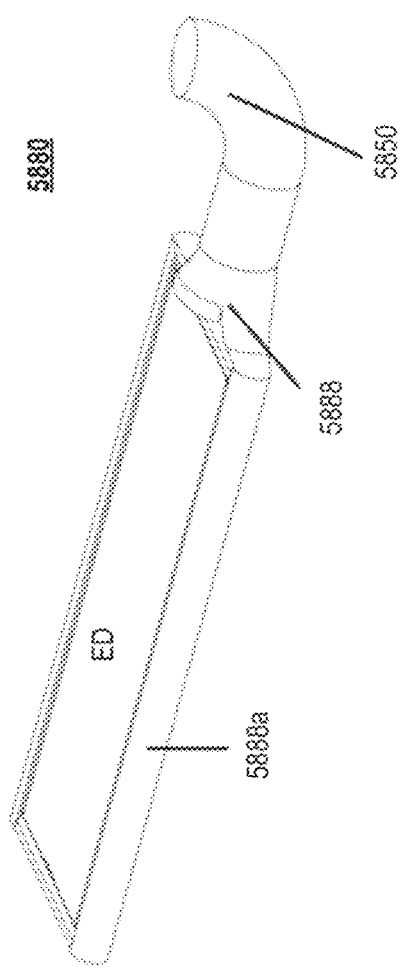

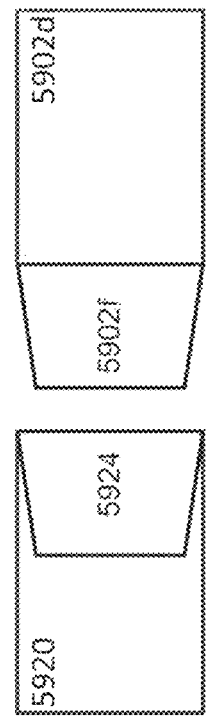
FIG. 63B
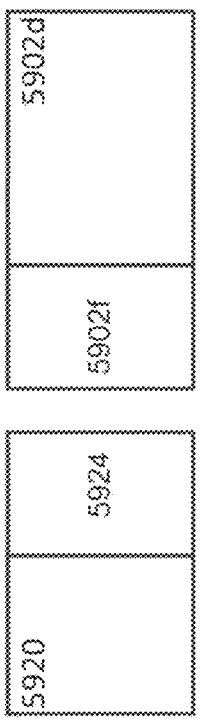
FIG. 63D
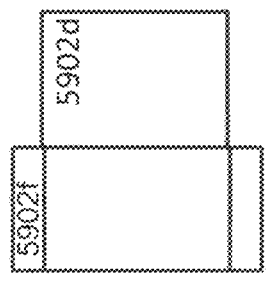
FIG. 63C
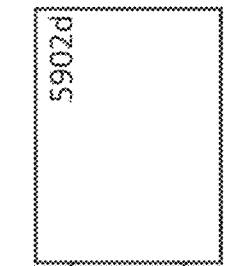
FIG. 63E
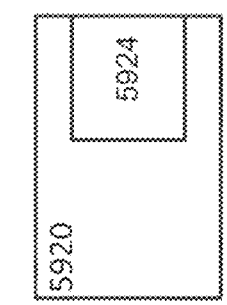

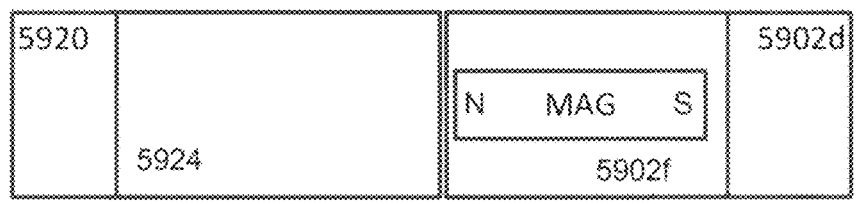
FIG. 63F
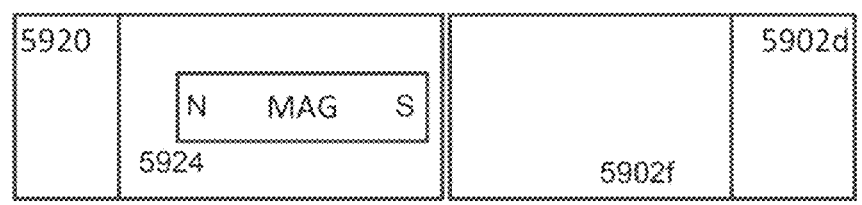
FIG. 63G
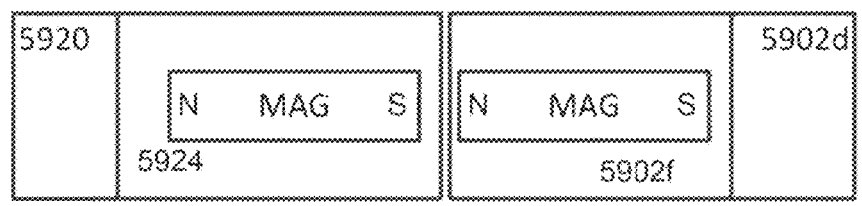
FIG. 63H
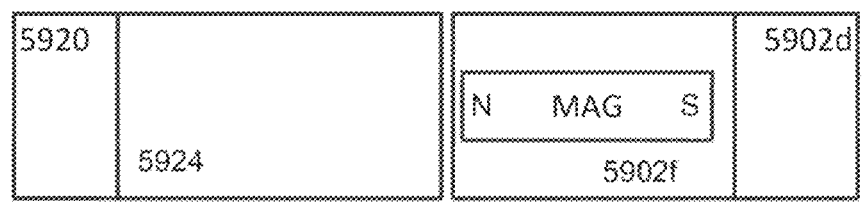
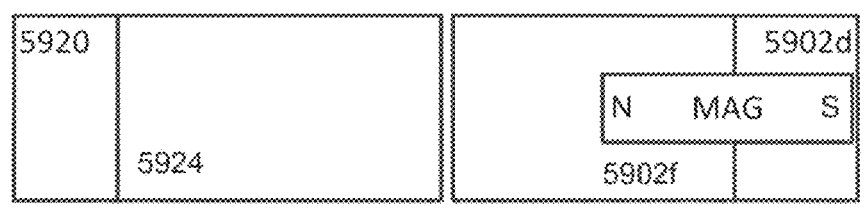
FIG. 63I

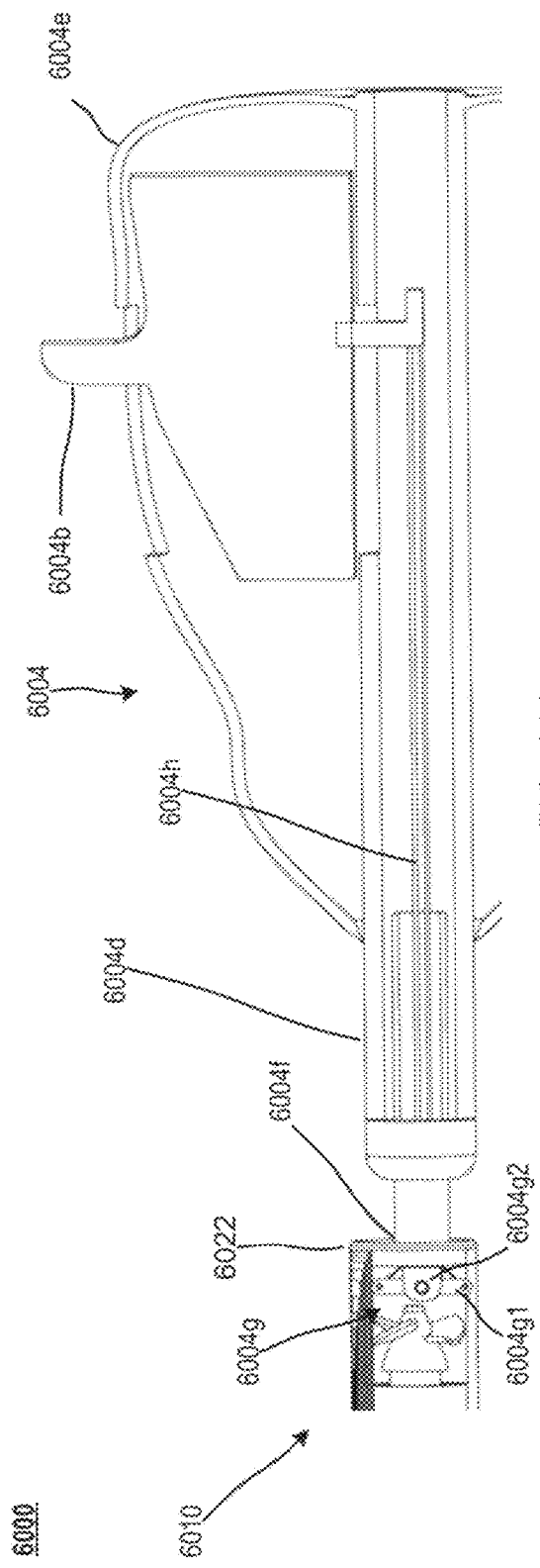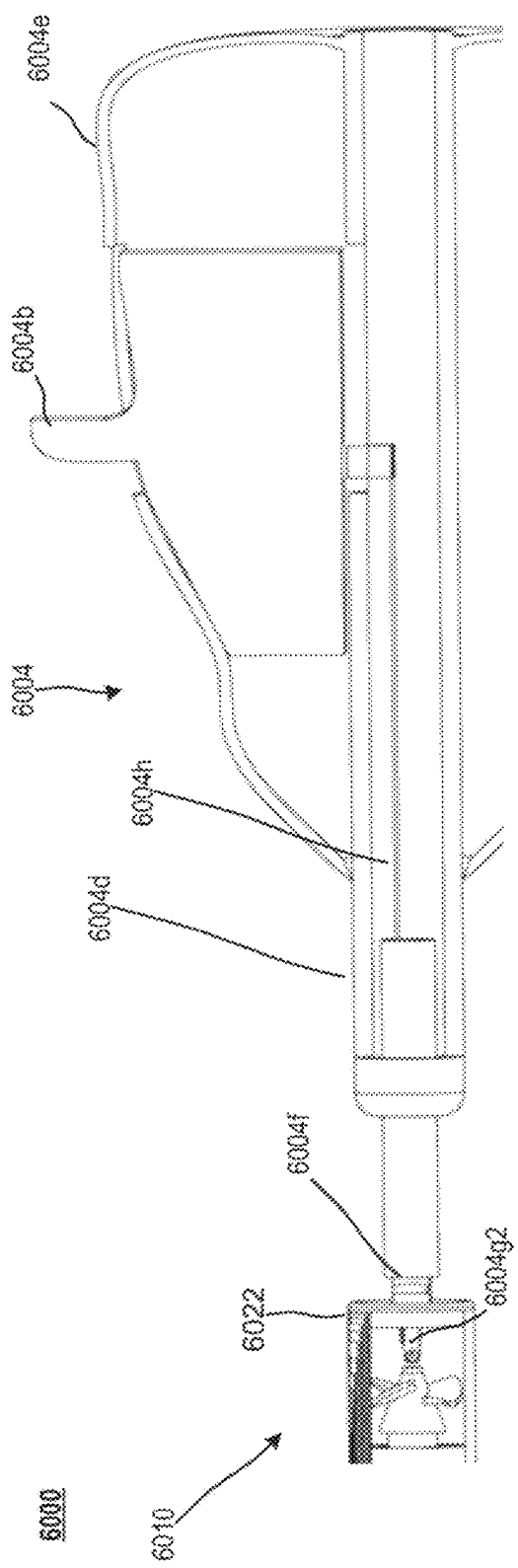

6400

6400

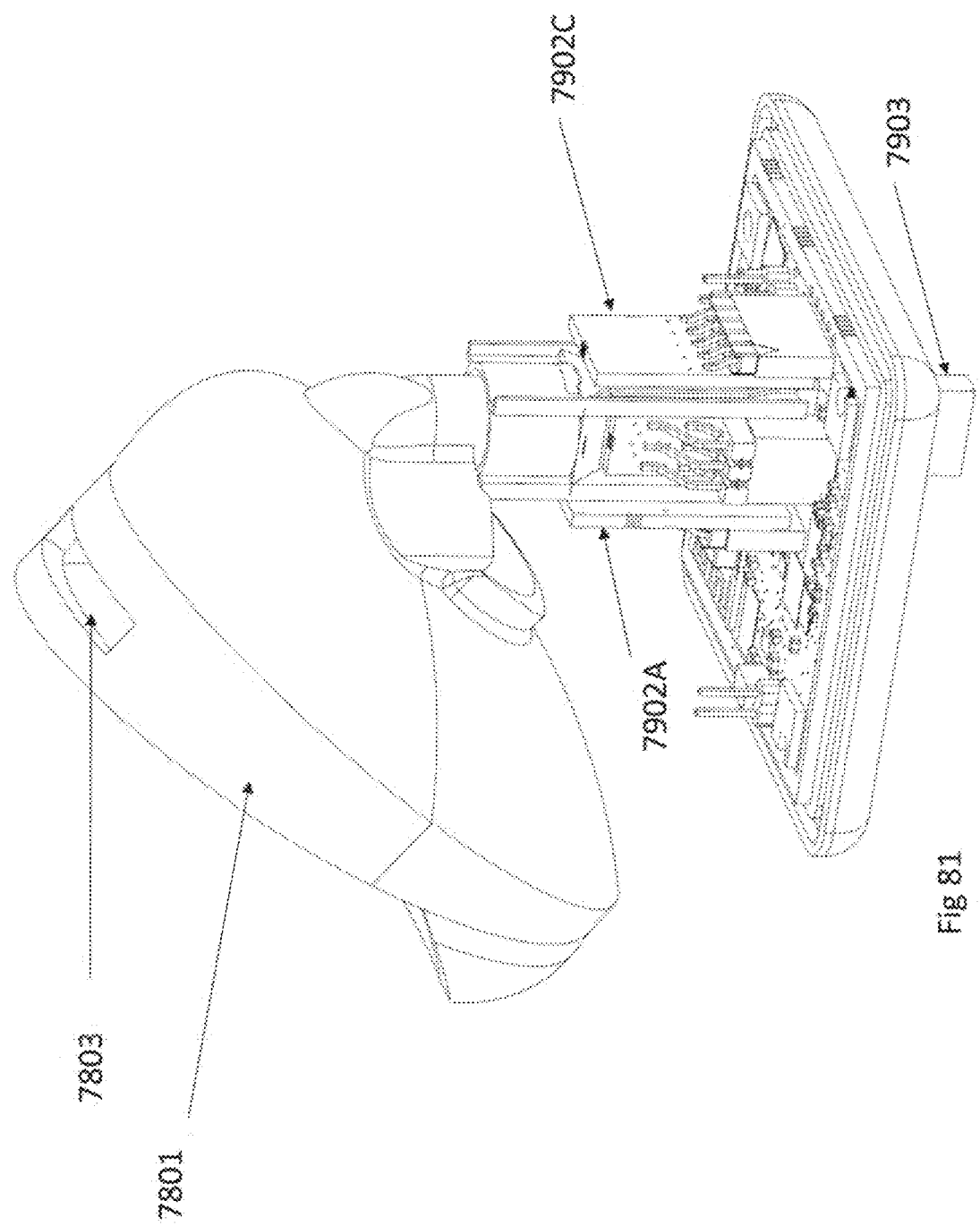

BODILY FLUID MANAGEMENT SYSTEM

CROSS REFERENCE TO RELATED APPLICATIONS

This application is a Continuation of PCT/US2022/025421, filed Apr. 19, 2022, which claims priority to and the benefit of U.S. Provisional Application Ser. No. 63/176,674, filed Apr. 19, 2021 and U.S. Provisional Application Ser. No. 63/323,203, filed Mar. 24, 2022. This application is also a Continuation-in-Part of PCT/US2021/013933, filed Jan. 19, 2021 which claims priority to and the benefit of U.S. Provisional Application Ser. No. 62/961,976, filed Jan. 16, 2020. Each of the prior-mentioned disclosures are herein incorporated by reference in their entirety.

BACKGROUND

Embodiments described herein relate generally to fluid management systems, and more particularly to systems for improved control of voiding of bodily fluid from an organ, such as a bladder, infection detection, and infection prevention.

Individuals with neurogenic bladder lack control of bladder function due to neurological impairment, and may require an external intervention to maintain healthy urological and renal health. Neurogenic bladder may be congenital, but can also arise from disease or due to injury (e.g., stroke, Parkinson's Disease, Alzheimer's, dementia, spinal cord injury, multiple sclerosis). Neurogenic bladder often causes chronic urinary incontinence or chronic urinary retention, both of which bring a significant cost to an individual's well-being and daily way of life. Individuals with chronic urinary incontinence are commonly treated with medication, electrical stimulation, surgical interventions, or implantation of a permanent or temporary valve mechanism. However, for individuals with chronic urinary retention, intermittent catheterization remains the most common method of treatment.

Intermittent catheterization is typically performed using a Clean Intermittent Catheterization (CIC) technique as part of an Intermittent Catheterization Program. In this technique, users insert a catheter at set time intervals throughout the day to relieve pressure and release urine. However, most prescribed CIC programs can significantly diminish an individual's quality of life. For example, the process can be inefficient and puts the user at risk of urinary tract infections, Genito-Urinary (GU) injury, and urethral trauma due to false passage. Furthermore, intermittent catheterization fails to remove a significant volume of residual urine, which then remains stagnant in the bladder. Because individuals with neurogenic bladder commonly lack bladder sensation and thus cannot accurately perceive bladder fullness, many are susceptible to bladder overfilling, resulting in urinary "accidents" and/or urinary reflux which presents a high risk of both infection and tissue damage to the upper urinary tract. Although individuals with neurogenic bladder on CIC programs commonly rely on a timed catheterization schedule, this approach is imprecise and may call for catheterization more frequently than necessary. Not surprisingly, intermittent catheterization creates a substantial emotional burden on both the patient and caregiver: the task is disruptive to normal daily life, is time consuming, uncomfortable, and puts the patient at risk of infection.

Urinary incontinence is a common indication that can arise from neurogenic bladder, as discussed above, or from a variety of other etiologies, including pregnancy, childbirth, menopause, hysterectomy, enlarged prostate, prostate cancer, obstruction, urinary tract infection, and constipation. Existing techniques and devices for controlling timing of urination have drawbacks.

Many individuals have problems with urinary tract infections, especially catheter users. Many individuals who catheterize regularly live with a constant state of bacterial growth within their bladder. Unfortunately, clinicians can often not always distinguish between colonization and a symptomatic urinary tract infection (UTI). This distinction is key because the over prescription and administration of antibiotics leads to antibiotic resistant infections.

Other indications or conditions in which control of fluid discharge from a body organ via a body lumen can include dialysis for diabetes, therapeutic paracentesis to relieve abdominal pressure or fluid due to ascites, chest tubes for removing fluids or blood from the chest cavity, drainage of fluid from the pleural lung space, or removal of excess cerebrospinal fluid from the hydrocephalus.

Accordingly, a strong need exists for improved methods and apparatus to manage bladder function that can reduce patient discomfort and risk of infection and injury for individuals with urinary retention or urinary incontinence.

SUMMARY

A fluid management system can include a catheter and an external controller, and may also include a delivery device to deliver the catheter into the user's body, and/or a retrieval device to remove the catheter from the user's body. The catheter can include a valve to selectively control the passage of fluid through a lumen of the catheter, and a pump to convey fluid through the lumen. The catheter can also include an anchor to secure the catheter in the user's body. The catheter can include electronics, including one or more sensors, a sterilizer, a communication module, an energy harvesting module, and a controller. The external controller can include a motor that can actuate the catheter's pump and/or valve, a power source, electronics including a communication module that can communicate with the communication module of the catheter, and a user interface through which a user can control the operation of the system.

A fluid management system can also include a non-catheter device that analyzes the biophysical, chemical, and biochemical properties of fluid to derive clinically relevant insights. The device can work in conjunction with a catheter or as a standalone device. The device can reside inside, around, or be part of a toilet to capture and analyze fluid.

BRIEF DESCRIPTION OF THE DRAWINGS

FIG. 4C is a schematic diagram of a delivery device usable with the bladder system of FIG. 1, according to an embodiment.

FIG. 4D is a schematic diagram of the delivery device of FIG. 4C and the catheter of the bladder system of FIG. 1.

FIGS. 11A and 11B are a partial cutaway views of a catheter and a side view of a valve in a closed and open configuration, respectively, according to an embodiment.

FIGS. 15A and 15B are a partial cutaway views of a catheter and a side view and perspective view, respectively, of a valve and pump, according to an embodiment.

FIG. 18 is a side view of a distal portion of a catheter with an anchor including struts, according to an embodiment, shown disposed in a user's bladder and urethra.

FIG. 19 is a side view of a distal portion of a catheter with an anchor including struts and having an integrated seal, according to an embodiment, shown disposed in a user's bladder and urethra.

FIG. 30 is a proximal perspective view of a proximal portion of a catheter with an external proximal anchor, according to an embodiment.

FIG. 31 is a proximal perspective view of a proximal portion of a catheter with an external proximal anchor, according to an embodiment.

FIG. 32 is a perspective view of electronics of a catheter, according to an embodiment.

FIGS. 37A and 37B are schematic illustrations of a pressure sensor, according to an embodiment.

FIGS. 38A and 38B are schematic illustrations of a pressure sensor, according to an embodiment.

FIG. 45 is a schematic illustration of a light-based sensor for measuring properties external to the catheter, according to an embodiment.

FIGS. 49A to 49C are schematic illustrations of different optical mechanisms for sterilization by a sterilizing light source on the wall of a catheter lumen, according to embodiments.

FIGS. 50A and 50B are partial perspective and end cross-sectional views, respectively, of a catheter with multiple lumens, according to an embodiment.

FIG. 51 is an end cross-sectional view of a catheter with multiple lumens, according to an embodiment.

FIG. 52 is a cutaway perspective view of a portion of a catheter, according to an embodiment.

FIG. 53 is a cutaway perspective view of a portion of a catheter, according to an embodiment.

FIGS. 54A to 54C are a cutaway side view, side view, and perspective view, respectively, of a catheter according to an embodiment.

FIG. 61 is a perspective view of an external controller coupled to an electronic device, according to an embodiment.

FIG. 62 is a perspective view of an external controller coupled to, and enclosing, an electronic device, according to an embodiment.

FIGS. 64A and 64B are partial, cutaway side views.

FIG. 81 is a perspective partial cross-sectional view of the external bladder management system of FIGS. 77A and 77B, illustrating the inner electrical components.

DETAILED DESCRIPTION

Figure 1:
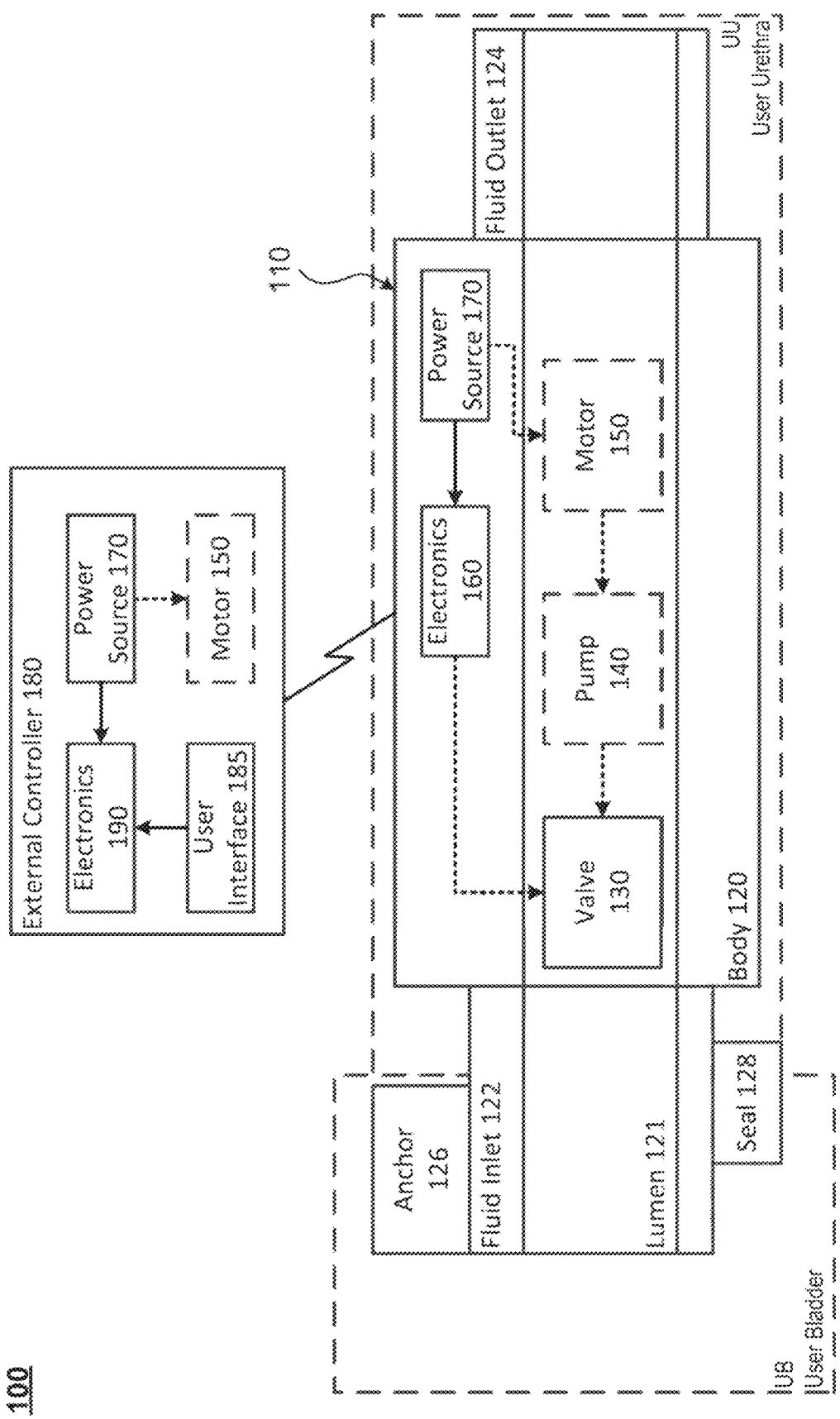
FIG. 1 is a schematic diagram of a bladder system including a catheter and an external controller, according to an embodiment.

Embodiments and implementations described herein relate to a fluid management system, in particular a bladder management system (also referred to herein as "transcatheter urinary bladder emptying device" or "bladder system") that can enable control over voiding (e.g. enabling voiding or preventing undesired voiding) of fluid from an organ, such as a bladder, and can also detect and/or help prevent infections of the organ or related organs, such as a bladder and/or urethra.

In some embodiments, a bladder management system (also referred to herein as "bladder system") can include a device that senses biophysical, chemical, and/or biochemical characteristics and/or changes in fluid from an organ and contributes to the generation of clinically relevant insights. This device can work in conjunction with a catheter, work in conjunction with a transcatheter urinary bladder emptying device, and/or as a stand-alone device (also referred to herein as "external bladder management system"). The device can physically attach to a catheter for the bladder system, or it can recognize the characteristics of fluid flowing through a catheter or bladder system. The device can reside on, in, or around a toilet and contain a lumen through which fluid passes. The device can contain destructive or non-destructive optical, chemical, or biophysical sensors that detect unique characteristics of fluid. The sensors can reside surrounding the lumen of the device such that they adequately capture the characteristics of fluid within the lumen. The device can be reusable and/or disposable. When characteristics of fluid from an organ, such as urine from a bladder, are detected, the device can record these data points and transmit (e.g., wirelessly) them to a database. This data-base can reside locally in the device, reside within a connected smartphone, or reside within a cloud-based infrastructure. Data in the database can be analyzed using artificial intelligence and/or machine learning to generate insights into the changes of the fluid characteristics over time for an individual or a specific population. These insights can represent changes in fluid characteristics or stagnancy of fluid characteristics.

In some embodiments, a bladder management system can include an extended-use, disposable, indwelling urinary catheter and an external controller that can control the operation of the catheter. This catheter can include a lumen for expelling urine from the user's bladder.

The catheter can include a valve that can be selectively closed to prevent urine flow, and selectively opened (such as by the external controller) to permit urine to flow from the bladder through the catheter and out of the urethra. The valve can be configured to be controlled (e.g., opened and closed) by signals from the external controller. Thus, the valve can act as a pressure relief mechanism to dispel pressure accumulating from fluid within the user's bladder.

The catheter can also include a pump to accelerate the flow rate of urine from the bladder (beyond the flow that would be achieved from gravitational force) and expel it through the urethra, with the urine passing through the open valve. In some embodiments, the pump can be configured to be controlled (e.g., started and stopped) and driven by the signals and power from the external controller. For example, the external controller can include a magnetic driver that uses moving magnetic fields to cause movement (e.g., rotation) of an impeller of the pump.

The catheter can also include a retaining portion such as an anchor to prevent migration of the catheter within the patient (e.g., translating further into the bladder and/or out of the bladder and urethra).

The catheter can also include sensors to monitor conditions in the bladder and/or urethra. Sensors can include a pressure sensor to monitor urine pressure in the bladder, one or more light or imaging sensors that can detect light intensity at one or more light wavelengths in one or more spatial locations to enable detection of conditions, materials, etc. in the bladder, the urethra, the surface (internal and/or external) of the catheter device, and/or of the urine in the bladder, the urethra, and/or the catheter. The light or imaging sensor(s) can include one or more source(s) of light at the one or more wavelengths, and/or the light source(s) can be separate from the light or imaging sensor(s).

The catheter can also include a communications system to communicate with (e.g., send information to, and receive information from) the external controller.

It can also include treatment devices, such as circuitry for delivering sterilizing light to the interior lumen of the catheter to reduce bacteria in the urine and/or on the catheter surface. Thus, the system may be configured to detect, prevent, and/or treat catheter associated urinary tract infections (CAUTI).

The catheter can be placed into position in the bladder and urethra, and removed therefrom, using insertion and/or extraction or retrieval device(s). The catheter can be placed by a trained individual such as a patient, a clinician, a nurse, or a caretaker. Once placed inside the bladder and urethra, the catheter can be fully internal (i.e., no portion of the catheter is visible from outside of the patient's body).

The passage of fluid in and out of the body is of interest for many organs throughout the body, as well as the passage of that fluid in an infection free manner. Therefore, although embodiments described herein are primarily related to the bladder of a person, such embodiments could be used in relation to any fluid-containing organ in a body. In addition, based on the particular needs of a user, the system can include various permutations of the embodiments described herein. For example, an embodiment for a user with just urinary incontinence may contain a valve or pressure relief mechanism, a retaining portion or anchor, a lumen for expelling urine, sensors, and/or sterilization circuitry, while not including other components of systems described herein. In another example embodiment, the device may consist of just the internal circuitry components, the retaining portion, and the fluid transport lumen.

The disclosed bladder systems can reduce the frequency with which a user must be catheterized, and correspondingly reduce the number of foreign objects entering the urethra.

FIG. 1 is a schematic diagram of a bladder system 100, including a catheter 110 and an external controller 180, according to an embodiment. The bladder system 100 is configured for controlled voiding of fluid from an organ of a user (e.g., a bladder of a human). For example, the bladder system 100 can be configured for removal of urine U from the user's bladder UB via the user's urethra UU. As shown in FIG. 1, the catheter 110 has a body 120 that may include (and may support and enclose) any one or more of a valve 130, a pump 140, a motor 150, electronics 160, and a power source 170.

Body 120 includes a fluid inlet 122 at an inlet, or distal, end thereof and a fluid outlet 124 at an outlet, or proximal, end thereof. The body 120 has a lumen 121 extending from the fluid inlet 122 to the fluid outlet 124, through which fluid (e.g., urine) may pass from the user bladder UB to the user urethra UU for discharge from the user's body. One or more anchors 126 and one or more seals 128 may be coupled to the body 120.

The anchor 126 is configured to secure at least a portion of the body 120 to a patient's anatomy to inhibit distal and/or proximal movement of catheter 110 relative to the user bladder UB and user urethra UU. Thus, the anchor 126 can be a retaining portion of the catheter 110. In some implementations, the anchor 126 is reconfigurable. For example, the anchor 126 can be configured to transition between a delivery configuration in which the anchor 126 is suitable to be inserted into the patient and delivered minimally or non-invasively through the patient's native anatomy (e.g., including the urethra) and into the patient's bladder, and a deployed configuration in which the anchor 126 secures at least a portion of the body 120 within the bladder UB, thereby preventing the body 120 from inadvertent displacement or exit from the bladder UB or the patient. In some implementations, the anchor 126 in its delivery configuration has a first cross-sectional area or diameter, and in its deployed configuration has a second cross-sectional area or diameter that is greater than the first cross-sectional area or diameter. In some implementations the anchor 126 can be delivered in a constrained arrangement, and when disposed within a target deployment location (e.g., within the bladder UB), the anchor 126 can be unconstrained and thereby assume its default or memory, deployed configuration. Additionally or alternatively, the anchor 126 can be transitioned between configurations via an external device (e.g., the external controller 180). In some implementations, the anchor 126 is self-deployed (e.g., it transitions from its delivery configuration to its deployed configuration without user manipulation beyond insertion of the anchor 126 into the target environment (e.g., bladder UB), while in some implementations, the anchor 126 is deployed as a separate step from insertion. For example, a user can separately actuate the anchor 126 to transition the anchor 126 from its delivery configuration to its deployed configuration, and vice versa (e.g., during removal of the catheter 110 from the patient).

In some embodiments, anchor 126 is configured to inhibit inadvertent proximal movement of body 120, but to permit intentional proximal movement (e.g., when the user desires to remove catheter 110). Thus, anchor 126 may be configured to collapse to a removal configuration, in which it has a smaller diameter than a deployed configuration, but not necessarily as small as the delivery configuration, and can be drawn proximally through user urethra UU without damaging the tissue.

Anchor 126 is shown in FIG. 1 as being disposed at the distal end of catheter 100 (e.g., at or coupled to fluid inlet 122), and as being deployable in user bladder UB to inhibit proximal displacement of catheter 110. The, or another, anchor 126 can also, or alternatively, be coupled to a more proximal portion of body 120 to engage user urethra UU, such that anchor 126 can inhibit both proximal and distal movement of catheter 110 relative to user bladder UB and user urethra UU. The, or another, anchor 126 can also, or alternatively, be coupled to the proximal end of body 120 (e.g., to fluid outlet 124) and configured to be disposed external to the user's body (e.g., at the external entrance to the user urethra UU and engageable with tissue surrounding the external entrance) in which position anchor 126 can inhibit distal movement of catheter 110 relative to user bladder UB and user urethra UU.

Seal 128 is coupled to body 120 and configured to engage with tissue of the user bladder UB and/or user urethra UU surrounding body 120 to occlude any space between the tissue and body 120 to inhibit the passage of fluid (e.g., urine) though such space. Fluid can therefore flow only through lumen 121, so that flow can be controlled by valve 130, and undesirable leakage of fluid around body 120 and out of user urethra UU can be prevented. Seal 128 may be part of, or constituted by, one or more anchors 126, or may be separate.

The valve 130 can selectively permit or prevent the flow of urine through lumen 121 (i.e., from the bladder to the urethra proximal to catheter 110). It can also provide relief from an overpressure condition in the bladder (i.e., provide a pressure failsafe function), and thus function as a pressure relief mechanism. Pump 140 is optional and is not included in all embodiments. If included, pump 140 may assist or augment the flow of urine through lumen 121. As indicated by the dashed arrow connecting pump 140 to valve 130, pump 140 may interact with valve 130 to control its operation (i.e., transition between open and closed states). For example, pump 140 may interact with valve 130 through creation of a pressure differential across valve 130, or through mechanical, magnetic, or other interaction. Pump 140 is driven by a motor 150, which may be part of catheter 110 (e.g., housed within body 120) or may be part of external controller 180. If motor 150 is part of catheter 110, then as indicated by the dashed arrow connecting them, motor 150 can drive pump 140 through a mechanical connection, or through a magnetic or other non-mechanical connection.

Power source 170 may be part of catheter 110 (e.g., housed within body 120), may be part of external controller 180, or may have components therefore distributed between catheter 110 and external controller 180. Power source 170 can provide power to electronics 160. Power source 170 may also provide power to motor 150 by a wired connection or a wireless connection. For example, power source 170 can provide power to motor 150 by a wired connection if motor 150 and power source 170 are both in the same component of system 100 (i.e., both in catheter 110 or both in external controller 180) or through a wireless connection (e.g., by inductive coupling) if motor 150 and power source 170 are in different components of system 100 (or if in the same component if it is otherwise desirable to avoid a wired connection). Power source 170 can be any suitable source of power/energy for use by other components of catheter 110 and/or external controller 180. For example, power source 170 can be a battery (primary or secondary), capacitor, or other mechanism for storing electrical energy.

The catheter 110 is configured to be communicatively couplable with the external controller 180, as described in further detail herein. As shown in FIG. 1, the external controller 180 includes electronics 190, user interface 185, and, as discussed above, may include motor 150 and some or all of power source 170. External controller 180 is configured to be manipulated or operated by a user to communicatively engage with or actuate one or more components of the catheter 110, as described in further detail herein.

The catheter 110 can be formed of any biocompatible material or combination of the same, and sized and shaped in any manner suitable to be delivered and implanted into a living object, such as a bladder of a human. In some implementations, for example, the catheter 110 can be sufficiently flexible to be safely inserted (and withdrawn) through a urethra of a patient and into (and out of) a bladder of the patient.

The valve 130 of the catheter 110 can be any valve type suitable to be transitioned between a closed configuration in which fluid communication between the fluid inlet 122 and the fluid outlet 124 through the lumen 121 via the valve 130 is blocked, and an open configuration in which fluid communication is allowed. In some implementations, the valve 130 is actuated (e.g., transitioned between from its closed configuration to its open configuration) in response to a fluid pressure within the environment in which the valve 130 is exposed reaching a threshold pressure. Said another way, the valve 130 can be configured to transition to its open configuration in response to pressure differential across the valve (i.e., between the distal side and the proximal side) reaching a sufficiently high level. In some implementations, the valve 130 can be mechanically configured to open in direct response to such fluid pressure, and in some implementations, the valve 130 can receive an electronic signal generated by or based on a reading from a pressure sensor (e.g., a pressure sensor disposed on the catheter 110 and configured to sense a fluid pressure within the lumen 121 or within a volume of the bladder outside of the catheter 110). Additionally or alternatively, in some implementations, the valve 130 can be externally actuated by the external controller 180, as described in various implementations below. Example methods of actuation include electronic signal communication or magnetic communication between the catheter 110 and the external controller 180.

The pump 140 can be any type of pump suitable to convey fluid (e.g., urine) from the fluid inlet 122 to the fluid outlet 124 through lumen 121 to augment the flow rate that could be produced by gravity and/or by the elasticity of the bladder. As noted above, the pump may also generate or augment a pressure differential across the valve 130 to cause the valve 130 to transition from its closed configuration to its open configuration. In some embodiments, pump 140 may be disposed on the distal side of the valve (i.e., closer to the bladder) and the pump 140 can be actuated to draw urine from the patient's bladder into the fluid inlet 122, through the lumen 121 and the valve 130, and out the fluid outlet 124. In other embodiments (e.g., as shown schematically in FIG. 1), the pump 140 may be disposed on the proximal side of valve 130, i.e. between valve 130 and fluid outlet 140. The pump 140 can be actuated in various ways, many of which are described below in specific implementations. In some implementations, for example, the pump 140 can be actuated by the external controller 180 (e.g., by a signal generated or sent by the external controller 180). Additionally or alternatively, the pump 140 can be actuated in response to a signal generated or sent by the electronics 160.

Figure 2:
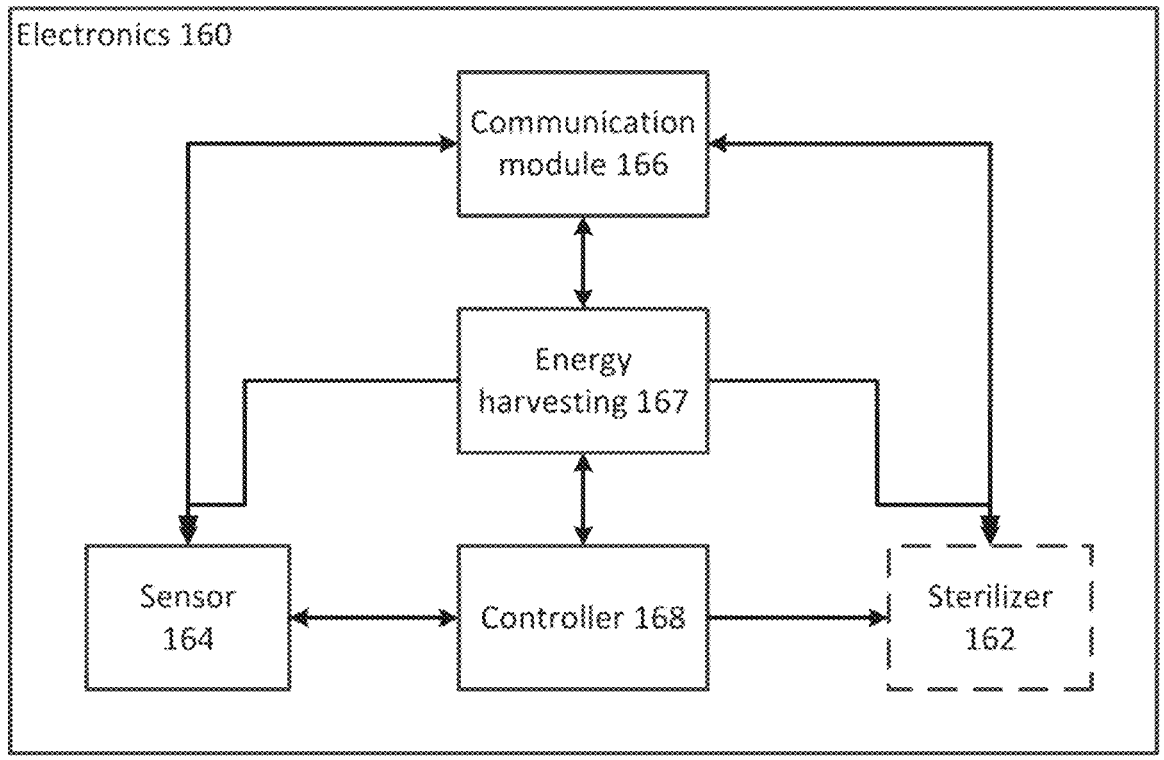
FIG. 2 is a schematic diagram of the electronics of the catheter of the bladder system of FIG. 1.

As shown schematically in FIG. 2, the electronics 160 can include any number of components suitable to perform various functions described herein, such as, for example, communication (short range, medium range, long range, and anywhere in between), memory storage, computing, signal processing, and the like, and others, as described in further detail herein. Example components of the electronics 160 can include one or more sterilizers 162, one or more sensors 164, a communication module 166, an energy harvesting circuit 167, and a controller 168.

The sensor 164 can include one or more sensors configured to sense various parameters. For example, sensor 164 can include one or more pressure sensors or transducers, which can detect fluid pressure within the lumen 121 and/or pressure within the environment in which the catheter 110 is exposed (e.g., a pressure of the bladder measured external to the catheter 110). Other parameters can include the pH of urine in lumen 121 or around catheter 110 (which can be measured with a pH sensor). Other parameters include bladder temperature, core body temperature, acute kidney injury through the secession of urine production, intra-abdominal pressure through embedded pressure sensors, glucose or sugar levels in the urine through glucose sensors, protein or albumin, ketones, leukocytes or other white blood cells or their corresponding esterases, albumen or bilirubin as an early sign of liver damage or disease, blood or its constituents presence, crystal formation, bladder spasticity through an embedded force or pressure sensor, autonomic dysreflexia through local perturbations in bladder or abdominal pressures and or coupled with symptomology screening, bacteria virility and invasiveness by monitoring how quickly it grows and changes the bladder local environment, bacteria culture type based on characteristic biophysical properties of each type of microorganism, early signs of cancer originating from the bladder or elsewhere in the body, determine the presence of kidney stones or urine that has a high likelihood of developing kidney stones, heart rate or EKG monitoring from external or internally embedded electrical or impedance sensors.

In some implementations, the sensor 164 is or includes one or more optical sensors, which can include one or more sources of light at one or more frequencies (e.g., visible, infrared, ultraviolet, etc.) and one or more corresponding optical detectors capable of measuring the intensity of light at the frequency(ies) emitted by the source(s). Such sensors can be configured to determine, for example, the degree of attenuation of the emitted light transmitted through, or reflected, refracted, diffracted, etc. a material (solid or fluid). For example, the sensor 164 can be configured to determine the degree of attenuation of emitted light transmitted through a fluid (such as urine) in the lumen 121 or external to catheter 121 or a solid (such as a wall of the catheter 110, and substances on the surface of the wall). The sensor 164 can also be configured to determine the degree of attenuation of emitted light reflected, refracted, diffracted etc. from a surface of the catheter 110 (i.e., an internal or external surface) or from a surface of the environment in which the catheter 110 is disposed (e.g., a bladder or urethra wall). Information collected by such sensors can be used to detect and/or quantify the presence of bacterial build up or colonization, biofilm formation, encrustations, obstructions, an increase in turbidity, downstream system infections, or the like. The sensor 164 can include other optical sensors, such as imaging sensors with which images of the interior or exterior of the catheter 110 and/or its environment can be acquired. The sensor(s) can provide data too, and receive control signals from controller 168. Various implementations of the sensor 164 are described in further detail herein.

In some embodiments, electronics 160 may include one or more sterilizers 162, which may be configured to sterilize one or more surfaces of the catheter 110 (e.g., the wall of lumen 121) and/or surfaces of the surrounding environment (e.g., a wall of the bladder and/or urethra). In some implementations, the sterilizer 162 is configured to be activated by a control signal from controller 168, such as in response to an indication by the sensor 164 (e.g., in response to the sensor 164 sensing the presence of an infection). Sterilizer 162 may be, for example, a source of ultraviolet (UV) light, such as light in the UVC portion of the spectrum. Sterilization could also be performed by a coating that releases anti-microbial chemicals, metals, or antibiotics.

Electronics 160 may include a communication module 166, by which electronics 160 (and catheter 110) can communicate (send and receive information) with external controller 180. Communication module 166 may include an antenna, such as an RFID antenna and associated circuitry. Energy harvesting circuitry 167 can harvest power received wirelessly by communication module 166 (e.g., from an antenna). Energy harvesting circuit 167 can provide power to sensor 164, sterilizer 162, and controller 168. Communication module 166 may send and receive data/signals to/from sensor 164, sterilizer 162, and controller 168, and can also transmit the data/signals (e.g., to the external controller or other components of system 100).

In some embodiments, the catheter could also provide the capability for drug delivery to the user, or to deliver other devices by or through the catheter.

As shown schematically in FIG. 1, the external controller 180 is configured to communicate with catheter 110, as described in further detail herein, and includes user interface 185, electronics 190, power source 170 (as described above), and, optionally, motor 150. User interface 185 can include any suitable mechanism by which a user can interact with external controller 180, including providing information to a user (by visual, aural, and/or tactile means) and receiving input (data, commands, etc.) from a user, such as by a touch screen, control buttons, switches, etc. User interface 185 can be coupled to electronics 190, so that information received from the user through user interface 185 can be provided to the electronics 190, and information can be provided by electronics 190 to user interface 185 for presentation to the user.

Figure 3:
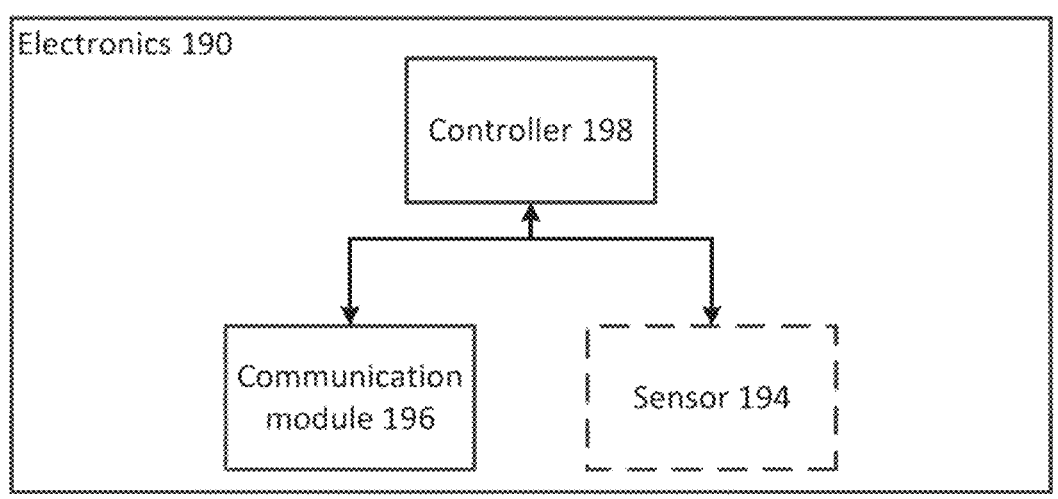
FIG. 3 is a schematic diagram of the electronics of the external controller of the bladder system of FIG. 1.

As shown schematically in FIG. 3, electronics 190 can include a communication module 196 and a controller 198. In some embodiments, electronics 190 can also include one or more sensors 194. Communication module 196 can be similar to communications module 166 (as shown in FIG. 2), and can communicate (send and receive data, control signals, etc.) with communications module 166 as a communication channel between external controller 180 and catheter 110. In some embodiments, communication module 196 can also communicate with other devices (e.g., a smart phone, tablet, computer, etc.) of a user, physician, or other health care provider. Controller 198 can be similar to controller 168 (as shown in FIG. 2), and can be configured to control the operation of electronics 190 and by extension external controller 180, to perform various functions, such as, for example, actuating or communicating with the electronics 160, the valve 130, the pump 140, and/or the motor 150 (in each case directly and/or through the electronics 160). The external controller 180 can therefore allow the user to control the catheter 110 to allow the user to urinate on-demand, to sterilize the catheter 110, to interrogate or monitor for the presence of bacteria and related complications, etc. Sensor(s) 194 can include sensors that can detect parameters or conditions relevant to the condition for which the bladder system is being used. For example, sensor 194 can include a near infrared spectroscopic sensor (for example with an infrared LED and associated sensor), which can be used to measure internal bladder volume non-invasively. The urine absorbs more of the IR signal from the LED before it is returned back to the associated sensor. Such a sensor can be used by placing the external controller (and sensor) in contact with the lower abdominal region, to take a measurement of bladder fullness.

The external controller 180 can have any suitable form factor. In some implementations, for example, the external controller 180 is a wand. In some embodiments, for example, the actuator is a smart device (e.g., a smart phone, smartwatch, activity tracker, etc.), software, a software phone, a hardware phone, or a wearable (e.g., piece of clothing with embedded electronics, such as an undergarment, belt, dedicated handle, etc.).

In use, for example, the catheter 110 can be inserted into the urethra of the patient (such as the user urethra UU of FIG. 1) until at least the fluid inlet 122 of the body 120 is disposed within the patient's bladder (such as the user bladder UB of FIG. 1), with the body 120 extending from the fluid inlet 122 within the bladder into the urethra such that the fluid outlet 124 is disposed within the urethra. In this manner, fluid can be conveyed from the fluid inlet 122 within the bladder to the fluid outlet 124 within the urethra, via the lumen 121, and then out the patient. With the body 120 delivered in this manner, the anchor 126 can be deployed to secure the body 120 in place within the bladder or urethra. The catheter 110 is then suited to convey fluid from the bladder on-demand (e.g., in response to a signal from the external controller 180, or in response to a particular fluid pressure).

Figure 4A:
FIG. 4A is a schematic diagram of a delivery device usable with the bladder system of FIG. 1, according to an embodiment.
Figure 4B:
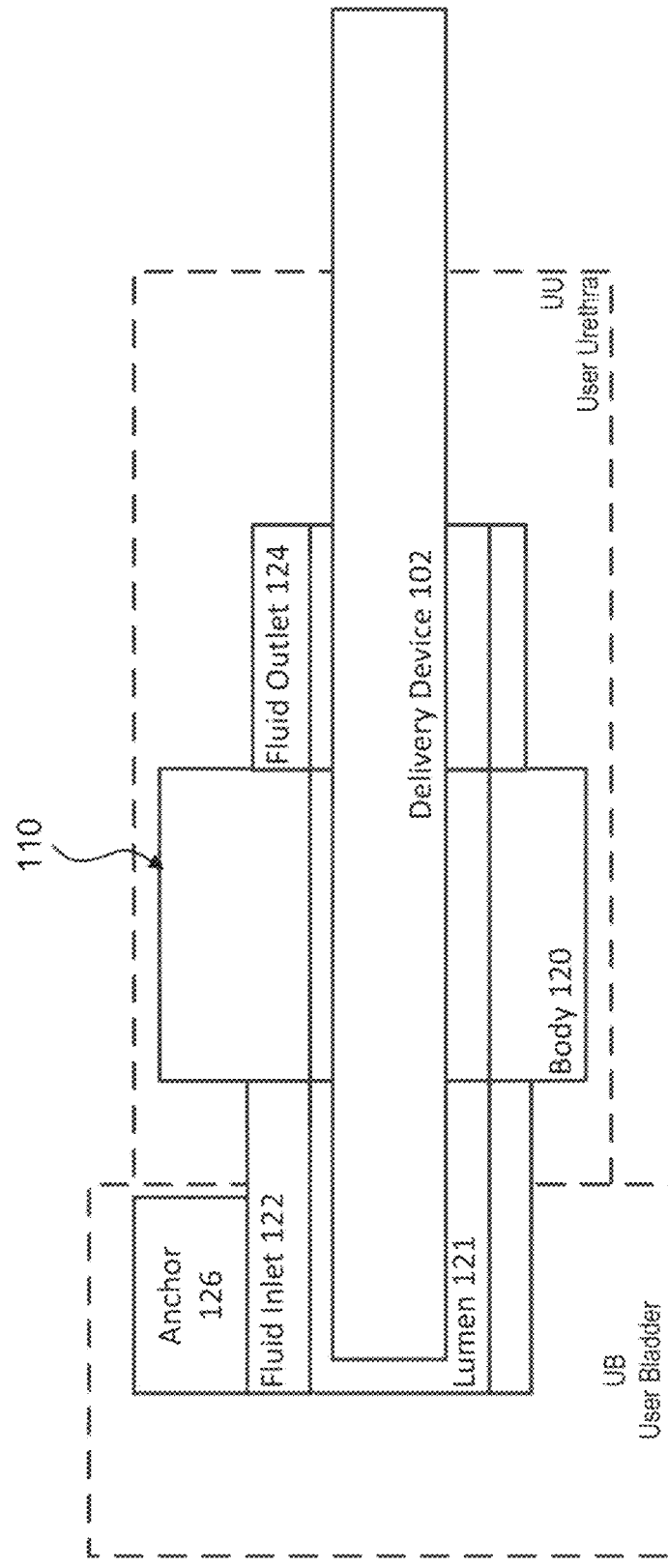
FIG. 4B is a schematic diagram of the delivery device of FIG. 4A and the catheter of the bladder system of FIG. 1.

As shown schematically in FIGS. 4A and 4B, catheter 110 can be inserted into position in a user's body (e.g. urethra and bladder) with the aid of a delivery device 102. Delivery device 102 can have a distal end with an actuator 102a that is coupleable with the distal end of catheter 110, and operatively connectable with anchor 126 to control deployment thereof. A proximal end of delivery device 102 can include a user control 102b by which a user can manipulate delivery device 102 and control actuator 102a. At least a distal portion of the body of delivery device 102 can be sized to fit within lumen 121 of catheter 110, as shown in FIG. 4B. In preparation for insertion of catheter 110 to the bladder and urethra of a user (such as user bladder UB and user urethra UU), catheter 110 can be disposed on delivery device 102. The distal ends of the catheter 110 and delivery device 102 can then be inserted into the entrance to user urethra UU, and the assembly urged distally through user urethra UU until the anchor 126 is disposed within user bladder UB, as shown in FIG. 4B. The user can then manipulate user control 102b to control actuator 102a to deploy (or allow to self-deploy) anchor 126 within user bladder UB. The user can then further manipulate user control 102b to cause actuator 102a to disengage from anchor 126 and/or fluid inlet 122 and withdraw delivery device 102 from catheter 110 and the user urethra UU.

As shown schematically in FIGS. 4C and 4D, an alternative design for a delivery device 102' can contain catheter 110, rather than being contained within catheter 110. Delivery device 102' can include a lumen 102c' sized to receive catheter 110 in a delivery configuration (e.g., a configuration in which anchor 126 has a smaller external diameter that can fit through the user urethra UU and within lumen 102c'). Delivery device can also have a user control 102b' at a proximal end thereof by which a user can manipulate delivery device 102'. At least a distal portion of the body of delivery device 102' can be sized to fit within user urethra UU, as shown in FIG. 4D. In preparation for insertion of catheter 110 to the bladder and urethra of a user, catheter 110 can be disposed in a delivery configuration within lumen 102c'. The distal ends of the catheter 110 and delivery device 102' can then be inserted into the entrance to user urethra UU, and the assembly urged distally through user urethra UU until the anchor 126 is disposed within user bladder UB, as shown in FIG. 4D. The user can then manipulate user control 102b discharge catheter 110 from the distal end of lumen 102c', and to deploy (or allow to self-deploy) anchor 126 within user bladder UB. For example, user control 102b' can include a push rod engageable with the proximal end of catheter 110 (e.g., fluid outlet 124) that is movable distally within lumen 102c' to allow a user to produce relative movement between catheter 110 and lumen 102c'. With anchor 126 deployed, the user can further manipulate user control 102b withdraw delivery device 102' proximally through user urethra UU, over catheter 110, and remove delivery device 102' from the user's body.

Figure 5A:
FIG. 5A is a schematic diagram of a retrieval device usable with the bladder system of FIG. 1, according to an embodiment.
Figure 5B:
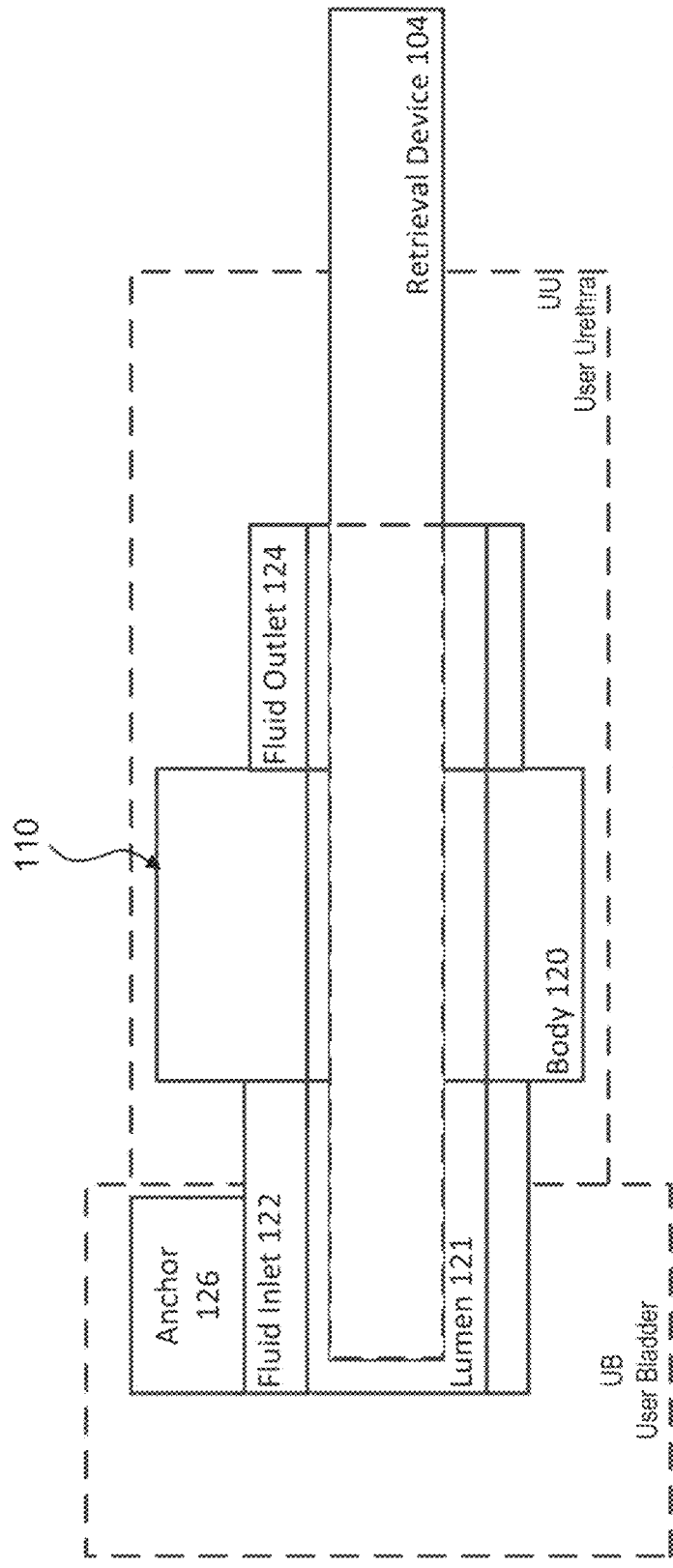
FIG. 5B is a schematic diagram of the retrieval device of FIG. 5A and the catheter of the bladder system of FIG. 1.

As shown schematically in FIGS. 5A and 5B, catheter 110 can be retrieved from a user's body (e.g., user urethra UU and user bladder UB) with the aid of a retrieval device 104. Retrieval device 104 can have a distal end with an actuator 104a and a proximal end with a user control 104b by which a user can manipulate retrieval device 104 and control actuator 104a. In some embodiments, actuator 104a can be configured to be is coupleable with the distal end of catheter 110, and operatively connectable with anchor 126 to control retraction thereof, and correspondingly, as indicated schematically in dashed lines in FIG. 5B, at least a distal portion of the body of retrieval device 104 can be sized to fit within lumen 121 of catheter 110. In such embodiments, to retrieve catheter 110 from the bladder and urethra of a user, the distal end of retrieval device 104 can be inserted into the entrance to user urethra UU, and the retrieval device urged distally through user urethra UU and lumen 121 until actuator 104a engages with anchor 126 and/or fluid inlet 122. The user can then manipulate user control 104b to control actuator 104a to retract anchor 126 from its deployed position and configuration within user bladder UB. The user can then withdraw the retrieval device 104 and catheter 110 proximally through the user urethra UU and remove it from the user's body.

In other embodiments, retrieval device 104 is shorter, and is configured so that actuator 104 engages only with the proximal end of catheter 110 (e.g., with a portion of fluid outlet 124). In such embodiments, to retrieve catheter 110 from the bladder and urethra of a user, the distal end of retrieval device 104 can be inserted into the entrance to user urethra UU, and the retrieval device urged distally through user urethra UU until actuator 104a securely engages with fluid outlet 124. The user can then withdraw the retrieval device 104 and catheter 110 proximally through the user urethra UU and remove it from the user's body.

In the following sections, each of the components of catheter 110 described above are described in more detail with reference to several different potential embodiments. Following the descriptions of individual components, several exemplary embodiments of catheters are shown that use specific combinations of embodiments of the components. However, these are non-limiting combinations of components, and any of the component embodiments described below can be used in different combinations (i.e., any embodiment of a component can be used with any embodiment of each other components).

Pump

The following section illustrates and describes several possible embodiments of pumps corresponding to pump 140 of catheter 110 described above.

Figure 6:
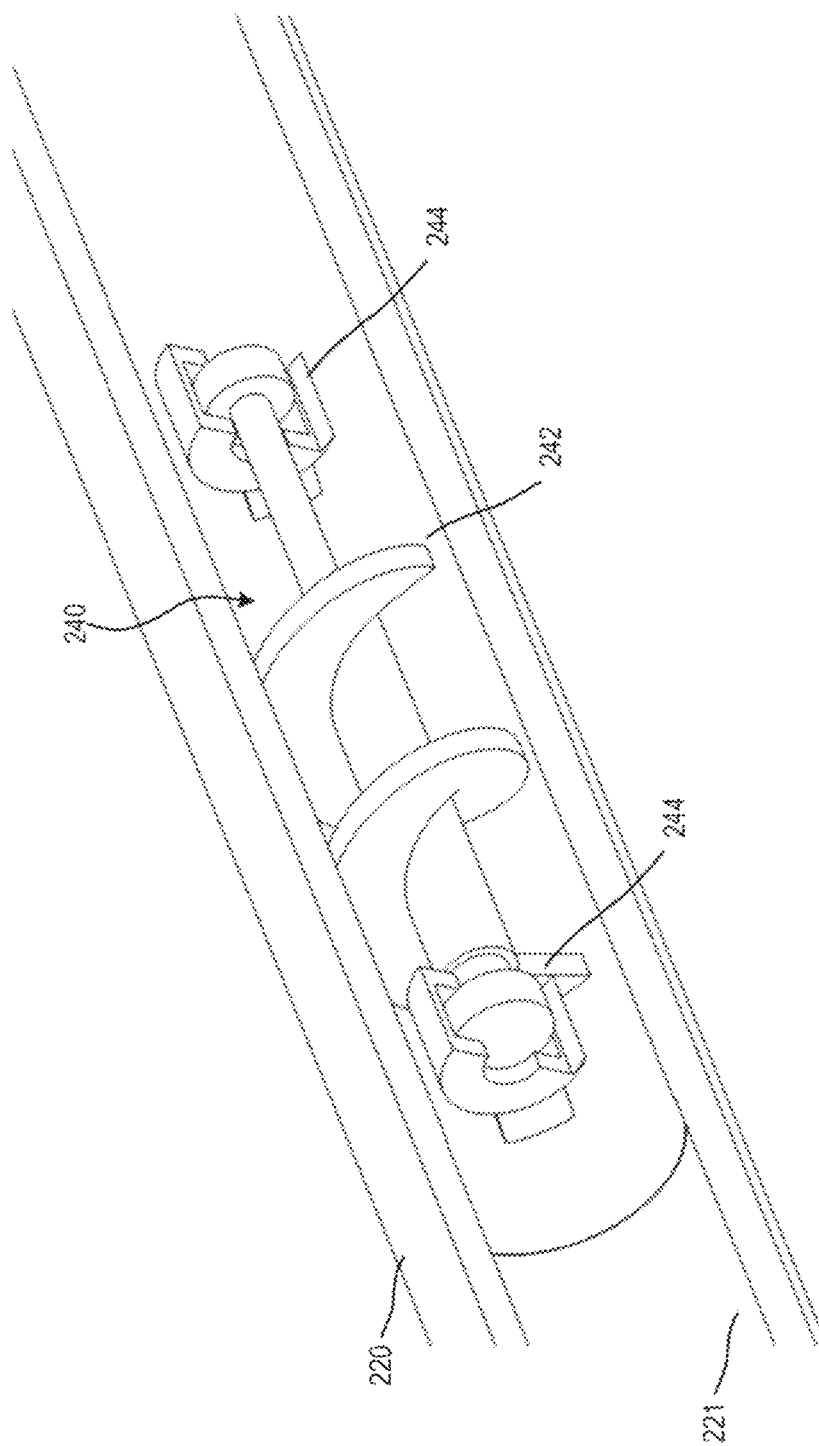
FIG. 6 is a partial cutaway view of a catheter and a perspective view of a pump, according to an embodiment.

FIG. 6 illustrates a pump 240 disposed in the lumen 221 of a catheter, formed in body 220 of the catheter. Pump 240 includes an impeller or turbine 242 that is configured to create a pressure gradient in fluid (urine) in lumen 221 when rotated, which pressure gradient can pull fluid (urine) out of the user's bladder. Turbine 242 is mounted for rotation in one or a series of bearings 244 to provide a low friction axis on which the turbine can spin. Pump 240 includes a magnetic core (not shown) which causes the turbine to rotate when the magnetic core is exposed to an external rotating magnetic field (e.g., generated by a motor such as motor 150 that includes, and can cause to rotate, one or more magnets (such as permanent magnets or electromagnets)). Turbine 242 can be formed of any suitable material or combination of materials. In some implementations, for example, the turbine includes polymer, metal, or a blend thereof in its composition. The rotating magnetic field generated from the external actuator (e.g., motor 150 in external controller 180) transmits torque to the impeller within the turbine 242. In the illustrated embodiment, turbine 242 is implemented as a continuous helical vane or screw, but turbine 242 can have any suitable shape, size, configuration, etc.

Figure 7:
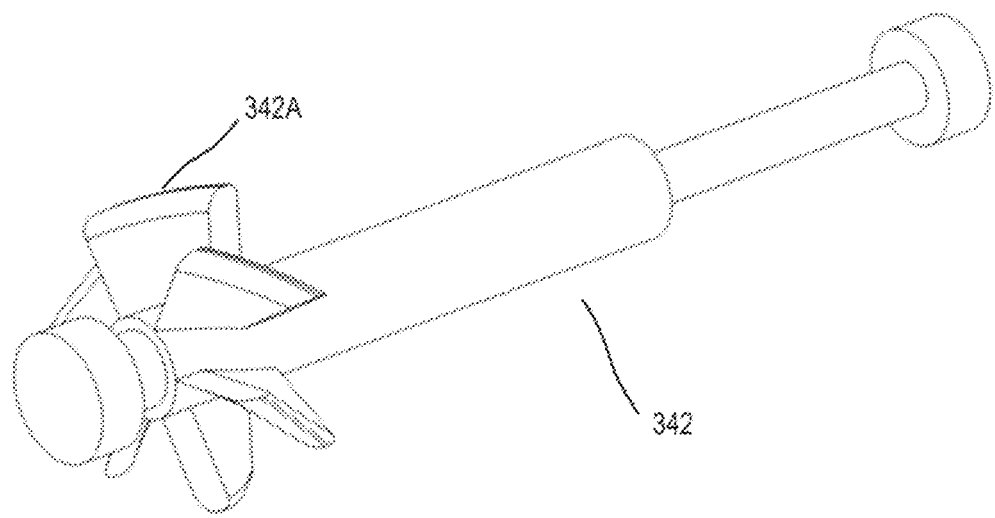
FIG. 7 is a perspective view of a pump, according to an embodiment.
Figure 8:
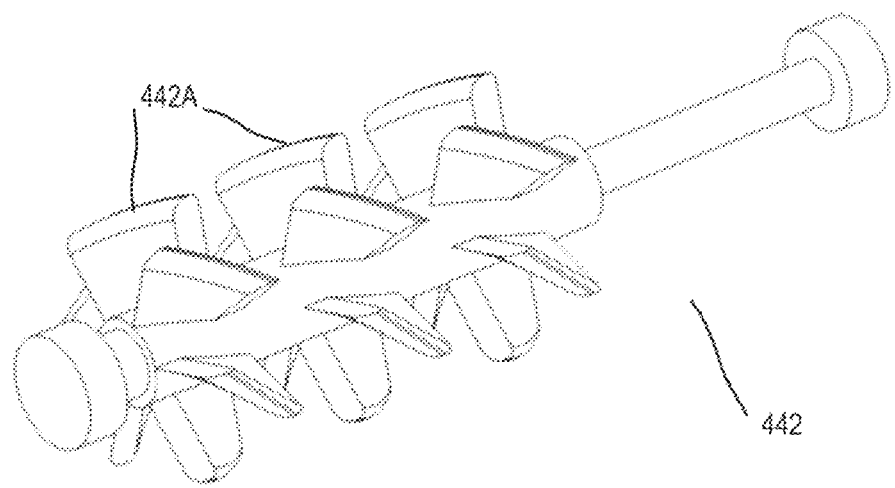
FIG. 8 is a perspective view of a pump, according to an embodiment.

For example, another embodiment of a turbine is shown in FIG. 7. Turbine 342 has a row of blades 342A. In another embodiment, shown in FIG. 8, a turbine 442 includes multiple rows of blades 442A.

The pump can be any other suitable type of pump. In some implementations, for example, the pump can take the form of a pneumatic pump, a linear pump, a centrifugal pump, a diaphragm pump, a lobe pump, a peristatic pump, an axial-flow pump, a plunger pump, a progressive cavity pump, or the like.

As discussed above in connection with bladder management system 100, the pump 140 is optional. Thus, in some embodiments, the catheter of a bladder management system can be configured to allow fluid to drain from the bladder using only gravity and/or the pressure generated within the bladder by the elasticity of the bladder, and as such, does not have a pump. This may be suitable for a bladder management system that is intended for users, for example, who have urinary incontinence. In some embodiments, the catheter of a bladder management system can include a pump and be configured to actively remove fluid from the bladder, replacing or supplementing the effect of gravity and/or the elasticity of the bladder (if either is applicable), thereby providing two methods for fluid removal.

Valve

As discussed above for bladder management system 100, the catheter can include a valve (e.g., valve 130) to selectively permit or prevent the flow of fluid (e.g., urine) through the lumen of the catheter, and to provide relief from an overpressure condition in the bladder (i.e., provide a pressure failsafe function). When bladder pressure reaches sustained, dangerous pressure levels, vesicoureteral reflux, or the reflux of urine into the ureters and up to the kidneys, may occur. This is common in patients with urinary tract infections, and those who intermittently catheterize to manage incontinence experience more urinary tract infections than those who do not. Repeated vesicoureteral reflux can cause kidney damage such as tissue scarring and can lead to chronic kidney disease or kidney failure. Thus, in some implementations, the valve in the catheter of the bladder management system may provide a pressure failsafe function to prevent vesicoureteral reflux. This function may be activated automatically, even if the pump is not activated (e.g., if a patient is noncompliant and does not activate the pump for urination). In some embodiments, the functions of the valve (e.g., pressure relief and control of flow through the lumen of the catheter, whether or not augmented by a pump) can be distributed in different mechanisms.

Both functions (pressure failsafe and lumen flow control) of the valve can be achieved with any suitable device that actuates in response to a threshold pressure (or pressure differential across the valve). The threshold pressure should be below a dangerous bladder pressure, which is clinically known to be about 40 cm of $H_2O$, although it varies from person to person. In some implementations, for example, a pressure failsafe may be in the form of a passive, mechanical check valve that uses a biasing mechanism, such as a spring, to urge a mechanical element, such as a ball, against a valve seat. When the fluid pressure (or pressure differential across the valve) exceeds a threshold value, the pressure overcomes the biasing force holding the mechanical element against the valve seat, forcing the valve open and allowing fluid to flow between the mechanical element and the valve seat.

The pump may contribute to the pressure, or pressure differential. For example, if the pump is on the distal side of the valve (i.e., the bladder side of the valve), then activation of the pump creates a pressure increase from its distal end to its proximal end, and thus augments the anatomically-produced pressure on the distal side of the valve, which can cause the valve to open even when the anatomical pressure (i.e., the amount by which the anatomical pressure exceeds the ambient pressure on the proximal side of the valve) is below the threshold pressure. In contrast, if the pump is on the proximal side of the valve, then activation of the pump creates a pressure increase from its distal end to its proximal end, and thus augments the anatomically-produced pressure drop across the valve, which again can cause the valve to open even when the anatomical pressure is below the threshold pressure.

Figure 9:
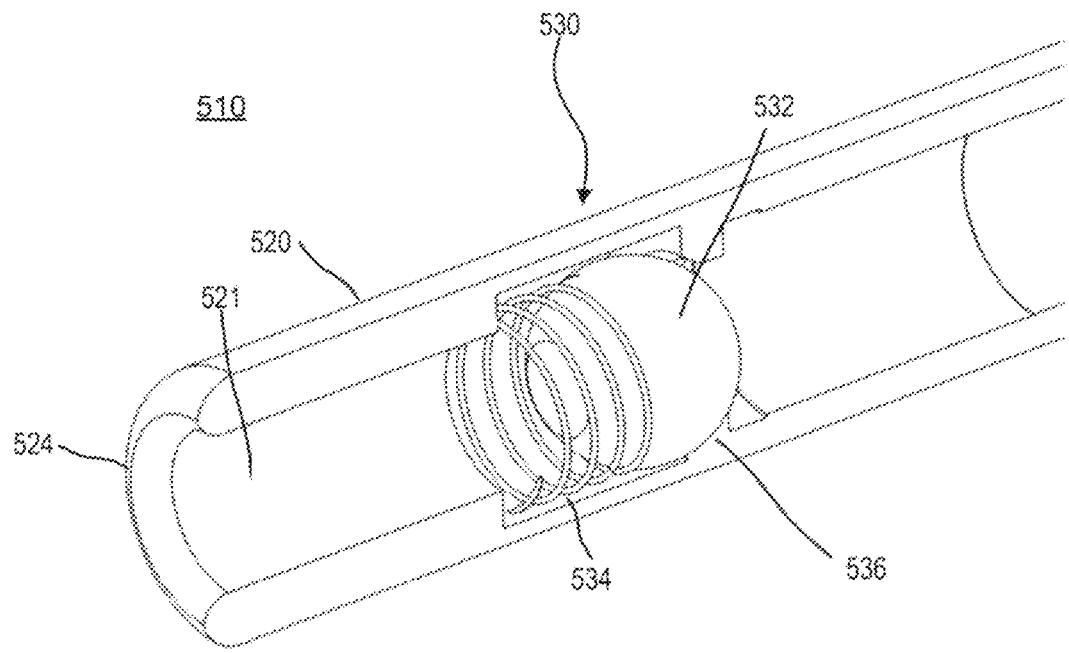
FIG. 9 is a partial cutaway view of a catheter and a perspective view of a valve, according to an embodiment.

One example of such a mechanical check valve is valve 530, shown in FIG. 9. Valve 530 is disposed in body 520 of catheter 510, in lumen 521 near fluid outlet 524. Ball 532 is biased by spring 534 against valve seat 536, in a normally-closed configuration as shown in FIG. 9. When the pressure of urine in the lumen 521 distal to the valve (i.e., closer to the bladder), which is approximately the bladder pressure, exceeds the threshold pressure, defined by the spring constant of spring 534 and the pre-bias with which the spring is compressed against the ball 532, the ball 532 is displaced proximally, against the spring 534 and away from valve seat 536. This creates an annular gap, or valve port (not shown in FIG. 9) between valve seat 536 and ball 532 through which urine can flow towards fluid outlet 524, thus relieving or lowering the pressure in the bladder.

Figure 10:
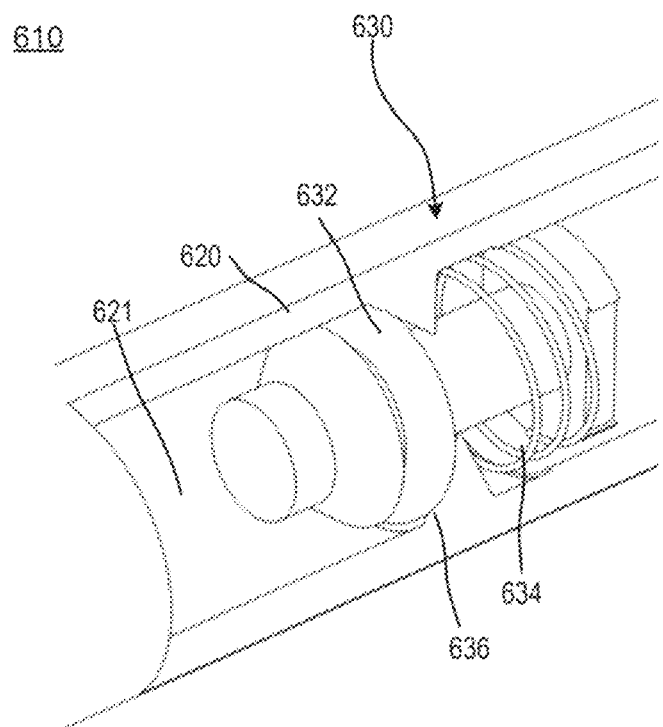
FIG. 10 is a partial cutaway view of a catheter and a perspective view of a valve, according to an embodiment.

Another example of a spring-biased mechanical check valve is valve 630, shown in FIG. 10. Valve 630 is disposed in catheter 610, in lumen 621. Piston 632 is biased by spring 634 (in this embodiment, disposed on the opposite site of valve seat 636 from piston 632) against valve seat 636, in a normally-closed configuration as shown in FIG. 10. When the pressure of urine in the lumen 621 distal to the valve exceeds the threshold pressure, defined by the spring constant of spring 634 and the pre-bias with which the spring is compressed, the piston 632 is displaced proximally, away from valve seat 636, creating an annular gap or valve port (not shown in FIG. 10) through which urine can flow towards fluid outlet 624 (not shown), thus relieving or lowering the pressure in the bladder.

Another example of a spring-biased mechanical check valve is valve 730, shown in FIGS. 11A and 11B. Valve 730 is disposed in catheter 710, in lumen 721. Piston 732 is disposed within lumen 711 in a sealing relationship with the wall of lumen 721. Piston 732 is biased by spring 734 to a normally closed, neutral position (shown in FIG. 11A) that is distal to valve ports 738. Valve ports 738, which are apertures formed through the wall of body 720, which provide fluidic communication between lumen 721 and the environment outside of body 720 (e.g., the urethra). When the pressure of urine in the lumen 721 distal to the valve exceeds the threshold pressure, defined by the spring constant of spring 734, the piston 732 is displaced proximally, past valve ports 738 (as shown in FIG. 11B), allowing urine to flow through valve ports 738 into the urethra, thus relieving or lowering the pressure in the bladder.

Figure 12:
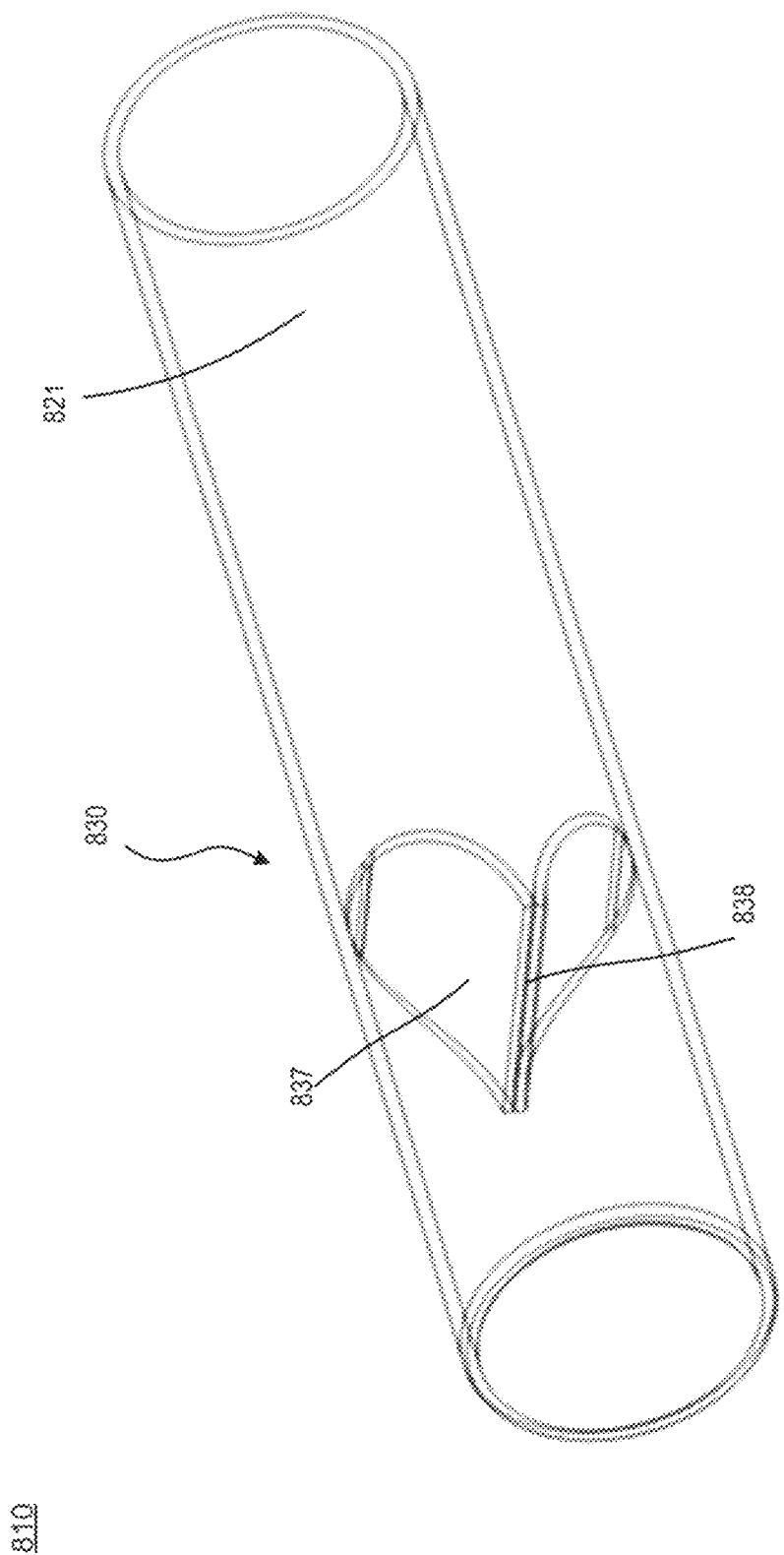
FIG. 12 is a partial cutaway view of a catheter and a perspective view of a valve, according to an embodiment.

In other embodiments, rather than using a mechanical spring to bias a valve member (ball or piston) against a valve seat, the valve can be formed with a resilient or elastomeric material and configured to define a normally closed valve port that can be forced open against the material's own resilient bias to open the valve port. One such embodiment is shown in FIG. 12. Valve 830 is configured as a "duck bill" valve, in which two opposed flaps 837 are normally in apposition with each other, forming a seal. The flaps can be separated, opening valve port 838, when the pressure of fluid between the flaps exceeds a threshold pressure. As shown in FIG. 12, valve 830 is disposed in lumen 821 of catheter 810. When the pressure of urine in lumen 821 distal to the valve exceeds the threshold pressure, the flaps 837 are forced apart, opening valve port 838, allowing urine to flow through valve port 838 into the urethra, thus relieving or lowering the pressure in the bladder.

In other embodiments, the leaflets of the duckbill valve can be attached to a linear or rotational actuator through a rigid, viscoelastic, or elastic connecting body such that when the actuator is moved from one position to another the actuator imparts a force on the connecting body which in turn opens or closes the valve.

Figure 13A:
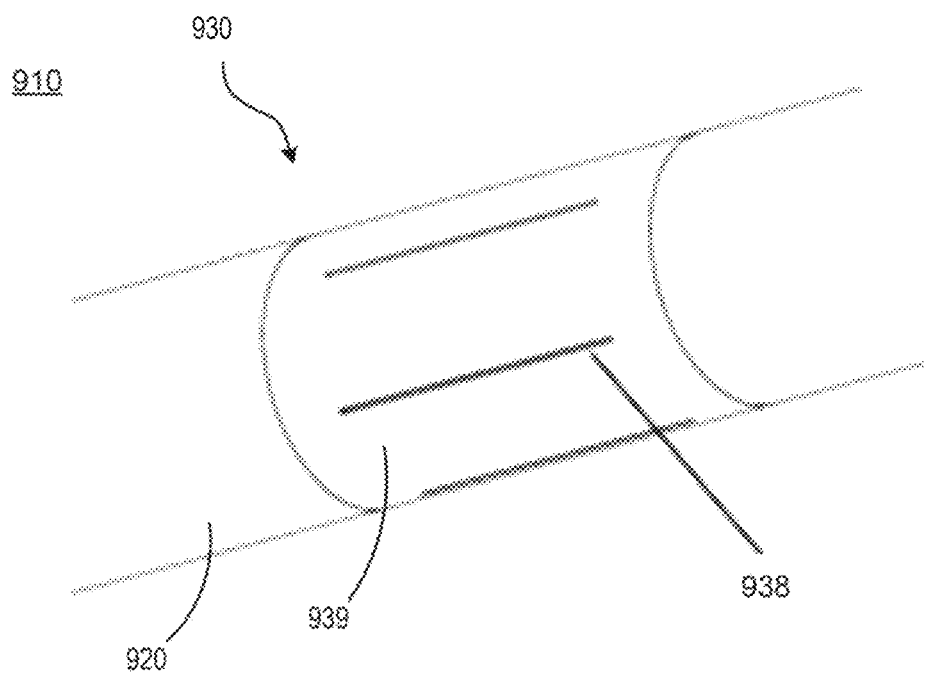
FIGS. 13A and 13B are perspective views of a portion of a catheter, and a pressure-relief device in a closed and open position, respectively, according to an embodiment.
Figure 13B:
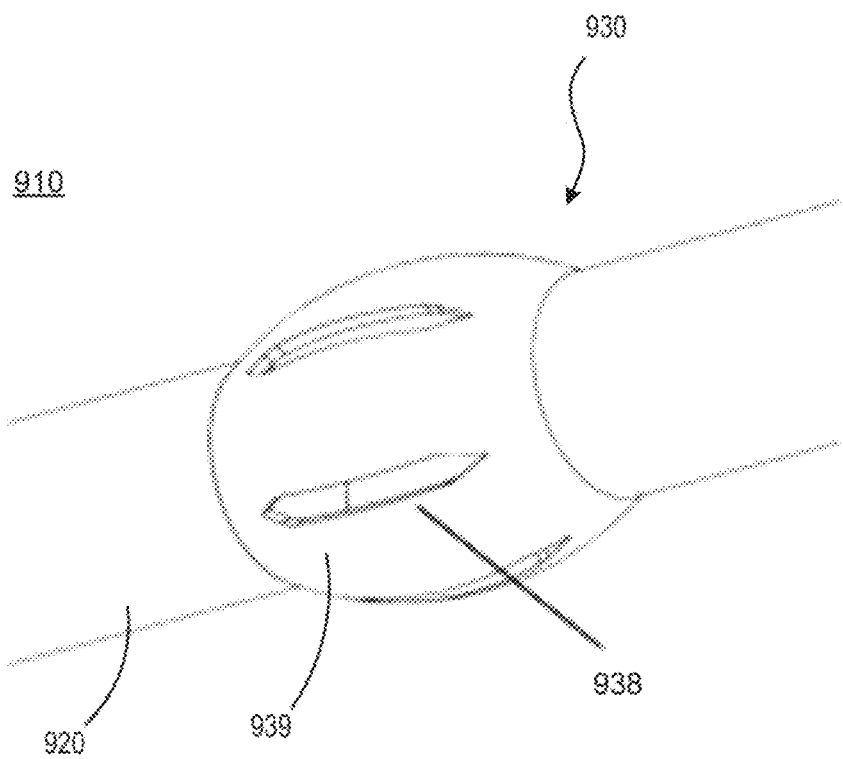

Another embodiment of an elastomeric valve is shown in FIGS. 13A and 13B. In this embodiment, the pressure relief function of the valve is separated from the lumen flow control function of the valve. Valve 930 is disposed in the wall of body 920 of catheter 910. Valve 930 includes multiple valve ports 938, each formed as slits in an elastomeric valve body 939. Valve ports 938 as normally closed, as shown in FIG. 13A. When the pressure of urine in the lumen (not shown) of catheter 910 distal to the valve exceeds the threshold pressure, the valve body 939 is elastically deformed or distended to a larger diameter, opening valve ports 938 (as shown in FIG. 13B), and allowing urine to flow through valve ports 938 into the urethra, thus relieving or lowering the pressure in the bladder. A separate valve can be disposed in the lumen of catheter 910 to selectively permit or prevent flow through the lumen, using any of the other valve mechanisms described herein.

In some embodiments, the valve can be actively actuated (opened or closed). For example, the valve can be actuated manually by a user action or automatically by a controller of the catheter and/or the external controller, instead of, or in addition to, being passively actuated in response to a pressure differential across the valve exceeding a threshold value. One example of such a valve is shown in FIGS. 14A to 14E. In this embodiment, catheter 1010 includes a pump 1040 and a valve 1030. In this embodiment, valve 1030 can be opened and closed by a rotary movement, rather than the translational movement employed by the valve embodiments described above. (As discussed in more detail below, it can also be opened and closed by translational movement.) Valve 1030 includes a valve seat 1036, which is implemented as a cylindrical body disposed in the lumen of catheter 1010. Valve seat 1036 has multiple valve ports or passages 1038a, through which fluid can pass from the distal side (nearer the bladder) to the proximal side of the valve seat 1036. Valve disk 1032 also has multiple valve ports or passages 1038b therethrough, is disposed concentrically with valve seat 1036, and is mounted for rotational movement relative to valve seat 1036 through a range of relative angular positions. In one angular position, shown in FIG. 14C, passages 1038a in valve seat 1036 do not overlap with passages 1038b in disk 1032. Thus, the solid portion of the distal face of disk 1032 occludes passages 1038a, valve 1030 is closed, and no fluid can flow therethrough. In another angular position, shown in FIG. 14D, passages 1038a and 1038b partially overlap, so that valve 1030 is partially open, and fluid can flow through a portion of the cross-sectional flow area of each of passages 1038a. In another angular position, shown in FIG. 14E, passages 1038a and 1038b are aligned, the valve 1030 is open, and fluid can flow through the full cross-sectional flow area of each of passages 1038a.

Figure 14A:
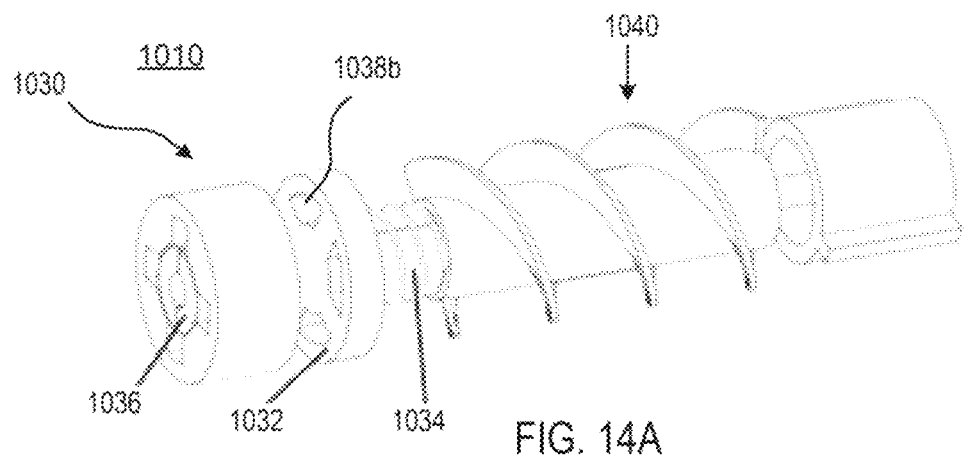
FIGS. 14A and 14B are perspective views of a valve and pump, with the valve shown in an axially open and closed position, respectively.
Figure 14B:
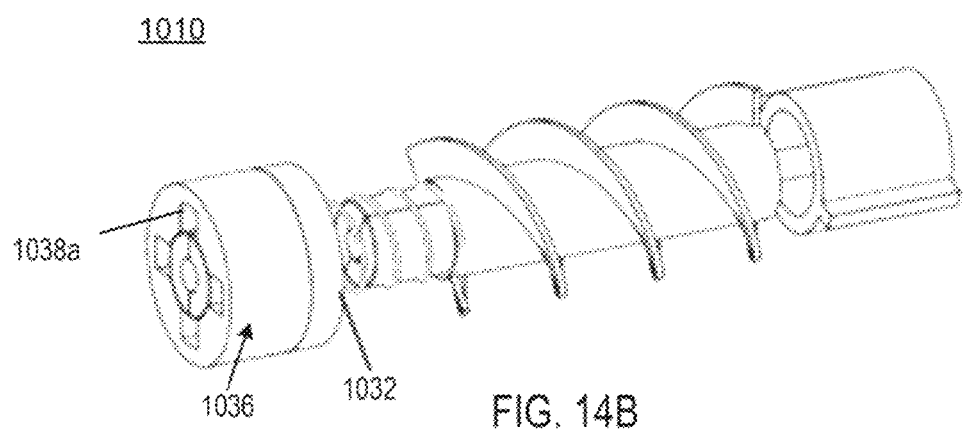
Figures 14C, 14D, 14E:
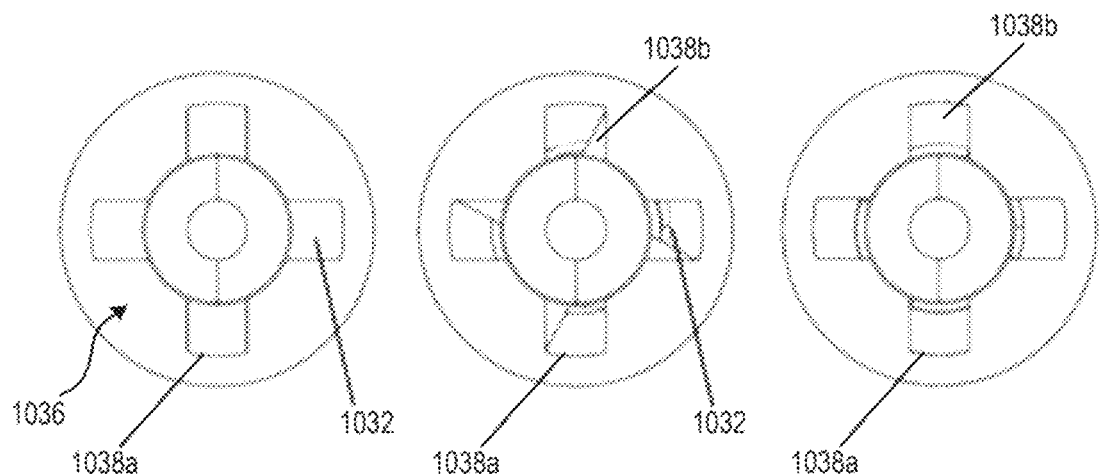
FIGS. 14C to 14E are end views of the valve of FIGS. 14A AND 14B, shown in a rotationally closed, partially open, and fully open position, respectively, according to an embodiment.

Each of valve seat 1036 and valve disk 1032 can contain magnets disposed therein, and their location and polarity configured so that the two components of the valve are magnetically biased towards the fully closed position shown in FIG. 14C. Thus, valve 1030 is normally closed. Valve 1030 can be opened by application of an external magnetic field, such as by a rotatable magnetic body disposed in the external controller of the bladder management system. Since valve seat 1036 is rotationally fixed, but valve disk 1032 is rotatable, the external magnetic field can interact with the magnets in valve disk 1032 to drive rotational movement thereof. Provided that the interaction of the external magnetic field and the magnets is valve disk 1032 is stronger than the interaction between the magnetic fields of the magnets in valve seat 1036 and valve disk 1032, the external magnetic field will produce rotation of the valve disk to open the valve. The rotational movement can be discrete (e.g., a fixed angular rotation to align valve ports 1038a and 1038b to open valve 1030 and keep it open until the magnetic field is changed) or it can be continuous (e.g., valve 1030 cycles continuously between fully closed, partially open, fully open, partially open, etc.), so that fluid can pass intermittently through valve ports 1038a, 1038b.

Valve 1030 can be configured so that the valve seat 1036 and valve disk 1032 are maintained in a fixed relative position axially (i.e., are in axial apposition to maintain a fluidic seal therebetween, such as in the relative positions shown in FIG. 14B) so that fluid can flow through the valve 1030 only when the valve disk 1032 is rotated relative to valve seat 1036 until valve ports 1038*a* and 1038*b* at least partially overlap angularly. However, valve 1030 can also be configured so that valve disk 1032 and valve seat 1036 can be moved axially relative to each other. If the valve disk 1032 are valve seat 1036 are spaced apart, as shown in FIG. 14A, then fluid can flow through valve ports 1038*a*, into the axial gap between valve seat 1036 and valve disk 1032, and then through valve ports 1038*b*. Thus, in the configuration shown in FIG. 14A, valve 1030 is axially open, and in the configuration shown in FIG. 14B, valve 1030 is axially closed (and is in a fully closed configuration assuming that valve ports 1038*a* and 1038*b* are not aligned). Magnets in valve seat 1036 and valve disk 1032 can be configured to magnetically bias the two components into the closed configuration. Valve 1030 can be selectively opened (i.e., changed from the axially closed position shown in FIG. 14B to the axially open configuration shown in FIG. 14A) by application of a suitable external magnetic field, such as one produced by magnets in the external controller of the bladder management system.

Alternatively, or additionally, valve 1030 can also include an optional, passive pressure relief mechanism, so that it can operate similar to the valve embodiments described above (i.e., to open when a bladder overpressure condition occurs). The magnets in valve seat 1036 and valve disk 1032 can be configured (for field strength, and relative orientation of magnetic poles) so that the strength of the interaction of their magnetic fields is low enough that the hydrostatic force applied to the distal face of disk 1036 by fluid in passages 1038*a* at a threshold pressure corresponding to a bladder overpressure condition is sufficient to force the valve disk 1032 away from valve seat 1036 in a proximal direction, to the axially open configuration shown in FIG. 14A. When the bladder overpressure condition has been relieved by the release or urine, the force of the urine on valve disk 1032 is reduced, and the magnetic interaction between the magnets in valve disk 1032 and valve seat 1036 can urge the components together, into the closed configuration of valve 1030 shown in FIG. 14B.

As shown in FIGS. 14A and 14B, valve 1030 may also include a spring 1034 that can augment or counterbalance, as appropriate, the magnetic interaction between valve disk 1032 and valve seat 1036. In some embodiments, the magnets in the two valve components can be arranged so that they provide the desired angular indexing (biasing towards a closed angular position) but produce little or no axial force (attraction or repulsion) between the components, in which case the spring 1034 provides the only axial biasing force on the valve disk 1032. If the magnets produce an axial force (attraction or repulsion between the valve components), the axial force (spring constant and preload) and its direction (compression or tension) can be selected to be additive to or subtractive from the force imposed by the magnets, to yield the desired axial hydrostatic force from urine pressure to cause the valve to open, and the restorative force to urge the valve 1030 to the closed position.

Other mechanisms can be used to provide for active actuation of the valve. Another embodiment of a valve is shown in FIGS. 15A and 15B. Catheter 1110 includes a valve 1130 and a pump 1140 disposed to control the flow of urine through lumen 1121 and allow the urine to be discharged from fluid outlet 1124. Valve 1130 includes a valve seat 1136 with which movable occluder 1132 can selectively engage. Occluder 1132 can be translated axially between a closed position (in sealing contact with valve seat 1136) and an open position (spaced from valve seat 1136, creating an annular opening or valve port therebetween) by a screw drive 1135. Screw drive 1135 can include a rotatable, threaded rod 1135*a*, that cooperates with an internally threaded journal or bearing 1135*c*. A magnetic drive member 1135*b* is coupled to one end of threaded rod 1135*a*, and occluder 1132 is coupled to the opposite end. Rotation of threaded rod 1135*a* in bearing 1135*c* causes threaded rod 1135*a*, and thus occluder 1132, to translate axially—rotation in one direction cause distal translation, and thus can bring occluder 1132 into sealing apposition with valve seat 1136 (closing valve 1130), while rotation in the other direction causes proximal translation of threaded rod 1135*a* and occluder 1132, spacing occluder 1132 from valve seat 1136 (opening valve 1130). Rotation of threaded rod 1135*a* can be caused by interaction of an external, rotating magnetic field (e.g., produced by a magnetic drive member in an external controller) with magnetic drive member 1135*b*. Thus, valve 1130 can be actively actuated (opened or closed). For example, the valve 1130 can be actuated manually by a user action or automatically by a controller of the catheter and/or the external controller.

Optionally, occluder 1132 can incorporate an automatic pressure relief function. As shown in FIGS. 15A and 15B, occluder 1132 can include an occluding head 1132*a*, a spring holder 1132*c*, and a spring 1132*b*. Occluding head 1132*a* can be coupled to spring holder 1132*c* for relative axial movement, and biased distally by spring 1132*b*. When valve 1130 is disposed in the closed configuration (i.e., by screw drive 1135 positioning occluder 1132 with occluder head 1132*a* in sealing apposition with valve seat 1136), valve 1130 can still open automatically in response to fluid pressure on the distal side of occluding head 1132*a* (i.e., bladder pressure) exceeding a threshold value, by proximal displacement of occluder head 1132*a* against the biasing force of spring 1132*b*. Although shown as a coil spring in FIGS. 15A and 15*b*, spring 1132*b* can be implemented in other ways, such as a viscoelastic gel or matrix whose mechanical and viscoelastic properties are tuned to compress at the proper pressure or volume threshold but still slowly enough to only open under a consistent pressure to resist opening under temporary spikes in volume or pressure. In other implementations, the tolerance between the occluding head 1132*a* and spring holder 1132*c* act as a dashpot to resist opening from acute changes or spikes in volume or pressure while still opening under consistent pressure thresholds.

Although catheter 1110 is shown in FIGS. 15A and 15B with the valve 1130 disposed distally (i.e., closer to the bladder) to pump 1140 in lumen 1121, it can alternatively be disposed proximally to pump 1140.

In another embodiment, an actively activated valve can include an iris mechanism, similar to a camera aperture mechanism.

In any of the embodiments above, the component specifications, such as spring constant for a spring, the length of a duck bill valve, can be varied to change the threshold pressure at which the valve opens, and relieves bladder pressure. A bladder management system can thus include different catheters, or a catheter with different valves, with different opening pressures, from which a health care giver or user can select to be appropriate for the user's specific condition or needs.

In some implementations, the pressure fail safe mechanism may be implemented as an active, rather than passive system. For example, a pressure sensor, such as a sensor 164, can continuously or periodically sense bladder pressure, and a controller, and release urine to relieve bladder pressure before a dangerous pressure is reached and in response to or based on the sensed bladder pressure reaching a threshold.

In some implementations, the pressure fail safe mechanism may be incorporated into the anchoring system. For example, the anchoring system can include a slit that opens or a support that flexes, under a threshold pressure to allow for fluid to pass around the catheter, between the catheter and the urethra wall, allowing for pressure relief before the organ reaches a dangerous pressure level.

Due to the natural spike in bladder pressure while laughing, coughing, or participating in other normal daily activities, in some implementations, the bladder management system may incorporate a valve or pressure failsafe mechanism that intentionally lags in response to bladder pressure exceeding the threshold pressure, to prevent urine leakage unless elevated bladder pressure is sustained. Said another way, the catheter can be configured to expel fluid from the bladder in response to the valve experiencing a threshold pressure for a sustained predetermined time period, and not before such time period is reached. In some implementations, for example, the catheter may include multiple valves in series, an elongated duck bill valve, an in-line dashpot, viscoelastic or anisotropic valve leaflets, a pump turbine that resists very fast rotation or a predefined threshold speed or acceleration of rotation, or another mechanism to introduce a lag to bladder depressurization for fail safe purposes. In some implementations, one or more of these lag-inducing mechanisms can be overridden through the on-demand pump activation.

Anchor, Seal

Distal displacement of the catheter into the bladder can cause uncomfortable and even painful bladder spasms, and proximal dislodgement of the device through the urethra could result in the catheter completely falling out of the patient's body. To limit or prevent displacement or dislodgment of the catheter of the bladder management system within the patient, the catheter can be configured to be anchored to the patient's anatomy. As discussed above for bladder management system 100, the catheter can include an anchoring mechanism (also referred to herein as an "anchor" or as a "retaining portion" of the catheter), either integral to, or formed as a separate component and then coupled to, the catheter. Uncontrolled flow of fluid (e.g., urine) through the user urethra, around the catheter body, is undesirable. Rather, fluid flow should only pass through the lumen of the catheter, controlled by the valve. Thus, as discussed above for bladder management system 100, the catheter can include a seal coupled to the catheter body and engageable with tissue of the bladder and/or urethra to inhibit the flow of fluid between the catheter body and the wall of the urethra. The seal may be constituted by, or formed as part of, the anchor.

In some implementations, the catheter can be anchored both in the bladder and at a proximal region of the urethra. In some implementations, this is accomplished using a Malecot-type structure on each end of the urethra, one internally at the neck of the bladder, and one externally at the proximal opening of the urethra. In some implementations, the external anchor can also serve to support a portion of the electronics of the catheter, such as a portion of the communication module, by which data from the one or more sensors can be accessed by the external controller.

In some instances, the catheter is anchored only internally. In such instances, the catheter can be anchored at one or more locations including, but not limited to, the prostate (for male users), intraurethral, or at the bladder neck.

Figure 16:
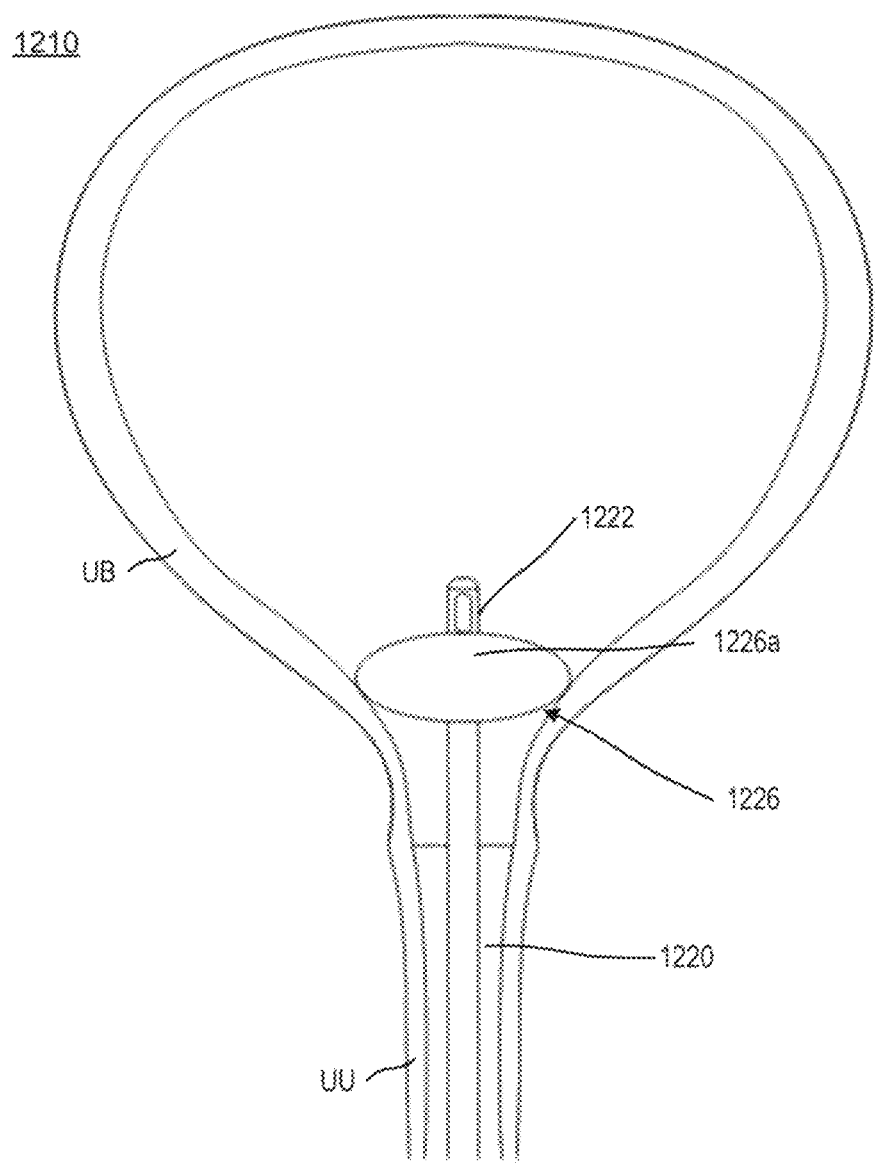
FIG. 16 is a side view of a distal portion of a catheter with an anchor including a balloon, according to an embodiment, shown disposed in a user's bladder and urethra.

In some embodiments, the anchor is implemented with one or more inflatable elements, or balloons. In such implementations, for example, the catheter can be delivered to the user's bladder with the anchor in a delivery configuration in which the balloon is deflated to fit within the urethra, and then when disposed within the bladder, the anchor can be transitioned to a deployed configuration in which the balloon is inflated such that it no longer fits through the urethra (i.e., it resists proximal movement of the catheter). FIG. 16 shows one embodiment of a balloon-based anchor. As shown in FIG. 16, catheter 1210 has a catheter body 1220 with an anchor 1226 disposed adjacent the fluid inlet 1222. The anchor 1226 includes a balloon 1226a. Anchor 1226 can be changed from a delivery configuration to a deployed configuration, by inflating the balloon 1226a by introduction of a fluid (e.g., gas or liquid) into the interior of the balloon 1226a. The fluid can be delivered via an inflation lumen (not shown) formed in the catheter body 1220, and coupleable at a proximal end of catheter body 1220 to a source of inflation fluid and in fluidic communication with the interior of balloon 1226a, such as by an inflation port or passage formed in the catheter body between the inflation lumen and the exterior of the catheter body (internal to balloon 1226a), in a conventional arrangement. Catheter 1210 can be introduced into the user's body by inserting the distal end of the catheter, with the anchor 1226 in the delivery configuration (i.e., with balloon 1226a uninflated), into the opening of the user urethra UU and moving catheter 1210 distally until fluid inlet 1222 is in the user bladder UB and anchor 1226 is disposed in the neck of the bladder. Anchor 1226 can then be changed to the deployed configuration by inflating balloon 1226a, to the condition shown in FIG. 16. The diameter of balloon 1226a is larger than the diameter of the urethra, inhibiting proximal movement of catheter 1210. Balloon 1226a can also be configured to sealingly engage the tissue of user bladder UB, serving the sealing function described for seal 128 in the embodiment of FIG. 1. When it is desired to remove catheter 1210 from the user's body, anchor 1226 is changed from the deployed configuration to a removal configuration (which may be the same as the delivery configuration, or may be a different configuration, but in which anchor 1226 can still be moved through the user urethra UU without excessive force or damage to the urethra) by removing inflation fluid from balloon 1226a via the inflation lumen.

Figure 17:
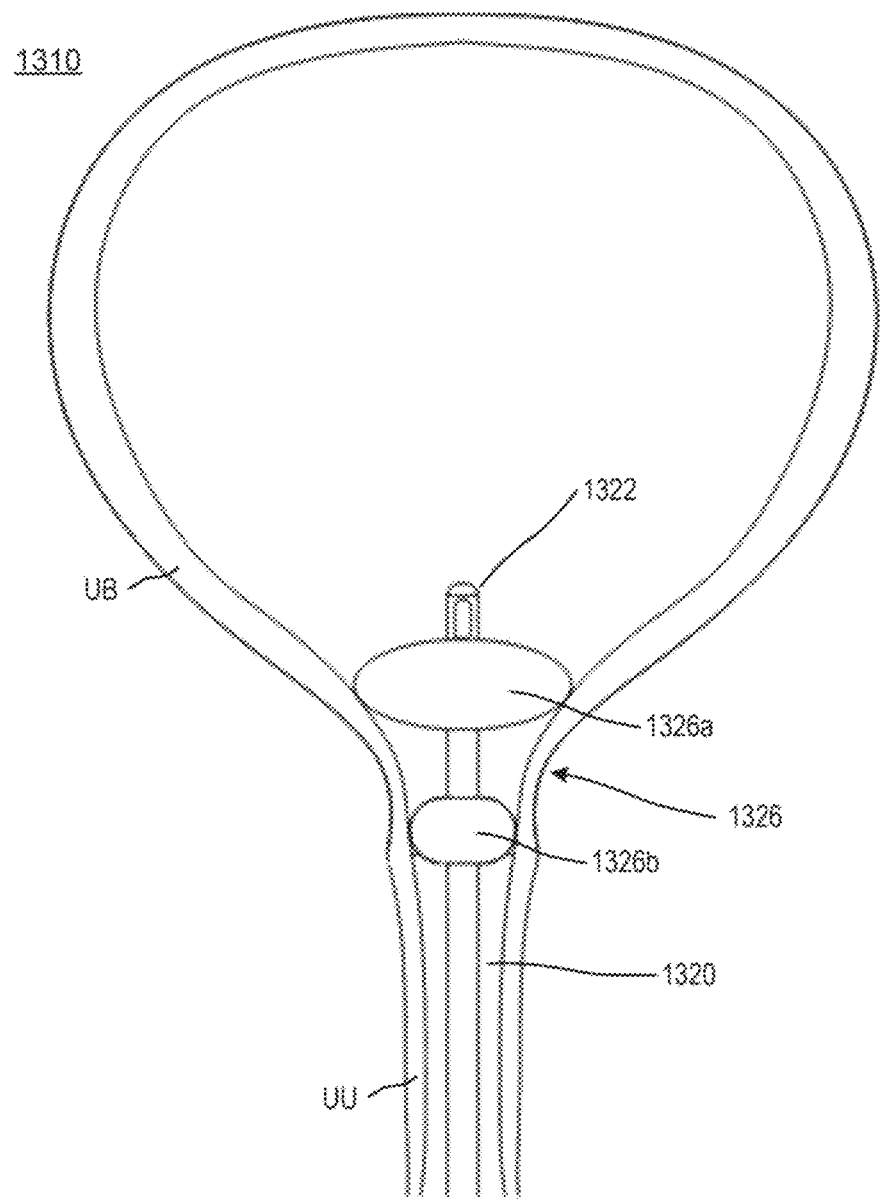
FIG. 17 is a side view of a distal portion of a catheter with an anchor including two balloons, according to an embodiment, shown disposed in a user's bladder and urethra.

FIG. 17 shows another embodiment of a balloon-based anchor. As shown in FIG. 17, catheter 1310 has a catheter body 1320 with an anchor 1326 disposed adjacent the fluid inlet 1322. The anchor 1326 includes a first, distal balloon 1326a and a second, proximal balloon 1326b. Distal balloon 1326a functions similarly to balloon 1226a, describe above. Proximal balloon 1326b is smaller in diameter than distal balloon 1326a and is configured to be disposed in the distal portion of user urethra UU. When in its deployed configuration, shown in FIG. 17, proximal balloon 1326b can slightly distend user urethra UU by stretching the tissue around the largest diameter portion of proximal balloon 1326b while a more distal portion of the urethra is not distended. This interaction with the user urethra UU serves three functions. The first function is to provide a secondary (to the distal balloon 1326a) stop to inhibit proximal migration of catheter 1310. The second function is to resist distal migration of catheter 1310. The third function is to form a fluid-tight seal with user urethra UU (essentially an artificial tissue sphincter seal) to ensure that urine does not pass proximally by proximal balloon 1326*b* and into user urethra on the outside of catheter body 1320, which could then leak undesirably from the user's body. Thus, proximal balloon 1326*b* serves the sealing function described for seal 128 in the embodiment of FIG. 1. Optionally, distal balloon 1326*a* may also provide a sealing function, such as with balloon 1226*a* in the embodiment of FIG. 16. Each of the two balloons can be inflated and deflated simultaneously, in the same manner as balloon 1226*a*, using a single inflation lumen, or can be inflated and deflated separately by use of two inflation lumens, one for each balloon.

Although the balloons in anchors 1226 and 1326 are shown as oval in cross section (oblate spheroids), other shapes for balloons can be cylindrical, conical, reverse conical, at least part of pyramidal, a dumbbell, a prolate spheroid, a sphere, a dome, or at least part of a spindle shape.

In some embodiments, the anchor can include or be formed from a plurality of discrete struts connected to the distal end of the catheter body, at or near the fluid inlet. The struts may be self-expanding or unfolding from a delivery configuration to a deployed configuration, or may require application of some force to change their configuration. One such embodiment is shown in FIG. 18. Catheter 1410 includes a body 1420 with a fluid inlet 1422 and an anchor 1426 coupled to, and extending distally from, fluid inlet 1422. Anchor 1426 includes a plurality of struts 1426*a* which, in the deployed configuration shown in FIG. 18, have distal portions that extend to a larger diameter than user urethra UU, thus resisting proximal migration of catheter 1410.

In another embodiment, such as catheter 1510 shown in FIG. 19, a seal 1528 can be associated with anchor 1526. In this embodiment, seal 1528 is formed as a sheet or webbing of fluid impermeable material (e.g., polymer) that interconnects struts 1526*a*, thus integrating the anchoring and sealing functions. Seal 1528 can form a fluid tight seal with the tissue of the bladder neck to prevent flow of urine into user urethra UU on the outside of catheter body 1520.

Figure 20B:
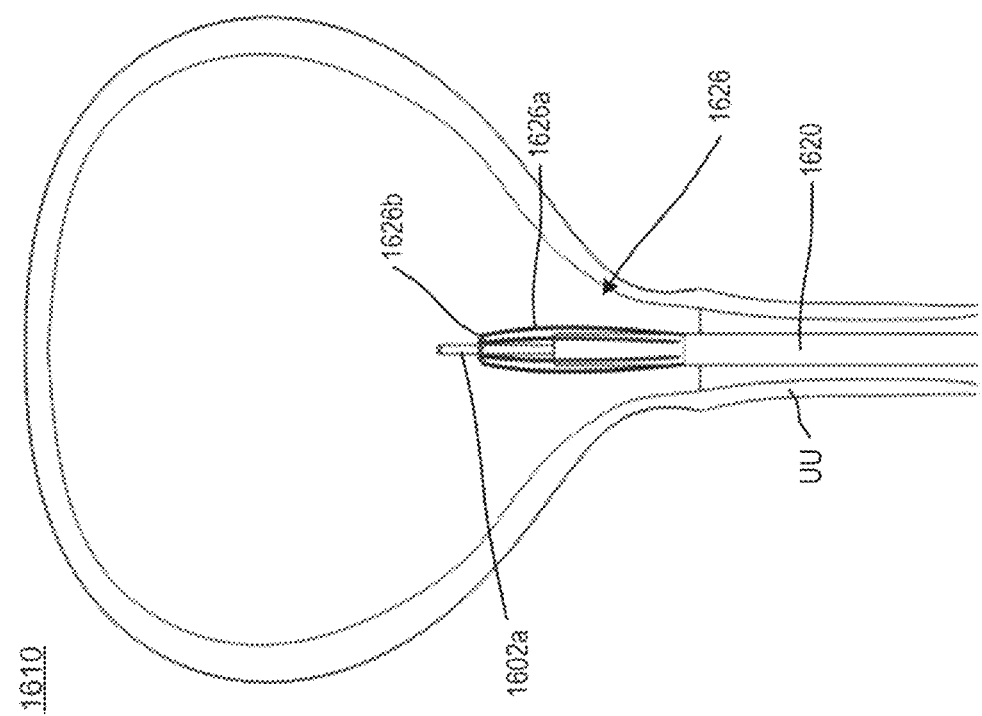
FIGS. 20A and 20B are side views of a distal portion of a catheter in a deployed and delivery configuration, respectively, according to an embodiment, shown disposed in a user's bladder and urethra.
Figure 20A:
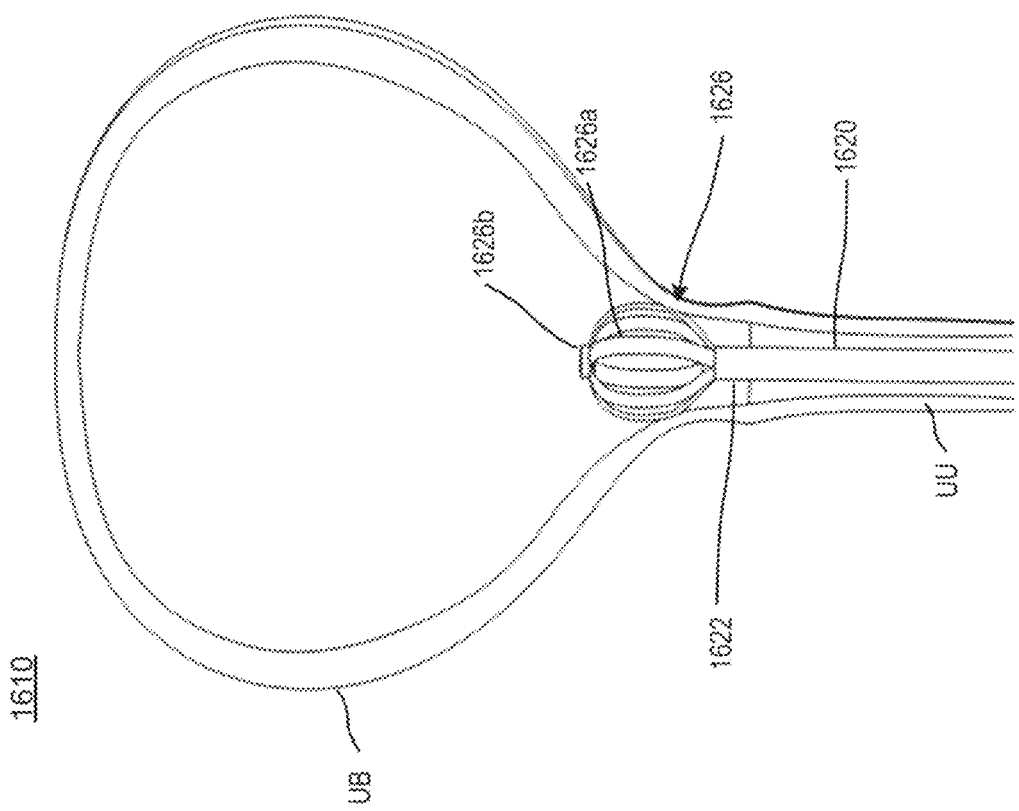

In some embodiments, the anchor can include multiple discrete struts with the distal ends joined together, while the proximal ends are coupled to the catheter body. One such embodiment is anchor 1626 of catheter 1610, shown in FIGS. 20A and 20B. The struts 1626*a* are at their proximal end to fluid inlet 1622 and are coupled together at their distal end by end cap 1626*b*. Struts 1626*a* may be formed to assume the shape shown in FIG. 20 when unconstrained or unstressed (i.e., the deployed configuration of anchor 1626). Anchor 1626 can be disposed in a smaller-diameter, delivery configuration, by being constrained radially (e.g., within the lumen of a delivery device, as described with reference to FIGS. 4C, 4D) and/or elongated axially (e.g., by displacing cap 1626*b* distally relative to fluid inlet 1622, such as by an actuator of a delivery device as described with reference to FIGS. 4A, 4B). The latter approach is illustrated in FIG. 20B, in which cap 1626*b* is displaced distally by a rod 1602*a* that is part of a delivery device. Anchor 1626 is thus in a delivery configuration in FIG. 20B (though a similar approach with a retrieval device, or a device usable both for delivery and retrieval, may be used to dispose anchor 1626 in a retrieval configuration).

Figure 21:
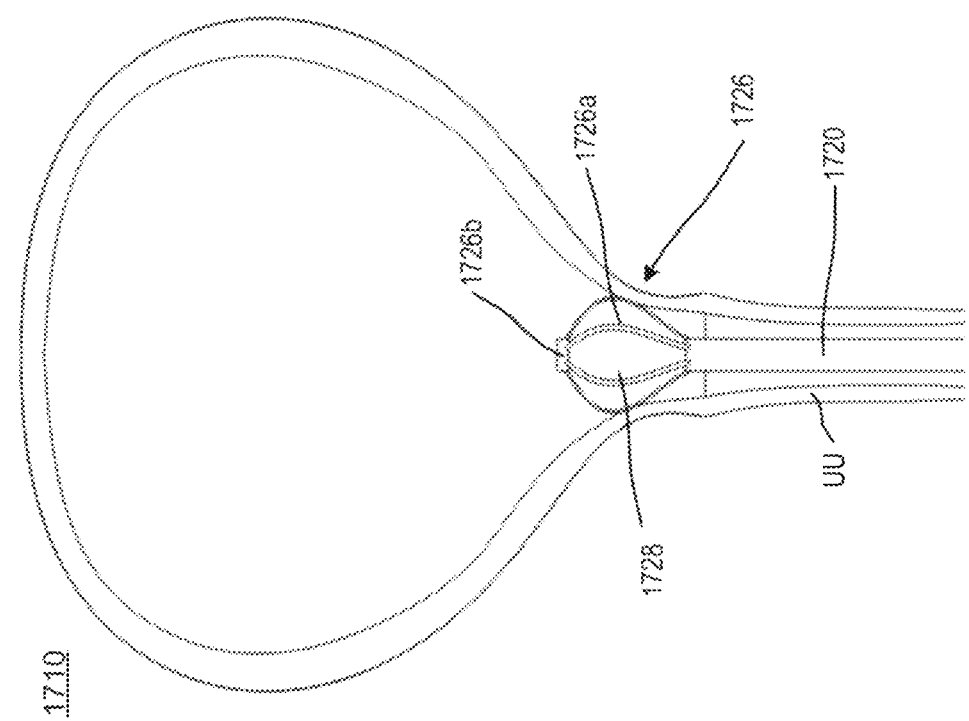
FIG. 21 is a side view of a distal portion of a catheter with an anchor including struts and an integrated seal, according to an embodiment, shown disposed in a user's bladder and urethra.

Similar to the catheter 1510 shown in FIG. 19, in another embodiment a seal can be associated with an anchor such as anchor 1626. Catheter 1710 shown in FIG. 21 includes a seal 1728 formed as a sheet or webbing of fluid impermeable material (e.g., polymer) that interconnects struts 1726*a* (joined together at their distal ends by cap 1726*b*), thus integrating the anchoring and sealing functions. Seal 1728 can form a fluid tight seal with the tissue of the bladder neck to prevent flow of urine into user urethra UU on the outside of catheter body 1520.

Figure 22:
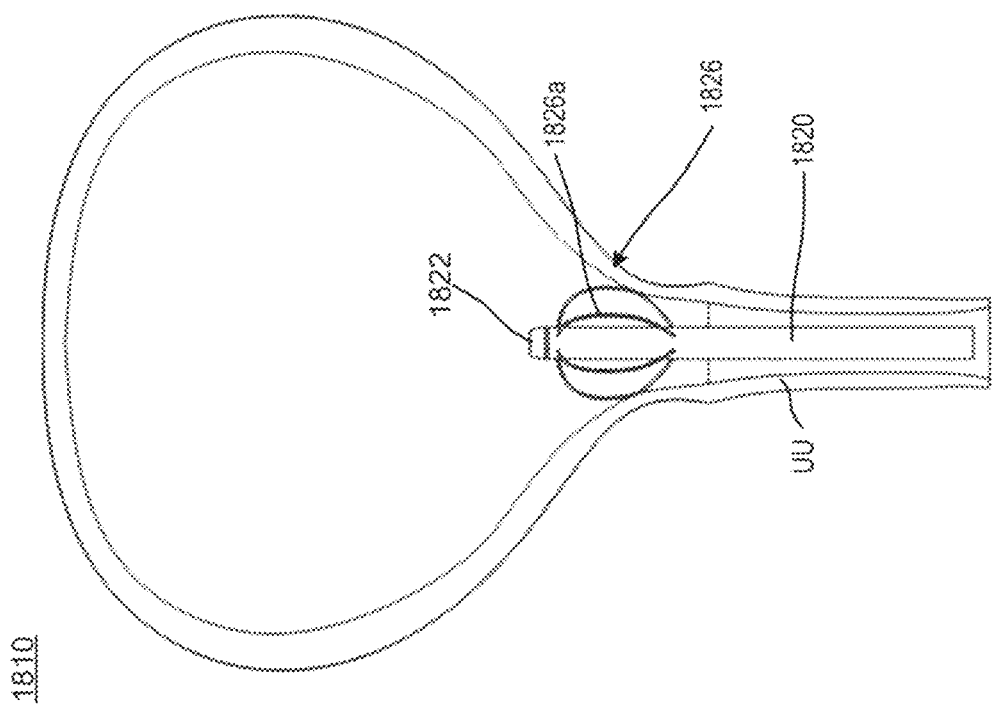
FIG. 22 is a side view of a distal portion of a catheter with an anchor including struts, according to an embodiment, shown disposed in a user's bladder and urethra.

In other embodiments, an anchor can be formed with struts that are coupled at both ends to the catheter body. An example of such an embodiment is catheter 1810, shown in FIG. 22. Catheter 1810 has an anchor 1826 disposed on catheter body 1820 near fluid inlet 1822, which includes a plurality of struts 1826*a*, each coupled at both its proximal end and distal end to catheter body 1820. Anchor 1826 is shown in its deployed configuration in FIG. 22.

Figure 23:
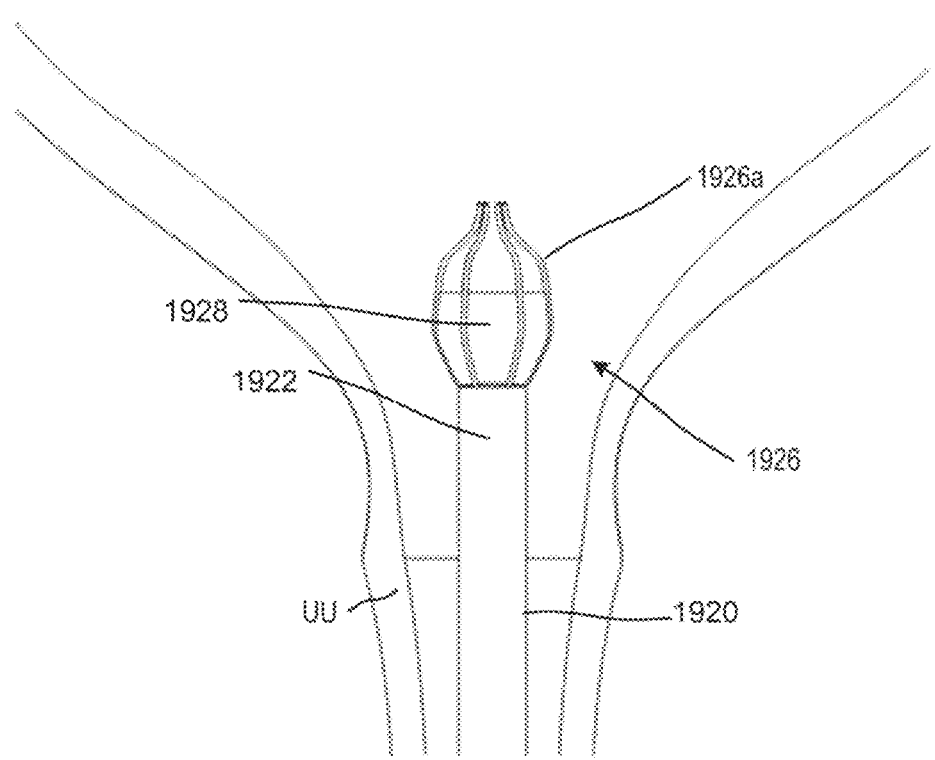
FIG. 23 is a side view of a distal portion of a catheter with an anchor including struts, according to an embodiment, shown disposed in a user's bladder and urethra.

In some embodiments, the struts can be shaped to facilitate distal delivery of the anchor through the urethra (i.e., the anchor need not be maintained/constrained in a delivery configuration until it is disposed distal to the urethra). One such embodiment is shown in FIG. 23. Catheter 1910 has an anchor 1926 coupled to fluid inlet 1922 at the distal end of body 1920. Struts 1926*a* are shaped with their distal tips spaced closely together, and form a shallow angle relative to the central axis of anchor 1926. Thus, the anchor 1926 can pass distally through user urethra UU without damaging tissue on the wall of the urethra, until the anchor 1926 extends into the user bladder before self-expanding into a deployed configuration (anchor 1926 is shown in FIG. 23 for ease of illustration in the smaller diameter configuration in which it can pass through the urethra). This embodiment also includes a seal 1928 integrated with anchor 1926, similar to other embodiments described above.

Figure 24B:
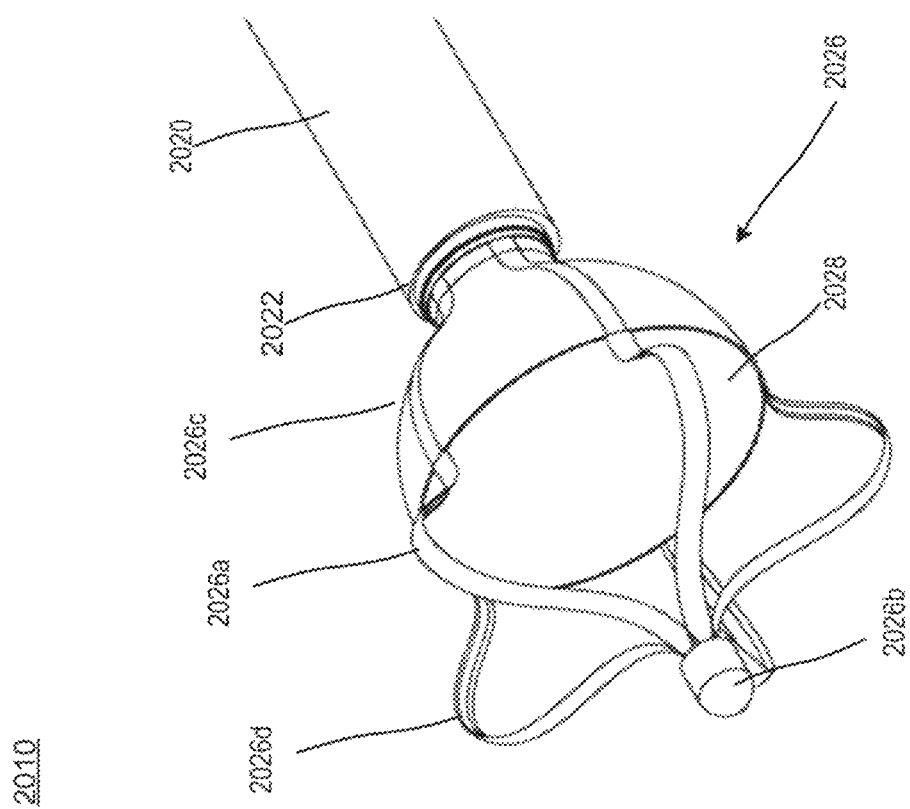
FIGS. 24A and 24B are proximal and distal perspective views, respectively, of a distal portion of a catheter with an anchor including struts and an integrated seal, according to an embodiment.
Figure 24A:
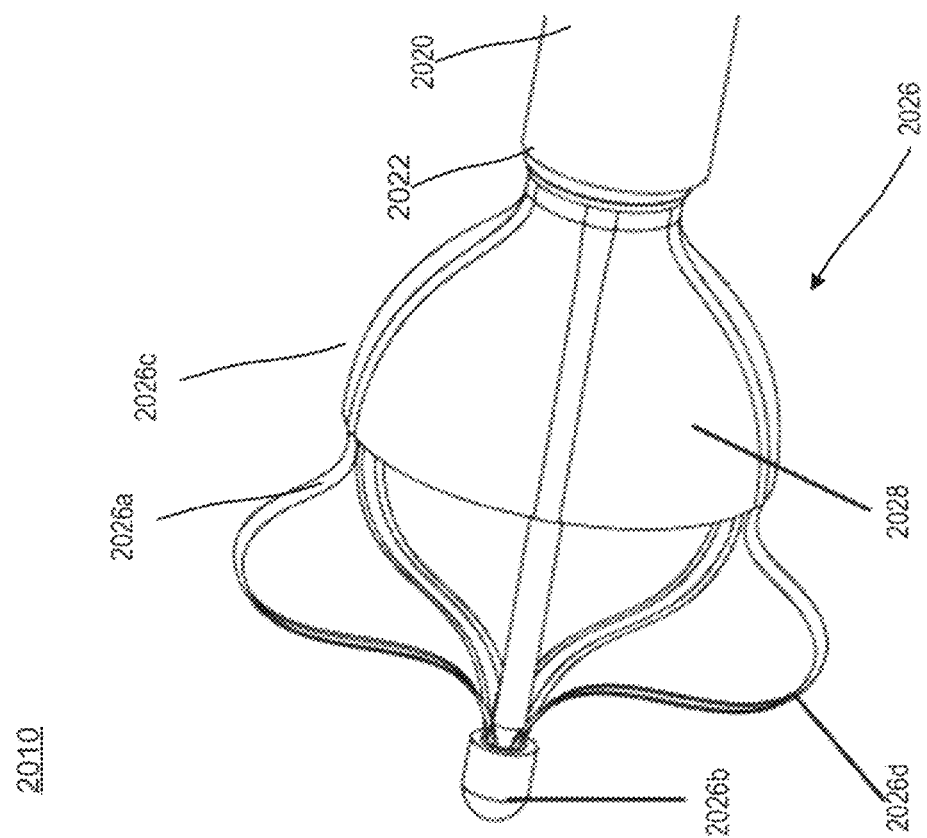

Another strut-based anchor embodiment with an integrated seal is shown in FIGS. 24A and 24B. Catheter 2010 includes a body 2020 with a fluid inlet 2022, an anchor 2026, and a seal 2028. Anchor 2026 is formed of struts 2026*a*, coupled at their proximal ends to fluid inlet 2022 and coupled together at their distal ends by cap 2026*b*. A seal 2028 is integrated with anchor 2026, with a sheet or web of material interconnecting struts 2026*a*. The struts 2026*a* are shaped with a compound curve that forms an anchor having a proximal portion 2026*c* than can be disposed in the entrance to the urethra from the bladder, with seal 2028 sealingly engaging tissue in that area, and a larger diameter distal portion 2026*d* that is larger than the entrance to the urethra and thus serves as an additional mechanism to inhibit proximal migration of catheter 2010 in the user's urethra. As with the embodiment described with reference to FIGS. 20A and 20B, anchor 2026 can be reconfigured from the deployed configuration shown in FIGS. 24A, 24B to a smaller-diameter delivery (or retrieval) configuration by displacing cap 2026*b* axially away from fluid inlet 2022, such as by an rod that is part of an actuator of a delivery and/or retrieval device.

Figure 25B:
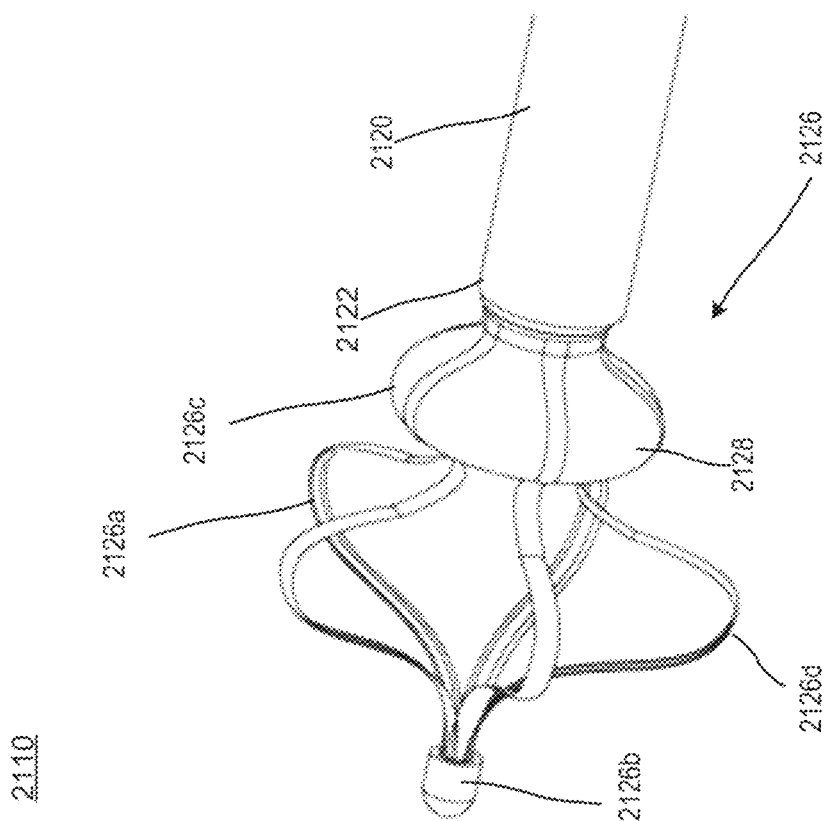
FIGS. 25A and 25B are proximal and distal perspective views, respectively, of a distal portion of a catheter with an anchor including struts and an integrated seal, according to an embodiment.
Figure 25A:
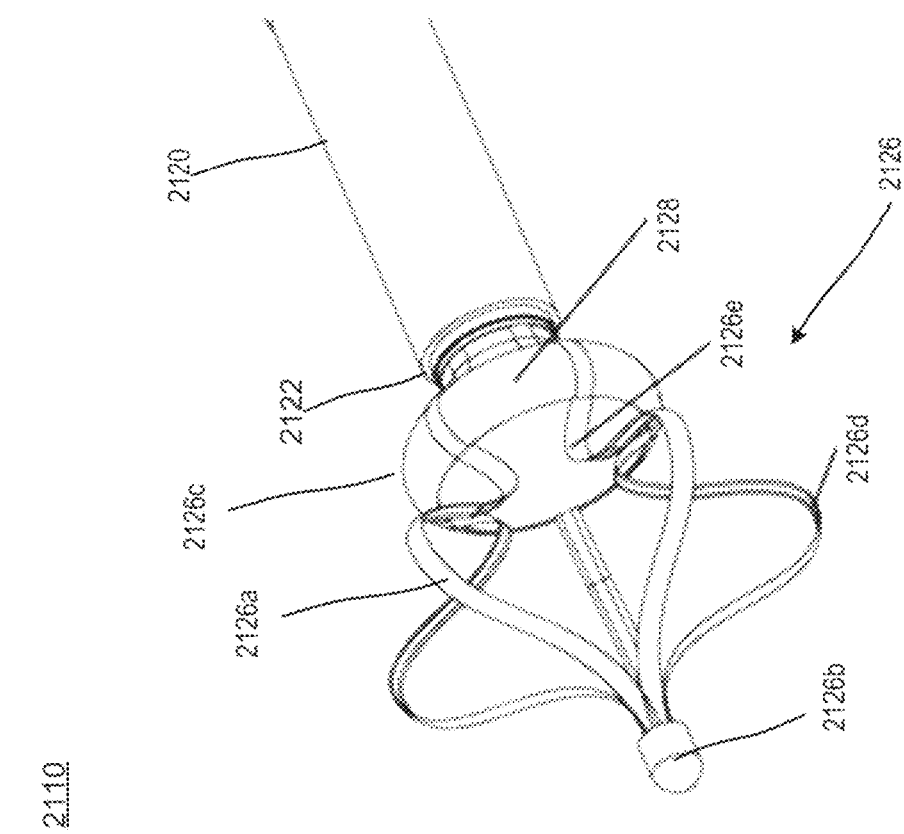

In other embodiments, strut-based anchors can be configured to provide similar functionality to the two-balloon embodiment described with reference to FIG. 17. That is, a proximal portion of the anchor can be configured to stretch or distend tissue in the urethra for sealing and to inhibit movement. One such embodiment is illustrated in FIGS. 25A and 25B. Catheter 2110 has a body 2120 with a fluid inlet 2122, an anchor 2126, and an integrated seal 2128. Anchor 2126 is formed with struts 2126*a*, coupled at their proximal ends to fluid inlet 2122 and at their distal ends by cap 2126*b*. Struts 2126*a* are shaped to form a smaller diameter proximal portion 2126*c* and a larger diameter distal portion 2126*d*, separated by a neck or waist 2126*e*. Anchor 2126 can be deployed with proximal portion 2126*c* disposed in the user urethra, similar to proximal balloon 1326*b* described with reference to FIG. 17, to provide sealing as well as resistant to both proximal and distal migration of catheter 2110. Distal portion 2126*d* can deployed in the user bladder, and function to further inhibit proximal migration. Anchor 2126 can be delivered, deployed, and retrieved similar to anchor 2026 described with reference to FIGS. 24A and 24B.

In embodiments of anchors formed with struts, any suitable number of struts can be incorporated, so that the cross-axonal shape of the expanded struts can be in a hexagonal, square, or any polygonal shape.

Figure 26B:
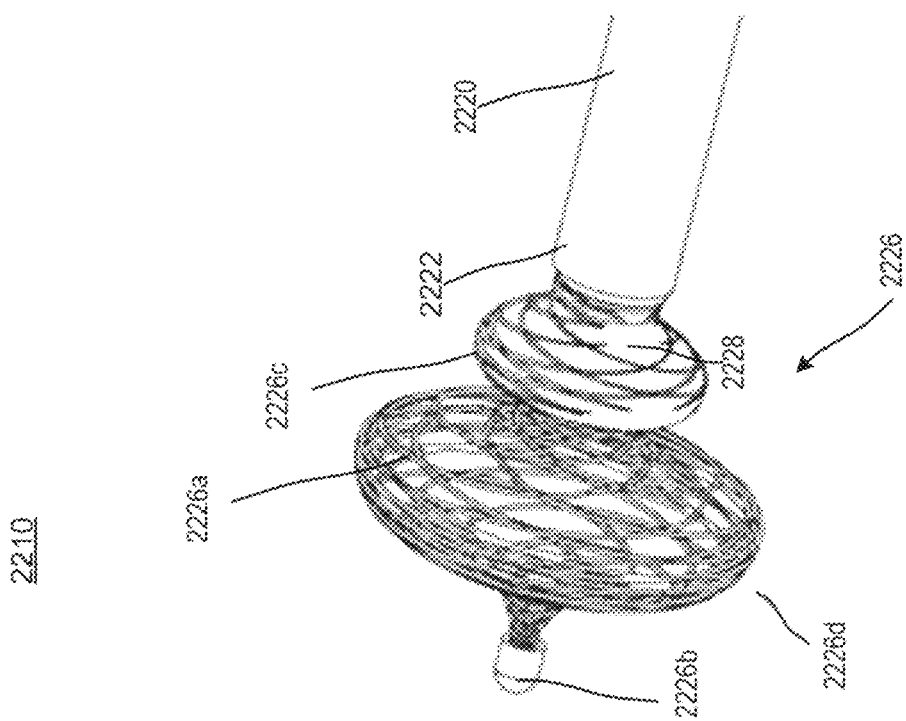
FIGS. 26A and 26B are proximal and distal perspective views, respectively, of a distal portion of a catheter with an anchor formed of braided wire and having an integrated seal, according to an embodiment.
Figure 26A:
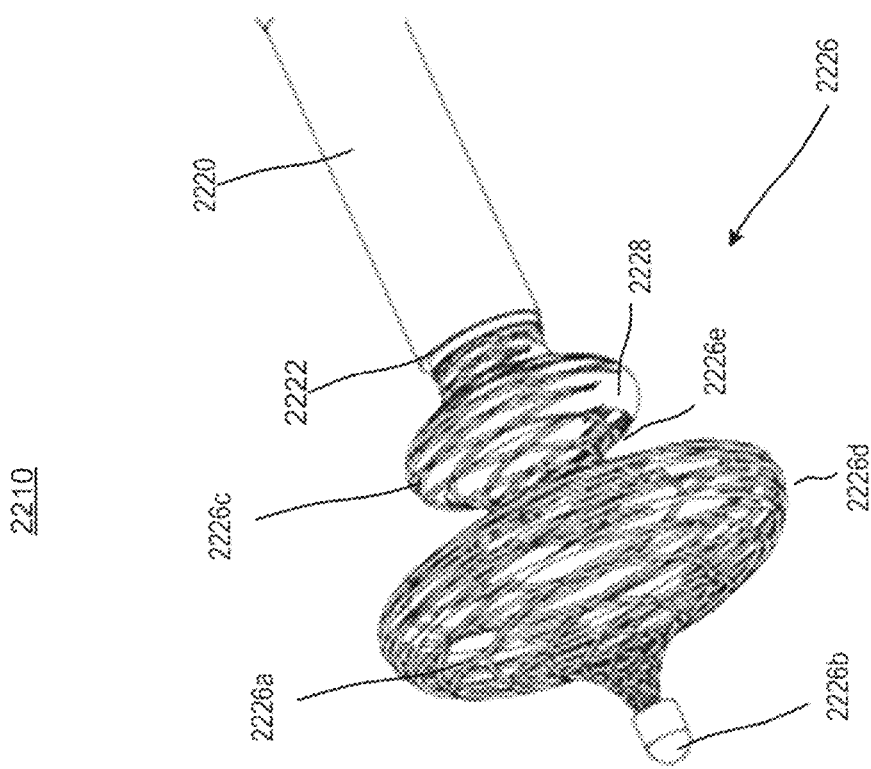

In other embodiments, rather than being formed with discrete struts, the anchor can be formed with wire (e.g., woven into a braid) with the shape defined by appropriately forming and setting the material of the wire, such as a shape memory material (e.g., nitinol). One such embodiment is shown in FIGS. 26A and 26B. Catheter 2210 has a body 2220 with a fluid inlet 2222, an anchor 2226, and an integrated seal 2228. Anchor 2226 is formed a plurality of wires 2226*a*, woven into a unitary braid, and coupled at their proximal ends to fluid inlet 2222 and at their distal ends by cap 2226*b*. Other than the braided construction, anchor 2226 is shaped, and functions, the same as anchor 2126 described with reference to FIGS. 25A and 25B (i.e., the braided wires 2226*a* are shaped to form a smaller diameter proximal portion 2226*c* and a larger diameter distal portion 2226*d*, separated by a neck or waist 2226*e*, and can be disposed in the user's urethra and bladder, and delivered, deployed, and retrieved int the same fashion).

Figure 27:
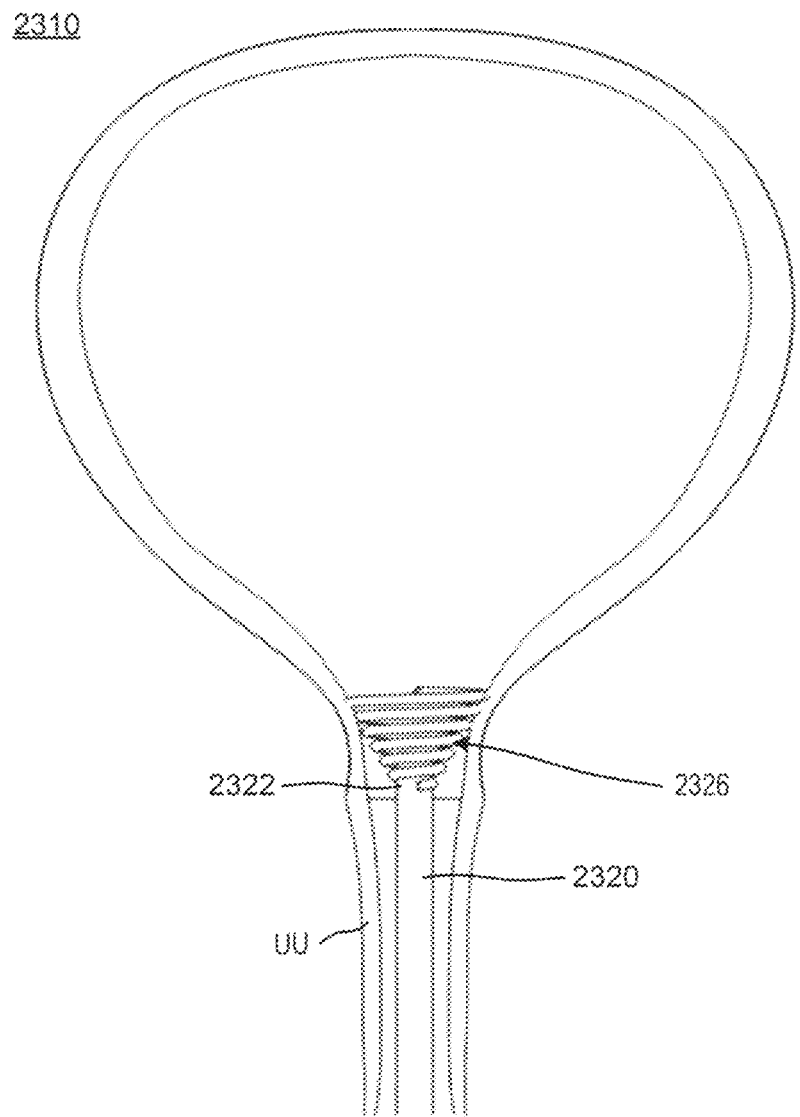
FIG. 27 is a side view of a distal portion of a catheter with an anchor formed of a coiled wire, according to an embodiment, shown disposed in a user's bladder and urethra.

In some embodiments, the anchor can be formed as a spiral coil. One such embodiment is shown in FIG. 27. Catheter 2310 includes of a self-expanding coiled section of wire, with a smaller diameter end coupled to fluid inlet 2322 of body 2320 and a larger diameter distal end, forming a conical or funnel shape that inhibits proximal migration of catheter 2310. As with other embodiments, anchor 2326 can include an integrated seal by coupling a sheet or web of material to the outer surface of the wire coil.

Figure 28B:
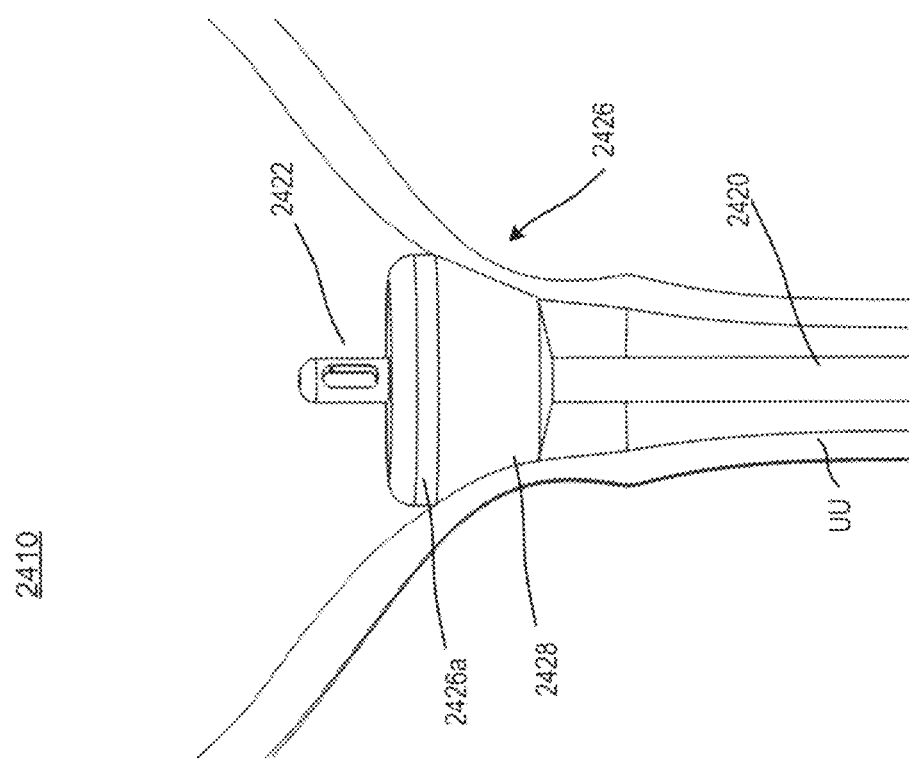
FIGS. 28A and 28B are side views of a distal portion of a catheter having an anchor formed of expandable foam, shown in a delivery and deployed configuration, respectively, according to an embodiment, shown disposed in a user's bladder and urethra.
Figure 28A:
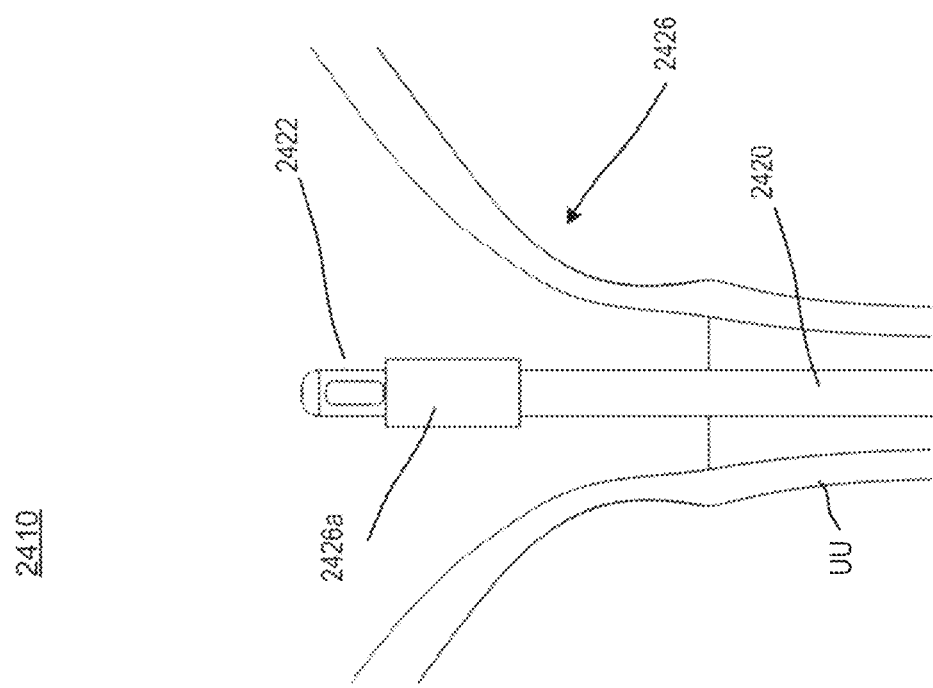

In some embodiments, the anchor can be formed from a self-expanding foam, or similar absorbent material. One such embodiment is shown in FIGS. 28A and 28B. Catheter 2410 has a body 2420 with a fluid inlet 2422, an anchor 2426, and an integrated seal 2428. Anchor 2426 includes an unitary anchor body 2426*a* that is formed of a material that expands by absorbing fluid (such as urine) to change from the smaller diameter delivery configuration shown in FIG. 28A to the larger diameter deployed configuration shown in FIG. 28B. In the deployed configuration, anchor body 2426*a* has a tapered, or frustoconical shape that can inhibit proximal migration of catheter 2410. At least the proximal face of anchor body 2426*a* can include a fluid impermeable coating 2428, which functions as a seal. The material forming anchor body 2426*a* can be, for example, a foam composed of a polymer, rayon, cotton, polyurethane, hyaluronan, hyaluronic acid, collagen, or any other shape memory polymer or blend. In some embodiments, the foam can be doped with a biocompatible material. The coating 2428 can be formed of PET, PEBA, polyether ether ketone (PEEK), PTFE, silicone, polystyrene (PS), polyurethane (PU), latex, or a copolymer thereof, and may have a thickness between 1 μm and 1 mm. The anchor body can be transition from its deployed (expanded) configuration to a retrieval (collapsed) configuration simply by withdrawing it proximally into the user urethra—the compressive force exerted by the urethral wall can expel the liquid (urine) that was absorbed by the foam.

As described above, an anchor can be disposed in locations other than, or in addition to, the distal end of the catheter (i.e., the anchoring function that inhibits proximal and/or distal migration of the catheter can be performed by structures proximal to the fluid inlet of the catheter, and/or at or proximal to the outlet end of the catheter).

Figure 29:
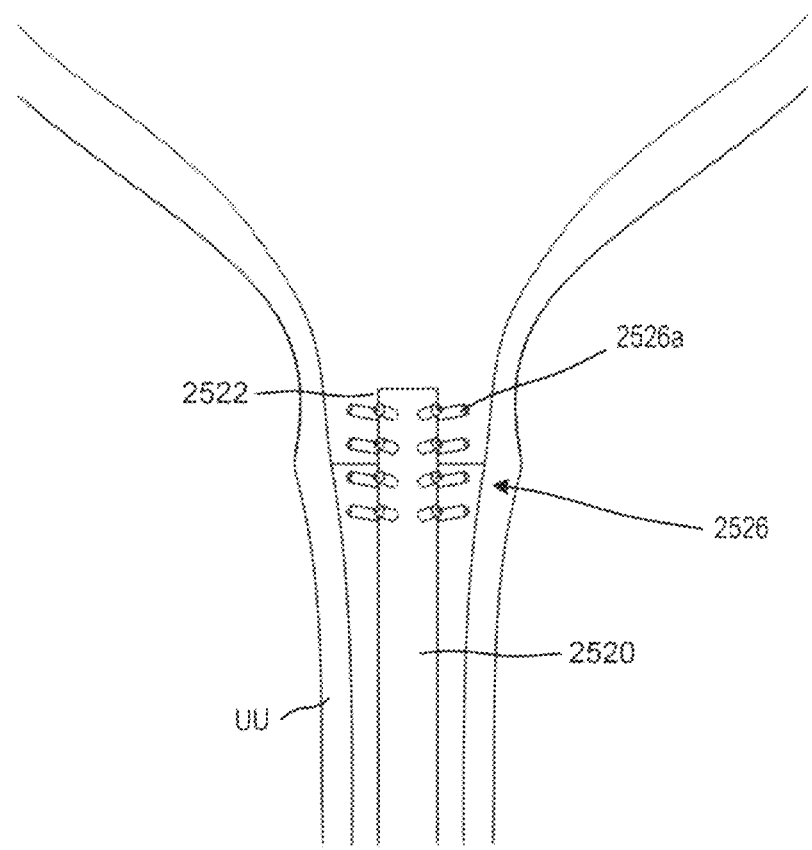
FIG. 29 is a side view of a distal portion of a catheter with a urethral anchor, according to an embodiment, shown disposed in a user's urethra.

An embodiment of a catheter with an anchor configured to be disposed in the urethra is shown in FIG. 29. Catheter 2510 has a body 2520 with a fluid inlet 2522, and an anchor 2526. Anchor 2526 is configured to be disposed in the user urethra UU and engage the tissue of the urethral wall to inhibit at least distal migration of catheter 2510. In the illustrated embodiment, anchor 2526 is formed of a plurality of small posts 2526*a* projecting laterally from body 2520. The posts 2526*a* are angled slightly distally, to preferentially resist distal movement of catheter 2520. The posts 2526*a* may be formed of any suitable material, such as polymer. Although shown in this embodiments as posts, other micro or macro surface modifications such as beads, teeth, foam-like material that expands after insertion, or other variations that provide outward pressure (or increased friction) in the user urethra to aid in inhibit movement of catheter 2510.

In some embodiments, the catheter can be also, or only, anchored at the external opening at the proximal end of the urethra (e.g., externally). An embodiment of a catheter with an anchor configured to be disposed in the urethra is shown in FIG. 30. Catheter 2610 has a body 2620 with a fluid outlet 2624, and an anchor 2626. Anchor 2626 is configured to be disposed externally to the user's body, proximal to the external entrance to the user's urethra, and to engage the external tissue around the entrance to the urethra, to inhibit at least distal migration of catheter 2510. In the illustrated embodiment, anchor 2526 is formed of a pair of loops 2626*a* projecting laterally from fluid outlet 2624 and having a lateral extent larger than the diameter of the urethra.

In another embodiment, shown in FIG. 31, catheter 2710 includes a body 2720, a fluid outlet 2724, and an anchor 2726, which includes a plate 2726*a* having a lateral extent larger than the diameter of the urethra.

Due to anatomy differences in the male and female urinary tract, in some embodiments, the catheter may be tailored for use by male versus female users. For example, the male catheter may be anchored by the prostate, and the female catheter may be relatively larger to inhibit migration.

Catheter Electronics, Power Source

As described above in connection with bladder management system 100 with reference to FIGS. 1 and 2, the catheter can include electronics, such as electronics 160, and a power source, such as power source 170. The electronics can include a communication module such as communication module 166, which can communicate with a corresponding communication module, such as communication module 196, in electronics, such as electronics 190, in an external controller, such as external controller 180. Exemplary implementations of the electronics (including communications modules) and power sources are described below.

Communication between an external controller and a catheter can be conducted wirelessly. Such wireless communication can be enabled by a communication module that includes a circuit with any suitable permutation of an embedded device, such as a tuning circuit, a power harvesting circuit, a wireless communication integrated circuit, a microprocessor, or a voltage boosting circuit. For example, the communication module can include an antenna and a wireless communication integrated circuit. Any of the subparts can be integrated into one or more integrated circuits.

In one potential configuration, wireless communication between the communication modules of the external controller and the catheter can be implemented using near field communication by transmitting (from the external controller) radio frequency (RF) energy in a specific frequency band, or array of bands. Exemplary bands include, but are not limited to, about: 13.7 MHz 13.56 MHz, 2.3 GHz, 125-134 kHz, 856 MHz, 960 MHz, 856-960 Mhz, 2.4 GHz, 915 MHz, 784 MHz, 218-219 MHz, 220 MHz, 3.5 GHz, 100 KHz-2.45 GHz, or any spectrum of frequency from about 9 KHz to about 3000 GHz. These transmitted RF waves induce harmonic resonance in the RF antenna, which in turn induces a flow of current in the RF antenna, which in turn charges capacitors in the power harvesting circuit to a minimum desired threshold of voltage. The tuning circuit aids the RF antenna to have the proper impedance to facilitate the harmonic resonance between the external communication device and the RF antenna. The induced voltage from the power harvesting circuit can awaken the catheter's communication module so that it can establish a wireless communication link with the external controller's communication module. Upon establishing a confirmed communication link, the wireless communication integrated circuit can transmit a signal to the catheter's controller (embedded microprocessor) via, but not limited to I2C protocols, analog, or any other suitable digital communication protocol. This transmitted signal wakes up, powers, and informs the catheter's controller to interrogate or otherwise communicate with the one or more sensors or other circuits included in the catheter electronics. These downstream interrogations can be sent through the boost circuit to increase the voltage or current of these signals to reach the voltage or current levels required of the sensors or circuits. Upon receiving data back from the downstream sensor or circuits, the catheter controller can transmit the data to the communication module's integrated circuit, which then transmits the data through the RF antenna to the external control's communication module.

In some embodiments, the RF antenna and the power harvesting circuit can directly interrogate downstream sensors or circuits. Based on the status of the catheter's user, the downstream sensors or circuits can attenuate the interrogation signal, causing a disturbance in the resonance frequency link with the external controller's communication module. The software in the external controller's communication module is then able to translate these changes in the resonance link utilizing algorithms based on, but not limited to, artificial intelligence, machine learning, regression analysis, or any other diagnostic based algorithm.

The antenna of the catheter's communication module can, in some embodiments, include one or more turns or coils of a conductive metal such but not limited to copper, gold, or silver, an can be tuned to operate at one or more frequencies, including, for example, from about 30 Hz to about 300 GHz. In some embodiments, the catheter's communication module can have multiple antennas tuned to one or more frequencies to allow for one or more separate communication channels for one or more external controller's communication modules to communicate with. For example, the circuit could include an antenna internally tuned to a specific frequency by the shape, length, and thickness of its coil. In some embodiments, the antenna can be printed directly into a printed circuit board along with other components of the electronics. An example of such an embodiment is shown in FIG. 32. Catheter 2810 includes a catheter body 2820 with a lumen 2821 and which contains electronics 2860. Electronics 2860 includes communication module 2866 implemented on a printed circuit board (PCB) 2866a. RF antenna 2866b in formed on, and RF energy harvesting and communicating integrated circuit 2866c is attached to, PCB 2866a. (Thus, communications module 2866 functions both for communications and for energy harvesting.) Electronics 2860 also includes a sterilizer 2862 (implemented as an LED), and two sensors 2864: a pressure sensor 2864a (implemented as a piezoelectric sensor) an optical sensor 2864b (implemented as an ultraviolet (UV) sensing photodiode that can sense light from sterilizer 2862, which thus also serves as part of the optical sensor), disposed to sense properties of fluid in lumen 2821.

In some embodiments, the antenna is wound around, on top of, or lateral to the catheter's lumen, and in others it can be positioned proximal or distal to the lumen. In some embodiments, the antenna is wound in relation to the catheter body in any combination of, but not limited to, the axial, circumferential, or radial directions.

Figure 33:
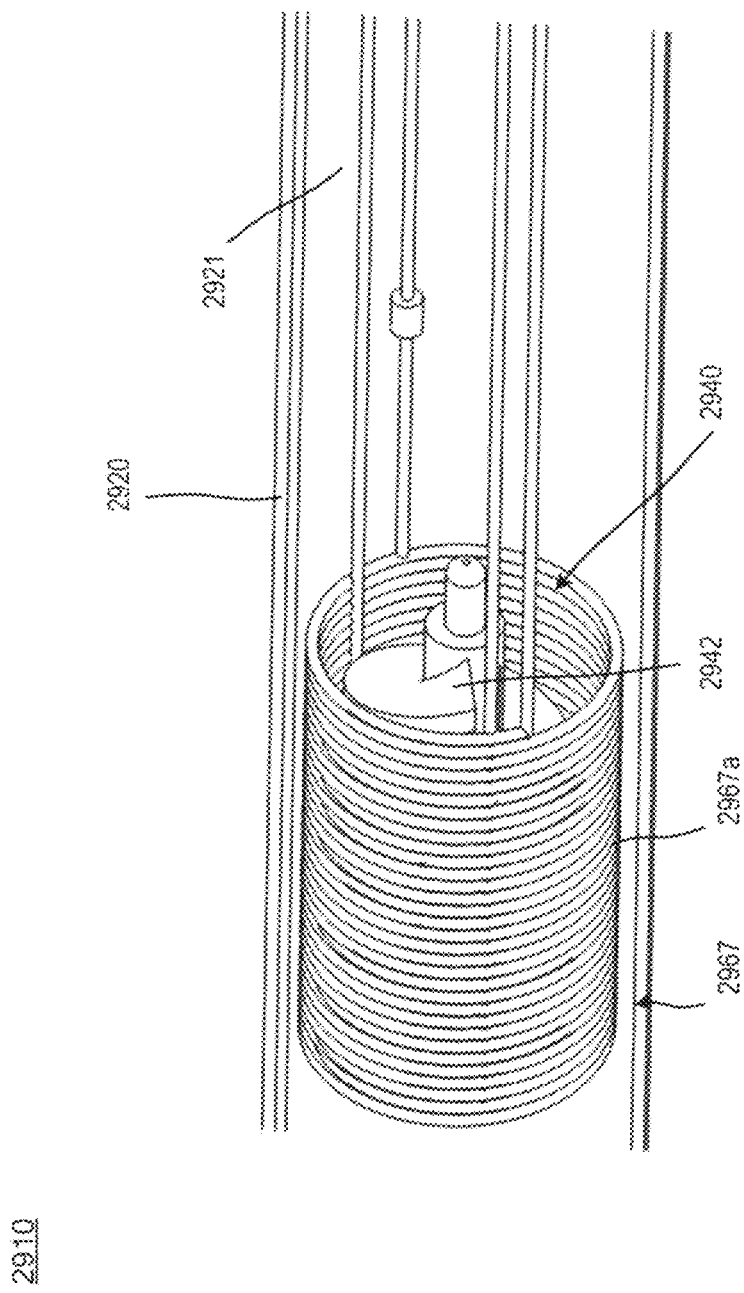
FIG. 33 is a perspective view of an energy harvesting circuit of a catheter, according to an embodiment.

In some embodiments, a power harvesting circuit can be separate from a communication module, and can harvest energy from the spinning of the impeller of the catheter's pump. One such embodiment is shown in FIG. 33. Catheter 2910 has a body 2920 and a lumen 2921, with a pump 2940 having a rotating impeller 2942 disposed to pump fluid through lumen 2921. Power harvesting circuit 2967 includes a coil 2967a disposed around impeller 2942. Rotation of impeller 2942 (driven by an external controller) generates a flow of current in coil 2967a, which can be used to power other components of the catheter's electronics, and/or charge a capacitor that can be used to power the components. In some embodiments, coil 2967a can also act as the RF antenna for the catheter's communication module.

In some embodiments, the power harvesting circuit can harvest energy from the user's body, using thermoelectric energy harvesting in which energy is harvested from the gradient of temperature from the body and the temperature change in the fluid as it travels through the catheter's lumen.

In some embodiments, the catheter's electronics can include a battery that is used to provide power to the sensors and circuits. In some embodiments, the energy harvested from the power harvesting circuit is used to recharge the battery.

Figure 34:
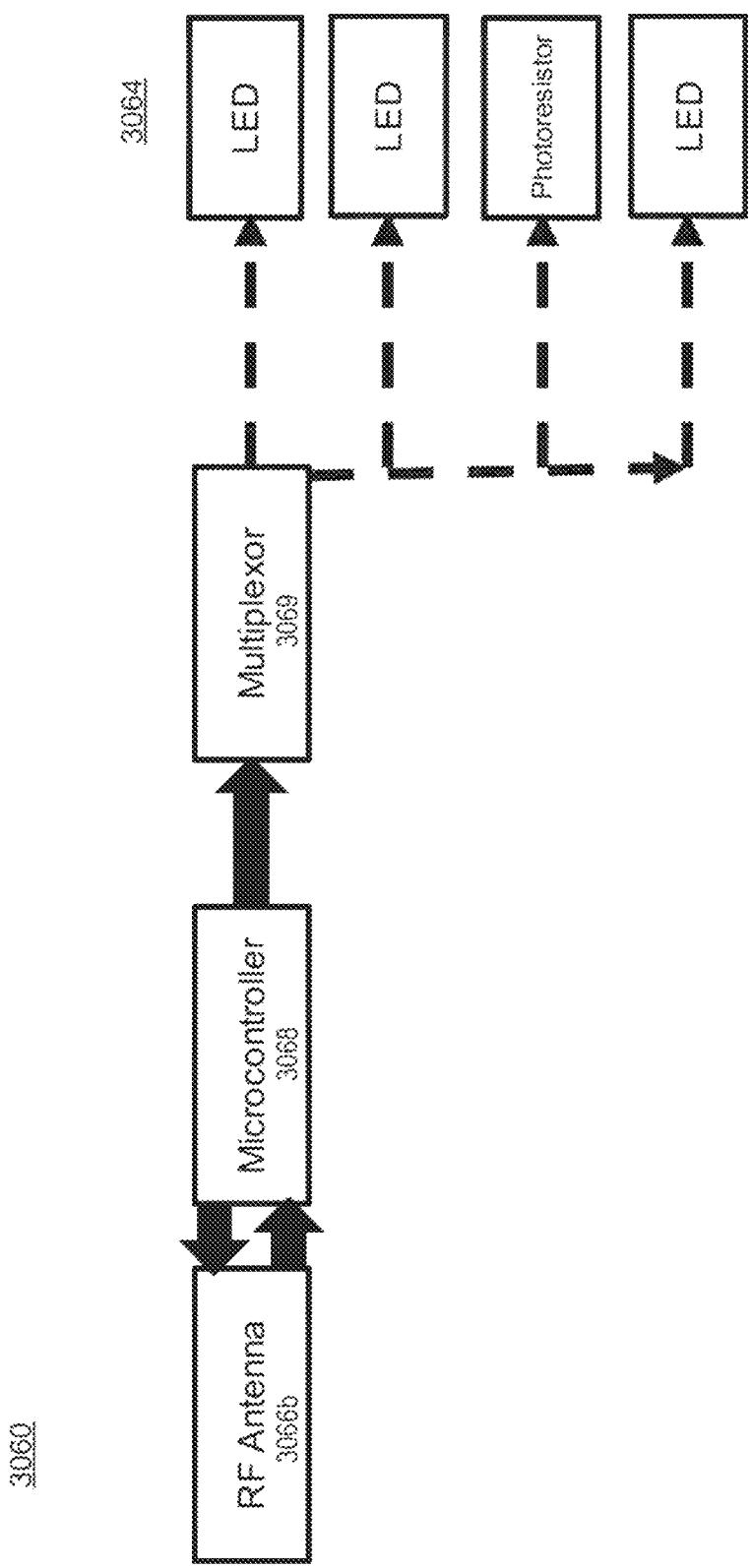
FIG. 34 is a schematic diagram of a catheter electronics that includes a multiplexor, according to an embodiment.

In some embodiments, the catheter's electronics can include a multiplexer circuit so that the catheter's controller can interrogate multiple sensors or other downstream circuits and concatenate their data outputs into a single data stream for communication to the external controller. Such an embodiment is illustrated schematically in FIG. 34. As shown in FIG. 34, electronics 3060 includes an antenna 3066b (e.g., an RF antenna) coupled to controller 3068 (e.g., a microcontroller). A multiplexor 3069 is coupled between controller 3068 and a plurality of sensors 3064, which may include optical sensors, pressure sensor, temperature sensors, etc. (e.g., LEDs and photoresistors). The multiplexor's switching circuit can cycle the I2C communication channel out of the controller 3068 to each sensor 3064 in turn. The controller 3068 can then compile the data from the interrogated sensors 3064 and relay it to the communication module of the external controller (e.g., for access by the user). In some embodiments, the controller can have multiple digital or analog input/output ports to communicate with multiple downstream components simultaneously.

Figure 35B:
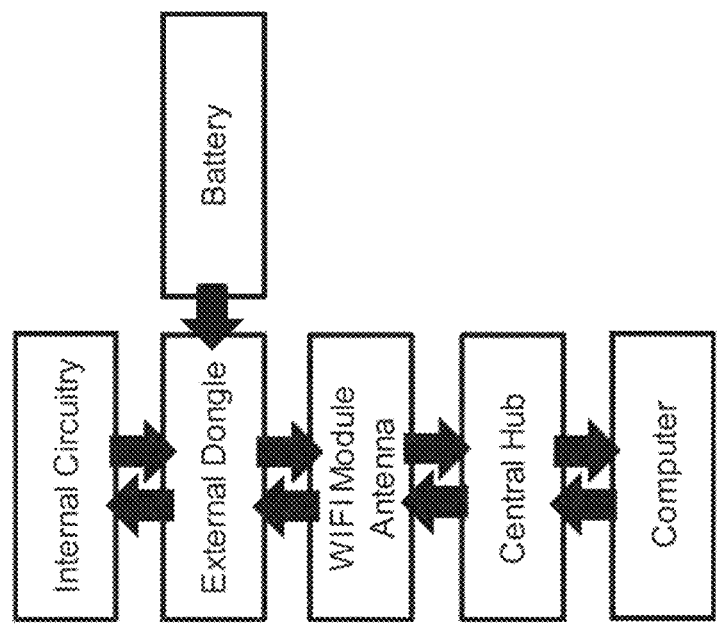
FIG. 35B is a schematic flow and power diagram of FIG. 35A, according to an embodiment.
Figure 35A:
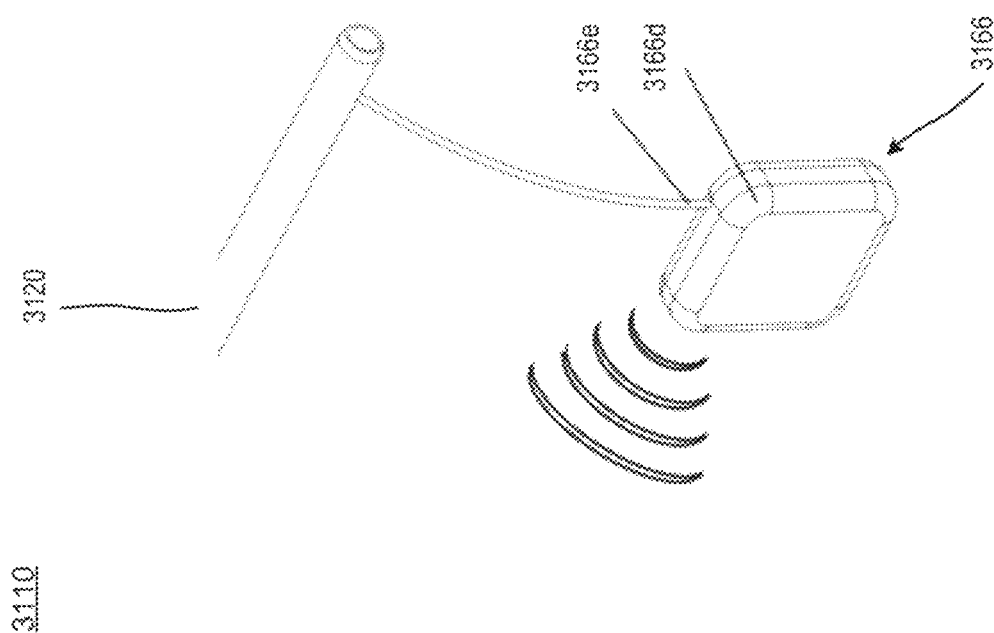
FIG. 35A is a schematic diagram of a catheter electronics housed partially in a wired dongle external to the catheter.

In some embodiments, the catheter's communication module can be external to the catheter, such as by being housed in a "dongle" or other housing that is wired to the other components of electronics in the catheter. One such embodiment is shown in FIG. 35A, and a flow diagram for power and communications is shown in FIG. 35B. As shown in FIG. 35A, catheter 3110 includes a body 3120 housing some of the components of electronics (not shown), such as sensors and other circuits. Communication module 3166 is housed in dongle 3166*d* external to the body of the user and connected to the other catheter electronics by a wire 3166*e*. Dongle 3166*d* can be free, attached to a fluid collection bag, or any other external surface. The communication module 3166 can be powered, for example, by a battery or wall outlet. Communication module 3166 can communicate with other devices, such as a communication module of an external controller, a central hub, or directly to any home or hospital monitoring devices electronic medical record systems, via, for example, any wireless or wired communication protocol, such as, but not limited to, WiFi or ZigBee. In some embodiments, the dongle 3166*d* extends to external of the urethra and has an external dock for interrogating the status of, and powering, communication module 3166 (or other components of the catheter electronics, via wire 3166*e*). FIG. 35B is a schematic flow diagram of the flow of energy or information between the internal circuitry (e.g., communication module 3166), the external circuitry, and a computer system external to the communication module 3166.

Figure 36:
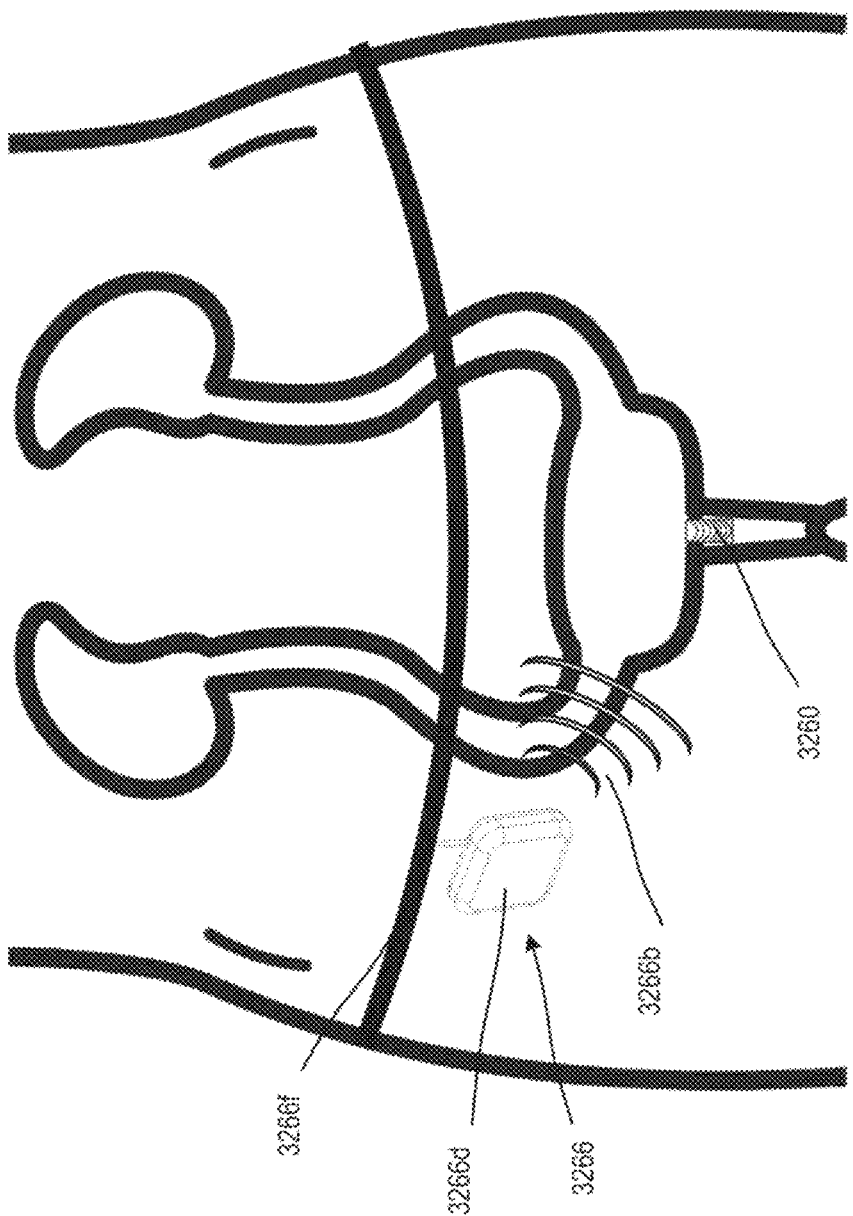
FIG. 36 is a schematic illustration of a catheter electronics housed partially in a dongle that communicates wirelessly with the other components of the catheter electronics, according to an embodiment.

In an alternative embodiment, shown in FIG. 36, communication module 3266 is housed in a dongle 3266*d* that is worn by the user, is powered by an external garment or band 3266*f* worn by the user, and communicates with the other components of electronics 3260 of the catheter by a wireless link 3266*b*.

Sensors

As described for bladder management system 100 with reference to FIGS. 1 and 2, as well as an external bladder management system, catheter electronics can include one or more sensors configured to sense various parameters. Such sensors can include pressure sensors or transducers, which can detect fluid pressure within the catheter lumen, the fluid containing organ (e.g., bladder), or the discharge lumen (e.g., urethra), or within the environment in which the catheter is exposed (e.g., a pressure of the bladder measured external to the catheter). Such pressure sensors can be placed anywhere on the catheter or device or elsewhere in the bladder management system, including but not exclusively in line with the device lumen, catheter lumen, the anchor, on the fluid outlet, or on the fluid inlet. In some embodiments, the pressure sensor can include a flexible membrane with one side in contact with the entrapped fluid and the other side having one or a series of piezoresistive elements in a Wheatstone bridge such that a change in relative or absolute pressure causes a relative or absolute change in the output from the sensor. Such an embodiment is shown in FIGS. 37A and 37B. Pressure sensor 3364 has a flexible membrane 3364*a* disposed in contact with a fluid FL, such as contained in a lumen 3321 (e.g., a catheter lumen, body lumen, etc.), Flexible membrane 3364*a* can be deflected or strained by increased pressure of the fluid in lumen 3321, as shown schematically in FIG. 37B. Piezoresistive elements or a Wheatstone bridge (strain gauge) (not shown) can detect the deflection, and associated circuitry can determine the pressure, and communicate it to the user (such as via catheter communication module and external controller communication module). In some embodiments, the whole pressure over time waveform can be stored and transmitted when the catheter electronics/pressure sensor is interrogated. In some embodiments, the pressure sensor transmits only a singular data point when interrogated, while in other embodiments, the pressure sensor transmits a series of data points. In some embodiments, the pressure sensor includes a capacitance-based pressure sensor, in which deflections of the flexible membrane, due to changes of fluid pressure, alters the distance between two conductive plates thereby altering their capacitance. This change in capacitance is then interrogated by upstream circuitry. In some embodiments, the deflection of the piezoresistive element induces a voltage and/or current that is read by an upstream circuit.

In some embodiments, the pressure sensing is correlated by the deflection of a spring connected to a plate in line with the fluid. One such embodiment is shown in FIGS. 38A and 38B. Sensor 3464 includes a first, movable plate 3464*a* that can be disposed in contact with fluid FL, and a second, fixed plate 3464*b*. A spring 3464*c*, which in some embodiments may be a piezoresistive element, is coupled between the two plates. When the pressure of the fluid FL changes, the movable plate 3364*a* compresses or decompresses (e.g., a change in length Δd) the spring 3364*c* such that it changes the resistance of the spring. This change in resistance is then read out by an embedded upstream circuit and correlated to a change in pressure.

Figure 39:
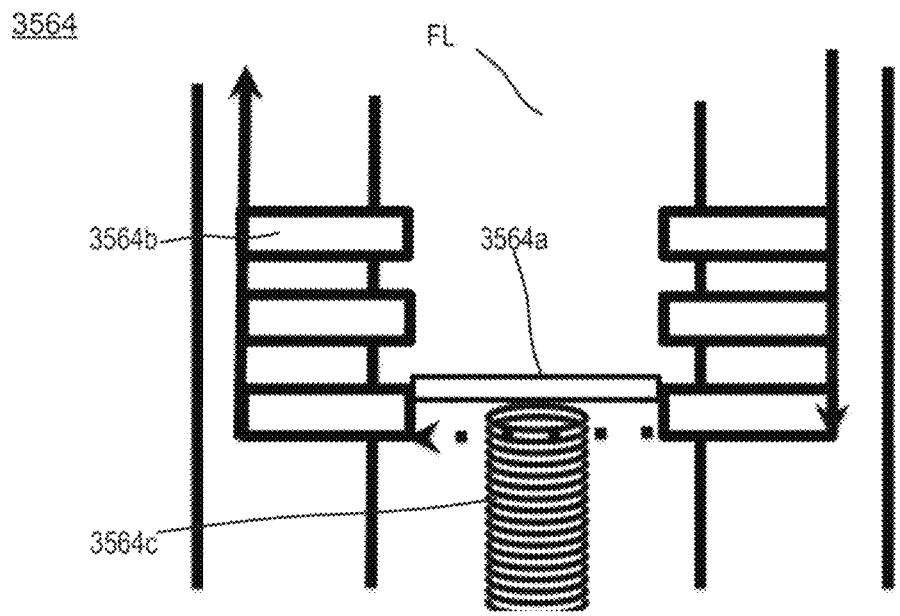
FIG. 39 is a schematic illustration of a conductive pressure sensor according to an embodiment.

Another embodiment of a pressure sensor is shown in FIG. 39. Pressure sensor 3564 includes a conductive plate 3564*a* exposed to a fluid FL and coupled to a spring 3564*c*. As spring 3564*c* compresses, plate 3564*a* bridges one of an array of connections 3564*b* along the length of the sensor 3564. Each connected bridge correlates to a different pressure level in the fluid FL.

Figure 40:
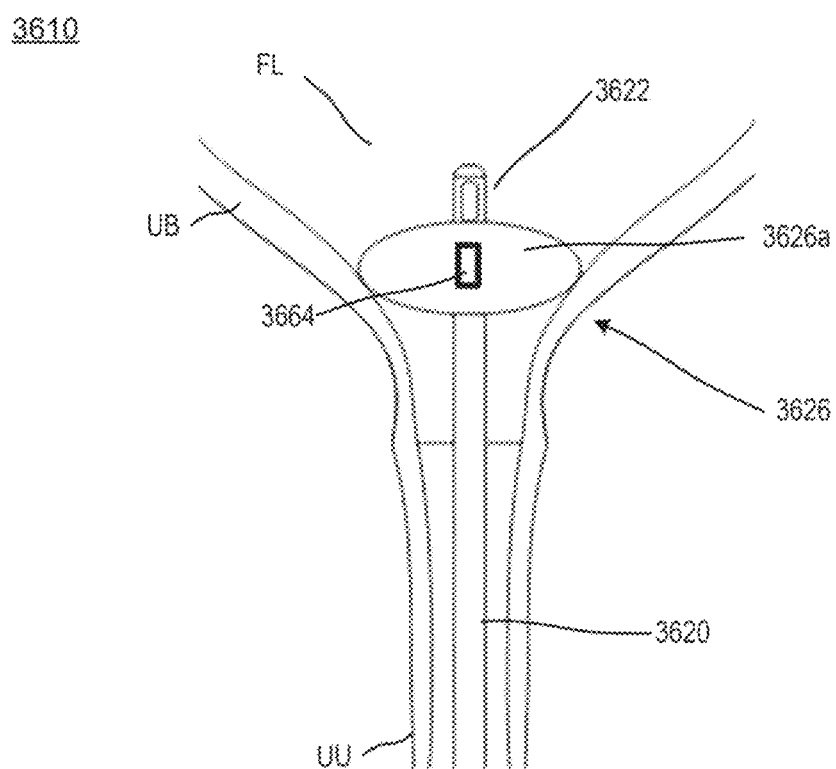
FIG. 40 is a schematic illustration of a pressure sensor disposed in a balloon of an anchor of a catheter, according to an embodiment.

As discussed above, pressure sensors can be disposed in various locations, depending on the fluid pressure to be measured. In one embodiment, shown in FIG. 40, a catheter 3610 has a body 3620, a fluid inlet 3622, and an anchor 3626 that includes a balloon 3626*a*. A pressure sensor 3664 is coupled to balloon 3626*a*. When the catheter 3610 is disposed as shown in FIG. 40 with the balloon 3626*a* disposed in the user bladder UB, the pressure sensor 3664 is configured to measure pressure of fluid FL in the bladder.

Figure 41:
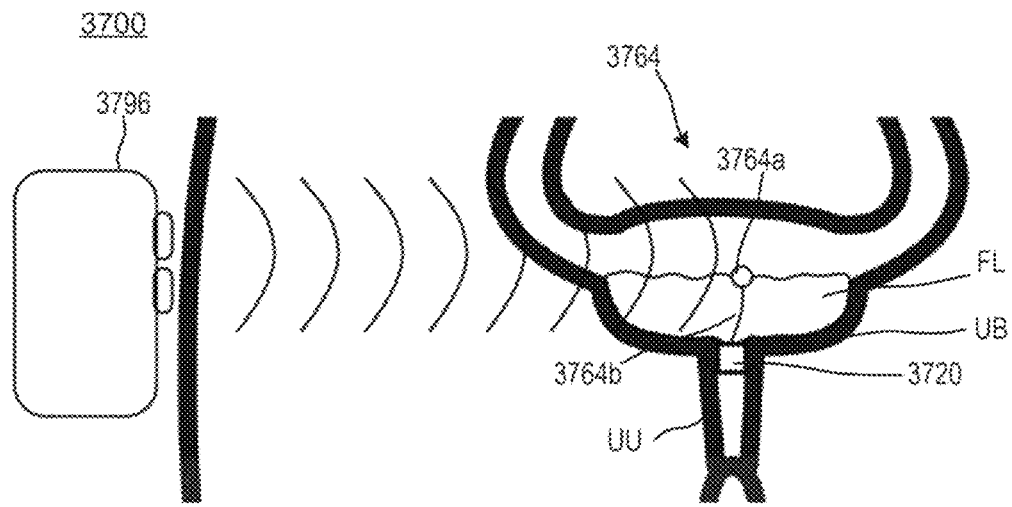
FIG. 41 is a schematic illustration of a fluid volume sensor tethered to a catheter, accordingly to an embodiment.

In some embodiments, a sensor can be configured to measure fluid volume or level, rather than pressure, and can be disposed in the fluid-containing organ, such as a bladder, rather than disposed on the catheter. One example is shown in FIG. 41, in which a bladder management system 3700 includes a sensor 3764 that is configured to measure the level or volume of fluid FL (urine) in user bladder UB, and communicate measurement data to communication module 3796 of an external controller (or other eternal device). In this embodiment, sensor 3764 includes a buoy 3764*a* that can float on the surface of fluid FL. Buoy 3764*a* is coupled to the body 3720 of the catheter (disposed in user urethra UU) by a tether 3764*b*. As the fluid FL builds in the organ, the buoy rises in height, which pulls the tether 3764*b* farther out of the catheter body, which correlates with an increase in the volume of fluid FL. Buoy 3764*a* contains an internal wireless communication circuit such that communication module 3796 can wirelessly interrogate its status in relation to the rest of the catheter.

Figure 42:
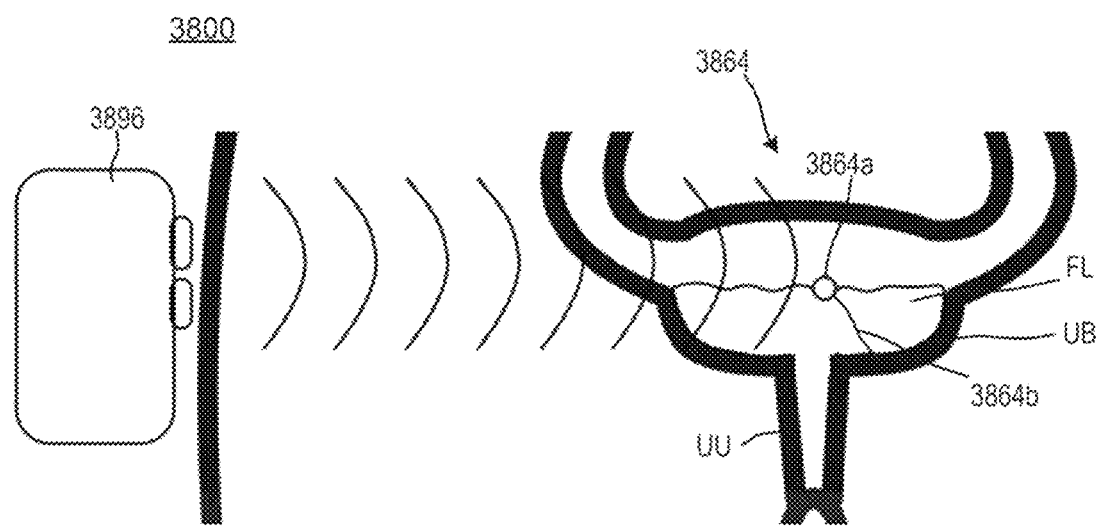
FIG. 42 is a schematic illustration of a fluid volume sensor tethered to a body organ, accordingly to an embodiment.

A similar embodiment is shown in FIG. 42. Bladder management system 3800 is similar to system 3700, except that buoy 3864*a* of sensor 3864 is not tethered to a device (i.e., is not dependent upon a catheter), but instead can be tethered to the wall of the organ of interest (e.g., user bladder UB in FIG. 42) by a tether 3864*b*.

In some embodiments, a sensor can be configured to measure the flow rate and/or flow characteristics and can be disposed in the fluid-containing organ, such as a bladder, or on an external bladder management system, rather than disposed on the catheter. Flow can be detected optically or acoustically, through various means both outside or inside the body. Flow can also be estimated based on the relative volume calculated and the amount of time the sensors recognize fluid passing through the lumen of the device.

In connection with any of the embodiments described herein, the bladder management system can report the absolute or relative volume of fluid in the organ of interest by correlating the measurements with a prior measured volume of the organ.

In some embodiments, the measured change in pressure or volume can trigger a small electric shock in the user in a part of their body which is sensate to notify them of their bladder levels. For example, one or more electrodes can be disposed on the exterior of the body of the catheter and configured so that when the catheter is disposed in the user's body, the electrode(s) can be in contact with the bladder, urethra, and/or other nearby tissue. The catheter's controller can cause power from the catheter's power source to provide bioelectronic neurostimulation to nearby or distant nerve bundles, to provide treatment or symptomatic relief from neuropathic pain, for the regulation of blood pressure by stimulating or inhibiting nerves or nervous system groups like the vagus nerve, the monitoring or regulation of heart rate, respiration, EKG signals, or to monitor for and inhibit autonomic dysreflexia.

External bladder management system and catheter electronics can include optical or light-based sensors that can measure other properties of fluid, material/organisms in the fluid and/or on surfaces of the catheter, etc. Techniques such as light-based spectroscopy measurements can identify various statuses of the user including but not limited to the presence of bacterial build up and colonization, biofilm formation, encrustations, obstructions, an increase in turbidity, or downstream systemic infections. In some embodiments, these spectroscopy measurements can be performed using but not limited to one or more combination of broad-spectrum UV, UVA, UVB, UVC, IR, any other range encompassed between about 10-about 400 nm, the visible light spectrum, and/or infrared sources of illumination. For example, as some species of bacteria grow in a bladder, they begin to release enzymes that greatly increase the concentration of nitrites in the urine. In some embodiments, since these nitrites adsorb UVC light, as their concentration increases, the corresponding sensor tracking the transmission of UVC light to it would measure a drop in UVC transmission correlating with an increase in nitrites and the early presence of the bacteria infection before significant colonization can occur. Additionally, in these embodiments, as the source of light that is used by the sensors to detect early signs of infection is inherently antibacterial, it has the additional effect of preventing or slowing the progression of infection in, on, around the catheter or inside the user's interrogated organ. Since signs of a growing bacterial infection lead to a chance in the transmission spectrum of one or more of the prior mentioned illumination sources (bacterial build up and colonization, biofilm formation, encrustations, obstructions, an increase in turbidity, and downstream systemic infections) this design can be used to track the progression of the infection from its very earliest signs to when it is fully grown and colonized to allow for early intervention.

In some embodiments, these light-based sensors can take the form of photodiodes, photoresistors, ambient light sensors, infrared detectors, phototransistors, photoelectric, or any form of optical sensor. In some embodiments, the bladder system includes one or more type of these sensors. In some embodiments, the bladder system includes one or more of these sensors arranged as singular units or arrays of units. In some embodiments, these sensors can be tuned to one or more single wavelengths of light, one or more spectrum of wavelengths, a combination of wavelengths and spectrum. In some embodiments, one or multiple sensors tuned to different wavelengths are used to monitor for chances in the transmission or adsorption of various light sources while calibrating to a spectrum that is not changing or changing in a predictable manner. In some embodiments, this changing data point is calibrated to a non-light-based data point such as temperature, pressure, or time. In some embodiments, the light sensors are opposite, adjacent, or any permutation of spatially offset of the light sources. In some embodiments, the source of illumination is embedded into the same integrated circuit as the photosensor.

Arrangements for light-based sensors are shown in the following embodiments. Referring back to FIG. 32, a light source 2862, such as a UVC LED, can be disposed on the wall of the lumen 2821 of the catheter 2821. (Light source 2862 can also function as a sterilizer, as described here, but for purposes of this discussion is treated as a part of the light-based sensor.) A light detector 2864b can be disposed on the wall of the lumen opposite light source 2862. Light from light source 2862 passes through fluid (e.g., urine) in the lumen 2810, and can be detected by light detector 2864b. The strength of the light signal received at sensor 2864b is indicative of the attenuation of the light from the light source 2862 by the fluid (or materials/organisms in the fluid). This arrangement of a light source and a light detector for a light-based sensor is shown schematically in FIG. 43A, in which a catheter 3910 includes a body 3920 with a lumen 3921, and a light-based sensor 3964 that includes a light source 3964a on one side of lumen 3921 and a light detector 3964b on the opposite side of the lumen 3921.

Figure 43B:
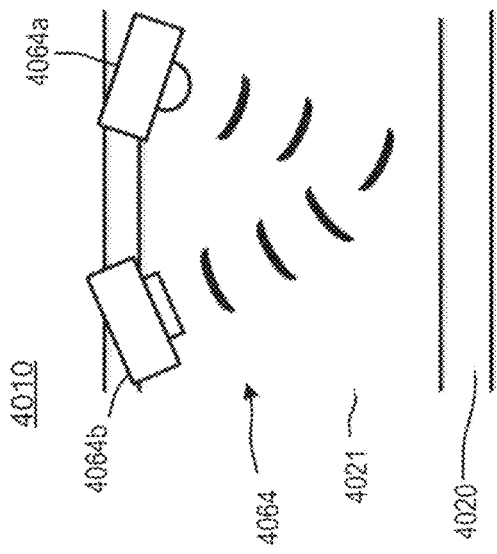
FIGS. 43A to 43C are schematic illustrations of arrangements of the components of light-based sensors, according to embodiments.
Figure 43C:
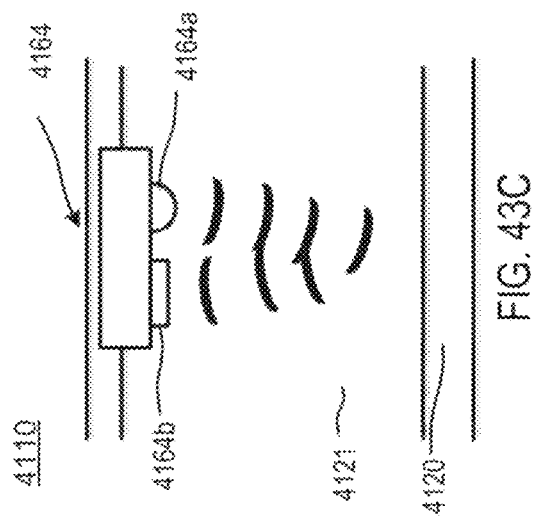
Figure 43A:
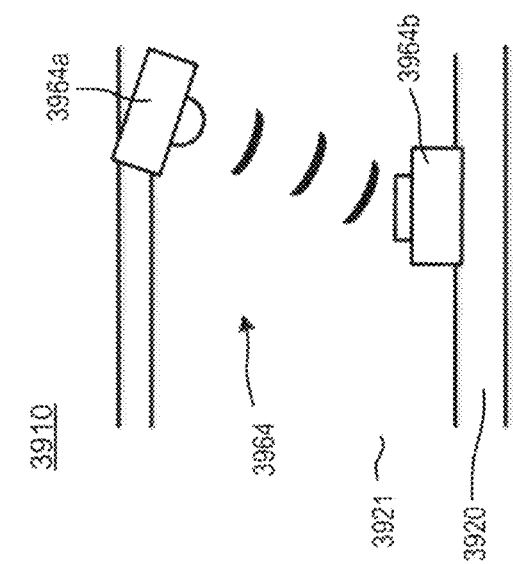
Figure 44A:
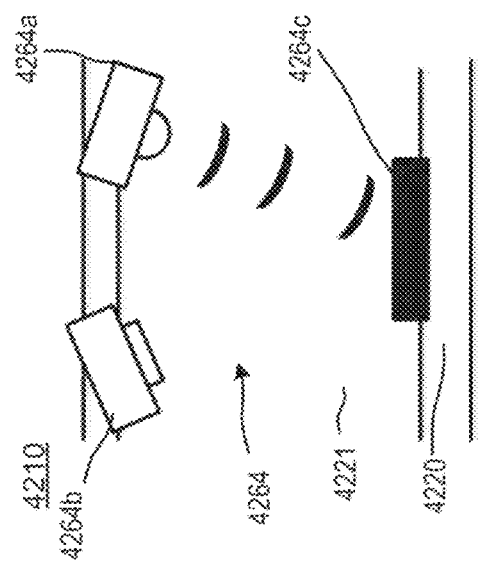
FIGS. 44A and 44B are schematic illustrations of a light-based pH sensor, according to an embodiment.
Figure 44B:
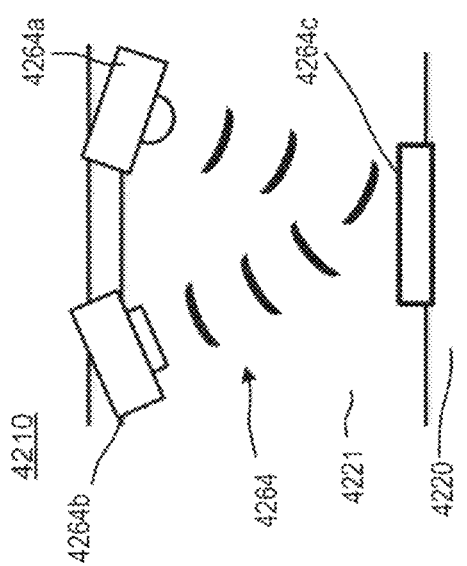

Other arrangements of light sources and detectors are shown in FIGS. 43B and 43C. As shown in FIG. 43B, catheter 4010 includes a light sensor 4064 with the light source 4064a and the light detector 4064b on the same side of lumen 4021. In this arrangement, the light passes through the fluid in lumen 4021 twice, and is also reflected off the wall of lumen 4021. Thus, sensor 4064 detects conditions in the fluid and on the wall of the lumen 4021. Catheter 4110 in FIG. 43C is similar to catheter 4010, except that the light source 4164a and the light detector 4164b are integrated into the same integrated circuit In some embodiments, other types of sensors can be included in the catheter. On such sensor type is a pH sensitive sensor. A pH sensor can be disposed on or in the walls of the catheter lumen such that is in contact with the fluid in the lumen. Such sensors can also be based on light—as the pH of the fluid changes, a light-based sensor is able to detect changes in its adsorption or transmission of any of the interrogating light sources described above. Such pH sensors can be disposed adjacent or opposite to the light source or sensors on the walls of the catheter lumen. One exemplary sensor arrangement is shown schematically in FIGS. 44A and 44B. Catheter 4210 includes a sensor 4264 with a light source 4264a and a light detector 4264b, arranged on the same wall of lumen 4221 of catheter body 4220. A pH sensitive substrate 4264c, disposed on the opposite side of lumen 4221, changes its reflectance, adsorption, or reflectance based on the pH of the fluid with which it is in contact (e.g., urine in lumen 4221). Thus, as shown in FIG. 44A, substrate 4264c may reflect a relatively large amount of the light from light source 4264a to light detector 4264b, or, as shown in FIG. 44B, substrate 4264c may absorb relatively more of the light, reducing the amount that can reach light detector 4264b.

As discussed above, light-based sensors may operate with light at one or more wavelengths, and more than one light-based sensor may be used in a catheter. Thus, the number and/or wavelengths may be selected to enable the catheter's sensors to detect multiple properties or characteristics of the fluid or material/organisms therein, or on the walls of the catheter or surrounding tissue.

In some embodiments, it may be useful to sense properties of fluid external to the catheter, and or of tissue on the wall of the body organ or lumen within which the catheter is disposed. Sensor arrangements for such embodiments can be similar to those described above. For example, as shown in FIG. 45, a catheter 4210 can have a light-based sensor 4264 disposed on an exterior wall of catheter body 4220, oriented towards the wall of the organ (such as user bladder UB) or lumen (such as user urethra UU) in which catheter 4210 is disposed. Light from light source 4264a passes through fluid surrounding catheter 4210, illuminates the tissue on the wall of the organ or lumen, and is received at detector 4264b.

Sterilizer

In some embodiments, the bladder management system can include components for internal sterilization of the catheter (e.g., with UV light) to kill present bacteria, mitigate bacterial build up and colonization, biofilm formation, and downstream systemic infections. Urinary tract infections are caused by bacterial invasion of the urinary tract by bacteria such as *Escherichia coli* (*E. coli*). UVC light of a wavelength of 200-280 nm is known to have germicidal effects which disrupt bacterial DNA and RNA, damaging these bacteria and thereby sterilizing the area. In some embodiments, the sterilizing light sources can be in the UVB (280-315 nm), UVA (315-400 nm), or any other range encompassed between about 10-about 400 nm. Some embodiments can contain one or more spectra of sterilizing radiation. In some embodiments, the sources of sterilizing radiation are directed inward to facilitate killing of bacteria in the internal lumen of the catheter; while in other embodiments, the sterilizing radiation is directed towards the inside of the fluid containing organ from the distal end of the catheter. In some embodiments, the radiation is directed radially away from the lumen of the catheter in order to sterilize the surface of the catheter or the area external to the catheter. In some embodiments, the external surface of the catheter is opaque to the sterilization radiation to prevent the radiation from escaping out of the internal lumen of the catheter. In some embodiments, the catheter is translucent to the radiation such that only the outer surface of the catheter receives enough radiation flux to sterilize while any surrounding tissue remains undamaged. In some embodiments, the catheter is transparent to the sterilizing radiation. In some embodiments, the internal surface, the body, or the external surface of the catheter lumen is reflective or refractive to the sterilizing radiation such that a single source can sterilize a larger area of interest.

Figure 47:
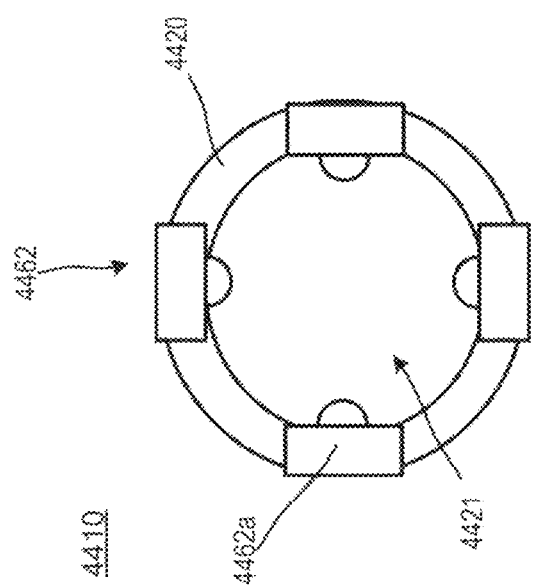
FIG. 47 is a schematic illustration of a sterilizer with an array of sterilizing light sources arranged circumferentially about the catheter lumen, according to an embodiment.
Figure 46:
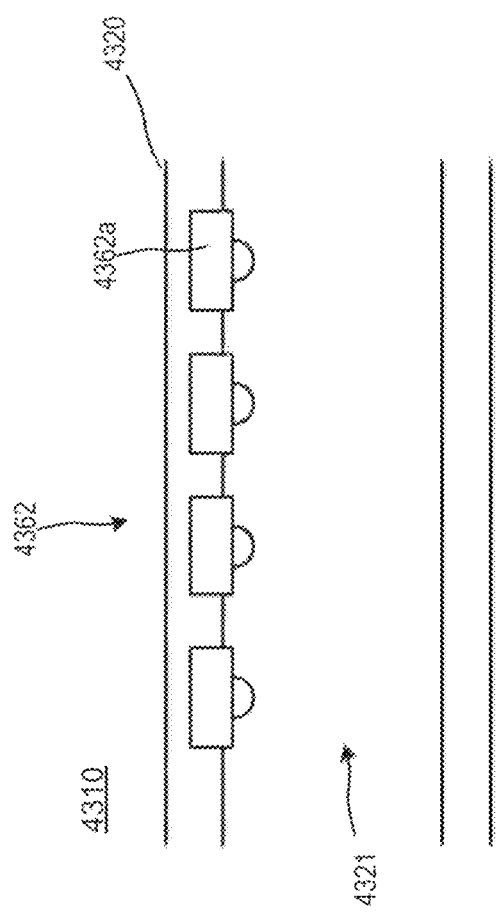
FIG. 46 is a schematic illustration of a sterilizer with an array of sterilizing light sources arranged axially along the catheter lumen, according to an embodiment.

In some embodiments the source of this sterilizing radiation is from light emitting diodes (LED) embedded into the wall of the catheter lumen. In some embodiments, the catheter contains any number of embedded LEDs from 1-100 as singular units, as an array, or a series of arrays. For example, as shown in FIG. 46, a catheter 4310 with body 4320 has a sterilizer 4362 disposed on a wall of lumen 4321. Sterilizer 4362 includes an array of sterilizing light sources 4362a (e.g., UV LEDs) disposed longitudinally along lumen 4321. In another embodiment, shown in FIG. 47, a catheter 4410 with body 4420 includes a sterilizer 4462 with an array of sterilizing light sources 4462a arranged circumferentially around lumen 4421.

Figure 48A:
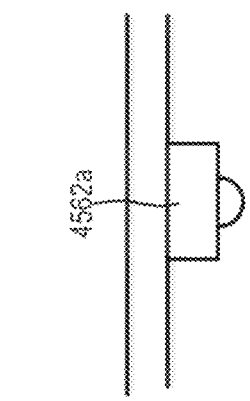
FIGS. 48A to 48E are schematic illustrations of different axial and circumferential orientations of a sterilizing light source, according to embodiments.
Figure 48B:
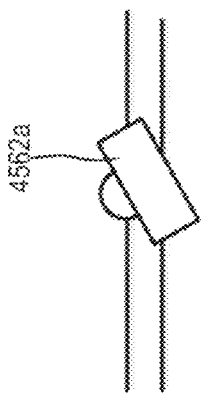
Figure 48C:
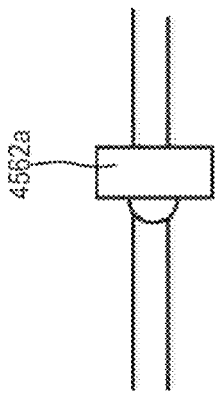
Figure 48D:
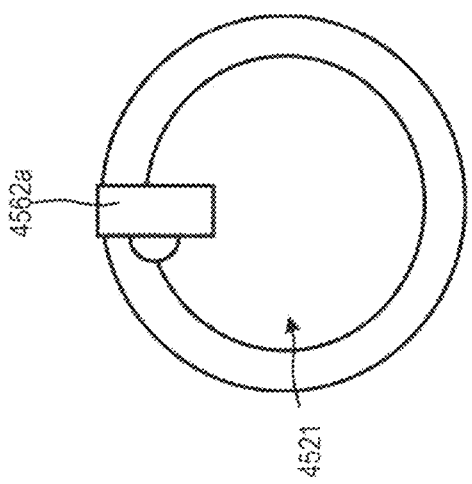
Figure 48E:
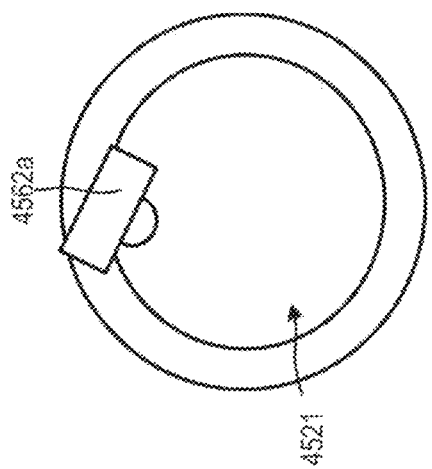

In some embodiments, the sterilizer's LEDs can be directed towards any direction in relation to the central axis of the lumen including but not limited to perpendicular towards, −180 to 180 degrees angled away from perpendicular, or parallel. In some embodiments, the LEDs can be orientated circumferentially, angled off circumferential, or any permutation of circumferential, radial, and axial offset. For example, as shown in FIGS. 48A to 48C, a sterilizer's sterilizing light source 4562a can be arranged to be directed toward the central axis of lumen 4521 (FIG. 48A), away from the central axis (FIG. 48B), or parallel to the central axis (FIG. 48C). The sterilizing light source 4562a can also be arranged to be directed circumferentially (FIG. 48D) to the lumen 4521 or angled off of circumferential (FIG. 48E) to the lumen 4521.

Different optical mechanisms can also be used by the sterilizer, as illustrated schematically in FIGS. 49A to 49C. As shown in FIG. 49A, sterilizing light source 4662a can be directed towards the lumen 4621, the wall of which is able to reflect the radiation, thereby sterilizing a large surface area of the lumen 4621. As shown in FIG. 49B, the wall of lumen 4621 can refract the radiation from sterilizing light source 4662a such that the lumen wall attenuates the radiation such that only up to the external surface of the catheter receives sufficient radiation to sterilize. As shown in FIG. 49C, the wall of lumen 4621 can refracts the radiation from a sterilizing light source 4662a down the lumen wall, increasing the area in which the light sterilizes.

In some embodiments, the embedded sources of sterilizing radiation are coupled to fiber optic cables to transmit the sterilizing radiation down the length of the catheter and radially around the fibers. Various embodiments can contain one or more embedded fibers coupled to one or more sources of embedded radiation emission.

Catheter Body

As discussed above in connection with the embodiment of FIG. 1, a catheter body (e.g., body 120) can include one or more lumens (e.g., lumen 121) for carrying fluid out of the body. In some embodiments, the catheter can also have one or more lumens or cavities for holding electronic components (e.g., components of electronics 160). One example embodiment is shown in FIGS. 50A, 50B. Catheter 4710 includes a body 4720 with a lumen 4721 for the transport of fluid. Body 4720 also has a separate lumen or cavity 4723 in which electronics 4760 can be disposed. Alternatively, electronics 4760 (or any other components of catheter 4710) can be completely embedded into the wall of the catheter. In some embodiments, the catheter body can include other lumens that are separate from the fluid transport lumen. For example, as shown in FIG. 51, catheter 4810 has a catheter body 4820 that includes a lumen 4821 for transport of fluid, and includes two other, smaller lumens 4823. These lumens can be used for a variety of purposes, such as carrying fluid for inflation/deflation of balloon anchors (described above), control wires or rods for manipulation of devices at the distal end of the catheter, and/or conductive wires to carry power or data.

In some embodiments, the catheter body can include a cavity or chamber to house components that can be disposed axially relative to the fluid transport lumen, rather than parallel to it. An example of such an arrangement is shown in FIG. 52. Catheter 4910 has a body 4920 that includes a lumen 4921 to transport fluid. A valve 4930 and pump 4940 are disposed in lumen 4921 (these components are similar to valve 1130 and pump 1140 illustrated in FIGS. 15A and 15B). In this embodiment, fluid outlet 4924 is implemented as a pair of lateral openings, rather than an axial opening as with other embodiments described above. Body 4920 further includes a closed chamber 4923 disposed proximally to fluid outlet 4924. Disposed in chamber 4923 are some components of electronics 4960 and an optional power supply 4970 (e.g., battery or capacitor). Other components of electronics 4960, such as antenna 4966b can be disposed on or in other portions of catheter body 4920 and connected to the components in cavity 4923 by conductive (wires or printed traces) or wireless connections. Cather body 4920 also includes at its proximal end a ring-shaped interface 4925 for engagement with a delivery and/or retrieval device, as described in more detail below. In an alternative embodiment, a fluid transport lumen can extend through or around chamber 4923, so that fluid outlet 4924 can be at the proximal end of the catheter body 4920, rather than on the sides as shown in FIG. 52.

In another embodiment, the catheter can include an alternative mechanism for driving pump 4940 and actuating valve 4930. Catheter 5010 shown in FIG. 53 is similar to catheter 4910 (e.g., includes a closed chamber 5023 similar to chamber 4023), but includes a motor 5050 which is coupled by an axle or drive shaft assembly 5058 to pump 5040 and, optionally, to valve 5030 (e.g., through separate, concentric shafts). Motor 5050 can be powered by an internal power source (battery, capacitor) and/or via remote power transmission from, for example, an external controller via antenna 5066b.

In some embodiments, the catheter can be anywhere from about 1 inch to about 1 meter in length, and the catheter can be anywhere from about 2 mm to about 30 mm in diameter. In some embodiments, the catheter composed of a combination of polymer, metal, or braided or coiled reinforcement using metal, polymer, or their combination to allow for pushability during insertion while maintaining sufficient flexibility to snake its way into position. In some embodiments, the catheter contains one or more radiopaque markers to aid in its proper delivery to the organ of interest located on, for example, the anchor, next to or adjacent the fluid inlet or the fluid outlet, on components of the electronics (e.g. PCB, antenna), and/or on the pump. In this manner, an operator can visualize the radiopaque markers from outside the patient during insertion.

Additionally, the catheter is in some embodiments composed of PET, PEBA, polyether ether ketone (PEEK), PTFE, silicone, polystyrene (PS), PU, latex, or a copolymer thereof. In some embodiments, the catheter lumen or lumens may feature a PTFE liner to facilitate lubricious translation and/or rotation with respect to other components. In some embodiments, one or more polyether block amide (PEBA) jackets are incorporated to reinforce the lumen, having a high durometer from 10 D to 90 D (Shore value) to maximize catheter pushability and flexibility, and reflowed to impart a circular cross-sectional profile to the catheter. In some embodiments, alternative lumens would house conductive wires, rigid printed circuit boards, or flexible printed circuit boards to serve as path for current transmission for the various electrical components in the body of the catheter. This conductive wire can be formed of a copper-based wire (e.g., copper, copper clad steel) and may feature a coating of insulation (e.g., PI, polyamide-imide). The gauge of the conductive wire is between 40 AWG and 15 AWG. In some embodiments, the polymers of the catheter may include radiopaque additives like barium sulfate in order to aid in fluoroscopic visualization.

In some embodiments, the bladder system is inserted and advanced over a guidewire placed through the urethral opening using standard cystoscopy methods and delivered to the organ of interest. In some embodiments, this guidewire can be used to keep an anchoring method from being deployed until the bladder system is in the proper position after which, upon releasing the guide wire and its removal, the anchor is released thus allowing for secured placement of the bladder system in the organ of interest.

Example Catheters

As discussed above, a catheter of a bladder management system can employ any combination of the various embodiments of the components described above. Several examples of catheters are illustrated and described below.

Figure 54B:
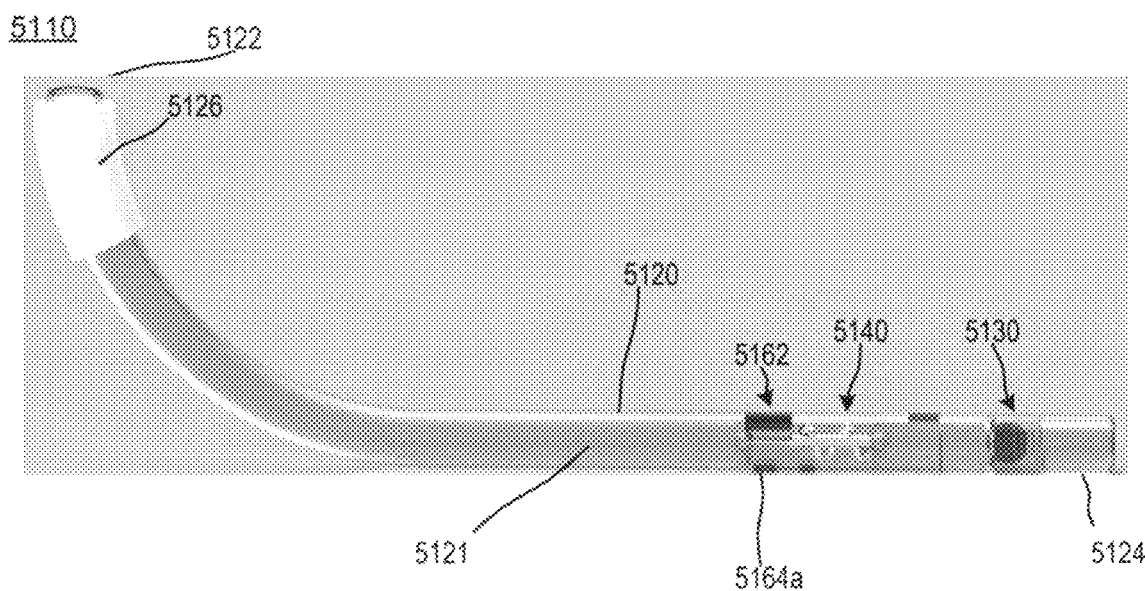
Figure 54C:
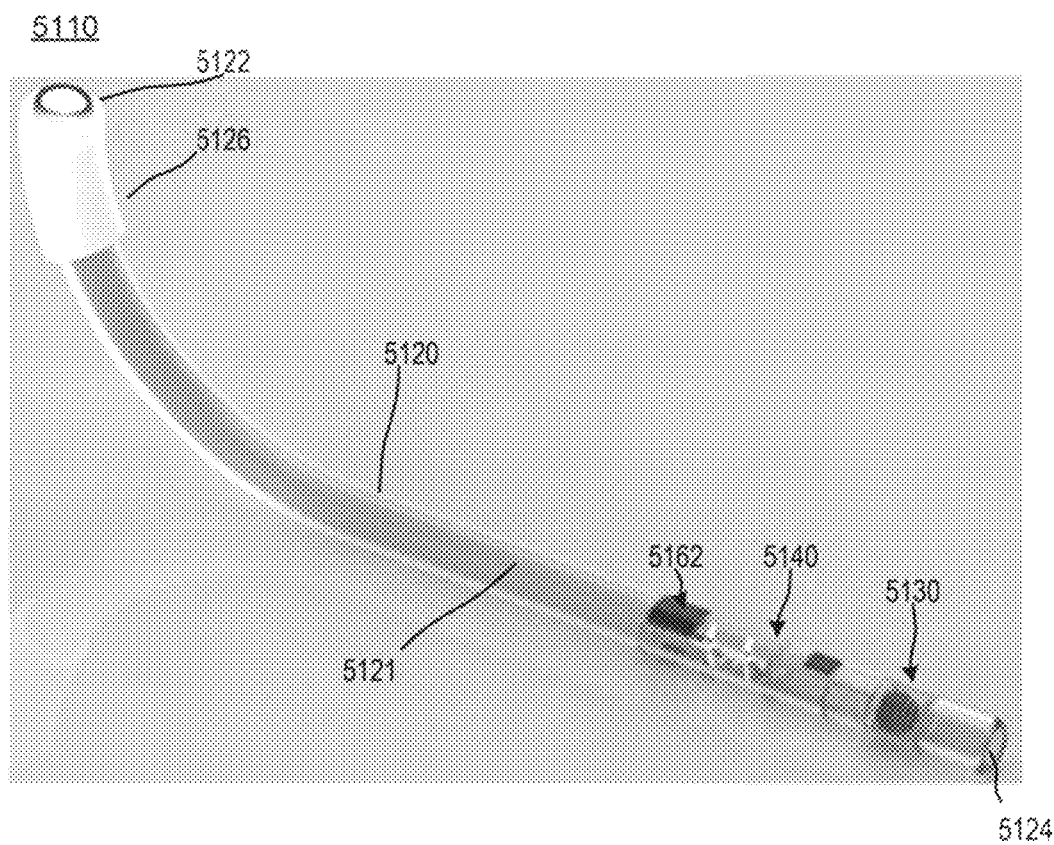

As shown in FIGS. 54A to 54C, catheter 5110 includes a body 5120 with a lumen 5121, fluid inlet 5122, and fluid outlet 5124. A valve 5130 is disposed in lumen 5121, and is implemented as a ball check valve, similar to the embodiment shown in FIG. 9. Valve 5130 is disposed proximally (downstream) to a pump 5140, which is similar to the pump shown in FIG. 6. Sensors include a light-based sensor with a light detector 5164a disposed on one wall of lumen 5121 and a pressure sensor 5164b disposed on the wall of lumen 5121. A sterilizer 5162 (which can also function as a light source for light detector 5164a) is disposed on an opposite wall of lumen 5121. An anchor 5126 is disposed at the distal end of body 5120—this embodiment uses a foam-based anchor such as that shown in FIGS. 28A and 28B, and is shown in its deployed configuration in FIG. 54A and in its delivery configuration in FIGS. 54B and 54C.

Figure 55:
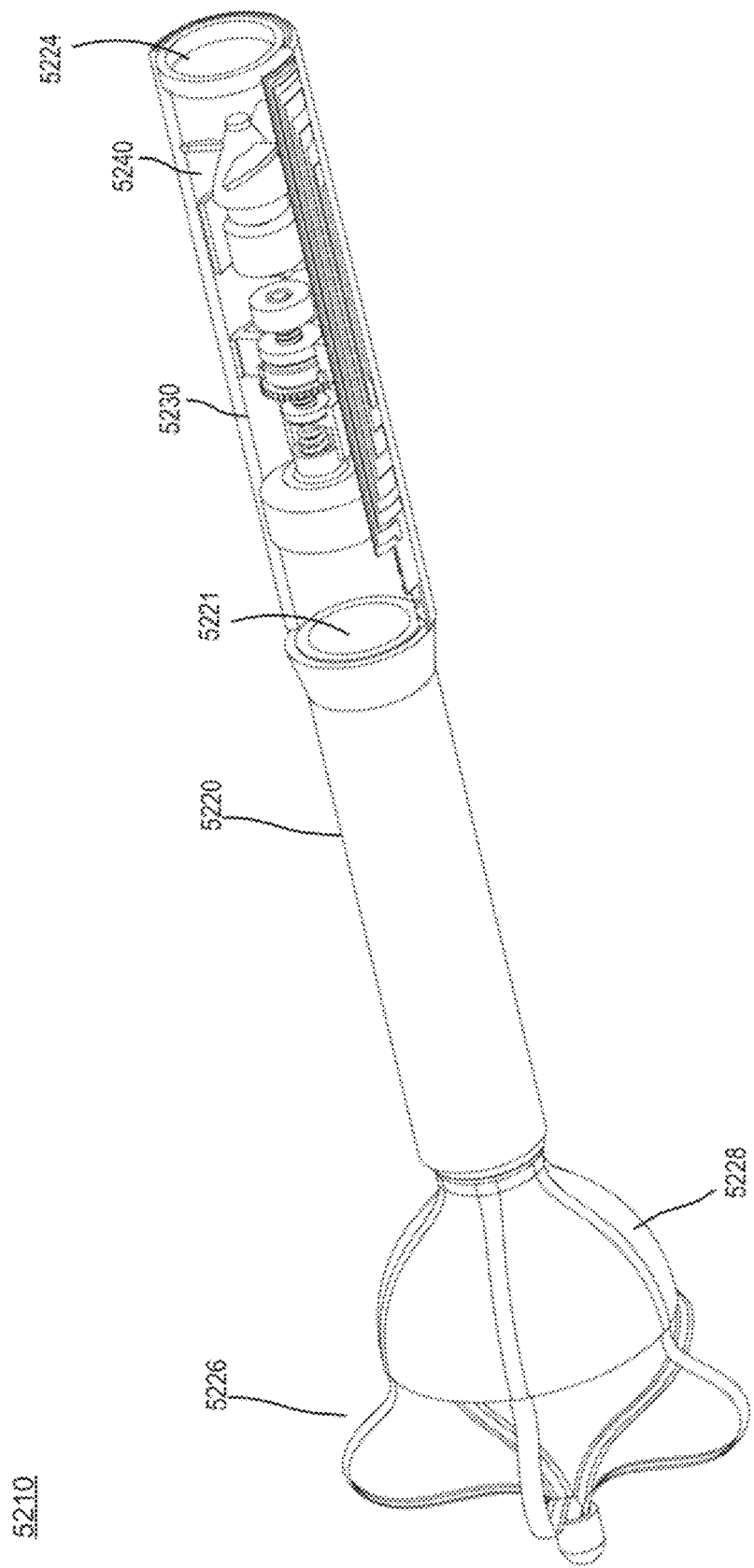
FIG. 55 is a side perspective view of a catheter, according to an embodiment.

As shown in FIG. 55, catheter 5210 a body 5220 with a lumen 5221, fluid inlet 5222, and fluid outlet 5224. A valve 5230 is disposed in lumen 5221. Valve 5230 is disposed distally (upstream) to a pump 5240. Valve 5230 and pump 5240 are the same as those described above with reference to FIGS. 15A and 15B. An anchor 5226 is disposed at the distal end of body 5220—this embodiment is similar to that shown in FIGS. 24A and 24B, includes a seal 5228, and is shown in its deployed configuration in FIG. 55.

External Controller

As described for bladder management system 100 with reference to FIGS. 1 and 3, a bladder system may include an external controller that can enable a user to control urination and for the user, other persons, or the bladder system automatically, to sterilize the catheter, and interrogate and monitor for, including but not limited to, the presence of bacterial build up and colonization, biofilm formation, encrustations, obstructions, an increase in turbidity, and downstream systemic infections.

In order for the user to urinate at their convenience, in some embodiments the external controller may include a user interface that allows the user to activate the catheter's pump on demand. As discussed above, in some implementations, the pump activation can override the pressure fail-safe check valve to actively drain the bladder of urine. In some embodiments, the external controller contains a magnetically polarized component that rotates, spins, or otherwise flips the magnetic poles to spin the diametrically magnetized core or bearing of the catheter's pump, thereby releasing urine.

In some embodiments, the external controller can include a movable magnet which can magnetically couples with a magnet of the catheter's valve to allow the fluid filled organ to drain through the valve.

In some embodiments, the external controller wirelessly interacts with the internally implanted circuit by transmitting RF energy in a specific frequency such as but not limited to 13.7 MHz to power UVC radiation to sterilize in, around, or up and down the length of the catheter, as described in more detail above.

In some embodiments, the external controller can also interrogate the catheter's sensor or sensors to measure properties of the fluid in or around, or surfaces of, the catheter body or catheter lumen. For example, as nitrite concentration increases with some bacterial growth and decreases UVC transmission, interrogation of the sensors would communicate the formation of bacterial growth, which causes urinary tract infections. Communicating this to the user allows for early treatment of urinary tract infections, or their prevention entirely.

In some embodiments, the external controller can utilize near infrared spectroscopy to interrogate the fluid filled organ to determine the pressure or volume of liquid in the organ.

An embodiment of a bladder management system with a catheter and an external controller is illustrated in FIGS. 56A to 56C, and 57. Bladder system 5300 includes catheter 5310 and external controller 5380. The catheter 5310 (which is similar to catheter 5210 shown in FIG. 55) includes valve 5330 and pump 5340 disposed in lumen 5321. In this embodiment, valve 5330 is similar to valve 1130 described with reference to FIGS. 15A and 15B, i.e., it can be externally actuated by magnetic interaction with the external controller 5380. In particular, valve 5330 includes a magnetic drive member 5335*b* that is coupled to one end of threaded rod 5335*a*, which cooperates with an internally threaded valve bearing 5335*c*. Occluder 5332 is coupled to the end of threaded rod 5335*a*. Rotation of magnetic drive member 5335*b*, and thus threaded rod 5335*a*, causes the occluder 5332 to translate axially—rotation in one direction causes distal translation, and thus can bring occluder 5332 into sealing apposition with valve seat 5336 (closing valve 5330), while rotation in the other direction causes proximal translation of threaded rod 5335*a* and occluder 5332, spacing occluder 5332 from valve seat 5336 (opening valve 5330). Rotation of threaded rod 5335*a* can be caused by interaction of an external, rotating magnetic field (e.g., produced by the magnetic drive member of the external controller 5380, as described below) with magnetic drive member 5335*b*. Thus, valve 5330 can be actively actuated (opened or closed).

Pump 5340 is similar to pump 1140 described with references to FIGS. 15A and 15B, and to pump 240 described with reference to FIG. 6, in that it can also be externally driven by magnetic interaction with the external controller 5380. Pump 5340 includes an impeller 5342 supported for rotation in pump bearing 5344, and coupled to magnetic pump drive member 5345. Rotation of impeller 5342 can be caused by interaction of an external, rotating magnetic field (e.g., produced by the magnetic drive member of the external controller 5380, as described below) with magnetic pump drive member 5345. Thus, pump 5340 can be driven by external controller 5380.

Figure 56B:
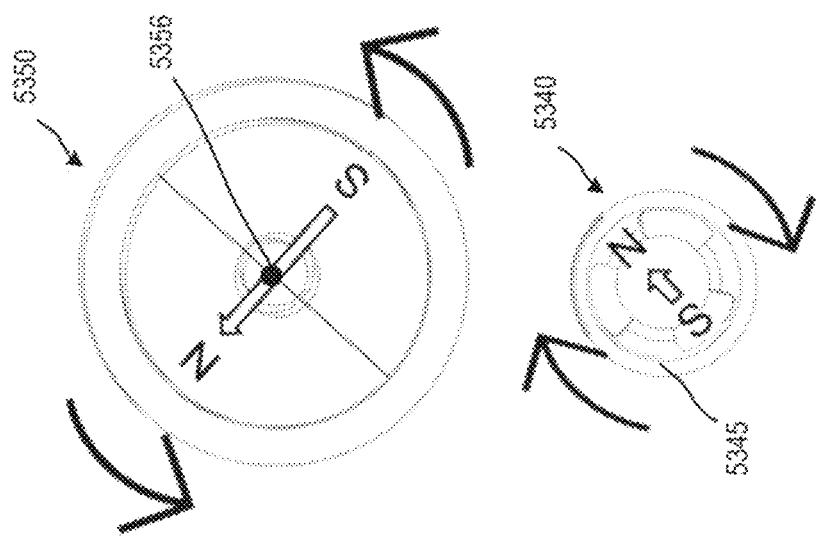
FIG. 56B is a schematic cross section view through the magnetic components of the catheter and external controller, according to an embodiment.
Figure 56A:
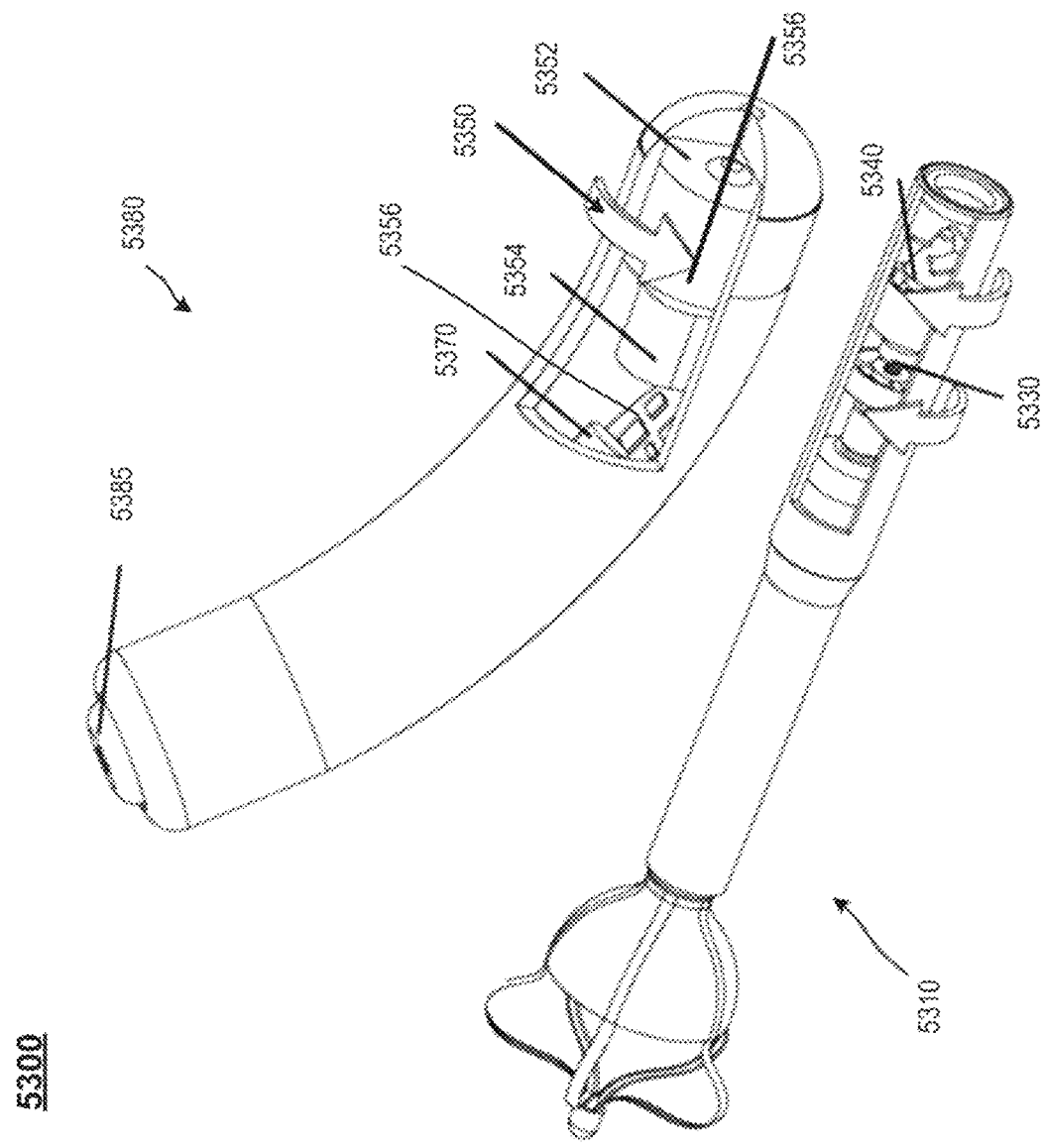
FIG. 56A is a perspective, partial cutaway view of a bladder system with a catheter and an external controller.
Figure 56C:
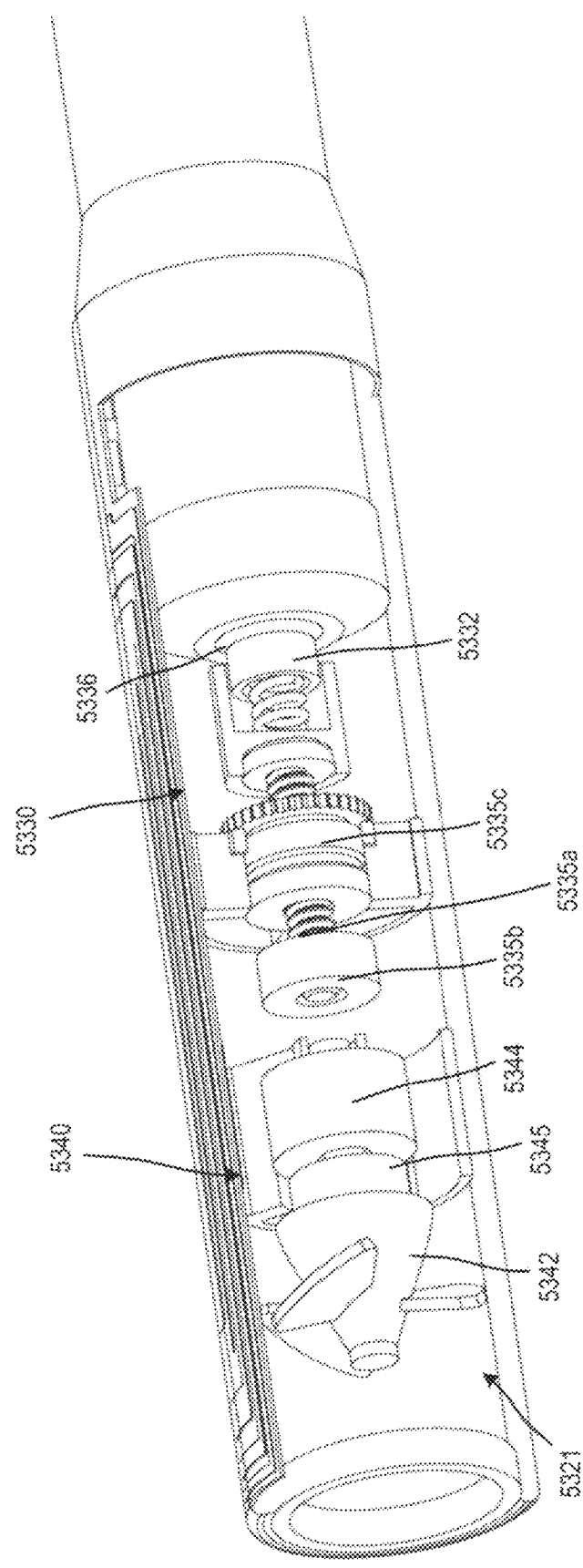
FIG. 56C is a perspective, partial cutaway view of the proximal portion of the catheter.
Figure 57:
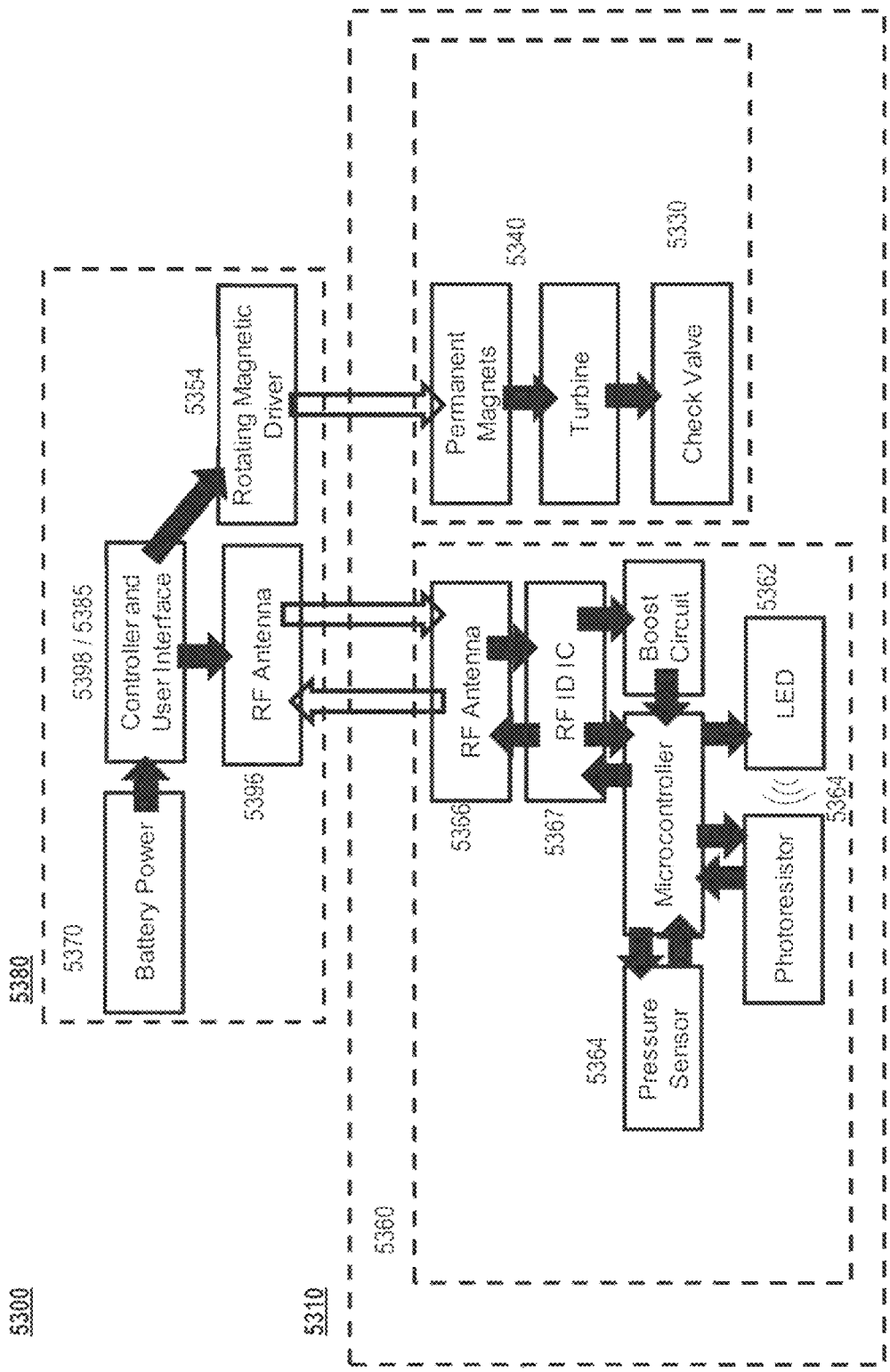
FIG. 57 is a schematic block diagram of the bladder system of FIGS. 56A to 56C.

External controller 5380 includes motor 5350, operable to actuate valve 5330 and/or drive pump 5340. Motor 5350 includes a magnetic component 5352 and a driver 5354. Magnetic component 5352 is mounted within external controller for rotation about a rotational axis 5356, and is to be rotationally driven by driver 5354. As shown in FIG. 56B (which is a cross-section through magnetic component 5352 of motor 5350 and a corresponding component of magnetic pump drive component 5345 of pump 5340), magnetic component 5352 has a diametric magnet (which may be implemented with a permanent magnet or electromagnet), with a north-south pole axis approximately orthogonal to rotational axis 5356. Correspondingly, magnetic pump drive component 5345 of pump 5340 has a diametric magnet, with a north-south pole axis approximately orthogonal to the rotational axis of pump 5340. The magnetic fields of magnetic components 5352 and 5345 can interact when they are brought sufficiently close together. Rotation of magnetic component 5352 can thus produce a corresponding, but opposite direction, rotation of magnetic pump drive component 5345, and thus the impeller 5342 of pump 5340, as indicated by the arrows in FIG. 56B. External controller 5380 can similarly actuate valve 5330 through interaction with magnetic drive component 5335*b*.

The rotation can be continuous, for example to continuously drive pump 5340 until a sufficient amount of fluid is drained from the organ (e.g., the user's bladder has been drained). In some embodiments, the rotation can be through a finite angle, for example to flip the orientation of the magnetic poles. This may be desirable, for example, in embodiments in which the valve can be magnetically actuated, such that driving the valve's magnetic poles through a single reversal of direction can transition the valve from a closed configuration to an open configuration to allow fluid to pass therethrough. When the user has determined that enough fluid has drained, the user can initiate another reversal of the magnetic poles of the valve and cause the valve to transition from the open configuration to the closed configuration.

The strengths of the magnets are preferably selected so that their magnetic fields interact sufficiently for motor 5350 to drive pump 5340 (and/or actuate valve 5330) when catheter 5310 is disposed in the body of a user, with pump 5340 and valve 5330 located in the user's urethra, and external controller 5380 is placed on or near the surface of the user's body, near the location of pump 5340 and valve 5330. External controller 5380 includes a power source 5370, which in this embodiment is a battery. Power source 5370 provides power for driver 5354, and for electronics 5390. External controller 5380 also includes a user interface 5385, which in this embodiment is simply a button or switch disposed on the end of the external controller 5380 opposite to motor 5350. A user can actuate the button while holding external controller 5380 close to their body near catheter 5310, to activate the driver 5354, and thus to activate the pump 5340. The activation of pump 5340 can be configured to transition valve 5330 from a closed configuration to an open configuration, such that fluid (e.g., urine) can pass through valve 5330 (e.g., to drain the user's bladder of urine).

External controller 5380 can have the same functionality, and interact with catheter 5310 in the same ways, as the external controller 180, described above with respect to FIGS. 1 to 3. The following description highlights some of the potential functionality and interactions, with additional reference to the schematic illustration of system 5300 in FIG. 57 to illustrate the flow of energy and data between the components of bladder system 5300, but without reference to specific structures or components in FIGS. 56A and 56B. For example, external controller 5380 can be communicatively coupled with catheter 5310 via a communication module 5396 (including an RF antenna) in the external controller 5380 and a communication module 5366 (also including an RF antenna) within the catheter 5310 for two-way information exchange. The communication module 5396 can wirelessly interact with communication module 5366 and/or energy harvester 5367 by transmitting radio frequency (RF) energy in a desired frequency or frequencies. For example, the communication module 5396 can transmit RF energy that can be used to power components of the catheter 5310, such as a sterilizer 5362 (e.g., to power UVC radiation to sterilize in, around, or up and down the length of the catheter 5310). The external controller 5380 can receive data/signals from sensors 5364 within the catheter, such as an optical sensor to measure changes in light transmission. For example, the external controller 5380 can receive data from sensors 5364 indicating a decreased transmission of UVC light due to increased nitrite concentration, which can communicate to the user formation of bacterial growth that can causes urinary tract infections. Communicating this to the user allows for early treatment of urinary tract infections, or their prevention entirely.

Figure 58:
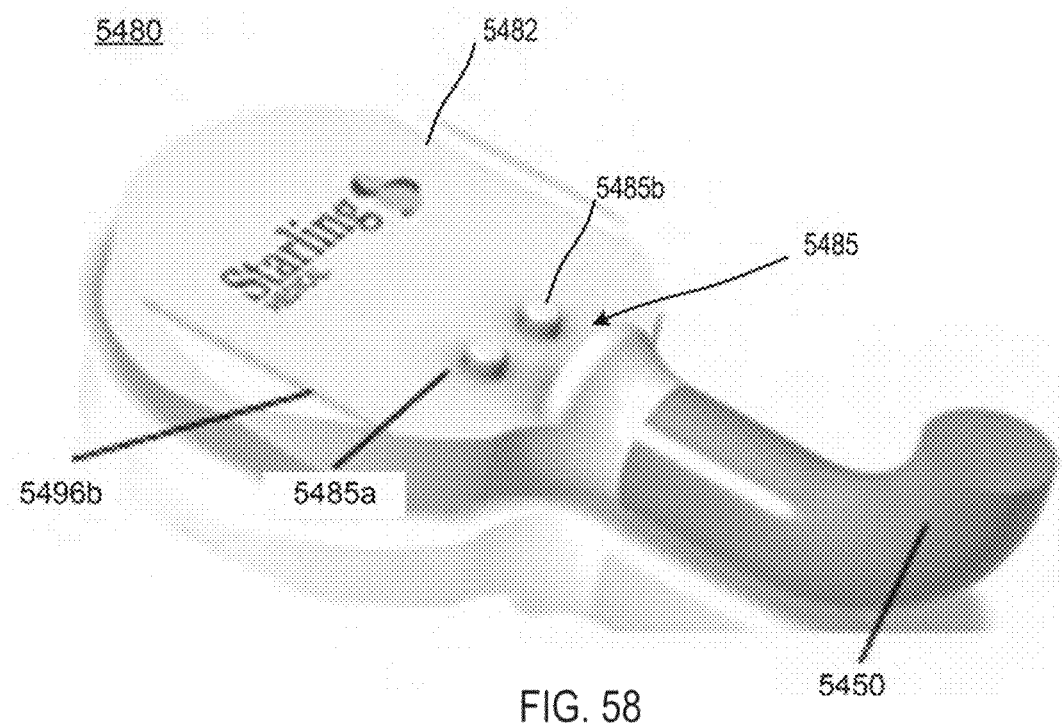
FIG. 58 is a perspective view of an external controller, according to an embodiment.
Figure 59:
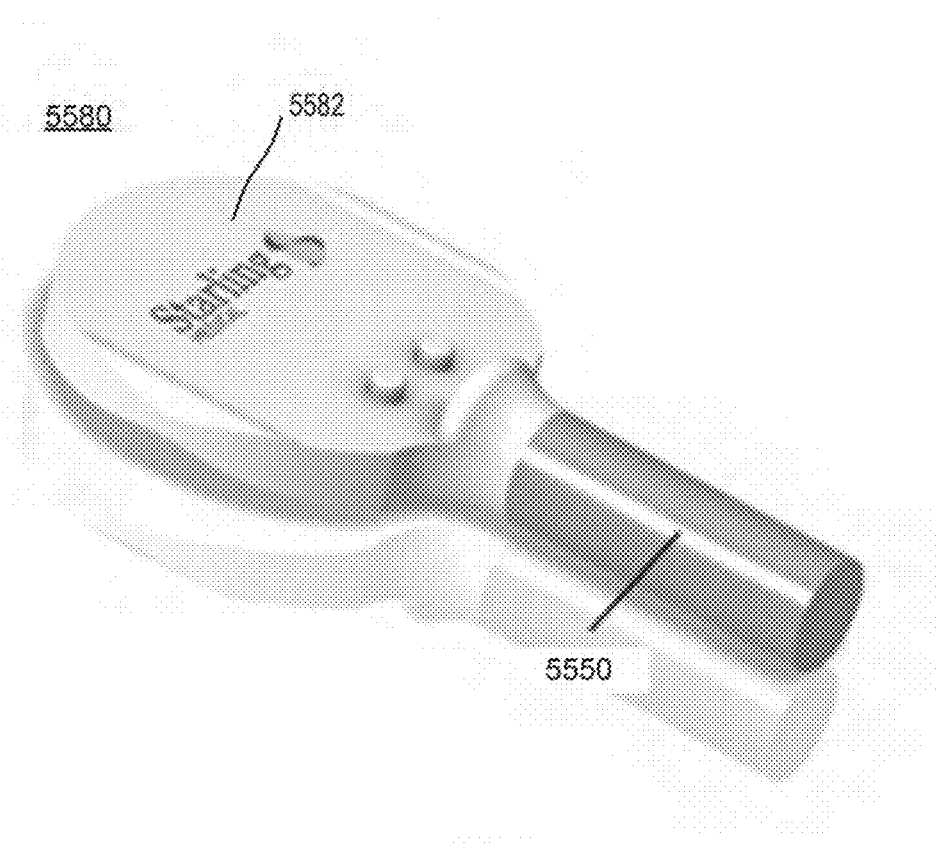
FIG. 59 is a perspective view of an external controller, according to an embodiment.

FIGS. 58 and 59 illustrate form factors for external controllers 5480 and 5580 respectively (which may include the same internal components as external controller 5380 described above), according to embodiments. In the embodiment shown in FIG. 58, the end of the controller that houses the motor 5450 is curved, terminating in a portion that is oriented approximately perpendicular to the handle portion 5482 of external controller 5480. This arrangement may provide a more convenient orientation for the user to grasp the handle portion 5482 while disposing the motor 5450 with the axis of rotation of the magnetic component of motor 5450 parallel to axis of rotation of the magnetic component of the catheter's pump. An RF antenna 5496b may be disposed in handle portion 5482. In this embodiment, user interface 5485 includes two buttons—button 5485a can be used to start and stop the catheter pump, and button 5485b can be used to initiate other electronics in the catheter, such as sensors and/or sterilizers. In the embodiment of FIG. 59, external controller 5580 is configured so that the end of the controller that houses the motor 5550 is straight, so that the end portion is oriented approximately parallel to the handle portion 5582 of external controller 5580.

In some embodiments, external controller 5480 or 5580 may be capable of communicating directly with other communications systems, such as with cell phone towers, a wireless router, or the internet through other communication portal, or a stand-alone communication unit which then in turn transfers the data to a centralized data hub through any potential wireless communication protocol.

In some embodiments, the external controller can be releasably coupled to a separate, general purpose electronic device, and the components and functions of the external controllers described above can be provided in part by the separate electronic device. For example, the electronic device can be a conventional smart phone or tablet, which typically include an internal power supply (battery), a port through which electrical power and data can be received by and sent/supplied from other devices coupled to the port, a touch screen that provides a user interface (display and input), a controller, an antenna (e.g., RF antenna) for near-field communication, and one or more wireless communication modules (such as Bluetooth or WiFi for communication with a local network, cellular for communication with a cellular network). Thus, an external controller coupleable to such a device can rely in whole or in part on the battery of the device for electrical power, on the touch screen of the device for the user interface, on the RF antenna of the device to communicate with the communication module of the catheter, and on the wireless communication module(s) for communication with other local or cellular networks.

Figure 60:
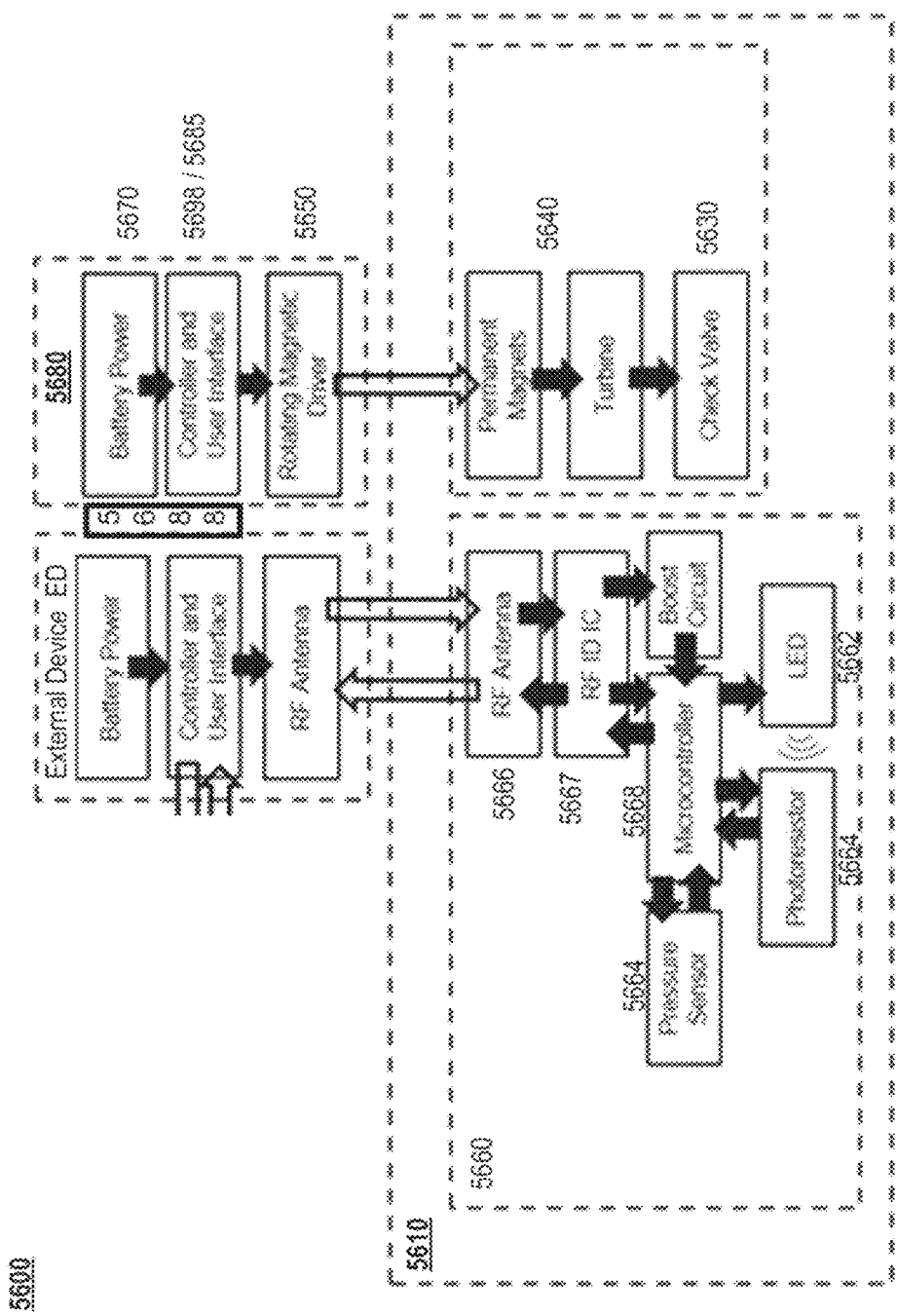
FIG. 60 is a schematic block diagram of a bladder system, according to an embodiment.

FIG. 60 is a schematic block diagram of a bladder system 5600 that includes an external controller releasable coupleable to an external device ED, as described above, and a catheter 5610, and illustrates the flow of power and communications among the components. The components of the catheter 5610 and external controller 5680 may be implemented, function, and interact with each other in accordance with any of the embodiments described above unless otherwise specified. External controller includes a motor 5650 with a rotating magnetic driver that can drive pump 5640 by causing permanent magnets coupled to the pump's turbine to rotate, driving the turbine, which may in turn actuate the valve 5630. Motor 5650 may be controlled by controller 5698 of the external controller 5680, and may also be controlled by a user interface 5685 that is part of external controller 5680. The components of external controller 5680 may draw power from an internal power source (such as a battery) 5670. External controller 5680 may be coupled by coupler 5688 to the external device, so that it is operatively coupled to the external device's battery (to draw power), user interface (such as a touch screen) (to receive user input/commands, and to exchange data such as from sensors 5664 on catheter 5610), and RF antenna (for communication with RF antenna 5666 and power harvesting circuit 5667 on catheter 5610, and, via controller 5668, with sensors 5664 and sterilizer 5662. Two possible implementation of such an external controller are shown in FIGS. 61 and 62.

FIG. 61 is a perspective view of an external controller 5780 coupled to an external device ED by a coupler 5788, accordingly to an embodiment. The arrangement of the controller is similar to that of the external controllers in FIGS. 56A, 56B, and 58, in that the end of the controller that houses the motor 5750 is curved, terminating in a portion that is oriented approximately perpendicular to the main plane of the external device ED.

FIG. 62 is a perspective view of an external controller 5880 coupled to an external device ED by a coupler 5888. The functionality of external controller 5800 is similar to that of external controller 5700, except that coupler 5888 includes an integrated case portion 5888a that can receive external device 5888. Case portion 5888a can also include an antenna (not shown) that can extend over a large portion, or all, of the surface of case portion 5888a beneath external device ED to provide a larger and more powerful antenna than the near-field antenna of the external device ED, thus enhancing communication between external controller 5880 and a catheter.

Delivery and Retrieval Devices

As discussed above with reference to FIGS. 4A to 4D, to facilitate delivery of the bladder system into a tubular organ like the urethra such that no part of the bladder system is external to the body, and/or to withdraw the bladder system from the organ, some embodiments of the bladder system can include a delivery system or device, and/or a retrieval system or device, or a combination delivery/retrieval system or device. The minimum functional requirement for the delivery device is to releasably engage with the catheter and transfer a distal force applied by the user to a proximal end of the delivery device (such as a handle) through the delivery device and to the catheter, to urge the catheter distally through the body lumen (such as a urethra) and, depending on the configuration of the catheter, until the distal end of the catheter (such as an anchor) is disposed in the body organ (such as a bladder). Thus, in some embodiments, the delivery device can include a long, relatively rigid body having a suitable interface to the catheter at is distal end, and a handle at its proximal end that can be grasped or manipulated by the user. It may also be advantageous for the delivery device to be able to transfer a proximal force, such as to partially or completely withdraw the catheter from the body lumen. This functionality is required for a retrieval device, or a combination delivery/retrieval device.

Figure 63A:
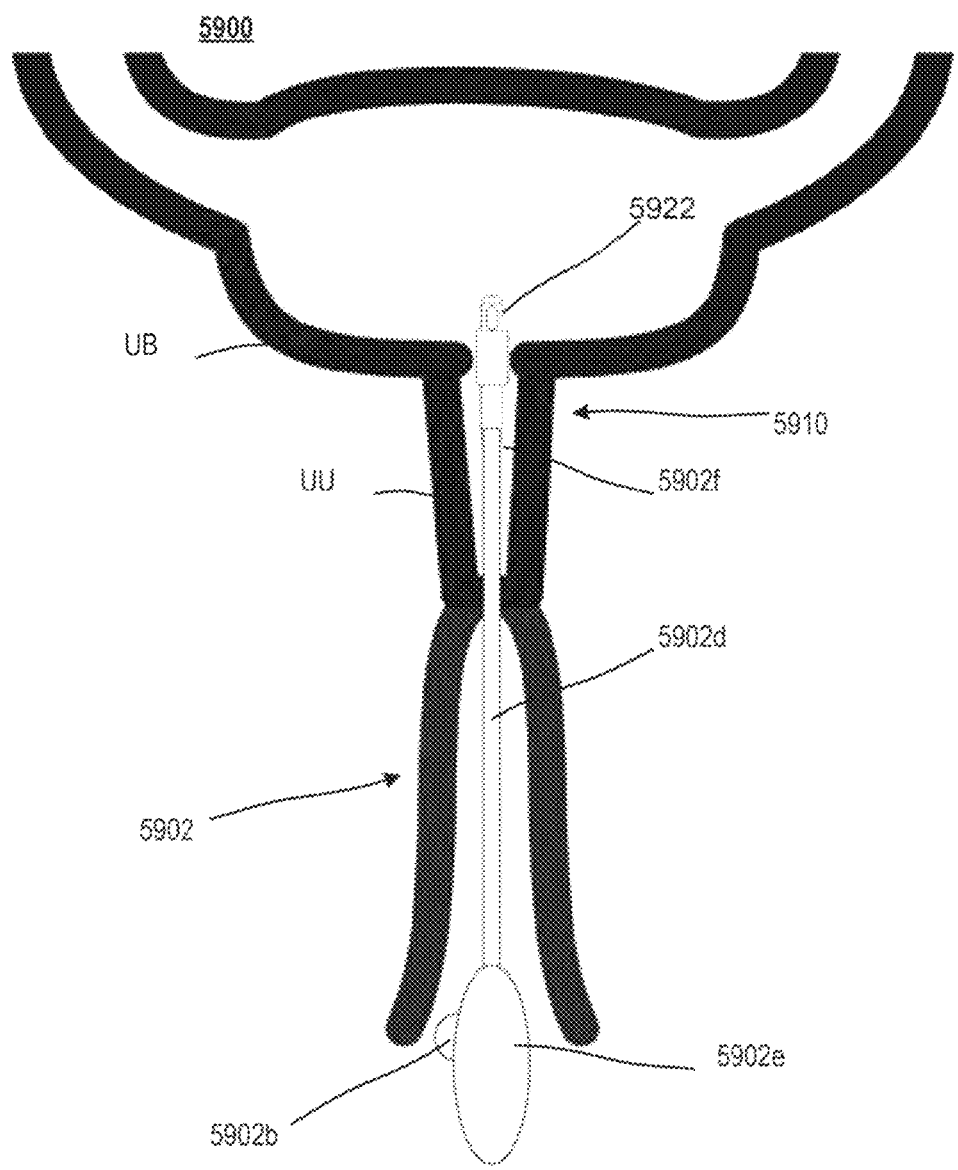
FIG. 63A shows a delivery/retrieval device and a catheter disposed in a user's body, according to an embodiment, and FIGS. 63B to 63I schematically illustrate various implementations of catheter interfaces and fluid outlets of the delivery device and catheter of FIG. 63A.

One such embodiment is shown in FIGS. 63A and 63B. In this embodiment, bladder system 5900 includes a catheter 5910 and a delivery device 5902 (though delivery device 5920 may also be usable as a retrieval device, so may be considered a delivery/retrieval device). Delivery device 5902 includes an elongated body portion 5902*d*, having at its distal end a catheter interface 5902*f* for catheter 5910. A handle 5902*e* is coupled to the proximal end of body portion 5902*d*, and a user control 5902*b* is disposed on handle 5902*e*. In FIG. 63A, the system is shown with the distal end of the body portion 5902*d* disposed in the user urethra UU, with catheter interface 5902*f* engaged with a proximal end of catheter 5910, and with the handle 5902*e* disposed outside the user's body. The distal end of catheter 5910 (with fluid inlet 5922) is disposed in the user bladder UB. Body portion 5902*d* is sufficiently long to enable the catheter 5910 to be delivered to its intended position in the user's body while the handle 5302*e* remains outside the user's body a sufficient distance to be grasped and manipulated by the user. For example, the length required would be longer for a catheter to be delivered into the body of a male than a catheter to be delivered into the body of a female. The body portion 5902*d* is also sufficiently rigid to transfer enough force from the user (applied to the handle) to the catheter 5910 to urge it through the urethra without buckling. It is also sufficiently flexible to conform sufficiently to any non-linearity of the body lumen (such as the urethra) that it does not damage the walls of the body lumen when inserted through it.

The catheter interface 5902*f* is configured to engage releasably with the catheter 5910 (such as to the proximal end), transmit the insertion force, and inhibit lateral displacement of the distal end of body portion 5902*d* from the catheter 5910, so that the body portion 5902*d* does not slip past the catheter 5910. The catheter interface 5902*f* may have a surface that abuts a corresponding surface of the proximal end of catheter 5910, such as at fluid outlet 5924, to transmit the force. As shown schematically in FIGS. 63B to 63D, mating surfaces of the fluid outlet 5924 and catheter interface 5902*f* may be perpendicular to the direction of insertion, with planar faces (FIG. 63B), may be angled, such as with two mating frustoconical surfaces (FIG. 63C), stepped, with catheter interface 5902*f* fitting inside a mating receptacle in fluid outlet 5924 (including the proximal end of the fluid lumen) (FIG. 63D) or having a larger receptacle that fits around the proximal end of catheter body 5920 (FIG. 63E), etc. Embodiments with non-planar interfaces (FIGS. 63C, 63D, 63E) provide both the insertion force transmission and lateral displacement inhibition functions, whereas a planar interface (FIG. 63B) may not provide the latter function.

None of the embodiments shown in FIGS. 63B to 63E provide a possibly desirable function of being able to transmit a proximally-directed force, such as if the user wishes to partially or fully withdraw the catheter 5910 from the body lumen, for example to reposition it before continuing the delivery, or to cease the delivery. Such a function may be provided by a mechanical interlock (as described in more detail below in connection with embodiments of a retrieval device), or may alternatively be provided through magnetic interaction between the catheter interface 5902*f* and catheter body 5920 (such as fluid outlet 5924). As shown in FIG. 63F, such magnetic interaction may be provided by disposing a magnet MAG (with poles N and S, which may be a permanent magnet or electromagnet) in catheter interface 5902*f* interacting with a ferromagnetic material embodying or included in some portion of body 5920 (including fluid outlet 5924) Alternatively, as shown in FIG. 63G, the magnet MAG can be included in fluid outlet 5924, while catheter interface 5902*f* includes a ferromagnetic material. In some embodiments, both fluid outlet 5924 and catheter interface 5902*f* can include a magnet, with opposing poles arranged to be adjacent to each other. The strength of the magnetic interaction can be selected to be sufficient to sustain desired proximally-directed forces applied by the user, such as to partially or fully withdraw the catheter from the body lumen, but insufficient to sustain a force that would be necessary to withdraw a catheter for which the anchor mechanism had deployed, permitting the catheter interface 5902*f* to be decoupled from fluid outlet 5924 after the anchor has deployed by applying a sufficient proximally-directed force.

In other embodiments, as shown schematically in FIG. 63I, the strength of the magnetic interaction may be selectively reduced, such as when delivery is complete and the delivery device 5902 is to be removed, by configuring the catheter interface 5902*f* so that the magnet MAG is movable between an engagement position (upper portion of FIG. 63I) and a disengagement position (lower portion of FIG. 63I). This movement may be controlled, for example, by a user control such a control 5902*b* shown in FIG. 63A. This embodiment may also be incorporated into a retrieval device, or a combination delivery/retrieval device. The distal end of the device can be inserted into the body lumen with the magnet MAG in the proximal position, until the catheter interface 5902*f* is close to, or in contact with, the fluid outlet 5924. The magnet MAG can then be moved to the distal position in which the magnetic interaction may be sufficiently strong to sustain application of a proximally-directed force sufficient to withdraw catheter 5910.

Figure 64C:
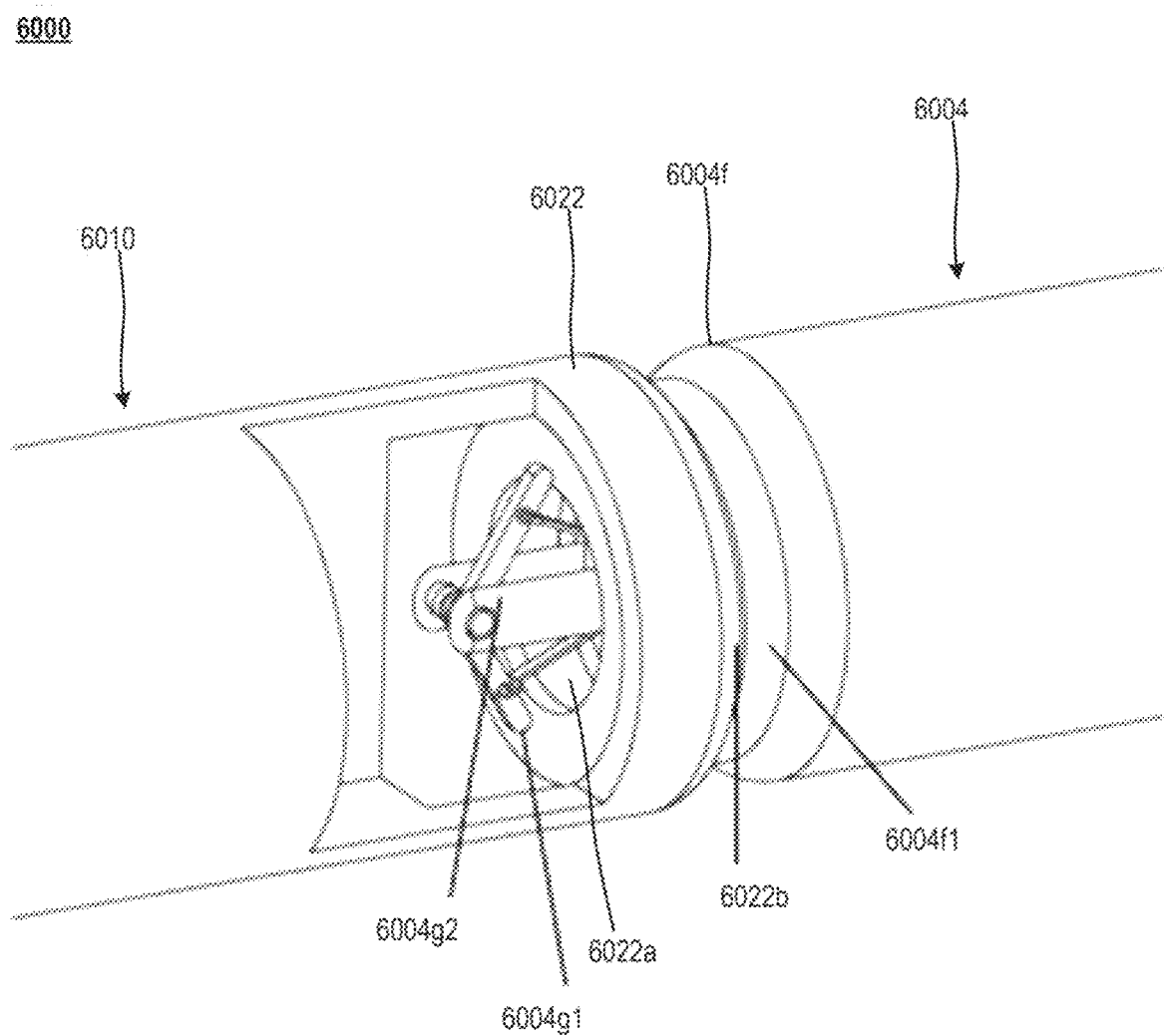
FIG. 64C is a partial, cutaway perspective view of a retrieval device and a proximal portion of a catheter, according to an embodiment.

FIGS. 64A to 64C illustrate a bladder system 6000 with a catheter 6010 and retrieval (or delivery and retrieval) device 6004. Retrieval device 6004 is similar to delivery/retrieval device 5902, including the magnet arrangement shown in FIG. 63H, but also includes a mechanical engagement or anchoring mechanism that can secure catheter 6010 to retrieval device 6004 while avoiding application of any distally-directed force to catheter 6010 during a retrieval procedure, which could undesirably push the catheter 6010 further into the user's bladder (or other body organ). Retrieval device 6004 includes a handle 6004*e*, a user control 6004*b* disposed on the handle 6004*e*, an elongate body portion 6004*d*, and a catheter interface 6004*f*. Engagement mechanism 6004*g* extends distally from catheter interface 6004*f*, and is coupled to user control 6004*b* by an actuator rod 6004*h*. A user can transition engagement mechanism 6004*g* between an engaged configuration (shown in FIG. 64A) and a disengaged configuration (shown in FIG. 64B) by moving the user control 6004*b* distally relative to handle 6004*e* (which moves actuator rod 6004*h* distally). Engagement mechanism 6004*g* is shown in FIG. 64C in an intermediate configuration between the engaged and disengaged configurations. Engagement mechanism includes a central post 6004*g*2 and a pair of arms 6004*g*1 pivotally coupled to central post 6004g2. In the engaged configuration, the arms 6004g1 extend laterally, spanning a distance that is greater than the diameter of the opening 6022a in the fluid outlet 6022. In this configuration, proximally-directed force applied to retrieval device 6004 is transmitted to catheter 6010 by the engagement of arms 6004g1 with the inner face of fluid outlet 6022. As shown in FIG. 64C, catheter interface 6004f can include a magnet 6004f1 at is distal face, and fluid outlet 6022 can include a corresponding magnet 6022b, and the magnets can generate a magnetic interaction that approximates catheter interface 6004f and fluid outlet 6022.

Retrieval device 6004 can be used as a delivery device by coupling catheter interface 6004f with fluid outlet 6022, transitioning engagement mechanism 6004g to the engaged configuration to secure the retrieval/delivery device 6004 to the catheter 6010. The user can apply distally-directed for to the handle 6004e to urge the catheter 6010 into the body lumen (user urethra) to the desired position. The user can then transition engagement mechanism 6004g to the disengaged configuration, and apply a proximally-directed force to handle 6004e, sufficient to overcome the magnetic attraction between magnets 6004f1 and 6022b, decoupling the delivery/retrieval device 6004 from catheter 6010, and withdraw delivery device 6004 from the user's body. The reverse process can be used to retrieve the catheter 6010. The user can dispose the engagement mechanism in the disengaged configuration, insert the distal end of delivery/retrieval device 6004 into the body lumen and move it distally until the catheter interface 6004f engages with fluid outlet 6002, then transition the engagement mechanism to the engaged configuration and apply proximally directed force to the handle 6004e to withdraw retrieval/delivery device 6004 and catheter 6010 from the user's body together.

As described above with reference to FIGS. 4A to 5B, a delivery device, retrieval device, or combined retrieval/delivery device can, in some embodiments, including an actuator that can be used to transition an anchor of a catheter between a delivery configuration and a deployed configuration. That is, during delivery of the catheter, the anchor can be disposed in the delivery configuration (e.g., collapsed to a smaller diameter) for insertion into and through the user's body lumen (e.g., urethra) and into the user's body organ (e.g., bladder), and may be maintained in that configuration by the actuator of the delivery device. Once the catheter has been properly placed, the user can use the actuator (via a user control on the delivery device) to transition the anchor to the deployed configuration. For retrieval, an actuator on the retrieval device can be used to transition the anchor from a deployed configuration to a retrieval configuration (which, as described above in connection the discussion of anchor embodiments) can be the same as the delivery configuration, or may be different. Since the anchor is disposed at or near the distal end of the catheter, the, or some portion of, the actuator of the delivery and/or retrieval device needs to extend to or near the distal end of the catheter. Several embodiments of such actuators, and corresponding catheters, are described below.

Figure 65:
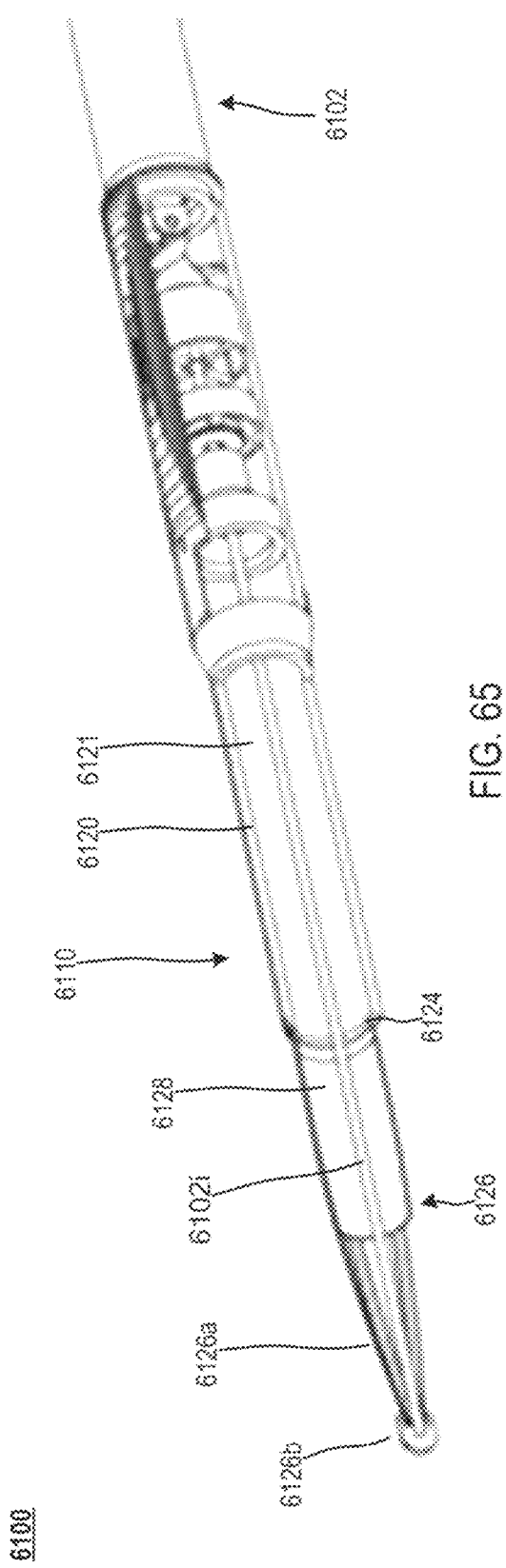
FIG. 65 is a partial cutaway side view of a delivery device and catheter, according to an embodiment.

FIG. 65 illustrates a bladder system 6100 with a catheter 6110 and a delivery device 6102. Catheter 6110 includes an anchor 6126, which is similar to anchor 2026 shown described above with reference to FIGS. 24A and 24B, and includes a seal 6128. Anchor 6126 is formed of multiple struts 6126a extending from the distal end of catheter body 6120, and joined at their distal ends by a cap 6126b. Delivery device 6102 (which can include a handle with user control, similar to the retrieval/delivery device 6004 describe above with reference to FIGS. 64A to 64C, includes an actuator with an anchor actuator rod 6102i. Catheter 6110 is configured so that a each internal component disposed within lumen 6121, such as the pump and valve, have a passage therethrough that can accommodate the anchor actuator rod 6102i. Thus, anchor actuator rod 6102i can extend from the distal end of delivery device 6102, into the fluid outlet of catheter 6110, through the internal components and the fluid lumen 6121 and extend out of the fluid inlet 6124 and through the interior of anchor 6126, and into cap 6126b. A distally-directed force applied by the user to the anchor actuator rod 6102i (via the user control on the handle, not shown) can transition the anchor 6126 into the delivery (or retrieval) configuration shown in FIG. 65, to enable the catheter to be delivered into (or retrieved from) the user's body lumen (e.g., urethra). Proximal movement of anchor actuator rod 6102i transitions anchor 6126 to its deployed configuration (e.g., by self expanding, as described above), and the anchor actuator rod 6102i can be withdrawn proximally through the catheter 6110, and withdrawn (with the rest of the delivery device) from the user's body lumen. The same configuration can be used in the reverse order with a retrieval device (or with the same device shown in FIG. 65 functioning as a delivery and retrieval device) to transition the anchor 6126 from the deployed configuration to a retrieval configuration, and withdraw the catheter 6110 from the user's body lumen.

Figure 66:
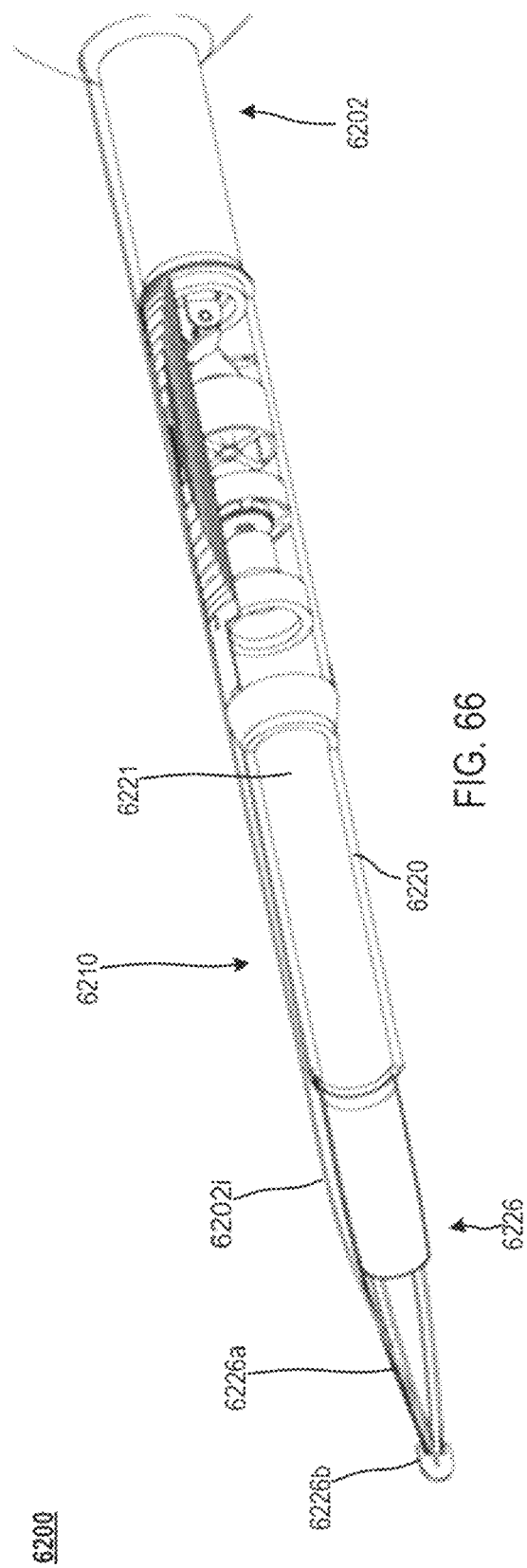
FIG. 66 is a partial cutaway side view of a delivery device and catheter, according to an embodiment.

Other configurations of the catheter and delivery/retrieval device and anchor actuator are contemplated. For example, FIG. 66 illustrates a bladder system 6200 with a catheter 6210 and a delivery device 6202, both of which are very similar to the catheter 6110 and delivery device 6102 described above. In this embodiment, anchor actuator rod 6202i does not pass through the fluid lumen 6221, but instead passes along the outside of catheter body 6220, then passes into anchor 6226, between struts 6226a and into engagement with cap 6226b. Optionally, guide loops (not shown) can be included on catheter body 6220 through which anchor actuator rod 6202i can be passed to guide the anchor actuator rod 6202i.

Figure 67A:
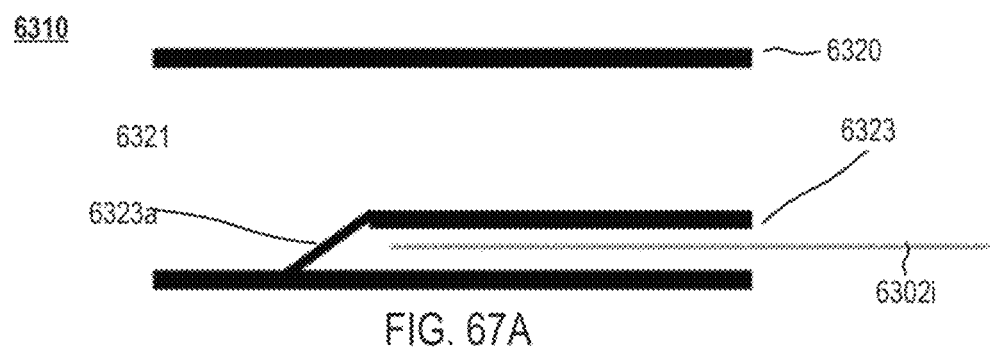
FIGS. 67A and 67B are schematic illustrations of a catheter lumen and an actuator rod for a delivery/retrieval device, according to an embodiment.
Figure 67B:
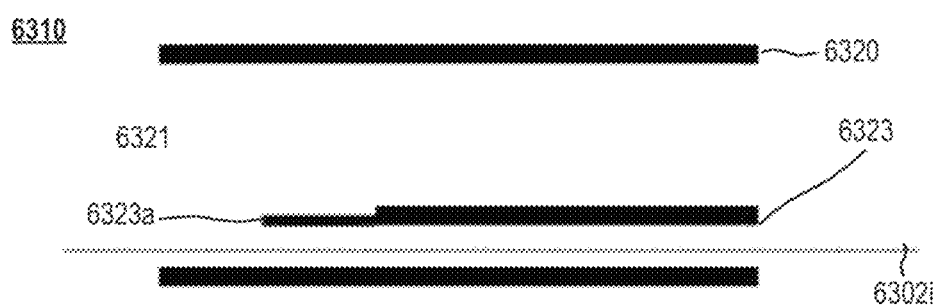

In other embodiments, a lumen for the anchor actuator rod can be formed in a wall of the catheter body, so that the anchor actuator rod does not pass through the catheter lumen or outside the catheter body. The lumen may be configured as described above with reference to FIG. 51. It may be advantageous for the lumen to have a self-closing mechanism so that the lumen does not provide a leakage path for fluid from the user's body organ when the anchor actuator rod is not disposed in the lumen. This is illustrated schematically in FIGS. 67A and 67B. Catheter 6310 includes has a catheter body defining a fluid lumen 6321 and an anchor actuator rod lumen 6323 with a movable closure 6323a. Anchor actuator rod 6302i can be inserted into anchor actuator rod lumen 6323 from the proximal end of catheter 6310 (FIG. 67A) and can be urged distally, toward the anchor (not shown) of catheter 6310, and can urge the closure 6232a from the closed position shown in FIG. 67A to the open position shown in FIG. 67A. When anchor actuator rod 6302i is no longer needed to maintain the anchor in a delivery configuration (i.e., after the catheter 6310 has been delivered to the desired location in the user's body), it can be withdrawn proximally and removed from anchor actuator rod lumen 6323 and from catheter 6310, allowing closure 6232a to transition from the open position to the closed position, prevent fluid from passing into and through anchor actuator rod lumen 6323 and thus preventing undesired fluid leakage.

In some embodiments, a retrieval device may be incorporated into the catheter. For example, a string, tether, or other flexible tension member may be attached to the proximal end of the catheter, such as at the fluid outlet, and be sufficiently long to extend proximally through the body lumen and outside of the body. A user may remove the catheter by grasping and applying a sufficient proximal force to the tension member.

In some embodiments, no additional delivery system is used.

Methods

Methods of delivery, use, and retrieval of bladder systems according to embodiments are described below.

Figure 68A:
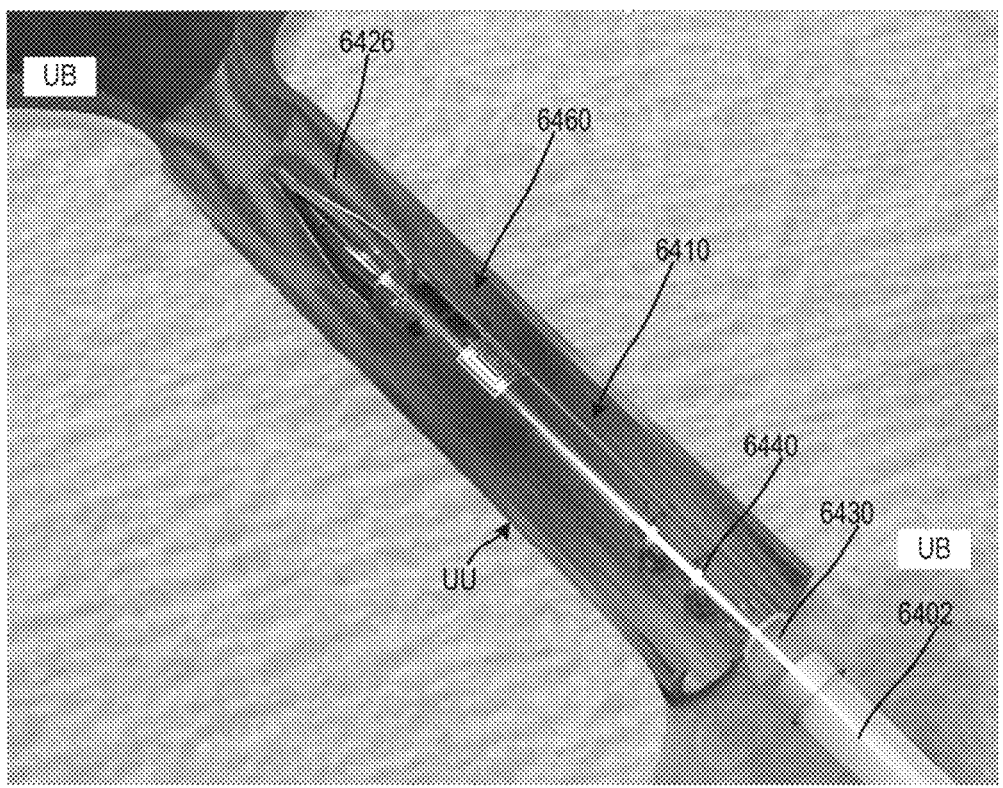
FIGS. 68A to 68D are illustrations of a catheter, delivery device, and external controller showing a sequence of operations for insertion and use of the catheter, according to an embodiment.

FIGS. 68A to 68D illustrate a bladder system 6400 and a sequence of operations with the bladder system 6400 to treat a user, and FIGS. 69A to 69D are flow charts illustrating steps in the sequence of operations 6500. Bladder system 6400 includes a catheter 6410, external controller 6480, and insertion device 6402. Catheter 6410 includes components according to embodiments described above. Valve 6430 is implemented as a duckbill type valve as described above with reference to FIG. 12, and is disposed proximal to pump 6440, which is implemented as a helical impeller as described above with reference to FIG. 6. Catheter 6410 further includes electronics 6460 similar to those describe above with reference to FIG. 32, and an anchor 6426 similar to the anchor described above with reference to FIG. 23. As shown in FIG. 68A, and steps 6501 to 6504 in FIG. 69A, catheter 6410 is coupled to delivery device 6402, into the entrance to user urethra UU with anchor 6426 disposed in a delivery configuration, and urged distally into user urethra UU toward user bladder UB.

Figure 68B:
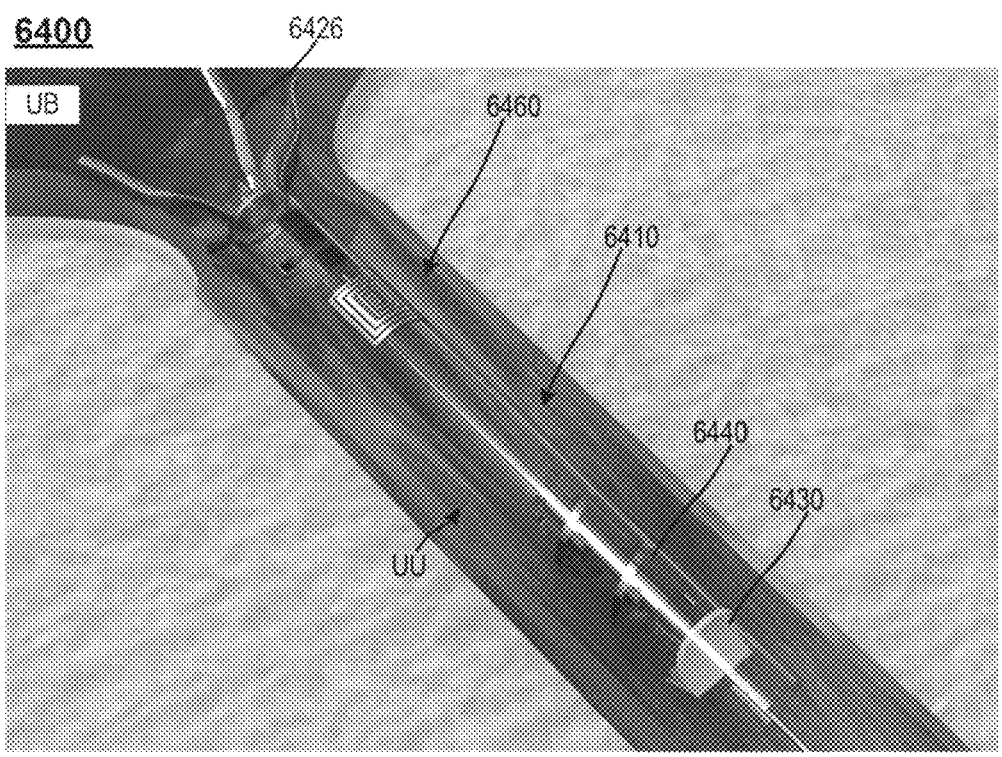
Figure 69A:
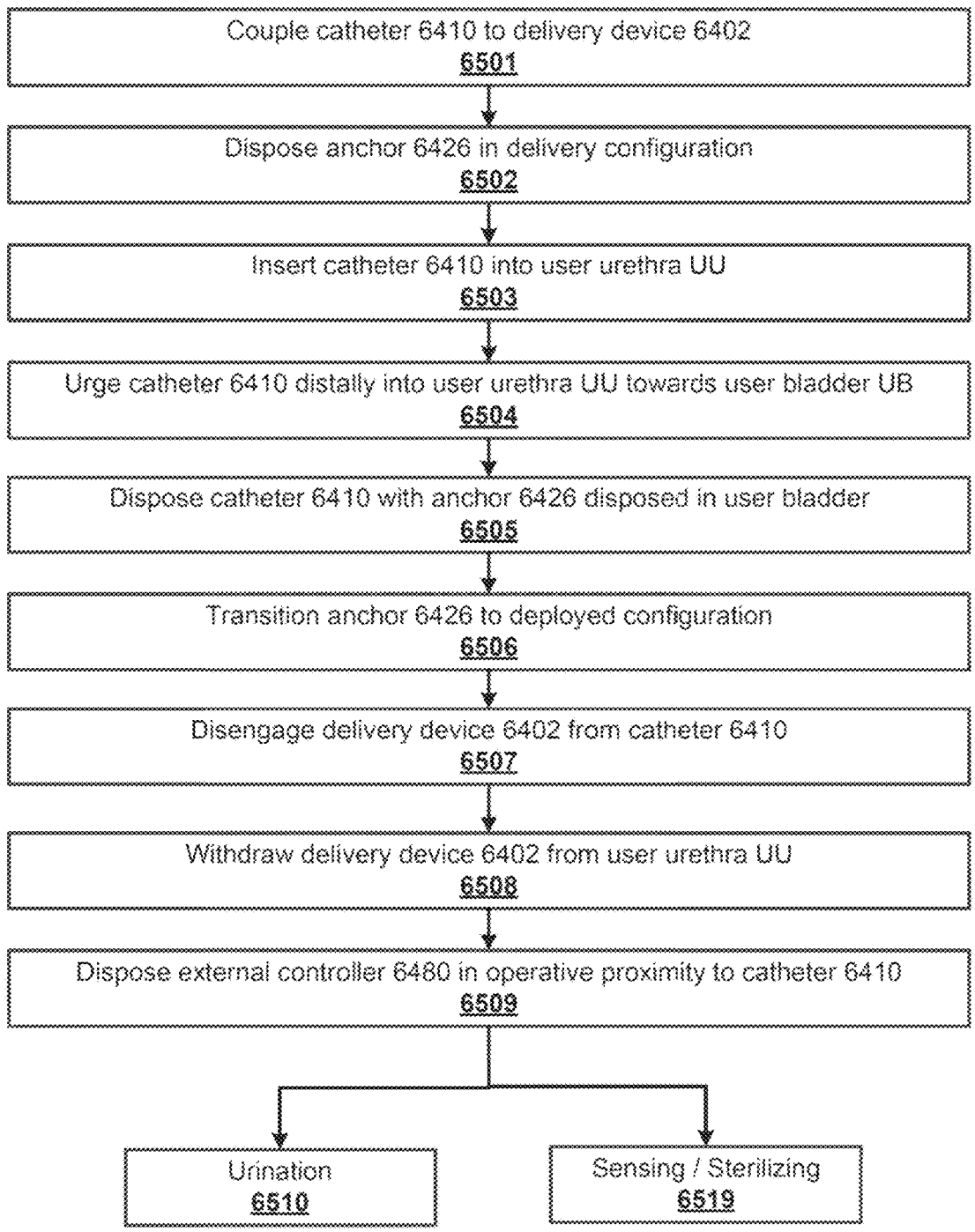
FIGS. 69A to 69C are flow charts showing the sequence of operations in FIGS. 68A to 68D.

As shown in steps 6505 to 6508 in FIG. 69A, catheter 6410 is moved further distally until anchor 6426 is disposed in user bladder UB, anchor 6426 is transitioned to the deployed configuration (in this embodiment by self-expanding), delivery device 6402 is disengaged from catheter 6410 and withdrawn from user urethra UU, resulting in the position and condition of catheter 6410 shown in FIG. 68B.

Figure 68C:
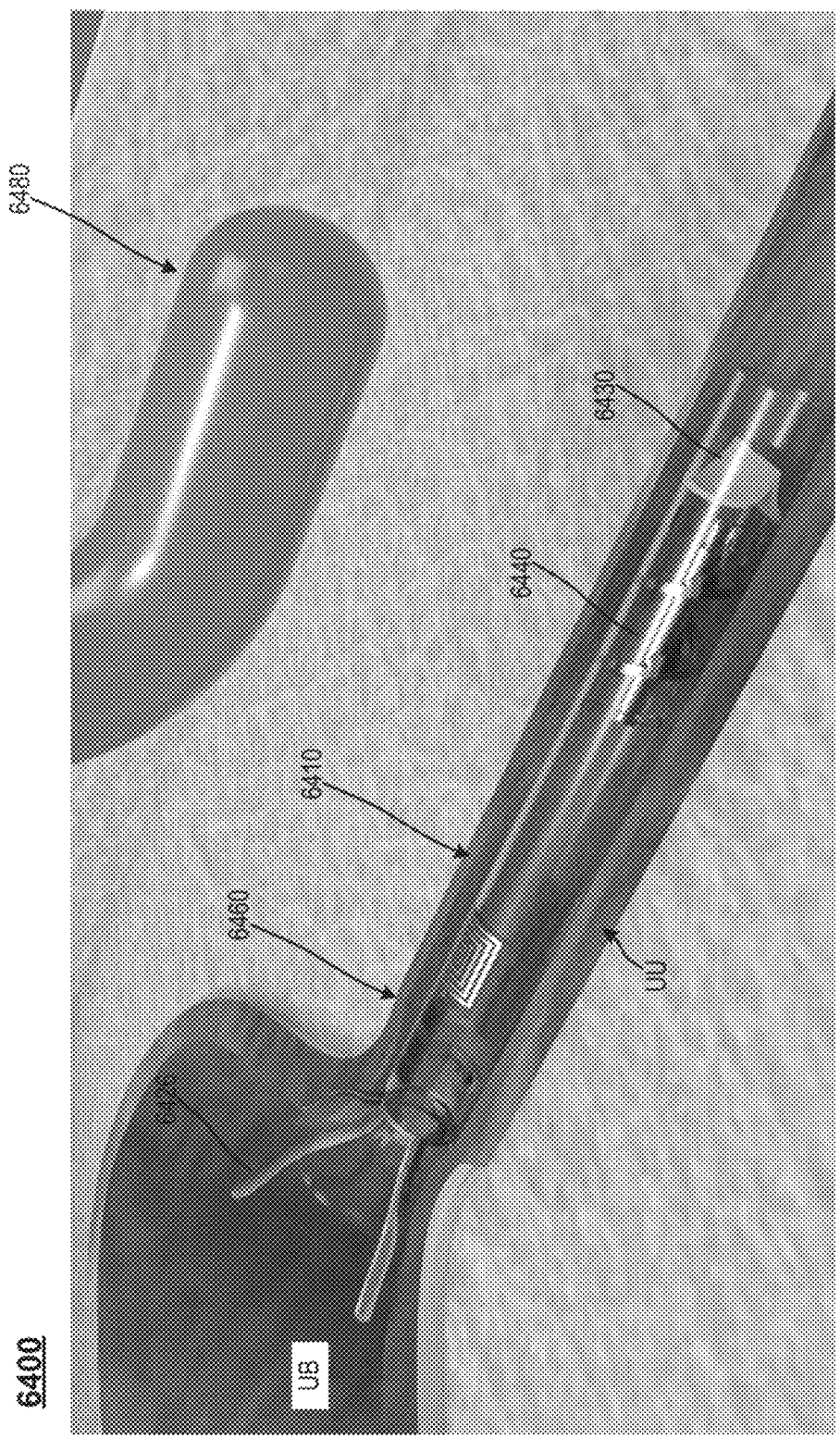
Figure 69B:
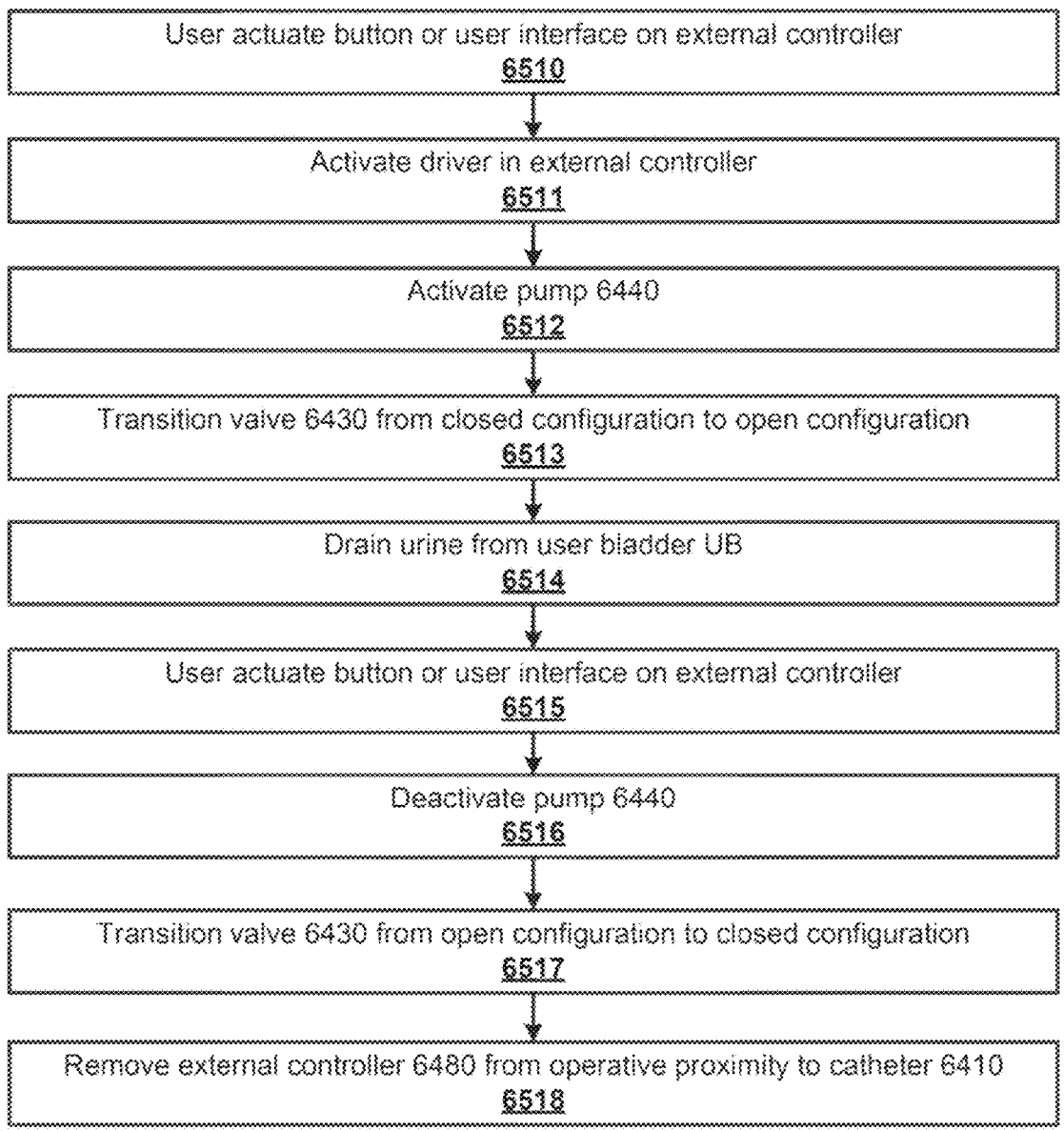
Figure 69C:
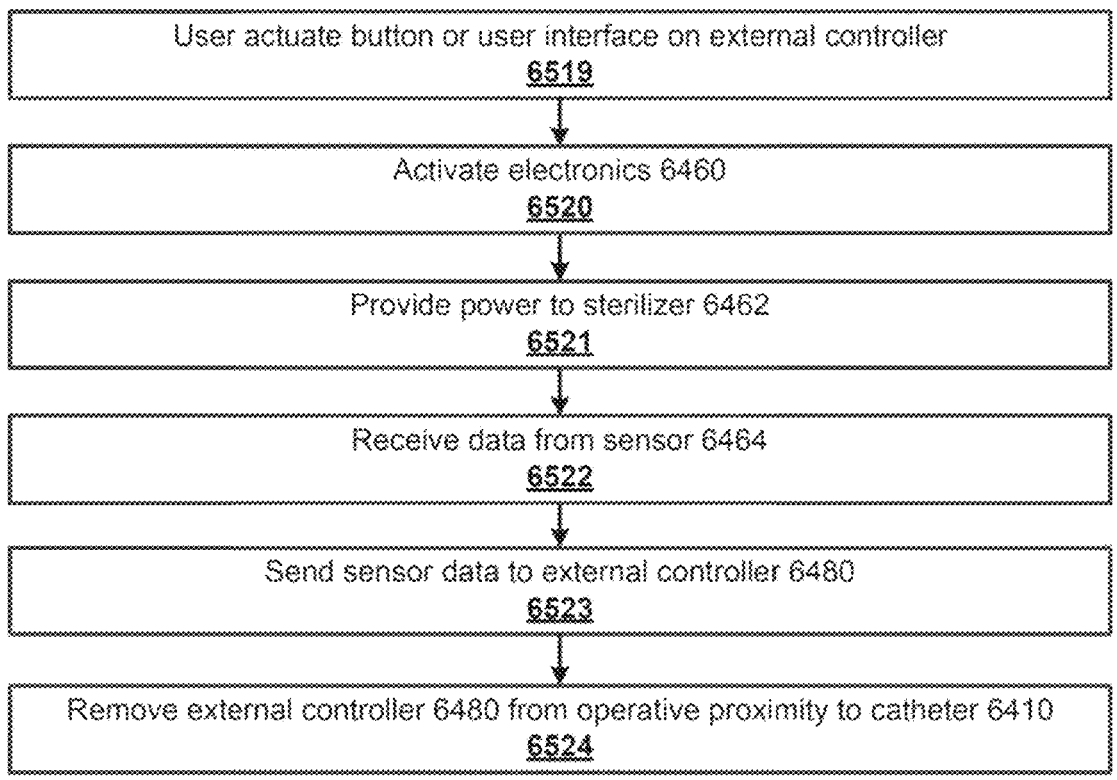

When a user wishes to release urine from the user bladder UB, then as shown in step 6510 in FIG. 69B, external controller 6480, which is similar to the external controller described above with reference to FIGS. 56A to 56C, is brought into operative proximity to catheter 6410, resulting in the position and condition of bladder system 6400 shown in FIG. 68C. As shown in steps 6510 to 6514, the user can then actuate a button or other user interface (not shown) on external controller 6480 to activate the driver in the external controller, and thus activate the pump 6440, creating a pressure differential across pump 6440 and drawing urine from user bladder UB. The pressure differential transitions valve 6430 from a closed configuration to an open configuration, such that the urine can pass through valve 6430. Urine then drains from the user bladder UB. When sufficient urine has been drained, then as shown in steps 6515 and 6516, the user can again actuate the button or other user interface on external controller to deactivate the driver on and thus deactivate pump 6440. As shown in step 6517, valve 6430 then transitions to the closed configuration. As shown in step 6518, the user can then remove the external controller 6480 from operative proximity to catheter 6410.

Figure 68D:
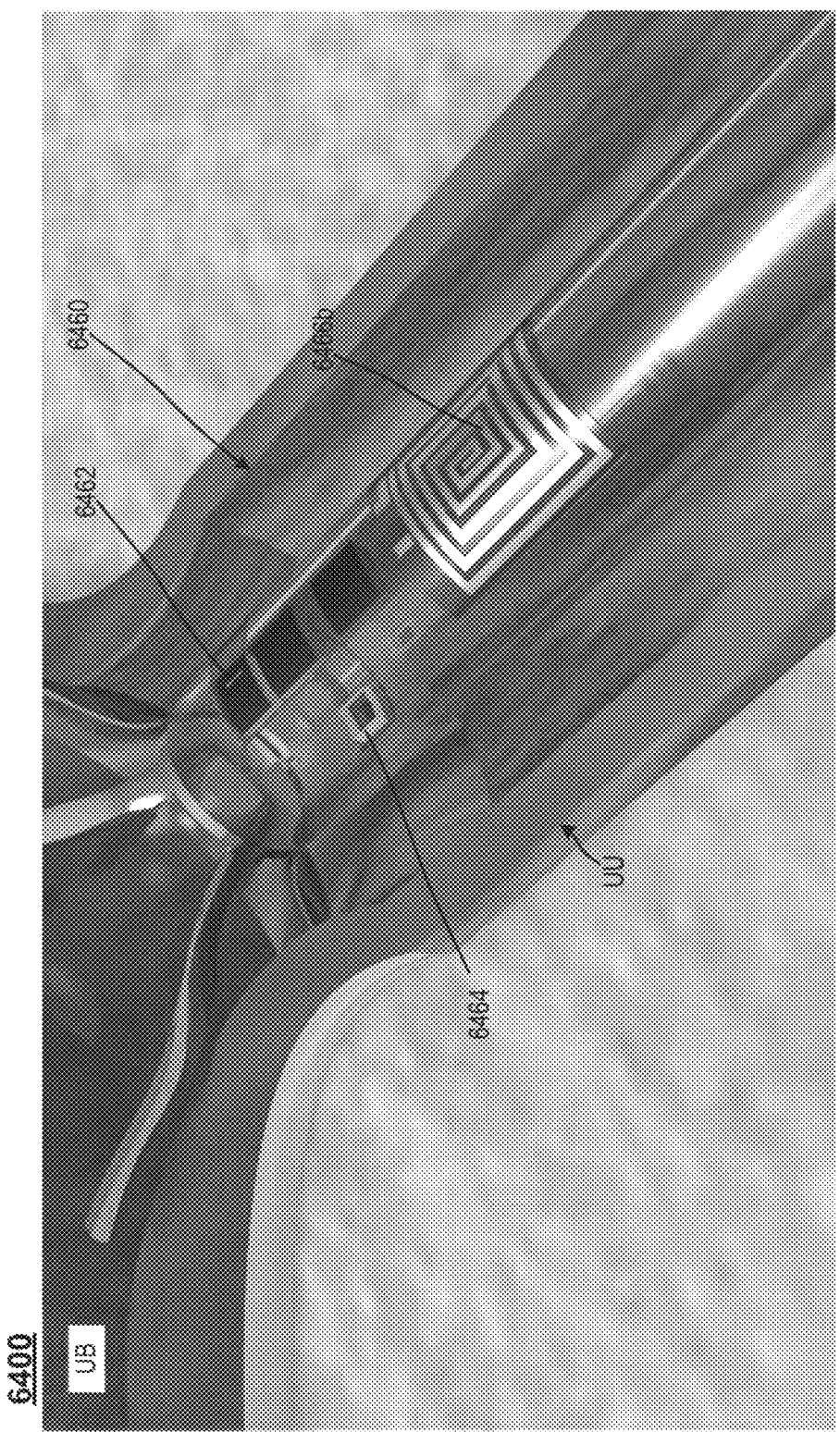

As shown in FIG. 68D, electronics 6460 of catheter 6410 includes an antenna 6466*b*, a sanitizer (e.g., UV LED) 6462, and light-based sensor 6464. When a user wishes to acquire data from sensor 6464, and/or sterilize catheter 6410 with sterilizer 6462, then after disposing external controller 6480 into operative proximity to catheter 6410 (shown in FIG. 68C and step 6509 in FIG. 69A), as shown in steps 6519 to 6523 in FIG. 69C, the user can actuate a button or other user interface (not shown) on external controller 6480. External controller 6480 can activate electronics 6460, which can provide power to sterilizer 6462 and receive data from sensor 6462 and send the data to external controller 6480. As shown in step 6524, the user can then remove the external controller 6480 from operative proximity to catheter 6410.

Figure 70A:
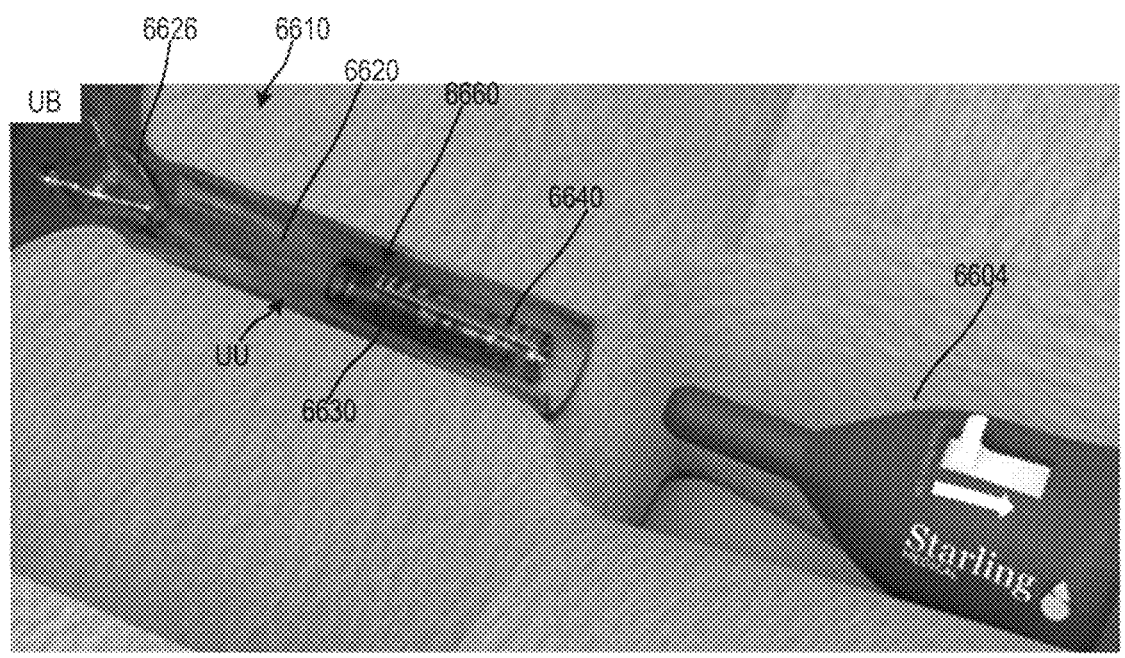
FIGS. 70A to 70D are illustrations of a catheter and retrieval device showing a sequence of operations for retrieval of the catheter, according to an embodiment.

When the catheter 6410 is no longer required, or needs to be replaced, it can be removed from the user's body. This sequence of operations is described below. FIGS. 70A to 70D illustrate a bladder system 6600 and a sequence of operations with the bladder system 6600 to treat a user, and FIG. 71 is a flow chart illustrating steps in the sequence of operations 6700. Bladder system 6600 includes a catheter 6610 and retrieval device 6604. Catheter 6610 is similar to catheter 5210 described above with reference to FIG. 55 and catheter 6010 describe above with reference to FIGS. 64A to 64C. Catheter 6610 includes a valve 6630 is implemented as a check-type valve, and is disposed distal to pump 6640. Catheter 6610 further includes electronics 6660 and an anchor 6626. Catheter 6610 is shown in FIG. 70A in an operative position in the user's body, with anchor 6626 disposed in the deployed configuration in user bladder UB and with catheter body 6620 disposed in user urethra UU. Retrieval device 6604 is similar to retrieval device 6004 describe above with reference to FIGS. 64A to 64C, and is shown in FIG. 70A near the user's body in preparation for use.

Figure 70B:
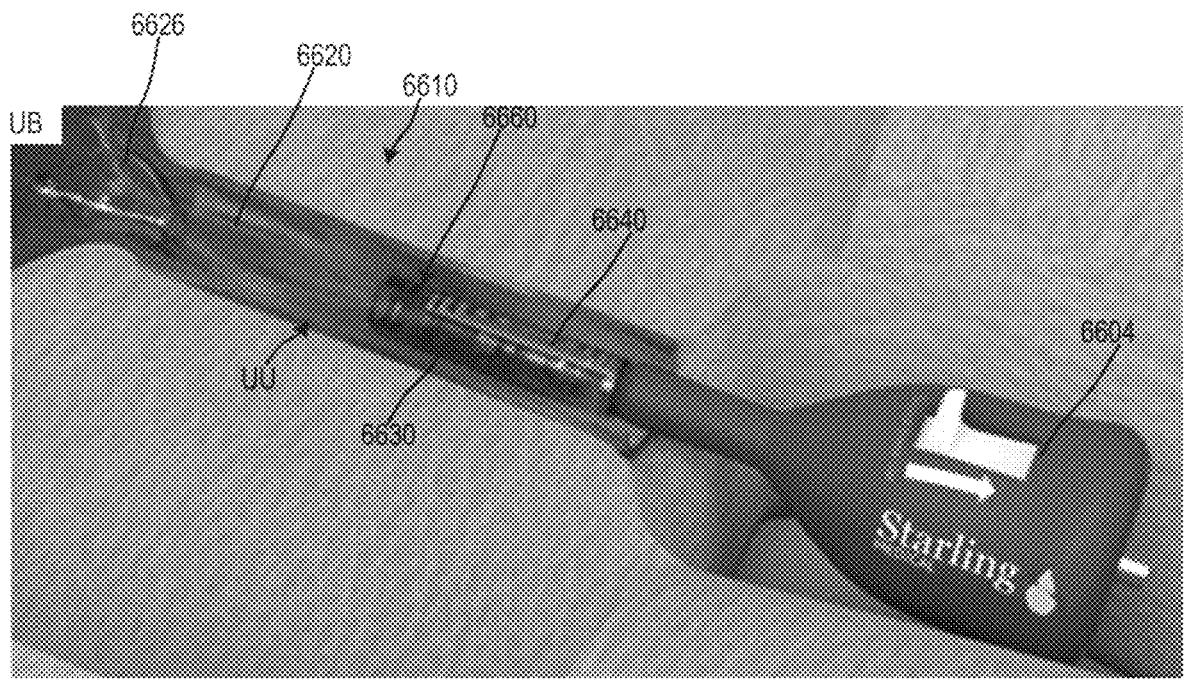
Figure 70C:
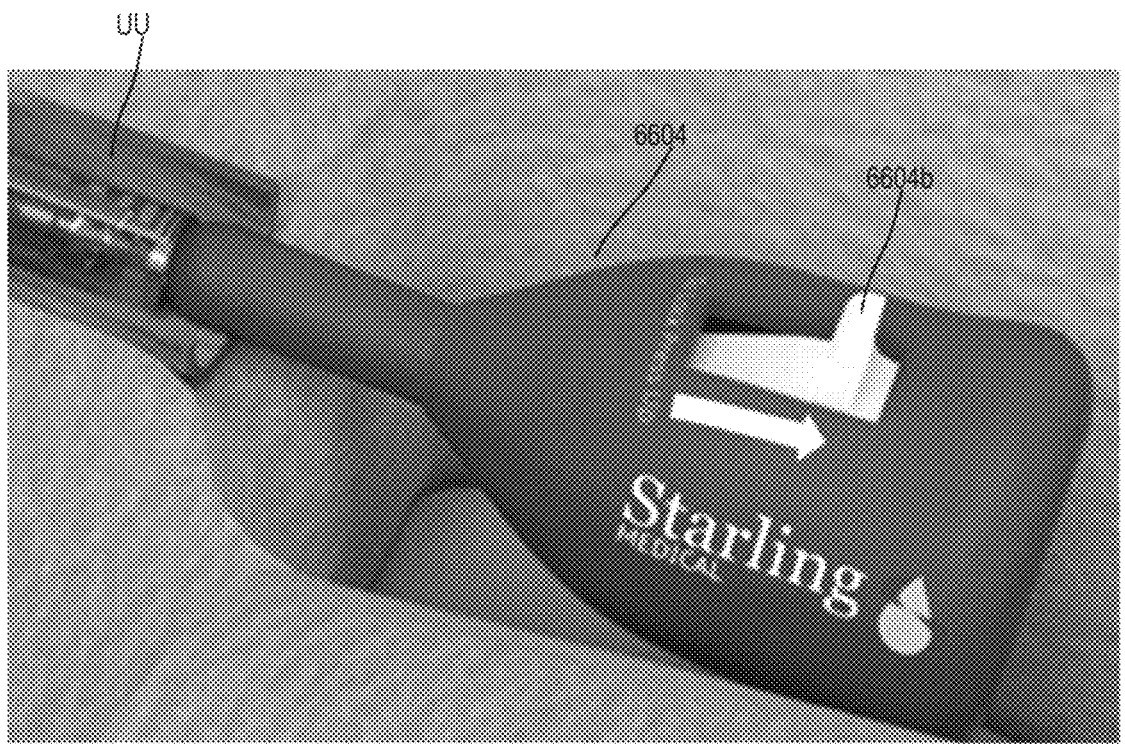
Figure 70D:
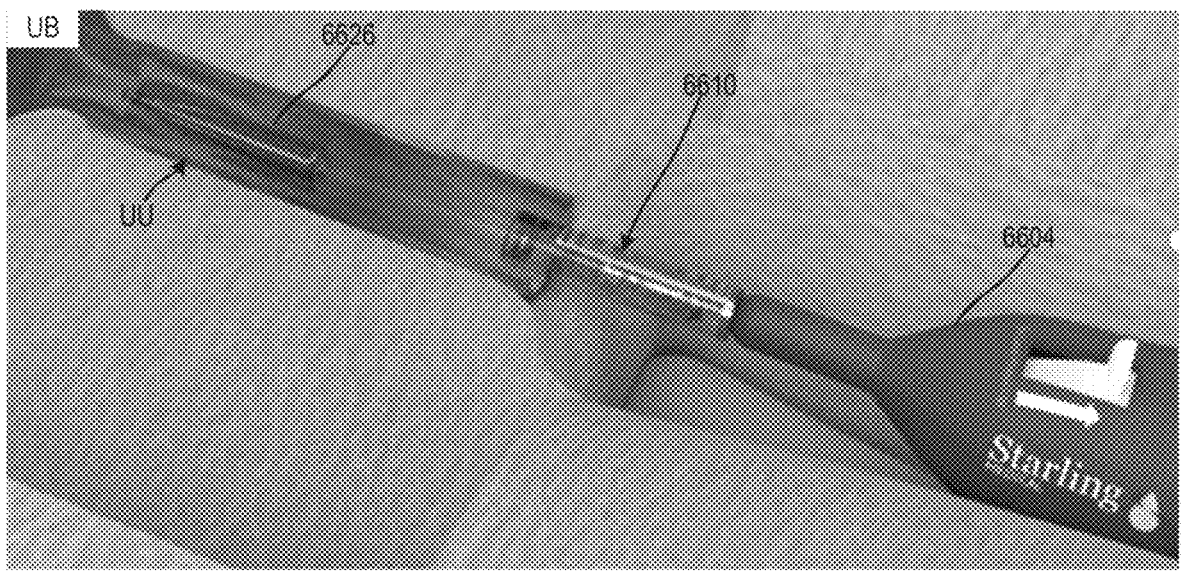
Figure 71:
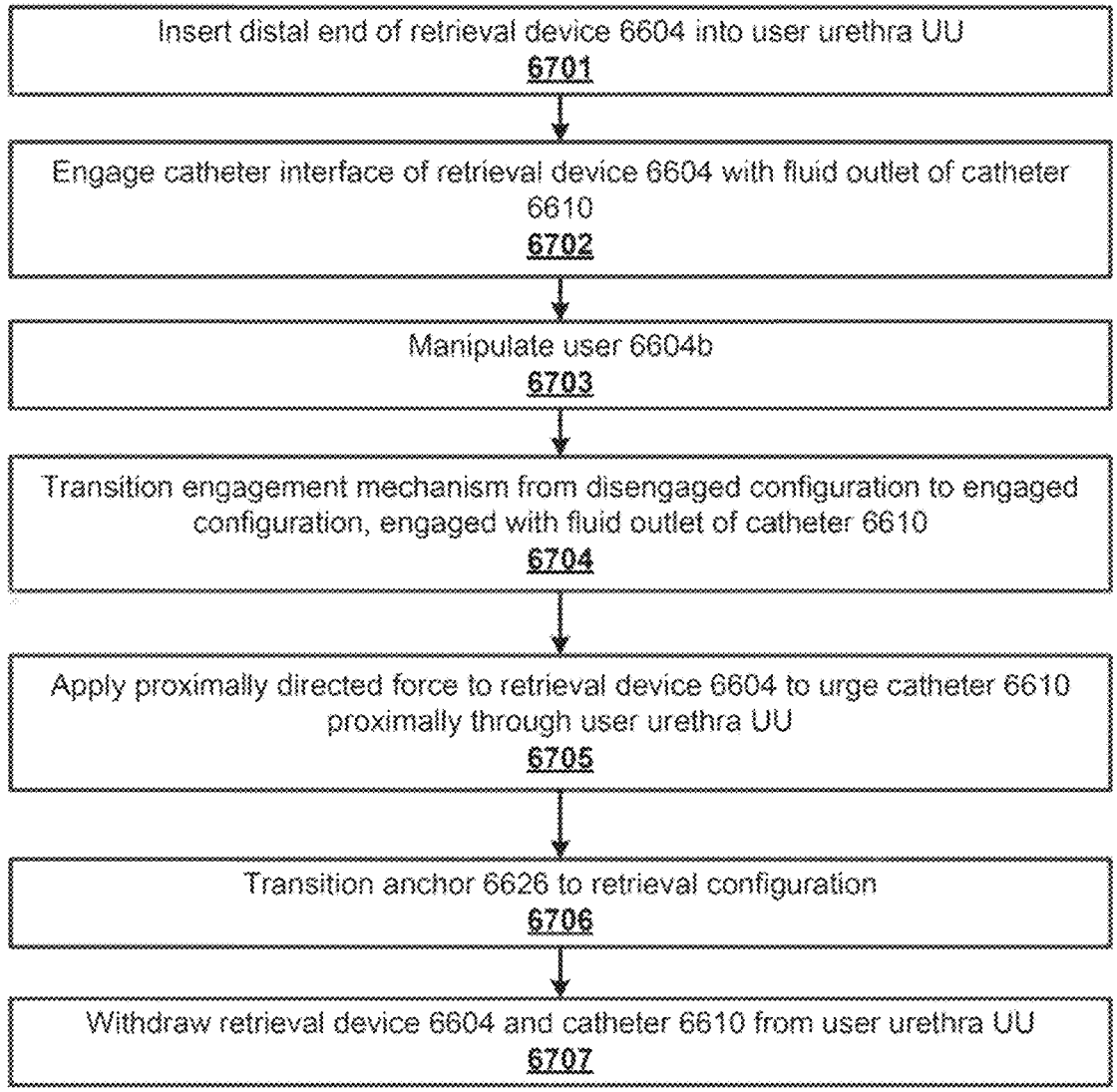
FIG. 71 is a flow chart showing the sequence of operations in FIGS. 70A to 70D.

As shown in steps 6701 and 6702 in FIG. 71, the distal end of retrieval device 6604 is inserted into user urethra UU and urged distally until the catheter interface is engaged with fluid outlet of catheter 6610, resulting in the position and condition of catheter 6610 and retrieval device 6604 shown in FIG. 70B.

As shown in steps 6703 and 6704 in FIG. 71, the user manipulates user control 6604*b*, moving it proximally. This movement, through the mechanisms described above with reference to FIGS. 64A to 64C, causes the engagement mechanism of the retrieval device 6604 to transition from a disengaged configuration to an engaged configuration, engaged with the fluid outlet of catheter 6610, resulting in the position and condition of catheter 6610 and retrieval device 6604 shown in FIG. 70C.

As shown in steps 6705 and 6706 in FIG. 71, the user can then apply a proximally directed force to the retrieval device 6604 to urge catheter 6610 proximally through user urethra UU. This movement causes anchor 6626 to transition from its deployed configuration to its retrieval configuration as it is drawn into user urethra UU, resulting in the position and condition of catheter 6610 and retrieval device 6604 shown in FIG. 70D. As shown in step 6707 in FIG. 71, the user than then withdraw retrieval device 6604 and catheter 6610 from the user's body together.

In some embodiments, a bladder management system may have a subset of the functionality of some of the bladder management system embodiments described above, and may be disposed only externally to the body of the user, and selectively couple to a conventional indwelling urinary catheter, or receive urine from the outlet of the user's urethra without the use of a catheter. As shown schematically in FIG. 72, bladder management system 6800 may 6880. Body 6820 may include (and may support and enclose) any one or more of a valve include including a body 6820 and an external controller 6830, electronics 6860, and a power source 6870. Body 6820 includes a fluid inlet 6822 at an inlet, or distal, end thereof and a fluid outlet 6824 at an outlet, or proximal, end thereof. The body 6820 has a lumen 6821 extending from the fluid inlet 6822 to the fluid outlet 6824, through which fluid (e.g., urine) from the user may pass. Urine originating from the user bladder UB may pass through the user urethra UU via a conventional indwelling urinary catheter IC (such as a Foley catheter) having a catheter outlet CO. The fluid inlet 6822 may be selectively coupled to the catheter outlet CO to receive urine therefrom. Alternatively, the user may not have an indwelling catheter IC disposed in their urethra, and instead may discharge urine into a collection device, such as a funnel (not shown in FIG. 72), and the fluid inlet 6822 may be selectively coupled to an outlet of the collection device to receive urine therefrom. Power source 6870 and electronics 6860 may be implemented, and function, as described above for the corresponding components of the other embodiments of bladder management systems described above. Urine (or other fluid) received at the fluid inlet 6822 may be passed through lumen 6821 and discharged directly from fluid outlet 6824 into a suitable receptacle (bag, toilet, etc.). In some embodiments, body 6820 may include a valve 6830 (which may be implemented, and function, as described above for the corresponding valves of the other embodiments of bladder management systems described above, e.g. under the control of electronics 6860 and by extension external controller 6880, or may be controlled manually by the user.

External controller 6880 can include a power source 6870, electronics 6890, and user interface 6885, each of which may be implemented, and function, as described above for the corresponding components of the other embodiments of bladder management systems described above. In some embodiments, some or all of the components of external controller may be integrated into body 6820. In some embodiments, bladder management system 6800 may be implemented as a single, urinary catheter accessory that incorporates all components into housing 6820.

Bladder management system 6800 may be used to manage bladder and urinary tract infections, e.g. by monitoring the status of such infections using sensors and techniques describe in detail above.

Figure 73:
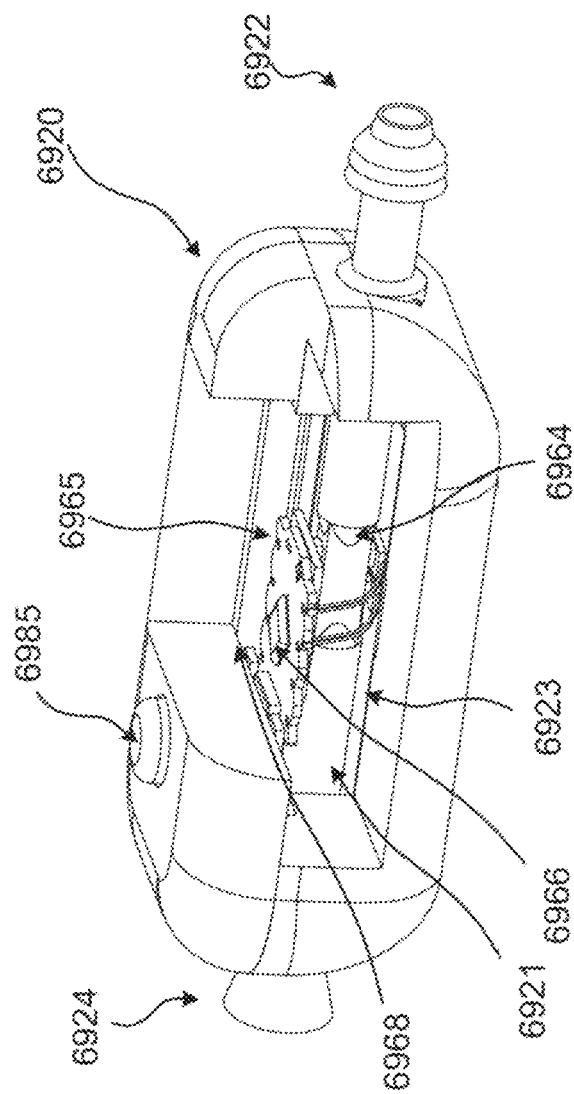
FIG. 73 is a perspective partial cross-sectional view of an external urinary catheter accessory, according to an embodiment.

An exemplary implementation of bladder management system 6800 is shown in FIG. 73. Bladder management system 6900 includes an external extended-use, disposable urinary catheter accessory for bladder and urinary tract infection management. In this embodiment, the accessory has a body 6920 with a fluid inlet 6922, a fluid outlet 6924, and a lumen 6921 extending between fluid inlet 6922 and fluid outlet 6924, and including a fluid analysis chamber 6923. Body 6920 also contains electronics that can include one or more light-based sensors, which can include multiple sensors 6964 and multiple LEDs 6865 (which may operate at any suitable wavelength, e.g. from 288 to 800 nm), as well as a controller 6968, wireless communication module 6966, and a user interface 6985. Bladder management system 6900 is configured to detect the early presence of urinary tract infections and other potential maladies such as cancer, renal failure, diabetes, or other maladies by communicating the results of the sensors 6964 wirelessly to an additional device such as, but not limited to, a smartphone.

Figure 74:
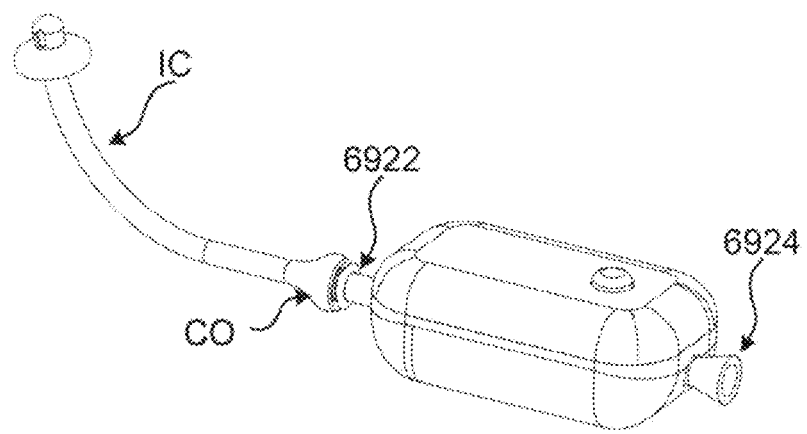
FIG. 74 is a perspective view of the external urinary catheter accessory of FIG. 73 shown coupled to the urine drainage port of a Foley catheter.
Figure 75:
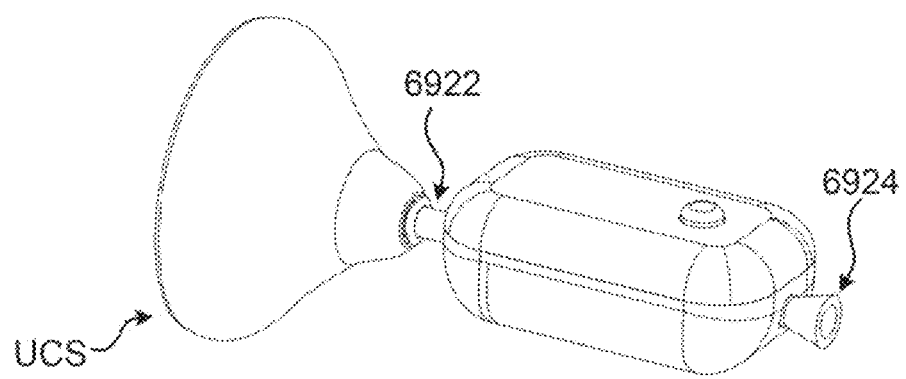
FIG. 75 is a perspective view of the external urinary catheter accessory of FIG. 73 shown coupled to the outlet of a urine collection funnel, accordingly to an embodiment.

As shown in FIG. 74, bladder management system 6900 may be selectively coupled to an intermittent urinary catheter or indwelling catheter IC, by coupling fluid inlet 6922 to catheter outlet CO. Urine discharged from the user's bladder through indwelling catheter IC may be received in fluid inlet 6922, pass through lumen 6921 and fluid analysis chamber 6923, and be discharged from fluid outlet 6924 into a receptacle such as a toilet or a bag. Urine passing through fluid analysis chamber 6923 may be analyzed using sensor 6964. Alternatively, as shown in FIG. 75, bladder management system 6900 may be selectively coupled to a funnel or other urine collection system UCS, obviating the need for a urinary catheter. In some embodiments, the urine collection system UCS can be mounted on, or in operative proximity to, a urinal or toilet bowl, with bladder management system 6900 releasable or fixedly coupled thereto, so that a user may urinate into the urine collection system UCS and after passing through bladder management system 6900, the urine is discharged into the urinal or toilet bowl.

In some embodiments, the fluid lumen 6921 can be selectively blocked by a valve (such as valve 6830 described above) disposed downstream of the fluid analysis chamber 6923. A user interface, such as button 6985, may be used to close the valve, activates the sensors 6964, relays the sensor data to a paired smartphone, and then open the valve to enable the urine to travel through the remainder of lumen 6921 and be discharged from outlet 6924. In some embodiments, the lumen 6921 may be implemented as multiple lumens of various sizes to enable efficient transport of fluid through the device so as not to accumulate in the device but create a stable column of fluid in fluid analysis chamber 6923 while fluid is being transported through the device.

Figure 76:
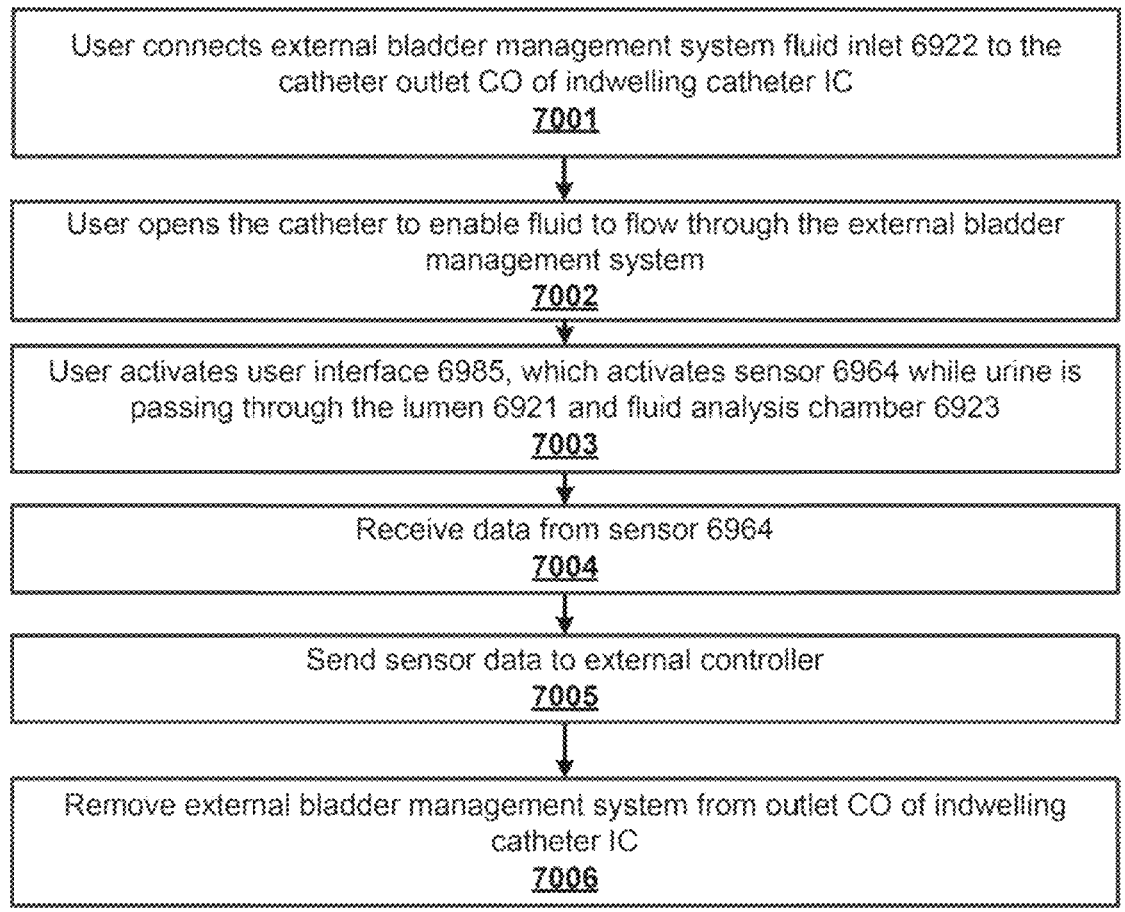
FIG. 76 is a flow chart illustrating use of an external urinary catheter accessor, according to an embodiment.

A sequence of operation of a bladder management system, such as systems 6900, is illustrated in the flow chart 7000 of FIG. 76. The user connects the fluid inlet 6921 of the external bladder management system 6900 to the outlet CO of indwelling catheter IC at 7001, such that fluid (e.g. urine) can only flow through lumen 6921. When ready, the user opens up the attached catheter allowing for fluid to be transported through bladder management system 6900, at 7002. As shown in 7003 and 7004, as fluid is transported through lumen 6921 and fluid analysis chamber 6923, the user can activate the user interface 6985, which activates the LEDs and corresponding light sensors 6964 to measure the composition of the fluid transporting passing through fluid management system 6900, and that composition data is captured by the controller 6968. Then in 7005, this data is relayed through the wireless communication module 6966 to, e.g. an external controller or smart phone. Then, at 6906, once the fluid has been fully emptied the external bladder management system 6900 is removed from the catheter IC.

Although embodiments described herein refer to emptying fluid from a bladder, the embodiments described herein can be used to selectively remove or empty fluid from organs other than a bladder. Such organs, for example, can include a chest cavity, intrapleural space, veins, arteries, chest tubes, a subarachnoid space in a head or spinal column, intestines, gastro-intestinal tract, pericardium, pleural space, or the like.

Detailed embodiments of the present disclosure have been disclosed herein or purposes of describing and illustrating claimed structures and methods that can be embodied in various forms, and are not intended to be exhaustive in any way, or limited to the disclosed embodiments. Many modifications and variations will be apparent without departing from the scope of the disclosed embodiments. The terminology used herein was chosen to best explain the principles of the one or more embodiments, practical applications, or technical improvements over current technologies, or to enable understanding of the embodiments disclosed herein. As described, details of well-known features and techniques can be omitted to avoid unnecessarily obscuring the embodiments of the present disclosure.

References in the specification to "one embodiment," "an embodiment," "an example embodiment," or the like, indicate that the embodiment described can include one or more particular features, structures, or characteristics, but it shall be understood that such particular features, structures, or characteristics may or may not be common to each and every disclosed embodiment disclosed herein. Moreover, such phrases do not necessarily refer to any one particular embodiment per se. As such, when one or more particular features, structures, or characteristics is described in connection with an embodiment, it is submitted that it is within the knowledge of those skilled in the art to affect such one or more features, structures, or characteristics in connection with other embodiments, where applicable, whether or not explicitly described.

Parameters, dimensions, materials, and configurations described herein are meant to be examples and that the actual parameters, dimensions, materials, and/or configurations will depend upon the specific application or applications for which the inventive teachings is/are used. It is, therefore, to be understood that the foregoing embodiments are presented by way of example only and that, within the scope of the appended claims and equivalents thereto; and that embodiments can be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

As used herein, the phrase "and/or" should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" phrase, whether related or unrelated to those elements specifically identified. Thus, as a non-limiting example, a reference to "A and/or B", when used in conjunction with open-ended language such as "comprising" or "including" can refer, in one embodiment, to A only (optionally including elements other than B); in another embodiment, to B only (optionally including elements other than A); in yet another embodiment, to both A and B (optionally including other elements); etc.

As used herein, the term, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein, the terms "about" and/or "approximately" when used in conjunction with values and/or ranges generally refer to those values and/or ranges near to a recited value and/or range. In some instances, the terms "about" and "approximately" may mean within ±10% of the recited value. For example, in some instances, "approximately a diameter of an instrument" may mean within ±10% of the diameter of the instrument. The terms "about" and "approximately" may be used interchangeably. Similarly, the term "substantially" when used in conjunction with physical and/or geometric feature(s), structure(s), characteristic(s), relationship(s), etc. is intended to convey that the feature(s), structure(s), characteristic(s), relationship(s), etc. so defined is/are nominally the feature(s), structure(s), characteristic(s), relationship(s), etc. As one example, a first quantity that is described as being "substantially equal" to a second quantity is intended to convey that, although equality may be desirable, some variance can occur. Such variance can result from manufacturing tolerances, limitations, approximations, and/or other practical considerations. Thus, the term "substantially."

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments described herein.

The specific configurations of the various components can also be varied. For example, the size and specific shape of the various components can be different from the embodiments shown, while still providing the functions as described herein. More specifically, the size and shape of the various components can be specifically selected for a desired or intended usage. Thus, it should be understood that the size, shape, and/or arrangement of the embodiments and/or components thereof can be adapted for a given use unless the context explicitly states otherwise.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

As used herein, a component and/or a device can be, for example, any assembly and/or set of operatively-coupled electrical components associated with performing a specific function, and can include, for example, a memory, a processor, electrical traces, optical connectors, software (executing in hardware) and/or the like.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

External Bladder Management System

Figure 72:
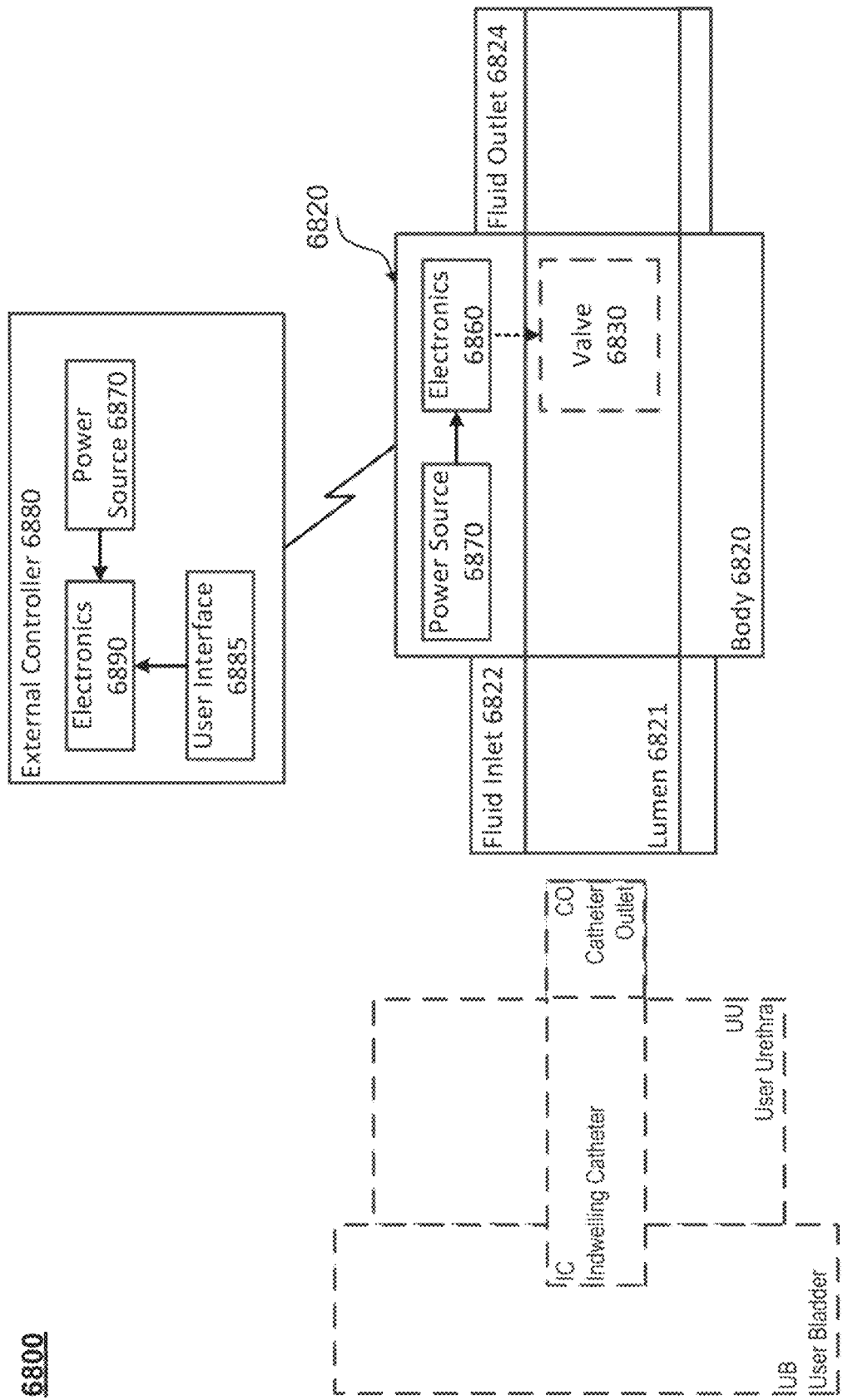
FIG. 72 is a schematic illustration of an external urinary catheter accessory, according to an embodiment.

As described above, a bladder management system may have a subset of the functionality of some of the bladder management system embodiments described herein, and may be disposed only externally to the body of the user, and receive urine from the outlet of the user's urethra with or without the use of a catheter (e.g., as shown and described with respect to the schematic illustration of FIG. 72.

In some embodiments, an external bladder management system, similar to or the same as discussed above, can work in conjunction with a bladder system or catheter and captures physical and chemical characteristics of fluid passing through its sensors. These characteristics can include, but are not limited to wavelength absorption peaks representative of, nitrite levels and other bacterial markers and metabolites, viral markers and metabolites such as those from the virus that causes COVID-19, markers of kidney stone presence and formation, markers and metabolites of cancers, flow rates and markers indicative of various voiding disorders such as benign prostatic hyperplasia, and proteins and sugars for measures of diabetes or kidney function. Data collected could also include flow, volume and/or duration of voiding. Analysis of data collected could lead to the inference of and/or the distinction between two conditions that traditionally have similar presentation, such as symptomatic urinary tract infections and urine colonization.

In some embodiments, the external bladder management system can physically interface with a fluid containing tube that is exiting the body. This fluid tube can be a urinary catheter, a peritoneal dialysis tube, a tube draining cerebrospinal fluid, a tube draining blood, or any other tube draining fluid from an organ inside the body. This physical interface between the fluid tube and the external bladder management system can create a seal to limit and/or prevent fluid leaks from the interface. It can be connected and disconnected by hand, or can be permanently connected such that it cannot be disconnected. This interface can connect via a standard luer lock or by any other means that securely attaches a fluid draining tube to the device.

In some embodiments, the external bladder management system can also act as a stand alone device that can work in conjunction with a fluid containing tube. In some embodiments, for example, a funnel or funnel-like basin can attach to the top of the bladder management system that captures fluid as it is drained into a receptacle, like a toilet. In this embodiment, a catheter draining urine can be held above the funnel connection and the funnel will collect fluid and channel it to drain through the lumen of the device. Once fluid enters the lumen of the device it can drain into the receptacle.

Figure 77A:
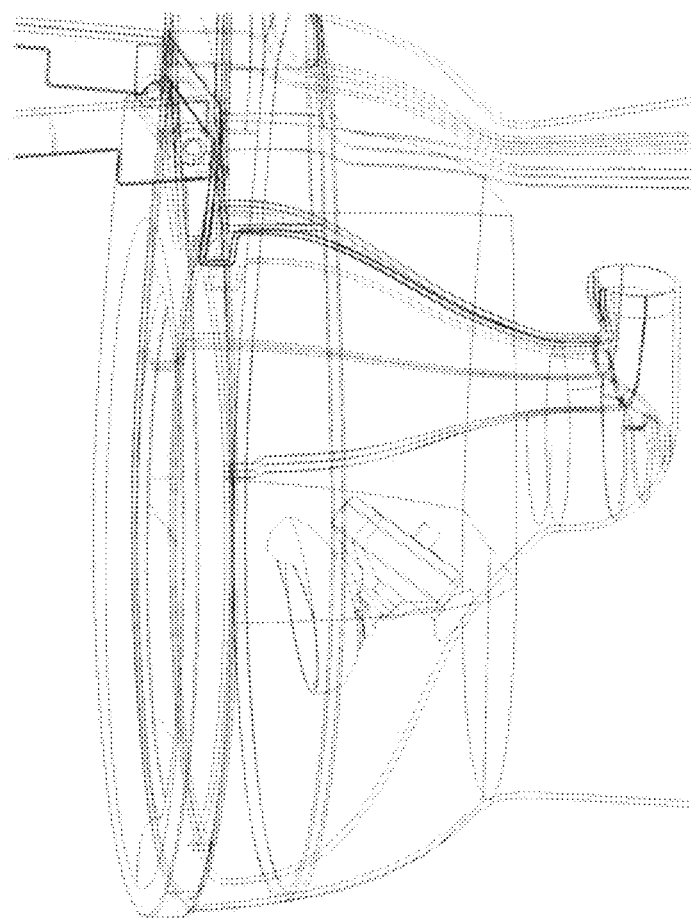
FIGS. 77A and 77B are perspective views of an external bladder management system placed inside of a standard toilet bowl, according to an embodiment.
Figure 77B:
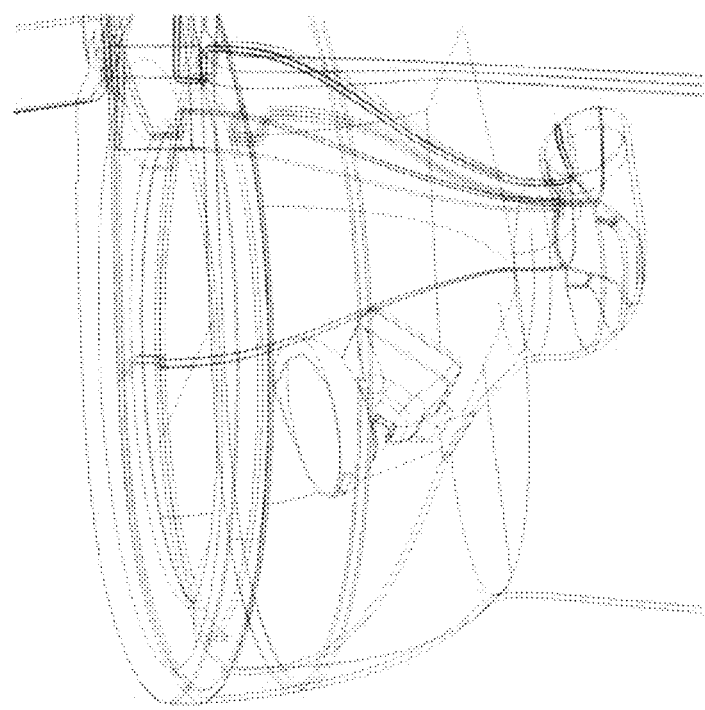
Figure 78:
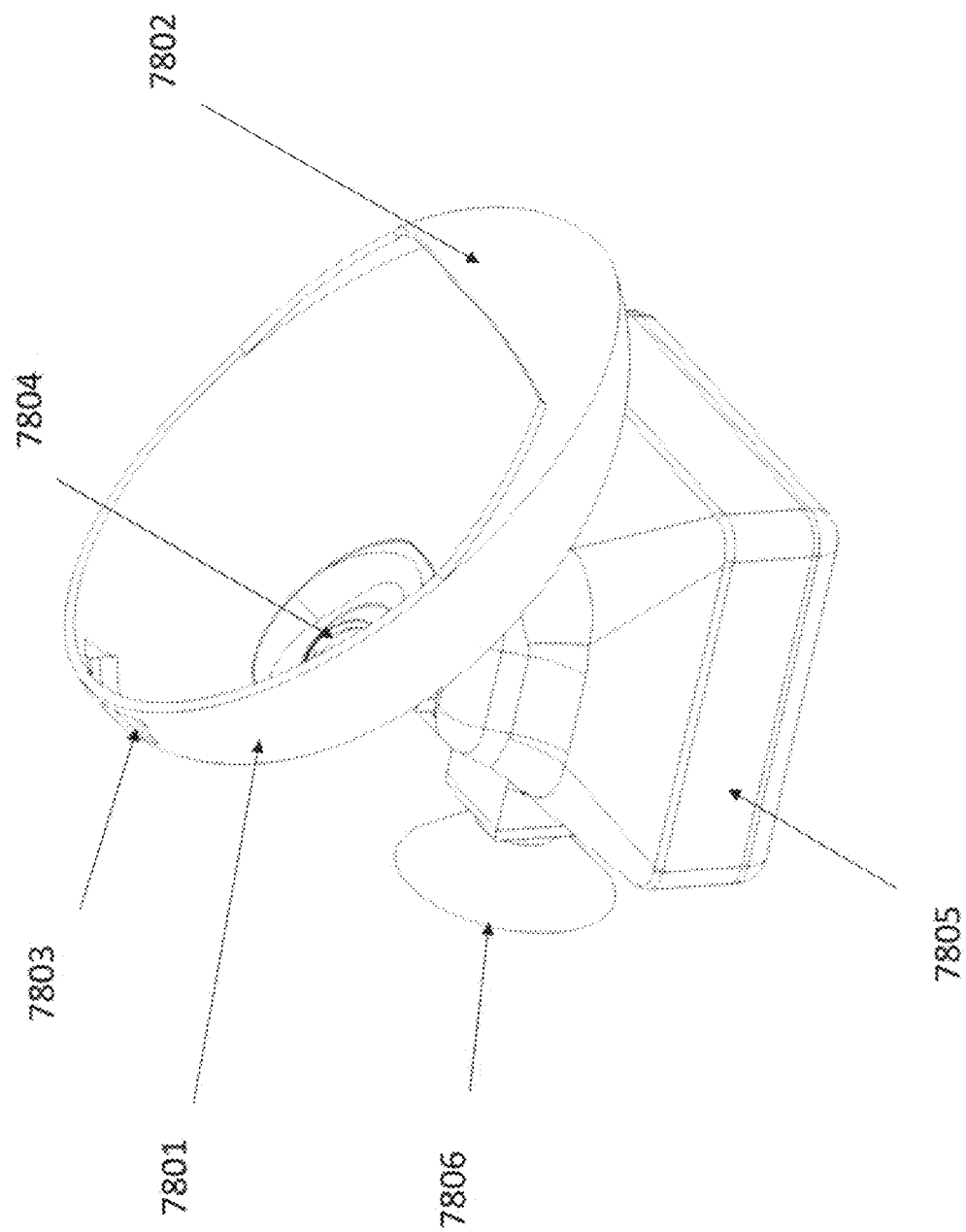
FIG. 78 is a close-up perspective view of the external bladder management system of FIGS. 77A and 77B, with a fluid collection funnel, suction cup attachment, and a circuitry and a fluid transfer holder.
Figure 79:
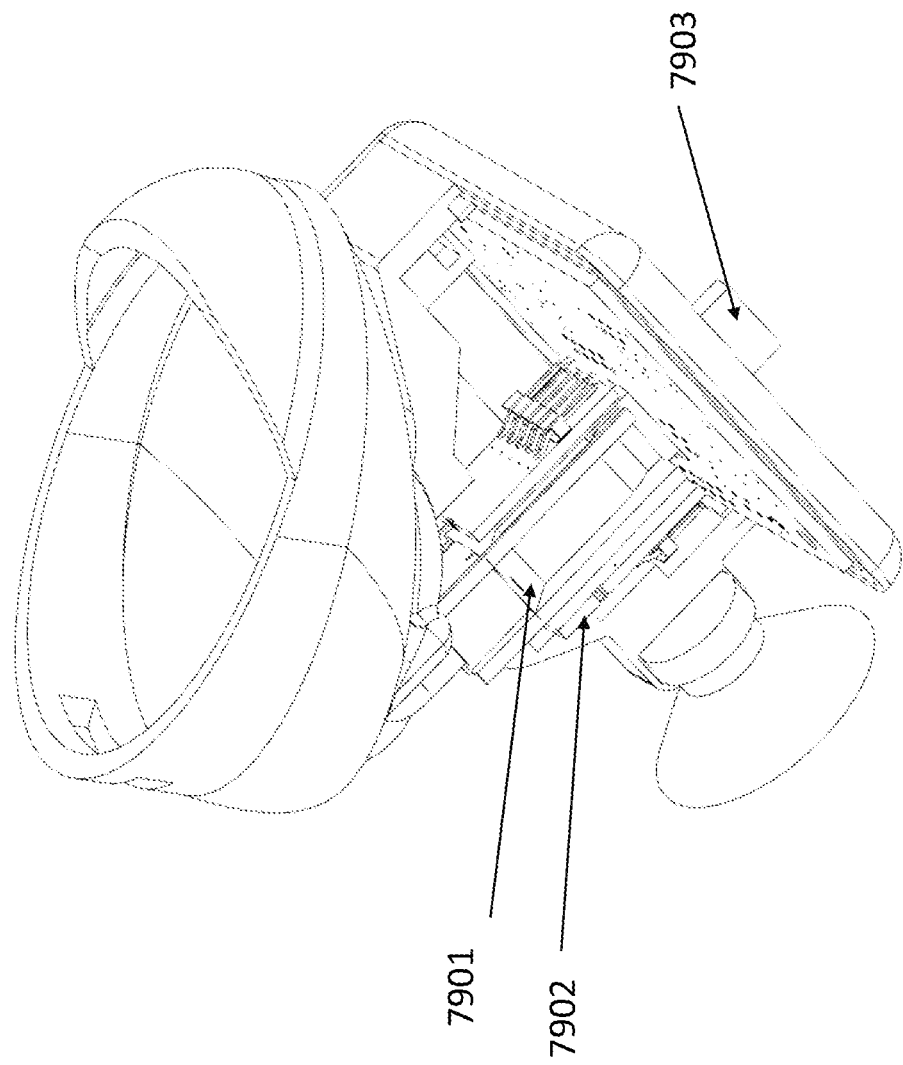
FIG. 79 is a perspective partial cross-sectional view of the external bladder management system of FIGS. 77A and 77B.

As shown in FIGS. 77A and 77B, external bladder management system 7100 can transiently or permanently reside within a fluid collection receptacle, like a toilet T, according to an embodiment. External bladder management system 7100 can be the same as or similar to, in form and/or function, any of the bladder management systems described herein. Thus, portions of the external bladder management system 7100 are not described in further detail herein. some details. As shown in FIGS. 77A-81, external bladder management system 7100 includes a body 7805 (e.g., can be similar to body 6820 or body 6920) coupled to a fluid capturing funnel 7801 (e.g., can be similar to fluid inlet 6822 or fluid inlet 6922) configured to collect the fluid, and an attachment mechanism 7806 to connect body 7805 and fluid capturing funnel 7801 to the fluid collection receptacle (in this example, a toilet T). The attachment mechanism 7806 can be any suitable attachment mechanism, such as, for example, a mechanical attachment, such as a clip, through magnetic attachment, such as a magnet on the device and a ferrous surface or magnetic surface on the receptacle, and/or through a suction-like attachment, as shown in FIG. 78, with reference to 7806. Body 7805 can connect to the T transiently or permanently and can contain one, some, all, or none of the aforementioned connection examples. In some embodiments, the external bladder management system 7100 be part of the fluid collection receptacle, e.g., such that it is integrated into the basin. Body 7805 can contain any or all of the electronics, sensors, and/or the like described in any of the embodiments herein. For example, the electronics may include a wireless transmitter to transmit data (e.g., fluid and/or urine analysis data) to a receiver external to the body and/or the fluid collection receptacle. Such a receiver, for example, can be a user's electronic device, such as a smart phone.

In some implementations, the funnel 7801 can be configured to be physically and/or operably coupled to a separate urinary catheter (e.g., such as those described in previous embodiments herein) such that fluid from a user's bladder can be transferred into the funnel 7801. In some implementations, the funnel 7801 can include a lip 7802 or similar structure such that when fluid (e.g., urine) is introduced into the funnel 7801 the fluid is redirected towards the middle of the funnel to discourage fluid from spilling out from the funnel 7801 or splashing back to the user. Funnel 7801 is fluidically coupled to a lumen 7804 (e.g., similar to lumen 6821 or lumen 6921) that is configured to route the fluid from funnel 7801 to an outport or outlet 7903 (e.g., similar to fluid outlet 6824 or fluid outlet 6924). In fluidic communication with lumen 7804 and between funnel 7801 and outport 7903 is a fluid testing chamber 7901 (e.g., similar to fluid analysis chamber 6923). In some implementations, outport 7903 is configured to limit fluid flow as it leaves the system 7100 such that even low fluid flows into the system 7100 can sufficiently fill testing chamber 7901 and such that a laminar flow profile is created in the chamber 7901. Said another way, outport 7903 can obstruct fluid flow such that the flow that moves through the fluid testing chamber 7901 is substantially laminar, to aid in testing and/or measuring. The funnel 7801 may be sufficiently sized to function as a reservoir to contain enough fluid (e.g., urine) to keep the volume within the fluid testing chamber 7901 sufficiently full during the testing phase, to produce consistent and repeatable testing and results. After the fluid is analyzed, it can flow out through the outport 7903, and discharged into the toilet bowl. Any suitable analysis can be performed on the fluid within the testing chamber 7901, using any suitable sensor(s) (e.g., similar to sensor 6964 and/or others described herein). Although not shown, in some implementations system 7100 can include a valve (e.g., similar to valve 6830) disposed downstream of the chamber 7901.

System 7100 can be powered through an external or internal battery pack containing commercially available batteries, disposable or rechargeable, or can be powered through active means (e.g., in some implementations system 7100 can include a power source similar to power source 6870). For example, as fluid passes through the system 7100, it could spin a turbine-like structure containing a magnetic core that is surrounded like copper wire that generates an electrical current to power the system 7100.

The system 7100 can be configured to communicate via WiFi, Bluetooth, NFC, cell phone signal, and/or other wireless signal (such as LTE, 3G, 4G, 5G, 5G+, etc) to a smartphone or similarly capable device or controller (e.g., similar to external controller 6880). Through this means of communication, system 7100 can share stored or actively collected data regarding the physical or chemical characteristics of the fluid being analyzed. This data can be stored locally on the external bladder management system 7100 temporarily or permanently. Once the data is transferred or communicated to a smartphone or database, the data can remain or self delete after a specified period of time.

Based on where the system 7100 resides within the fluid collection receptacle T, in this case a toilet, the external bladder management system 7100 can be cleaned and recalibrated by flushing the toilet either through the shape of the fluid collection funnel or just through its positioning in the toilet T. As shown, in this embodiment, system 7100 also includes an aperture 7803 through which clean or fresh toilet water can enter the funnel 7801 to clean therein for subsequent use. In some embodiments, funnel 7801 can include any suitable number (e.g., one or more) of apertures or openings through which fresh water or similar fluid can flow to clean system 7100. The body 7805 and funnel-like attachment 7806 can be situated near the basin of the toilet such that water flowing down the sides while flushed can be routed through the funnel and lumen of the device. The flow of water through the device can wash or rinse any remaining bodily fluid or residue. Once the system 7100 has been washed or rinsed, it can calibrate its optical or acoustic sensors. In addition, in this embodiment, system 7100 can track build-up of biofilm or other fluid components on the optical chamber and warn a user or an AI system that the optical sensors have come out of a predetermined range and thus the system 7100 needs to be cleaned further or replaced with one or more new components of the system 7100. In addition, upon activation the system 7100 can go through a self calibration step first to determine if the optical properties of the test chamber are in a predetermined range and adjust the output of the light sources or sensitivity of its sensors to calibrate their output such that measured properties of the test chamber are with a predetermined range.

The embodiment may include the addition of destructive chemical or physical tests, such as optical test strips that change color in the presence of a specific antigen, protein, marker or chemical signal. Optical sensors can be embedded in the device in such a way that they recognize any change in the color of the optical test strip and record that data. These destructive tests integrated into the embodiment may test for qualitative or quantitative metabolites or markers of the body's metabolic physiology (sugars, proteins, etc.), ions and vitamins (magnesium, calcium, zinc, etc.), and indicators of pathology (viral particles, bacteria-associated antigens, parasitic antigens, etc.).

In some implementations, system 7100 may include the addition of a fluid testing chamber that when filled from the top by the fluid collection portion transfers fluid through in a laminar flow profile past the embedded optical sensors in the device. This chamber can be made out of a non-UV absorbing polymer like a poly methacrylic or glass material. In addition, the chamber can have multiple thicknesses to enable measuring through smaller or larger portions of the tested fluid as shown in 7901. Different wavelengths have different base absorbance through urine, and so some wavelengths may need to pass through different path length than others. To accommodate for this, the fluid testing chamber 7901 may have a varying pathlengths through its inner volume (or air gap), between its walls. Said another way, a path length across a first portion of the fluid testing chamber 7901 may be different than a path length across a second, different, portion of the fluid testing chamber 7901. In some instances, the wall thickness of the fluid testing chamber 7901 can vary across its length to provide for such varying path lengths. Said another way, the inner volume or air gap through the fluid testing chamber 7901 may vary in cross-sectional area.

Figure 82:
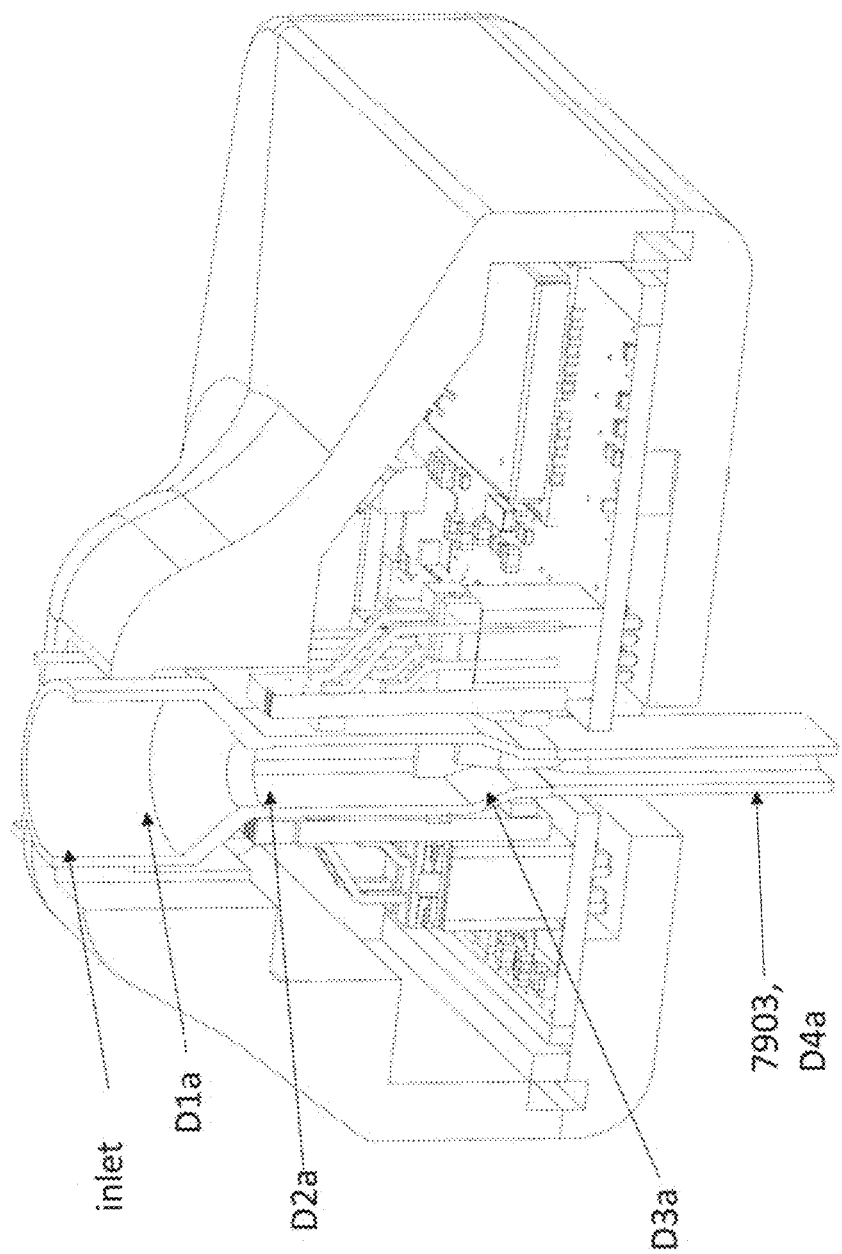
FIGS. 82 and 83 are partial cross-sectional views of the external bladder management system of FIGS. 77A and 77B.
Figure 83:
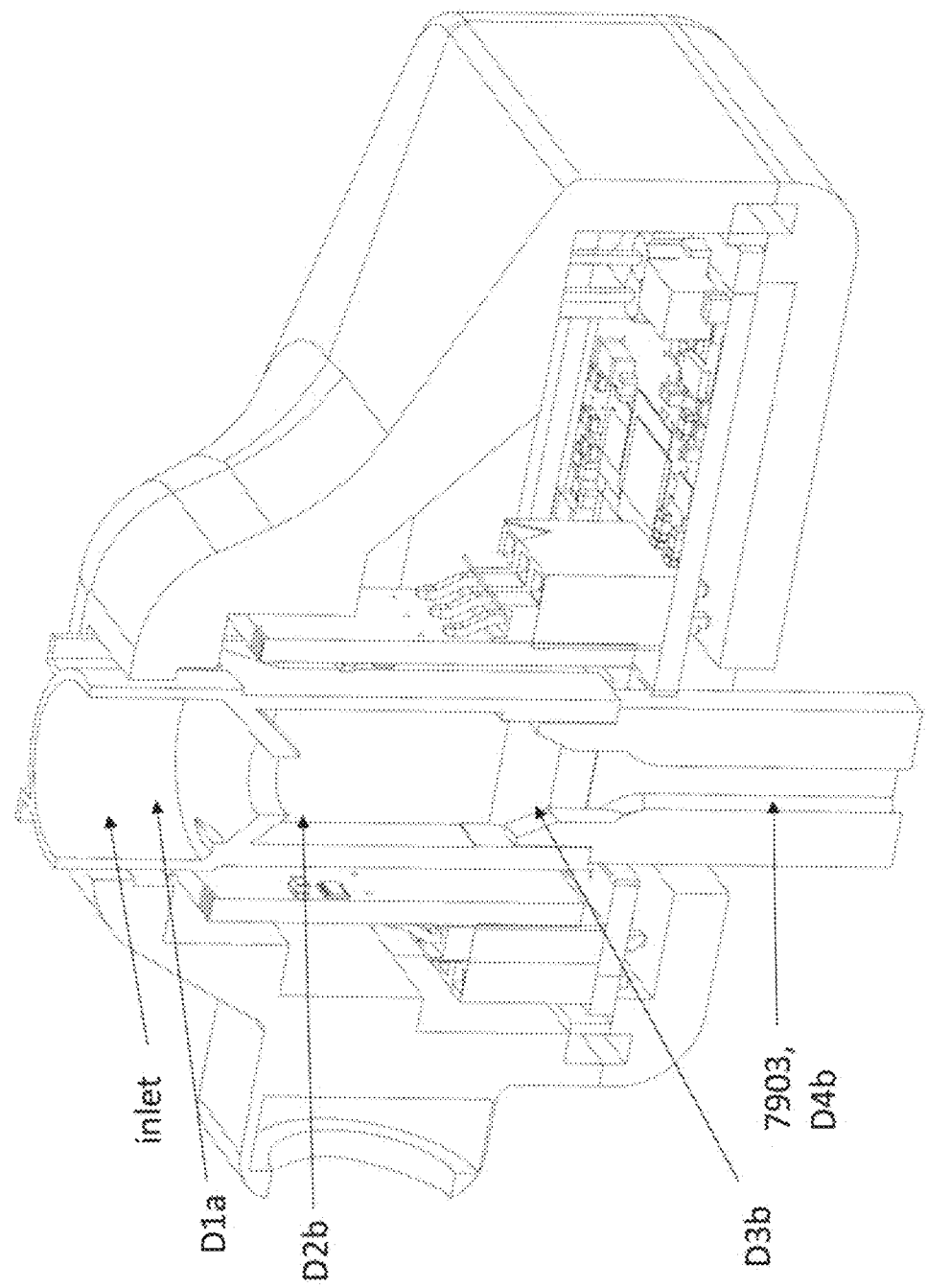

FIGS. 82 and 83 illustrate in partial-cross-section, as an example implementation, a fluid testing chamber 7901 having an inner volume that narrows along its longitudinal axis. More specifically, as shown in FIG. 82, which is a cross-sectional view taken along the testing chamber's 7901 relatively short lateral axis (e.g., its width), the fluid testing chamber 7901 has three reductions in cross-sectional area (e.g., and diameter, length, and/or width in some instances, depending on the shape of that particular portion or region) (referred to as D1a, D2a, D3a, and D4a), from its inlet to its outlet (which in this case is the fluid outlet 7903). The ratio of cross-sectional areas can be any suitable values such that laminar flow is maintained through the testing chamber 7901 and/or the testing chamber 7901 remains substantially full of fluid (e.g., urine) during its testing phase. An example ratio of cross-sectional areas, includes, for example, 17:11:3.7:1.86, for D1a, D2a, D3a, D4a, respectively. In some implementations, the ratios can be different, such as, for example, +/−5%, 10%, 15%, or 20% (or any percentages therebetween) of the above example.

FIG. 83, which is a cross-sectional view taken along the testing chamber's 7901 relatively long lateral axis (e.g., its length), shows that the fluid testing chamber 7901 has three reductions in cross-sectional area (e.g., and diameter, length, and/or width in some instances, depending on the shape of that particular portion or region) (referred to as D1b, D2b, D3b and D4b) from its inlet to its outlet. The ratio of cross-sectional areas can be any suitable values such that laminar flow is maintained through the testing chamber 7901 and/or the testing chamber 7901 remains substantially full of fluid (e.g., urine) during its testing phase. An example ratio of cross-sectional areas, includes, for example, 17:11.9:4.8:3, for D1b, D2b, D3b, D4b, respectively. In some implementations, the ratios can be different, such as, for example, +/−5%, 10%, 15%, or 20% (or any percentages therebetween) of the above example. Further, in this manner, the net result is a transition of flow from a cylindrical flow profile to rectangular flow profile that is limited to a laminar flow profile. In other implementations, a testing chamber can have any suitable number of transitions (e.g., less than or more than three).

In this implementation, from the inlet of the fluid testing chamber 7901 to the outlet of the fluid testing chamber 7901, its inner volume is reduced to limit fluid flow, thereby encouraging accumulation of fluid upstream the fluid testing chamber 7901 (e.g., within the funnel), and thereby encouraging both a laminar flow profile through the testing chamber 7901 and a testing chamber 7901 full of fluid during testing, to promote more reliable and repeatable testing.

In some implementations, system 7100 may include the addition of pressure, weight, sound, or light-based flow sensors in the fluid collection portion, alongside the other sensing elements, or at the outport of the device. These measurements can then be used to extract out several physiological or fluid measurements related to the fluid being introduced into the devices or its source such as peak flow rate, total flow rate, total time of fluid introduction, or residual volume remaining in the source.

Figure 80B:
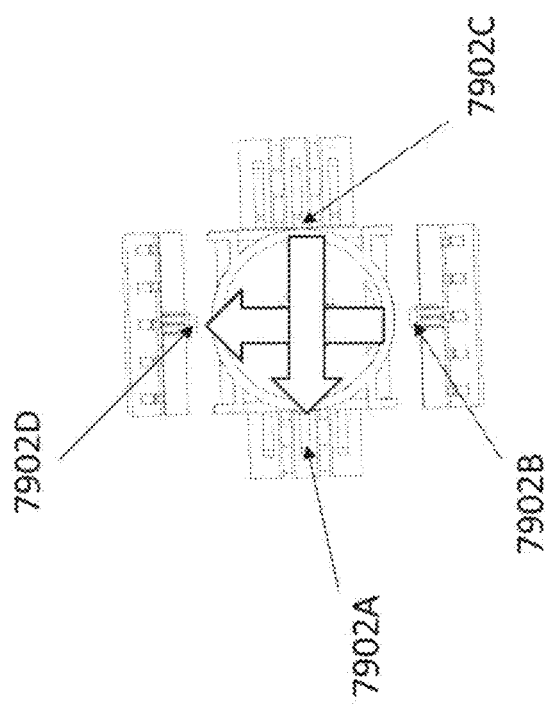
FIGS. 80A and 80B are a perspective partial cross-sectional and a top view, respectively, of the external bladder management system of FIGS. 77A and 77B, including sensors arranged on all 4 sides of a fluid transfer component.
Figure 80A:
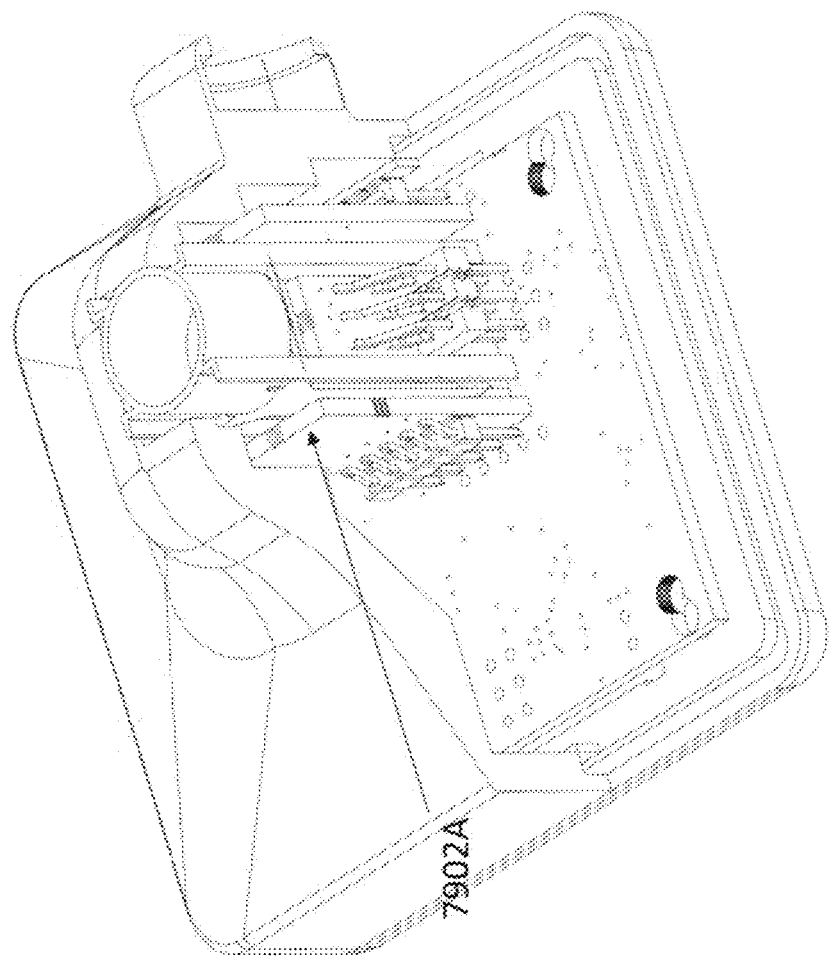

System 7100 may also include one or more printed circuit boards (PCBs) 7902 holding or configured to hold one or more optical or spectral sensors, arranged to sense fluid within the testing chamber 7910. In this embodiment, system 7100 includes four PCBs 7902A, 7902B, 7902C, 7902D, each vertically mounted and disposed circumferentially about the testing chamber 7901, as shown in FIGS. 80A and 80B, and collectively configured to perform spectroscopy on the fluid passing through the testing chamber 7901. In such a 4-way arrangement, as shown, system 7100 can analyze a sample within the testing chamber 7901 from multiple wavelengths and multiple, and e.g., custom, pathlengths, e.g., based on variations in PCBs (their emitters), their location, orientation, and/or programmed operation, and/or the structure of the testing chamber 7901. In some implementations, the PCBs 7902A, 7902B, 7902C, 7902D are the same, while in some implementations, they are different. Similar to as described in previous embodiments, the spectral or optical sensors may include a light source or emitter configured to convey light (e.g., at a predefined wavelength) across the fluid testing chamber and an optical detector capable of measuring an intensity of the light as the light exits the fluid testing chamber. The light can be conveyed at any suitable wavelength, such as, for example, 280 nanometers, 365 nanometers, 444 nanometers, 468 nanometers, 485 nanometers, 515 nanometers, 520 nanometers, 615 nanometers, 632 nanometers, 940 nanometers, 1350 nanometers, and/or the link, and any suitable wavelength therebetween.

Each PCB may include any suitable number of emitters and/or detectors, and can be arranged any suitable distance from a corresponding PCB. In some implementations, for example, the system may include four pairs of emitters and detectors, each emitter being configured to emit a relatively unique wavelength. In other implementations, more than four pairs may be used. For example, as shown in FIG. 80B, PCB 7902C includes three emitters, and PCB 7902A, located across the testing chamber 7901, includes three detectors, each configured to sense an intensity of the light from a corresponding emitter (e.g., LEDs) from PCB 7902C.

Similarly, as shown in this example, PCB 7902B includes five emitters, and PCB 7902D, located across the testing chamber 7901, includes five detectors, each configured to sense an intensity of the light from a corresponding emitter (e.g., LED) from PCB 7902B. As shown in FIG. 81, in this illustrated implementation, testing chamber 7901 defines a volume to contain the fluid for testing and transfer from the fluid inlet to the fluid outlet, and that volume decreasing in cross-sectional area from its inlet to its outlet, such that the distance (and light pathlength) from PCB 7902C to PCB 7902A is less than the distance (and light pathlength) from PCB 7902B to PCB 7902D. In this manner, various wavelengths can be used to test the fluid (e.g., urine). For example, UVC light, which may require a relatively short pathlength, can be used with PCBs 7902A and 7902C, and visible light, which may be suitable with a relatively longer pathlength, can be used with PCBs 7902 and 7902D. Urine, for example, has different transmissibility and/or attenuation at different wavelengths, and so this can be leveraged by the variations described herein.

In some embodiments, bladder management system 7100 may include one or more impedance sensors (not shown) operably and/or electrically coupleable to the optical sensors/PCBs, in an open circuit configuration by default, and configured to interact with fluid (e.g., urine), to thereby close or complete the circuit/electrical coupling with the optical sensors/PCBs, to thereby trigger the optical sensors to test the fluid/urine. Said another way, the one or more impedance sensors can function as spectroscopy triggers to cause the optical sensors to emitter and detect light to test the fluid. In this manner, for example, the bladder management system 7100 can conserve power, and, for example, only test fluid when fluid, such as urine, has entered the system. Given the lack of salt content in fresh toilet water, for example, a fluid flush with fresh toilet water, unlike urine, would not trigger the impedance sensor(s) to complete the circuit.

What is claimed is:
1. A system configured to reside within a urine collection receptacle, comprising:
 a body housing a fluid testing chamber, the fluid testing chamber being fluidically coupled to a fluid inlet and a fluid outlet;
 a fluid capturing funnel fluidically coupled to the fluid inlet;
 an attachment mechanism coupled to and extending from the body and configured to couple the body to the urine collection receptacle;
 a first optical sensor disposed within the body and including (1) a first emitter configured to convey via a first path a first light across the fluid testing chamber, and (2) a first optical detector configured to measure an intensity of the first light as the first light exits the fluid testing chamber; and
 a second optical sensor disposed within the body and including (1) a second emitter configured to convey via a second path a second light across the fluid testing chamber, and (2) a second optical detector configured to measure an intensity of the second light as the second light exits the fluid testing chamber, the first path and the second path being independent,
 the fluid testing chamber defining an internal volume through which fluid received by the fluid capturing funnel can be conveyed and tested by the first optical sensor and the second optical sensor, the fluid capturing funnel and the fluid testing chamber being collectively configured to maintain within the volume of the fluid testing chamber a volume of fluid sufficient for optical testing of the fluid.

2. The system of claim 1, wherein a first wall of the fluid testing chamber configured to receive the first light has a first thickness, and a second wall of the fluid testing chamber configured to receive the second light has a second thickness different from the first thickness.

3. The system of claim 1, wherein the internal volume of the fluid testing chamber varies in cross-sectional area.

4. The system of claim 1, wherein the fluid inlet defines a lumen through which fluid enters the fluid testing chamber and the fluid outlet defines a lumen through which fluid exits the fluid testing chamber, the lumen of the fluid inlet having a cross-sectional area greater than a cross-sectional area of the lumen of the fluid outlet.

5. The system of claim 1, wherein the funnel is configured to receive flush fluid from plumbing coupled to the urine collection receptacle for flushing the funnel for subsequent use and when the body is coupled to the urine collection receptacle.

6. The system of claim 1, wherein the funnel defines a lip configured to bias fluid introduced to the funnel towards the fluid inlet of the body and limit splashing of the fluid outside the funnel.

7. The system of claim 1, further comprising a transmitter configured to wirelessly transmit a signal representative of the intensity to a receiver external to the body.

8. The system of claim 1, wherein the volume has a rectangular cross-sectional area having a width different than its length, and planar walls configured to receive the conveyed optical light.

9. The system of claim 1, wherein the first emitter is coupled to a first printed circuit board that is disposed adjacent a first side of the fluid testing chamber, the first optical detector being disposed adjacent a second side, opposite the first side, of the fluid testing chamber, the second emitter being coupled to a third printed circuit board that is disposed adjacent a third side of the fluid testing chamber, the second optical detector being disposed adjacent a fourth side, opposite the third side, of the fluid testing chamber.

10. The system of claim 9, wherein the first emitter includes a light-emitting diode (LED) and the second emitter includes an LED.

11. The system of claim 1, further comprising a sensor configured to indicate when urine has entered the system, the first optical sensor and the second optical sensor configured to test the urine only in response to the indication.

12. The system of claim 1, wherein the fluid capturing funnel and the fluid testing chamber are collectively configured to encourage accumulation of fluid within a testing region between the emitter and the optical detector such that the testing region is fully occupied by fluid as the light is conveyed from the emitter to the optical detector.

13. The system of claim 1, wherein the first emitter is axially aligned with the first optical detector, and the second emitter is axially aligned with the second optical detector.

14. The system of claim 1, wherein with respect to fluid flow the first optical sensor is disposed upstream of the second optical sensor, the first path being greater than the second path, and the wall thickness of the fluid testing chamber through which the first path and the second path cross is equal.

15. The system of claim 1, wherein the first emitter and the first optical detector are laterally displaced by a first distance, and the second emitter and the second optical detector are laterally displaced by a second distance, the first distance being different from the second distance.

16. The system of claim 1, wherein the first optical sensor is configured such that the first path is a direct path, and the second optical sensor is configured such that the second path is a direct path.

17. A system, comprising:
a body housing a fluid testing chamber, the fluid testing chamber being fluidically coupled to a fluid inlet and a fluid outlet;
a fluid capturing reservoir fluidically coupled to the fluid inlet;
an attachment mechanism coupled to and extending from the body and configured to couple the body to a urine collection receptacle;
a first optical sensor disposed within the body and including (1) a first emitter configured to convey light a first pathlength across a first portion of an inner volume of the fluid testing chamber when the first portion through which the first pathlength crosses contains only urine received by the fluid capturing reservoir, and (2) a first optical detector capable of measuring an intensity of the light emitted by the first emitter as the light exits the inner volume of the fluid testing chamber;
a second optical sensor disposed within the body and including (1) a second emitter configured to convey light a second pathlength across a second portion of the inner volume of the fluid testing chamber when the second portion through which the second pathlength crosses contains only urine received by the fluid capturing reservoir, and (2) a second optical detector capable of measuring an intensity of the light emitted by the second emitter as the light exits the inner volume of the fluid testing chamber, the first pathlength being different than the second pathlength; and
a controller operably couplable to the first optical sensor and the second optical sensor, the controller configured to determine if optical properties of the fluid testing chamber are in a predetermined range and adjust at least one of (1) an output of the first or second emitter, or (2) a sensitivity of the first or second optical detector when the optical properties are not in the predetermined range.

18. The system of claim 17, wherein the inner volume of the fluid testing chamber varies in cross-sectional area along its longitudinal axis.

19. The system of claim 17, wherein the inner volume has a rectangular cross-sectional area having a width different than its length.

20. The system of claim 17, wherein the first emitter includes a light-emitting diode (LED), and the second emitter includes an LED.

21. The system of claim 17, further comprising a sensor configured to indicate when urine has entered the system, the first emitter and the second emitter each configured to emit light only in response to the urine contacting the sensor.

22. A system configured to reside within a urine collection receptacle, comprising:
a body housing a fluid testing chamber, the fluid testing chamber being fluidically coupled to a fluid inlet and a fluid outlet;
a fluid capturing reservoir fluidically coupled to the fluid inlet;
a first optical sensor disposed within the body and including (1) a first emitter configured to convey light at a first wavelength and first pathlength across an inner volume of the fluid testing chamber, and (2) a first optical detector arranged to measure an intensity of the light from only the first emitter as the light exits the inner volume of the fluid testing chamber; and a second optical sensor disposed within the body and including (1) a second emitter configured to convey light at a second wavelength and second pathlength across the inner volume of the fluid testing chamber, and (2) a second optical detector arranged to measure an intensity of the light from only the second emitter as the light exits the inner volume of the fluid testing chamber, the first wavelength being different than the second wavelength, and the first pathlength being different than the second pathlength, the inner volume of the fluid testing chamber having a cross-sectional area that reduces along its longitudinal axis from an end of the fluid testing chamber coupled to the fluid inlet to an end of the fluid testing chamber coupled to the fluid outlet.

23. The system of claim 22, wherein the first emitter includes a light-emitting diode (LED), and the second emitter includes an LED.

24. A system configured to reside within a urine collection receptacle, comprising:
 a body housing a fluid testing chamber;
 an attachment mechanism coupled to and extending from the body and configured to couple the body to the urine collection receptacle;
 a fluid capturing funnel fluidically coupled to an inlet-side of the fluid testing chamber such that fluid received in the fluid capturing funnel travels from the fluid capturing funnel to the fluid testing chamber when the body is coupled to the urine collection receptacle with the fluid capturing funnel disposed above the fluid testing chamber;
 a first optical sensor disposed within the body and including (1) a first emitter configured to convey light across the fluid testing chamber, and (2) a second optical detector capable of measuring an intensity of the light as the light exits the fluid testing chamber; and
 a second optical sensor disposed within the body and including (1) a second emitter configured to convey light across the fluid testing chamber, and (2) a second optical detector configured to measure an intensity of the second light as the second light exits the fluid testing chamber,
the first emitter and the first optical detector being laterally displaced by a first distance, and the second emitter and the second optical detector being laterally displaced by a second distance, the first distance being different from the second distance,
the fluid capturing funnel and the fluid testing chamber collectively configured such that the fluid testing chamber is fully occupied with the fluid for a period of time sufficient for the light to be conveyed from the first emitter and the second emitter, through the fluid, and to the first optical detector and the second optical detector.

25. The system of claim 24, wherein the optical sensor is a first optical sensor, the emitter is a first emitter, the light is first light, and the optical detector is a first optical detector, the system further comprising a second optical sensor disposed within the body and including a second emitter configured to convey second light across the fluid testing chamber and a second optical detector capable of measuring an intensity of the second light as the second light exits the fluid testing chamber, the first light traveling a first path length across the fluid testing chamber and the second light traveling a second path length across the fluid testing chamber, the first path length being different from the second path length.

26. The system of claim 24, wherein the inlet-side defines a lumen through which fluid enters the fluid testing chamber and an outlet-side of the fluid testing chamber defines a lumen through which fluid exits the bladder management system, the lumen of the inlet-side having a cross-sectional area greater than a cross-sectional area of the lumen of the outlet-side.

27. The system of claim 24, wherein the funnel is configured to receive flush fluid from plumbing coupled to the urine collection receptacle for flushing the funnel for subsequent use and when the body is coupled to the urine collection receptacle.

28. The system of claim 24, further comprising a sensor configured to indicate when urine has entered the system, the first optical sensor and the second optical sensor configured to test the urine only in response to the indication.

29. A system configured to reside within a urine collection receptacle, comprising:
 a body housing a fluid testing chamber, the fluid testing chamber being fluidically coupled to a fluid inlet and a fluid outlet;
 a fluid capturing funnel fluidically coupled to the fluid inlet;
 an attachment mechanism coupled to and extending from the body and configured to couple the body to the urine collection receptacle;
 a first optical sensor disposed within the body and including (1) a first emitter configured to convey light across the fluid testing chamber, and (2) a first optical detector capable of measuring an intensity of the light as the light exits the fluid testing chamber, the first emitter being disposed adjacent a first side of the fluid testing chamber and the first optical detector being disposed adjacent a second side, opposite the first side, of the fluid testing chamber; and
 a second optical sensor disposed within the body and including (1) a second emitter configured to convey light across the fluid testing chamber, and (2) a second optical detector capable of measuring an intensity of the light as the light exits the fluid testing chamber, the second emitter being disposed adjacent a third side of the fluid testing chamber, the second optical detector being disposed adjacent a fourth side, opposite the third side, of the fluid testing chamber,
the fluid testing chamber defining an internal volume through which fluid received by the fluid capturing funnel can be conveyed and tested by the first optical sensor and the second optical sensor, the fluid capturing funnel and the fluid testing chamber being collectively configured to maintain within the volume of the fluid testing chamber a volume of fluid sufficient for optical testing of the fluid.

30. The system of claim 29, wherein a first wall of the second side of the fluid testing chamber has a first thickness, and a second wall of the fourth wall fluid testing chamber has a second thickness different from the first thickness.

31. The system of claim 29, wherein the internal volume of the fluid testing chamber varies in cross-sectional area.

32. The system of claim 29, wherein the fluid inlet defines a lumen through which fluid enters the fluid testing chamber and the fluid outlet defines a lumen through which fluid exits the fluid testing chamber, the lumen of the fluid inlet having a cross-sectional area greater than a cross-sectional area of the lumen of the fluid outlet.

33. The system of claim 29, wherein the funnel is configured to receive flush fluid from plumbing coupled to the urine collection receptacle for flushing the funnel for subsequent use and when the body is coupled to the urine collection receptacle.

34. The system of claim 29, wherein the funnel defines a lip configured to bias fluid introduced to the funnel towards the fluid inlet of the body and limit splashing of the fluid outside the funnel.

35. The system of claim 29, further comprising a transmitter configured to wirelessly transmit a signal representative of the intensity to a receiver external to the body.

36. The system of claim 29, wherein the internal volume has a rectangular cross-sectional area having a width different than its length, and planar walls configured to receive the conveyed optical light.

37. The system of claim 29, wherein the first emitter is coupled to a first printed circuit board that is disposed adjacent a first side of the fluid testing chamber, the first optical detector being disposed adjacent a second side, opposite the first side, of the fluid testing chamber, the second emitter being coupled to a third printed circuit board that is disposed adjacent a third side of the fluid testing chamber, the second optical detector being disposed adjacent a fourth side, opposite the third side, of the fluid testing chamber.

38. The system of claim 29, wherein the first emitter includes a light-emitting diode (LED) and the second emitter includes an LED.

39. The system of claim 29, further comprising a sensor configured to indicate when urine has entered the system, the first optical sensor and the second optical sensor configured to test the urine only in response to the indication.

* * * * *